(12) United States Patent
Chen et al.

(10) Patent No.: US 11,844,925 B2
(45) Date of Patent: Dec. 19, 2023

(54) FLUID INFUSION SYSTEMS

(71) Applicant: MEDTRONIC MINIMED, INC., Northridge, CA (US)

(72) Inventors: Shixin Chen, Simi Valley, CA (US); Eric Allan Larson, Simi Valley, CA (US); Hsiao-Yu S. Kow, Ladera Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 84 days.

(21) Appl. No.: 16/893,128

(22) Filed: Jun. 4, 2020

(65) Prior Publication Data
US 2020/0384196 A1    Dec. 10, 2020

Related U.S. Application Data

(60) Provisional application No. 62/858,304, filed on Jun. 6, 2019.

(51) Int. Cl.
*A61M 5/142*    (2006.01)
*A61M 39/10*    (2006.01)
(Continued)

(52) U.S. Cl.
CPC ........ *A61M 5/14248* (2013.01); *A61M 5/162* (2013.01); *A61M 5/16831* (2013.01);
(Continued)

(58) Field of Classification Search
CPC ................ A61N 5/142; A61N 5/14244; A61N 5/14248; A61N 5/16831; A61N 5/16836;
(Continued)

(56) References Cited

U.S. PATENT DOCUMENTS

| 4,562,751 A | 1/1986 | Nason et al. |
| 4,678,408 A | 7/1987 | Nason et al. |

(Continued)

FOREIGN PATENT DOCUMENTS

| EP | 3354306 A1 | 8/2018 | |
| EP | 3539591 A1 * | 9/2019 | ............ A61M 39/14 |

(Continued)

OTHER PUBLICATIONS

Response to Invitation to Pay Additional Fees dated Sep. 25, 2020 from International Application No. PCT/US2020/036290, filed Oct. 21, 2020, 4 pp.

(Continued)

*Primary Examiner* — Tiffany Legette
(74) *Attorney, Agent, or Firm* — Shumaker & Sieffert, P.A.

(57) ABSTRACT

Fluid infusion systems such as a portable fluid infusion device includes a housing configured to accommodate a removable fluid reservoir. The housing has a largest dimension and a smallest dimension. The portable fluid infusion device includes a drive system configured to be serially coupled to the removable fluid reservoir such that a combined dimension of the drive system and the removable fluid reservoir is less than or equal to the largest dimension. The portable fluid infusion device includes a planar battery configured to supply power to the drive system. The planar battery has a plurality of faces comprising one or more faces having a largest area, and the planar battery being situated such that the one or more faces are parallel to the largest dimension and the smallest dimension.

11 Claims, 93 Drawing Sheets

(51) Int. Cl.
*A61M 5/172* (2006.01)
*A61M 5/162* (2006.01)
*A61M 37/00* (2006.01)
*A61M 5/168* (2006.01)

(52) U.S. Cl.
CPC ...... *A61M 5/1723* (2013.01); *A61M 37/0015* (2013.01); *A61M 39/10* (2013.01); *A61M 2005/14252* (2013.01); *A61M 2037/0023* (2013.01); *A61M 2205/50* (2013.01); *A61M 2205/8206* (2013.01); *A61M 2205/8243* (2013.01); *A61M 2230/201* (2013.01)

(58) Field of Classification Search
CPC ...... A61N 5/1723; A61M 2005/14252; A61M 2005/14573; A61M 2005/1726; A61M 2205/8206; A61M 5/142; A61M 5/14244; A61M 5/14248; A61M 5/16831; A61M 5/16836; A61M 5/1723; A61M 2005/1588; A61M 5/1452; A61B 5/4839; A61B 5/14865; A61B 5/14532; A61B 5/14514
See application file for complete search history.

(56) References Cited

U.S. PATENT DOCUMENTS

| | | |
|---|---|---|
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,814,020 A * | 9/1998 | Gross ............... A61M 5/14593 604/141 |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Arsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,892,085 B2 | 5/2005 | McIvor et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,905,868 B2 | 3/2011 | Moberg et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,435,209 B2 | 5/2013 | Hanson et al. |
| 8,474,332 B2 | 7/2013 | Bente, IV |
| 8,545,445 B2 | 10/2013 | Kamen et al. |
| 8,628,510 B2 | 1/2014 | Bazargan et al. |
| 8,674,288 B2 | 3/2014 | Hanson et al. |
| 9,295,786 B2 | 3/2016 | Gottlieb et al. |
| 9,636,450 B2 | 5/2017 | Hoss et al. |
| 9,974,903 B1 | 5/2018 | Davis et al. |
| 10,632,253 B2 | 4/2020 | Uchiyama et al. |
| 2002/0072733 A1 | 6/2002 | Flaherty |
| 2004/0220551 A1 | 11/2004 | Flaherty et al. |
| 2006/0224141 A1 | 10/2006 | Rush et al. |
| 2006/0253085 A1 | 11/2006 | Geismar et al. |
| 2007/0123819 A1 | 5/2007 | Mernoe et al. |
| 2007/0219480 A1 * | 9/2007 | Kamen ................ B23P 15/00 604/20 |
| 2008/0132773 A1 | 6/2008 | Burnes et al. |
| 2008/0269687 A1 | 10/2008 | Chong et al. |
| 2008/0281297 A1 | 11/2008 | Pesach et al. |
| 2009/0062767 A1 | 3/2009 | Van Antwerp et al. |
| 2009/0099523 A1 * | 4/2009 | Grant ................ A61M 5/5086 604/151 |
| 2009/0299290 A1 | 12/2009 | Moberg et al. |

(56) References Cited

U.S. PATENT DOCUMENTS

| | | | |
|---|---|---|---|
| 2009/0299301 A1 | 12/2009 | Gottlieb et al. | |
| 2010/0160861 A1 | 6/2010 | Causey, III et al. | |
| 2010/0198187 A1* | 8/2010 | Yodfat | A61M 5/142 604/131 |
| 2011/0137257 A1 | 6/2011 | Gyrn et al. | |
| 2012/0004602 A1 | 1/2012 | Hanson et al. | |
| 2012/0053522 A1 | 3/2012 | Yodfat et al. | |
| 2012/0078216 A1* | 3/2012 | Smith | A61M 5/145 604/93.01 |
| 2012/0238849 A1 | 9/2012 | Holtzclaw et al. | |
| 2012/0265003 A1 | 10/2012 | D'Ambrosio et al. | |
| 2012/0330228 A1* | 12/2012 | Day | A61M 5/20 604/82 |
| 2013/0023816 A1 | 1/2013 | Bachinski et al. | |
| 2013/0310630 A1 | 11/2013 | Smith et al. | |
| 2014/0207064 A1 | 7/2014 | Yavorsky | |
| 2015/0025503 A1 | 1/2015 | Searle et al. | |
| 2015/0174304 A1* | 6/2015 | Askem | A61F 13/0246 604/319 |
| 2016/0015887 A1 | 1/2016 | Pananen et al. | |
| 2016/0220798 A1 | 8/2016 | Netzel et al. | |
| 2017/0072118 A1 | 3/2017 | Makower et al. | |
| 2017/0100534 A1* | 4/2017 | Fukikoshi | A61M 5/1456 |
| 2017/0246366 A1 | 8/2017 | Rudser | |
| 2017/0312454 A1* | 11/2017 | Chattaraj | A61M 39/24 |
| 2018/0169322 A1 | 6/2018 | Chiu et al. | |
| 2018/0214636 A1 | 8/2018 | Amirouche | |
| 2018/0236163 A1 | 8/2018 | Stefanov et al. | |
| 2018/0250458 A1 | 9/2018 | Petersen et al. | |
| 2019/0117256 A1 | 4/2019 | Jager | |
| 2019/0134297 A1 | 5/2019 | Kamen et al. | |
| 2019/0307952 A1 | 10/2019 | Butler et al. | |
| 2019/0351134 A1 | 11/2019 | Cook et al. | |
| 2020/0114069 A1 | 4/2020 | Searle et al. | |
| 2020/0163389 A1 | 5/2020 | Sur | |
| 2020/0352485 A1 | 11/2020 | Antonio et al. | |
| 2020/0384192 A1 | 12/2020 | Garai et al. | |
| 2020/0384193 A1 | 12/2020 | Chiu et al. | |
| 2020/0384197 A1 | 12/2020 | Chiu et al. | |

FOREIGN PATENT DOCUMENTS

| | | | |
|---|---|---|---|
| EP | 3539592 A1 * | 9/2019 | A61M 39/14 |
| WO | 2008139458 A2 | 11/2008 | |
| WO | 2009013734 A2 | 1/2009 | |
| WO | 2010/042814 A2 | 4/2010 | |
| WO | 2013058879 A3 | 4/2013 | |
| WO | 2015027174 A1 | 2/2015 | |
| WO | 2017051619 A1 | 3/2017 | |
| WO | 2020184160 A1 | 9/2020 | |

OTHER PUBLICATIONS

International Search Report and Written Opinion of International Application No. PCT/US2020/036290, dated Oct. 30, 2020, 26 pp.
Invitation to Pay Additional Fees and, Where Applicable, Protest Fee, and Partial International Search Report from International Application No. PCT/US2020/036290, dated Sep. 25, 2020, 16 pp.
International Preliminary Report on Patentability from International Application No. PCT/US2020/036290, dated Dec. 16, 2021, 17 pp.

* cited by examiner

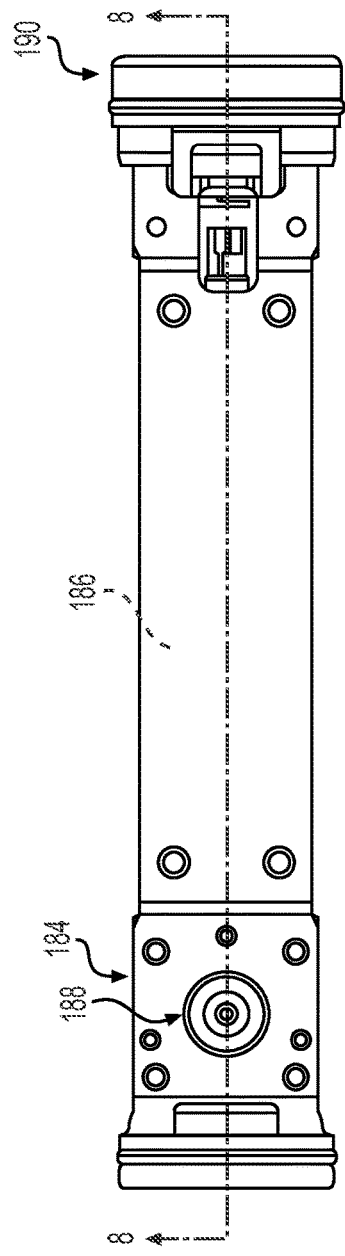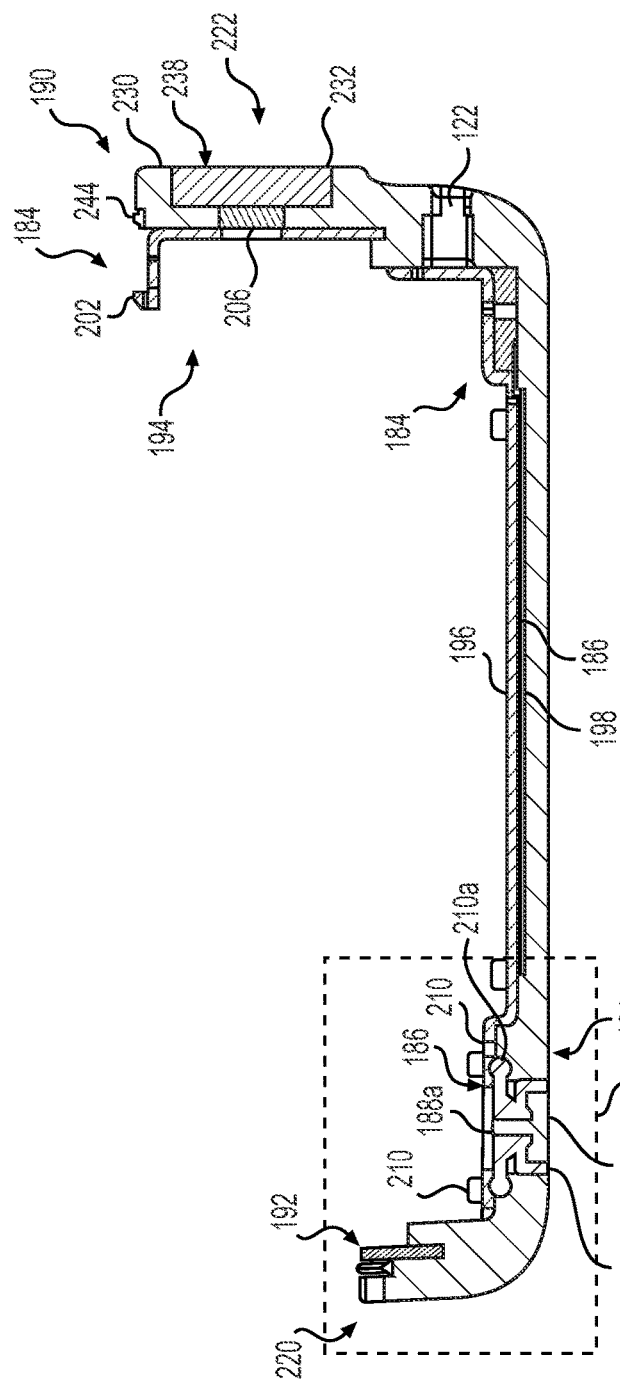

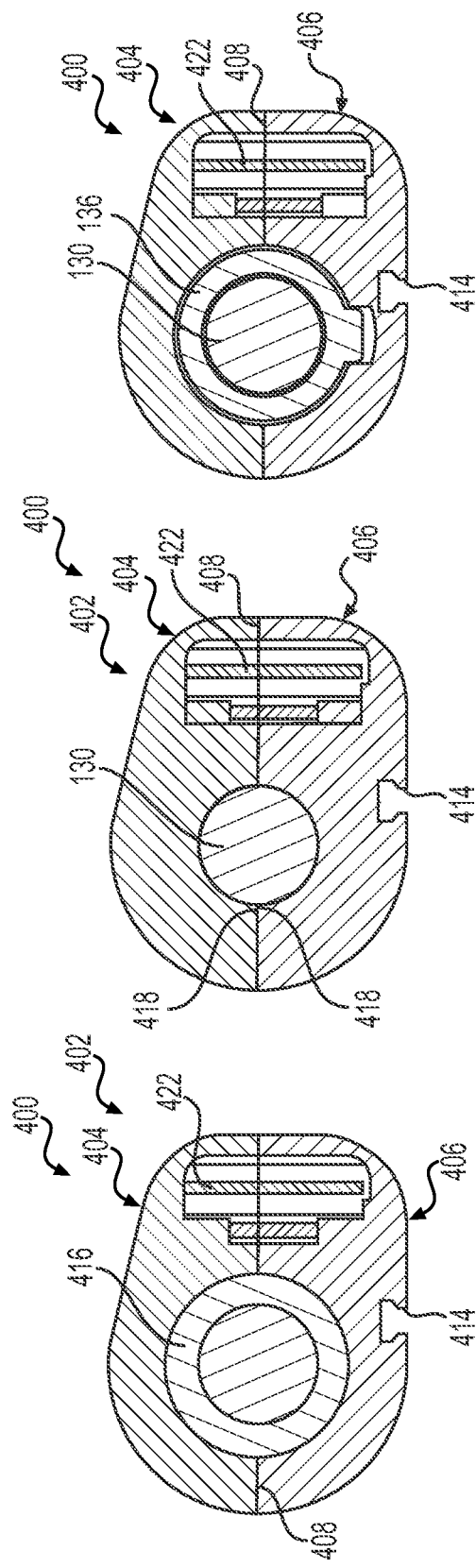

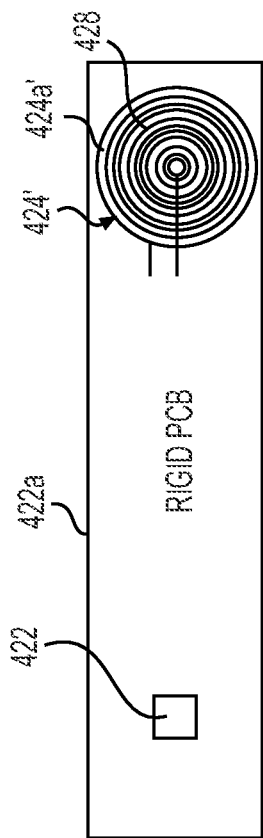
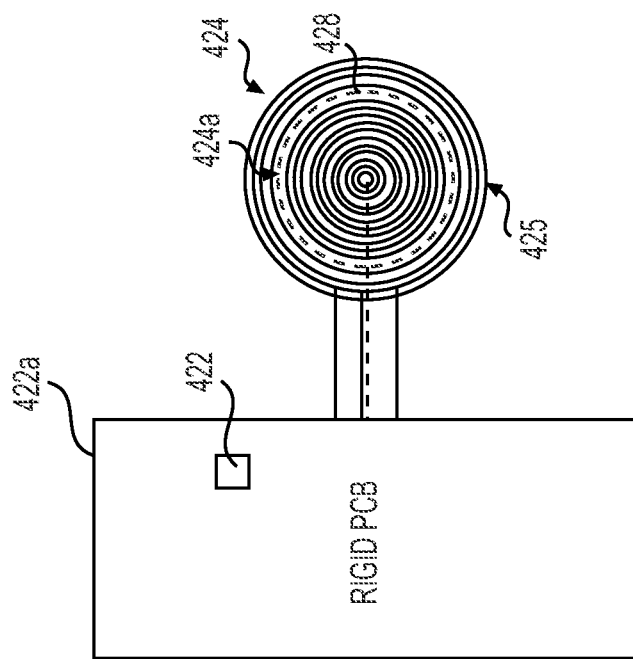

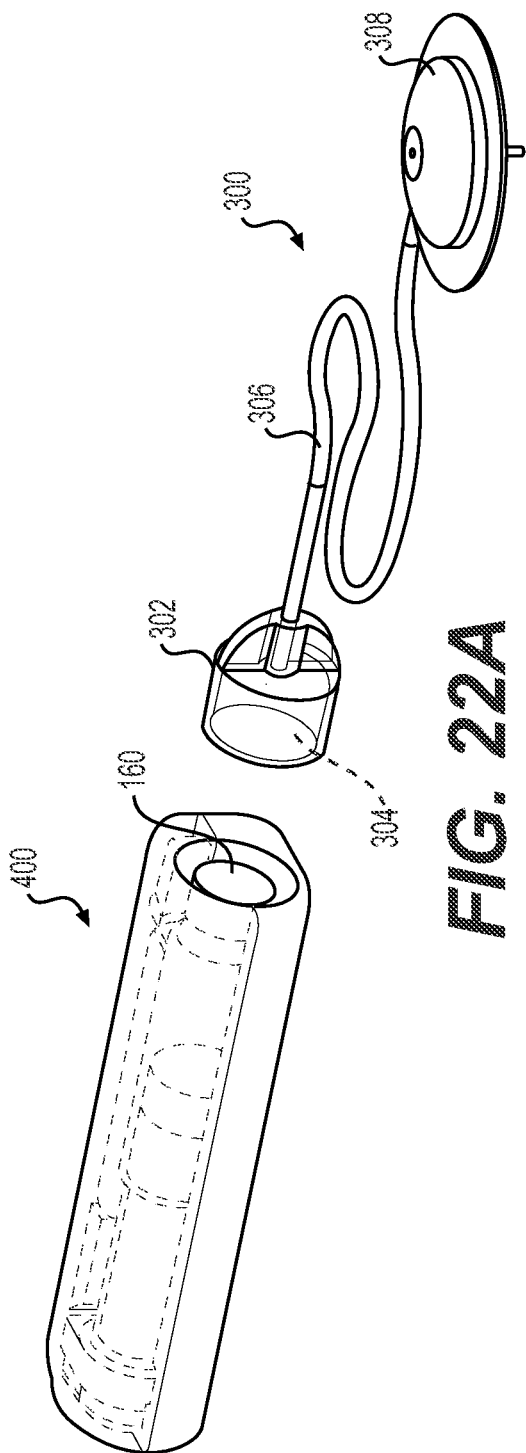
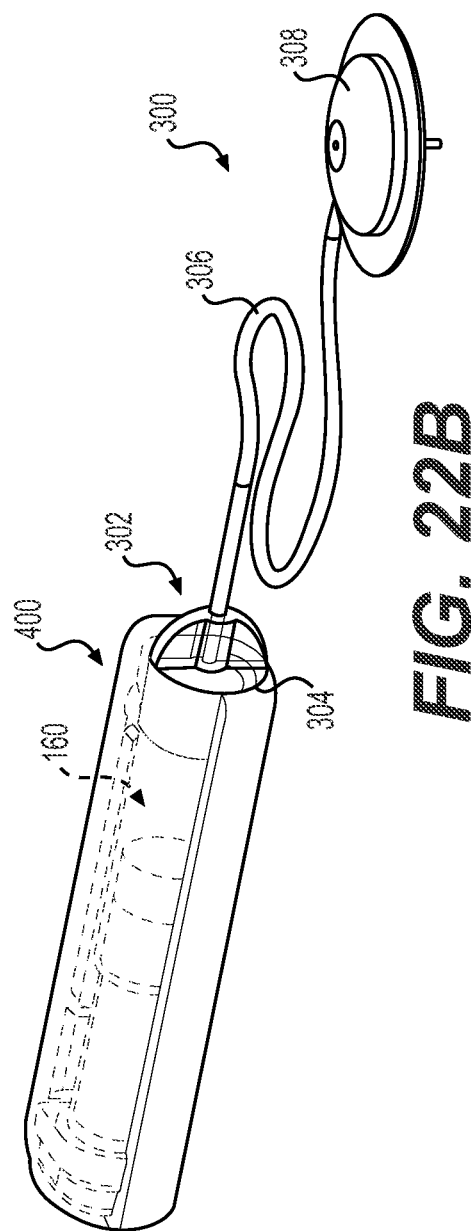

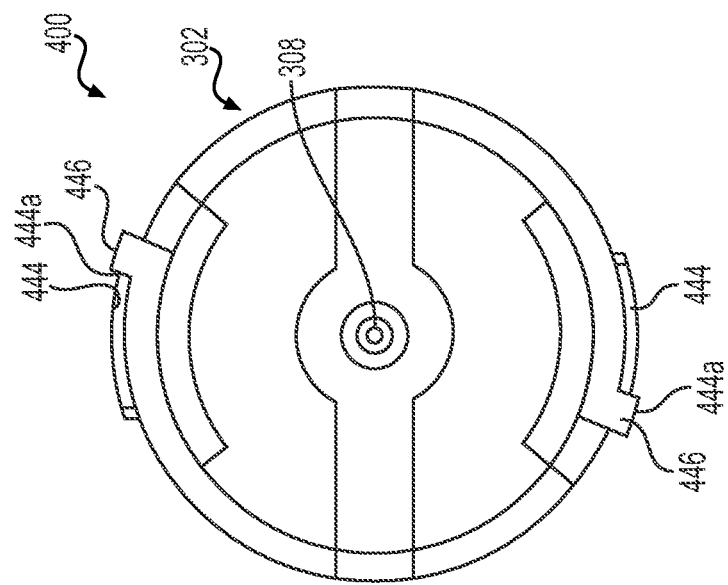
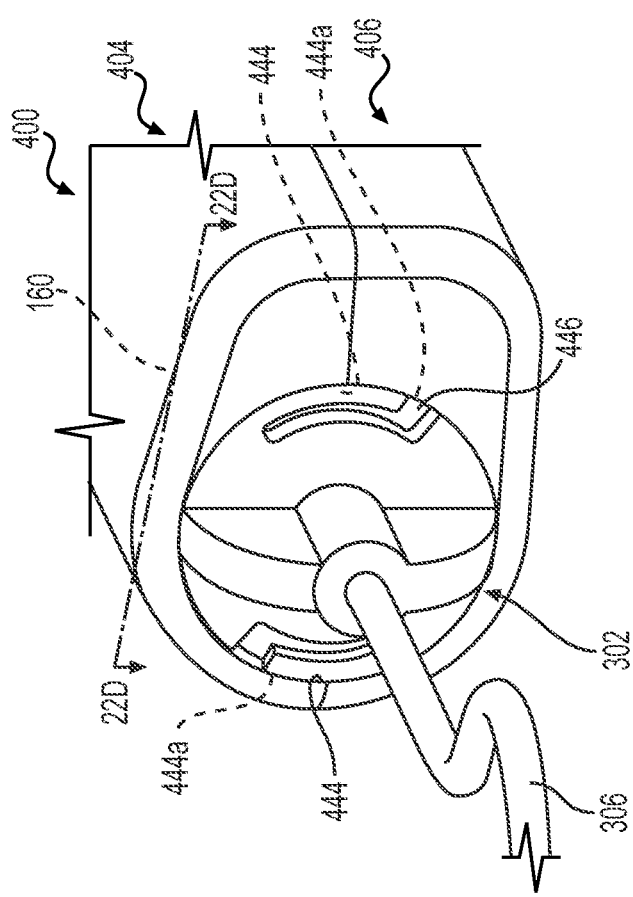
FIG. 22D
FIG. 22C

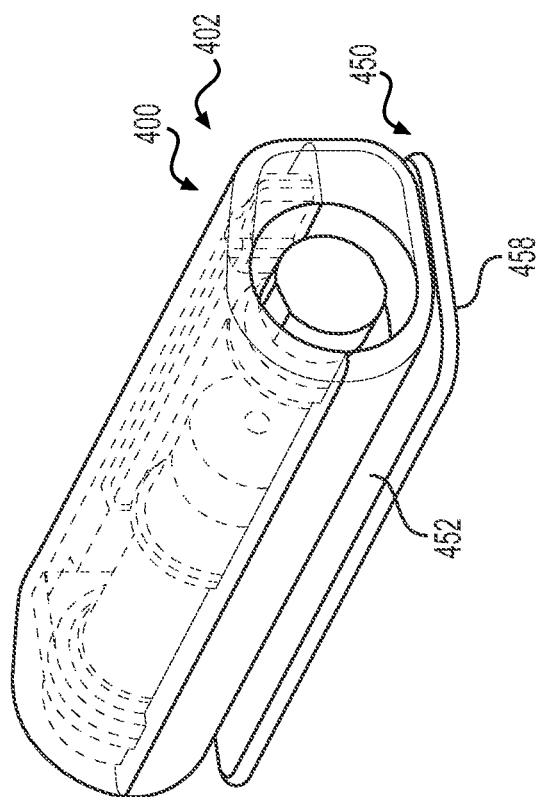
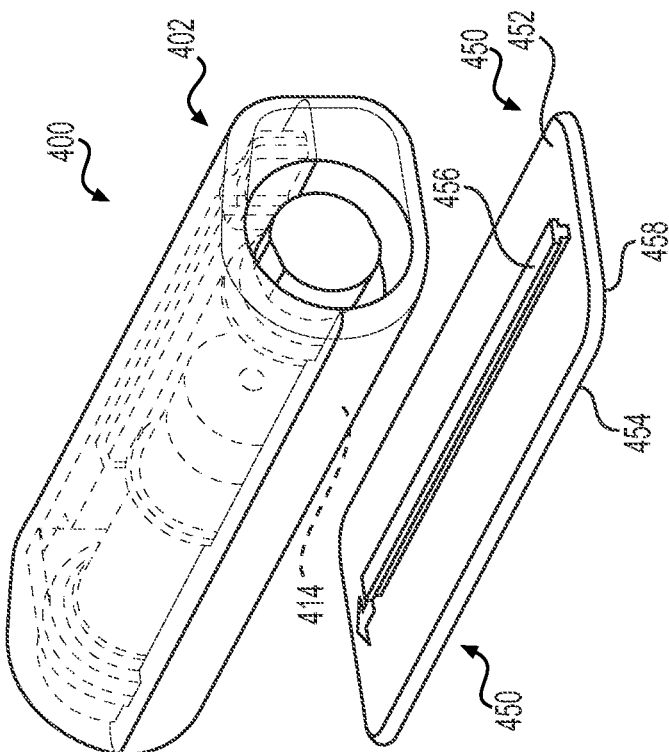

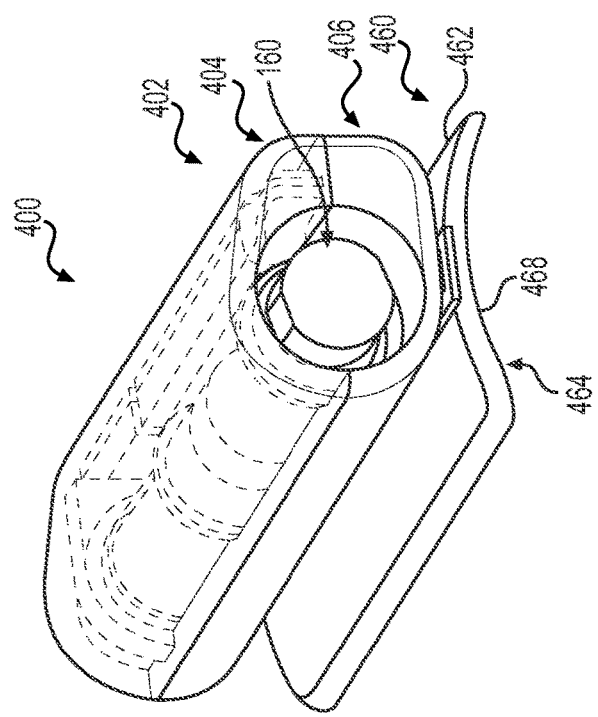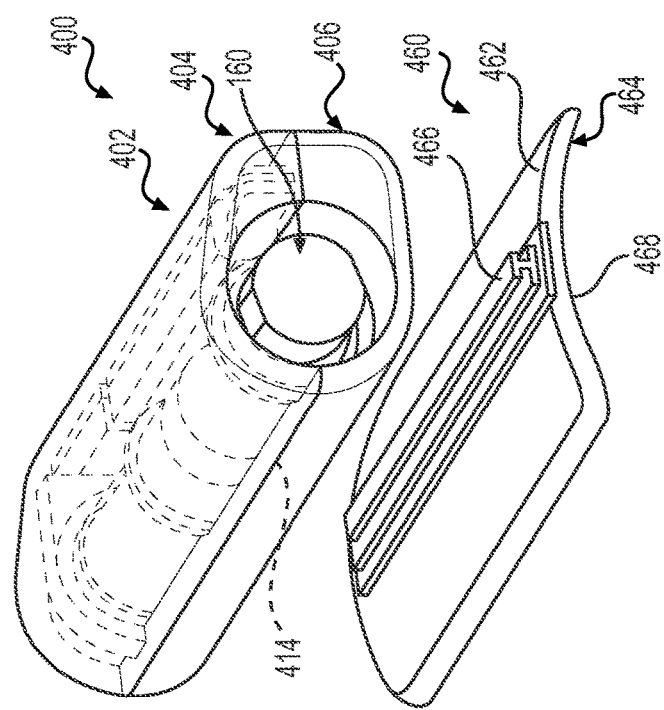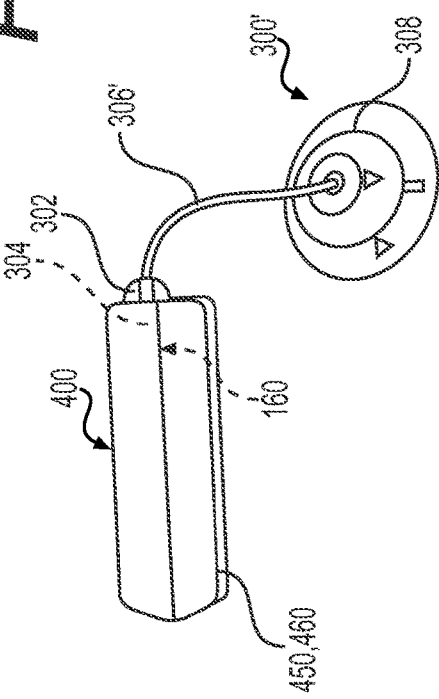

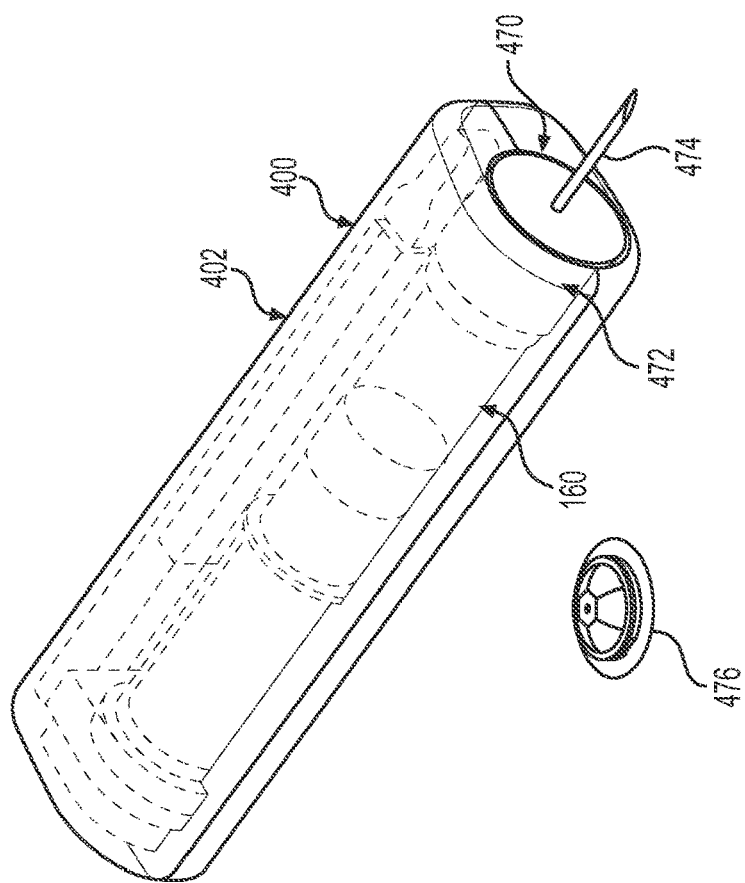
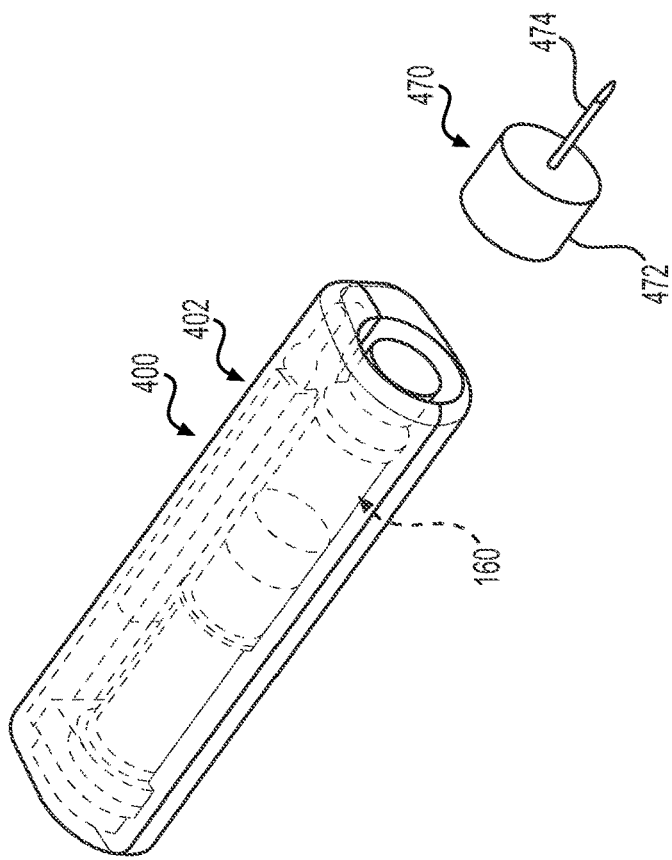

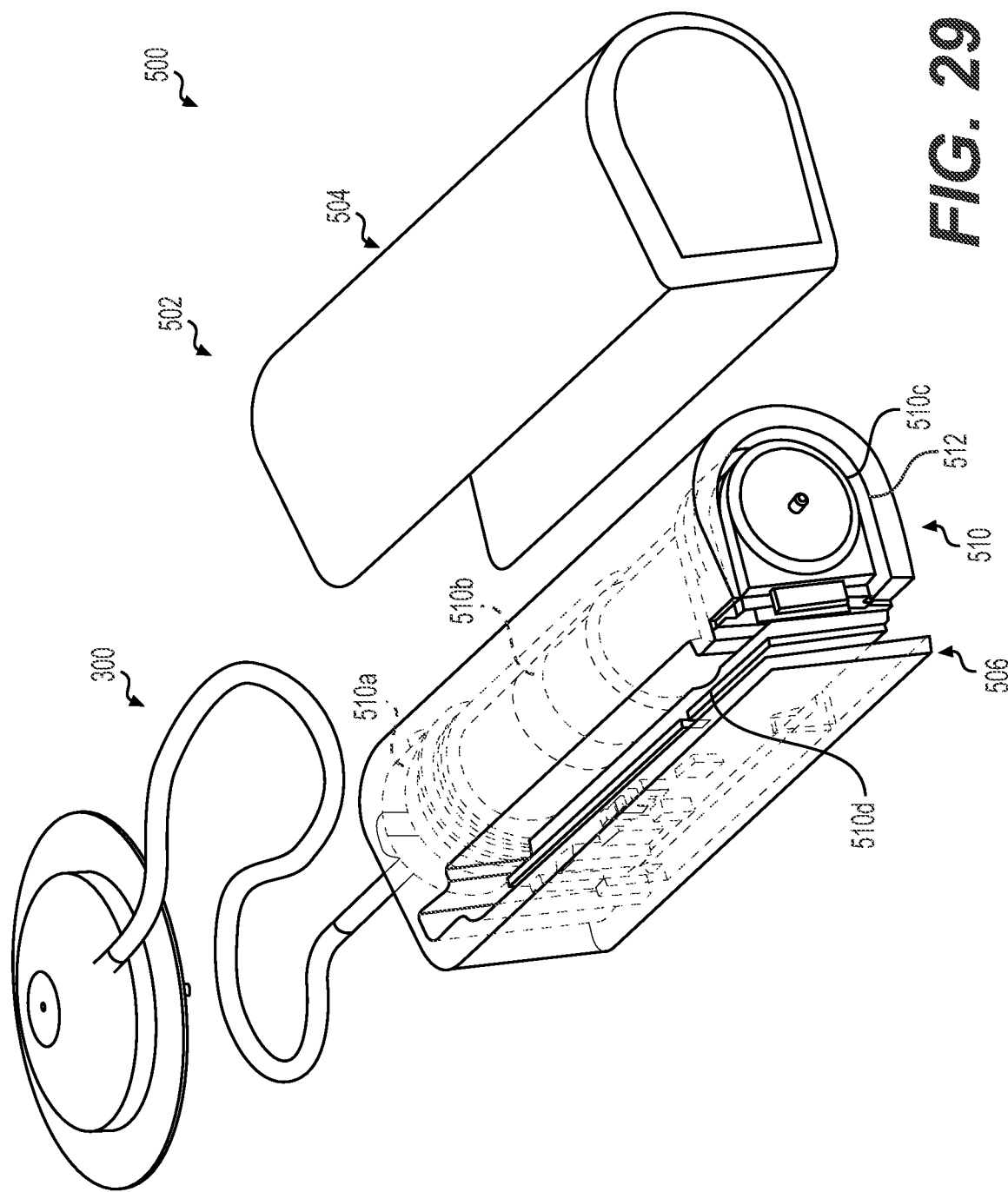

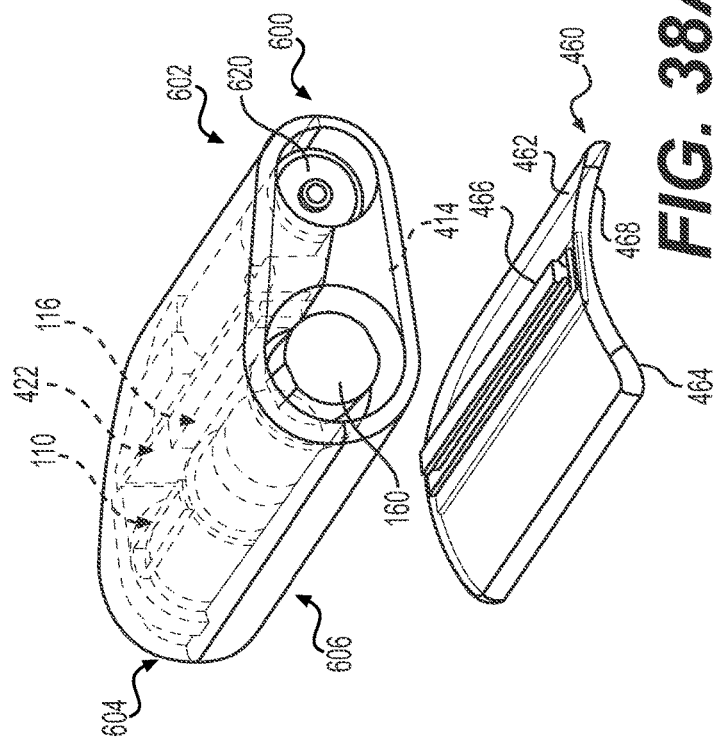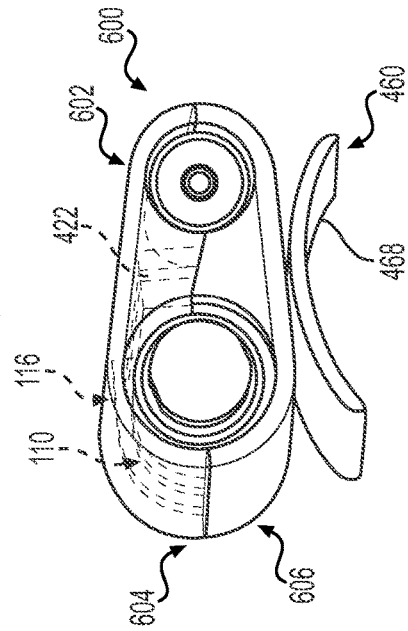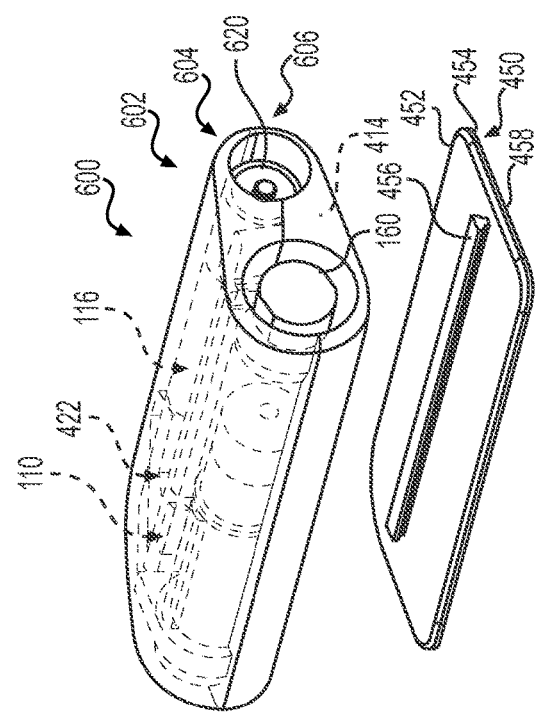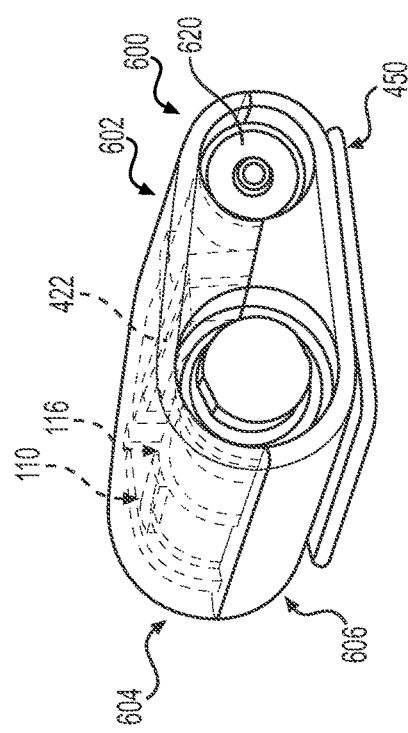

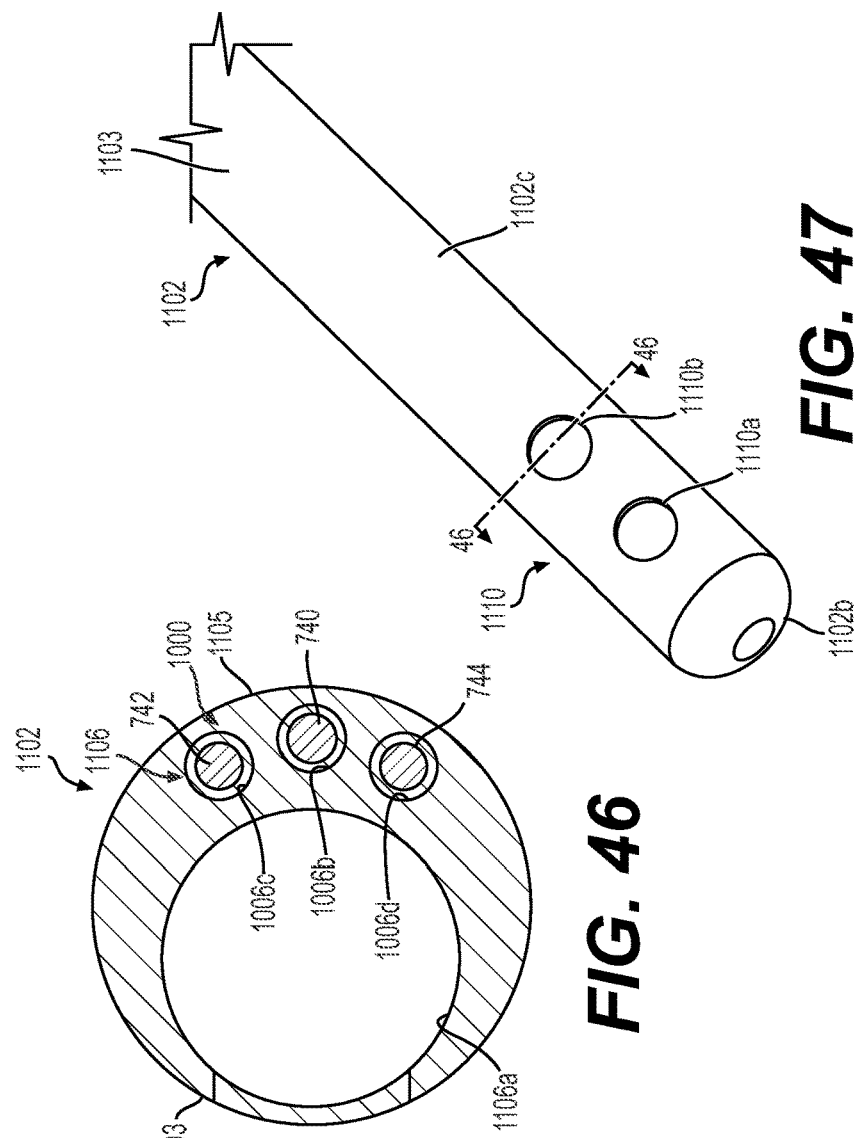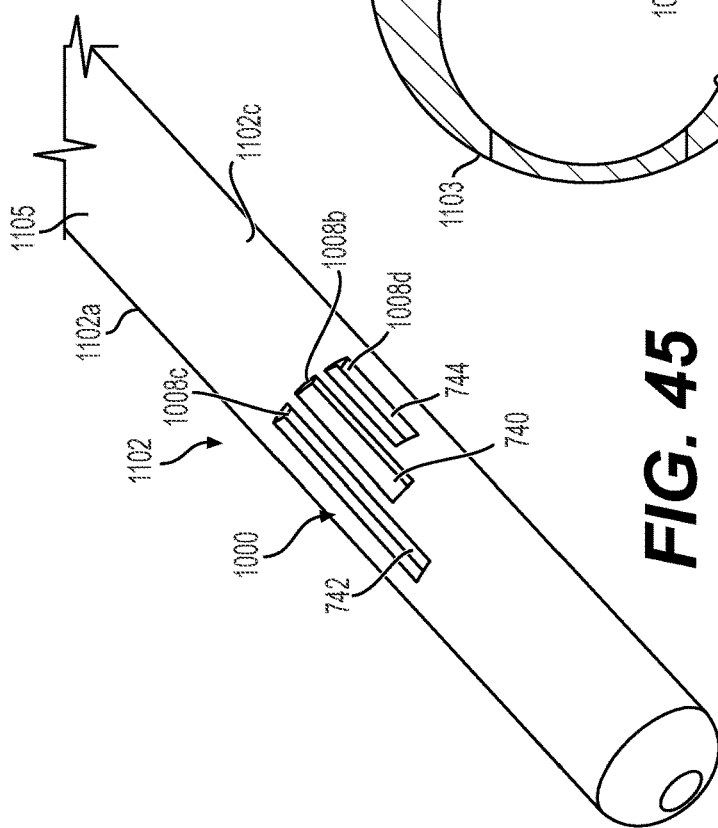

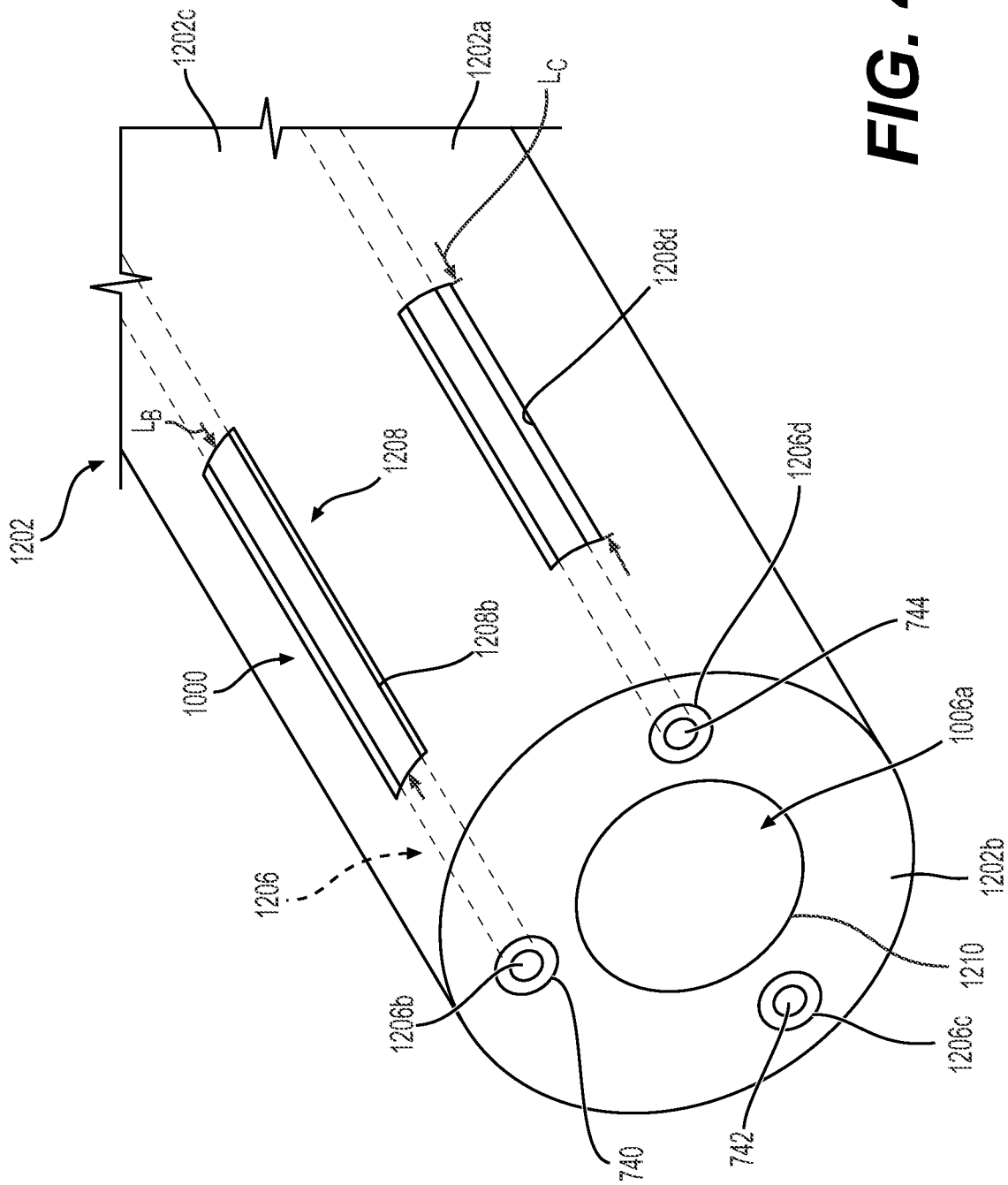

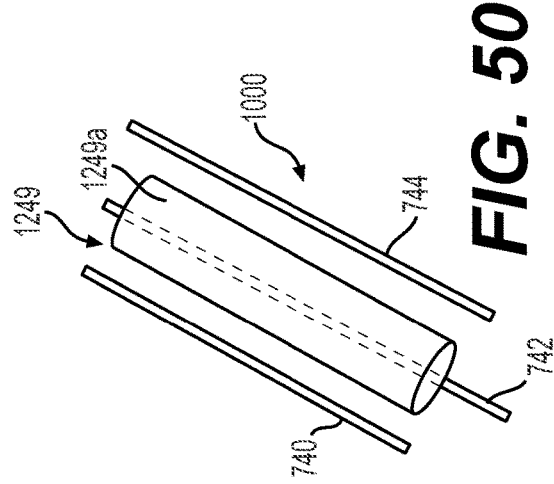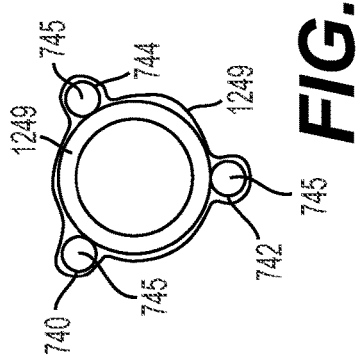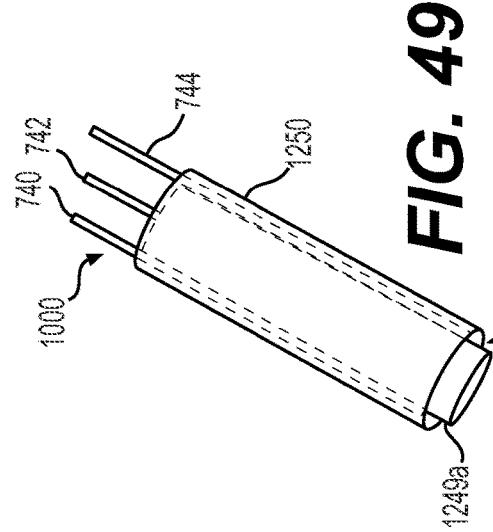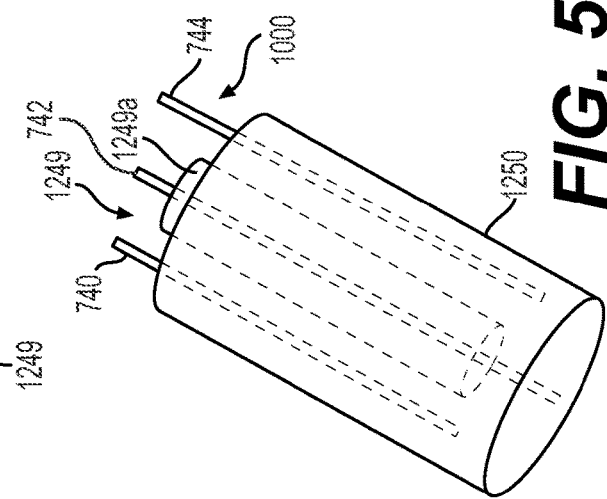

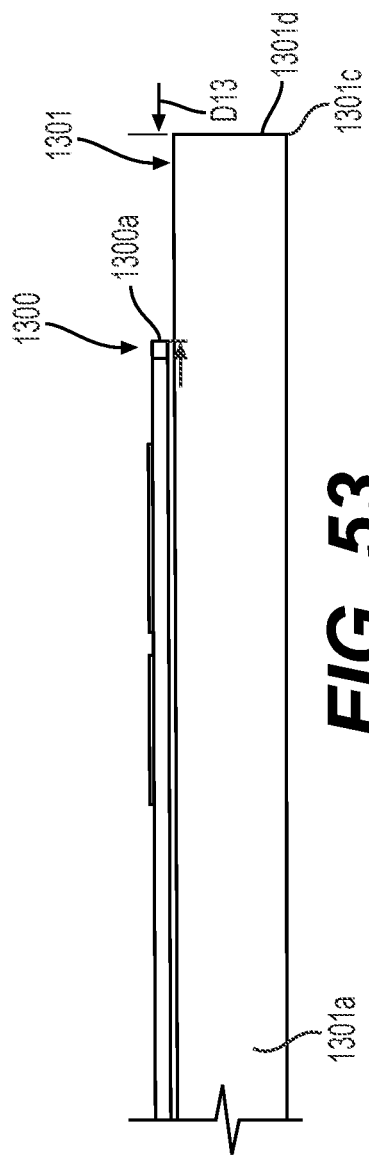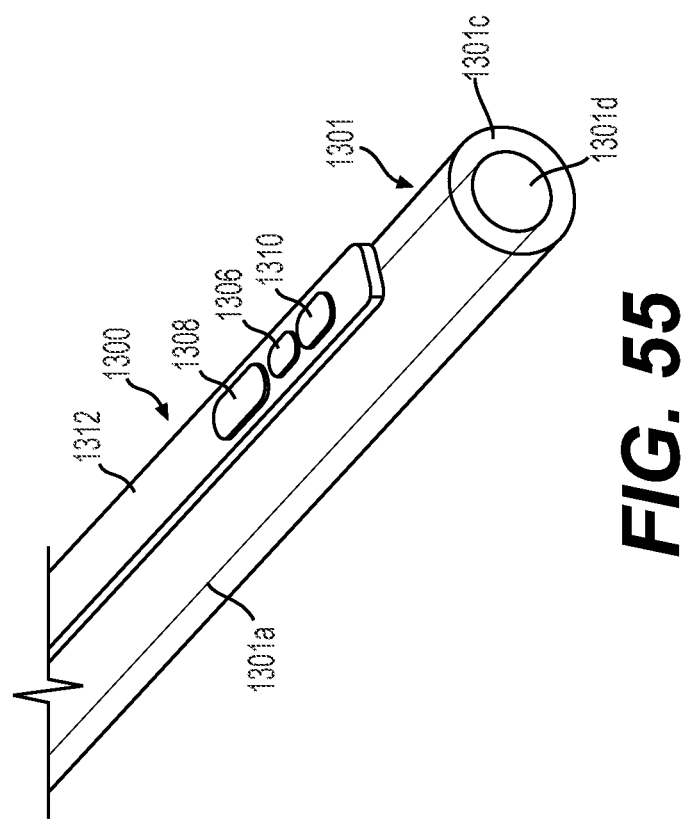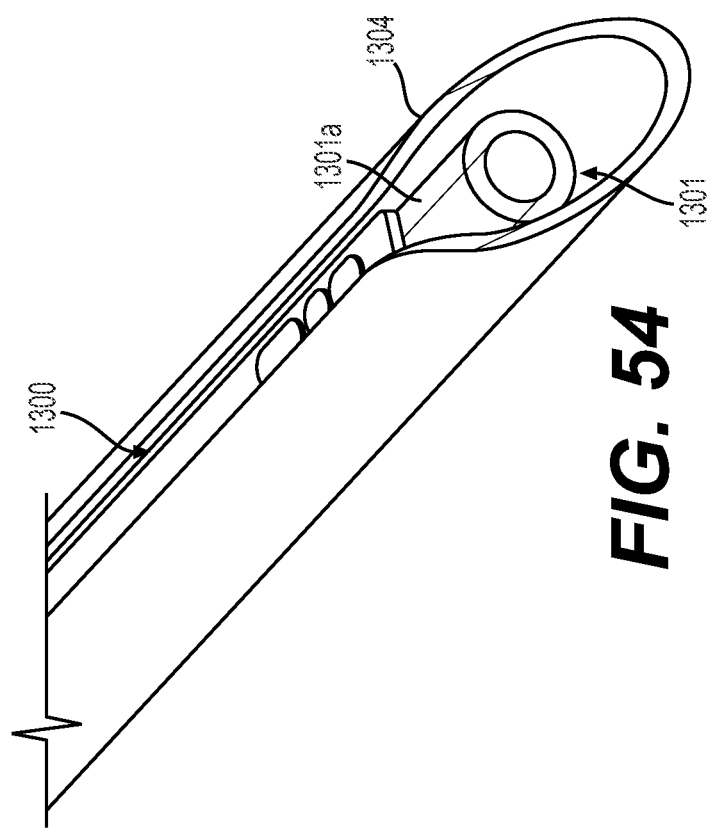

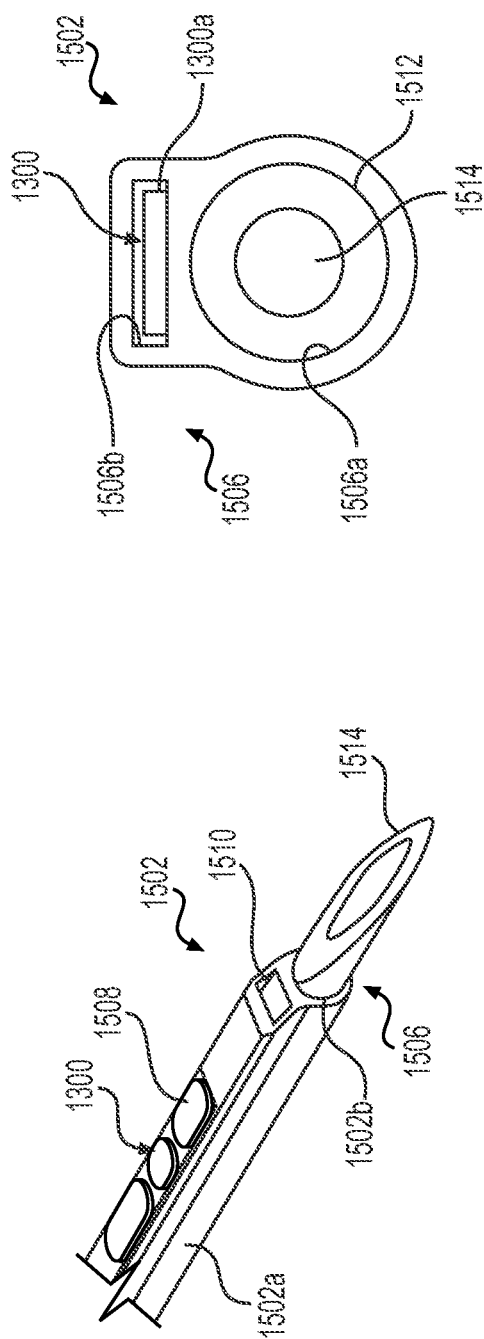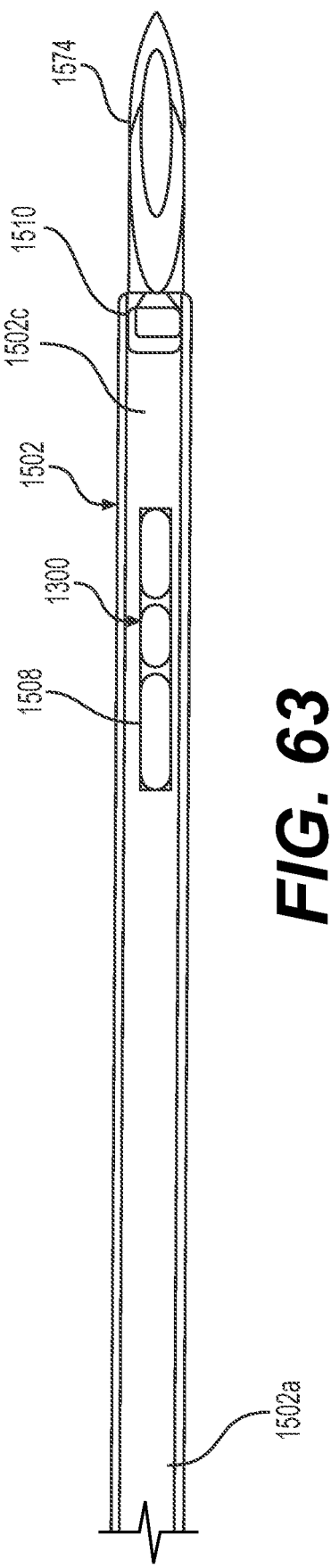
FIG. 61
FIG. 62
FIG. 63

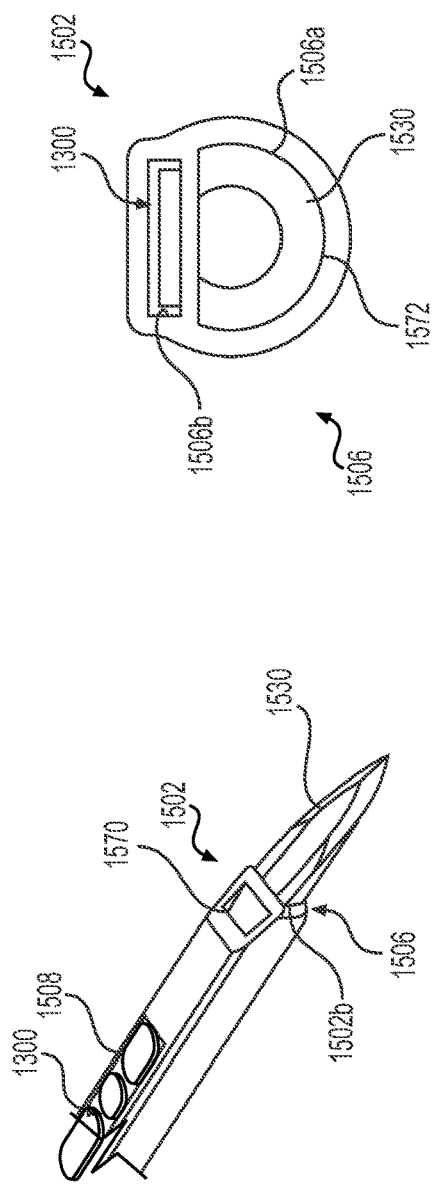
FIG. 65
FIG. 64
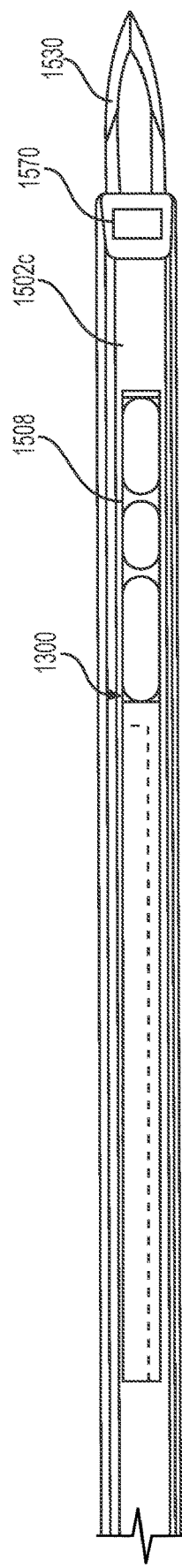
FIG. 66

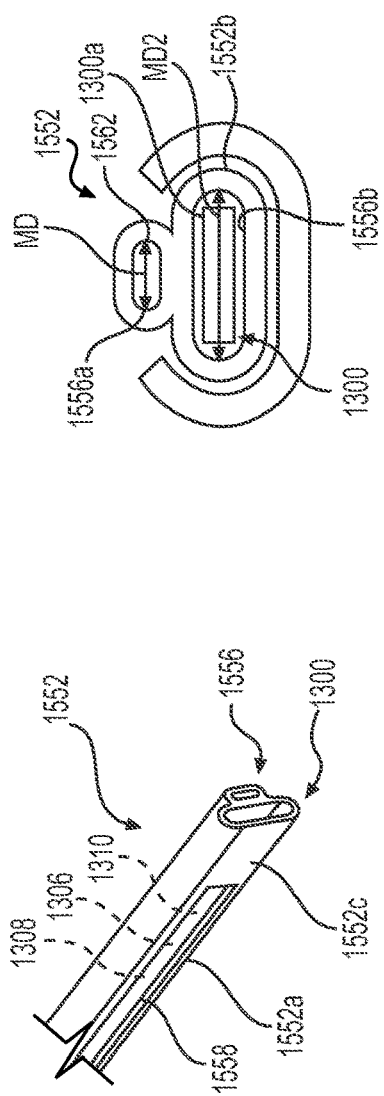
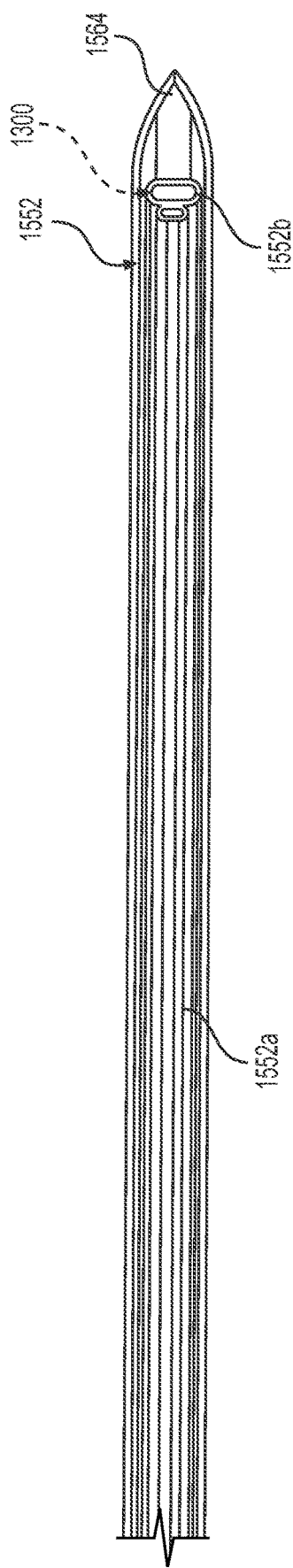
FIG. 67
FIG. 68
FIG. 69

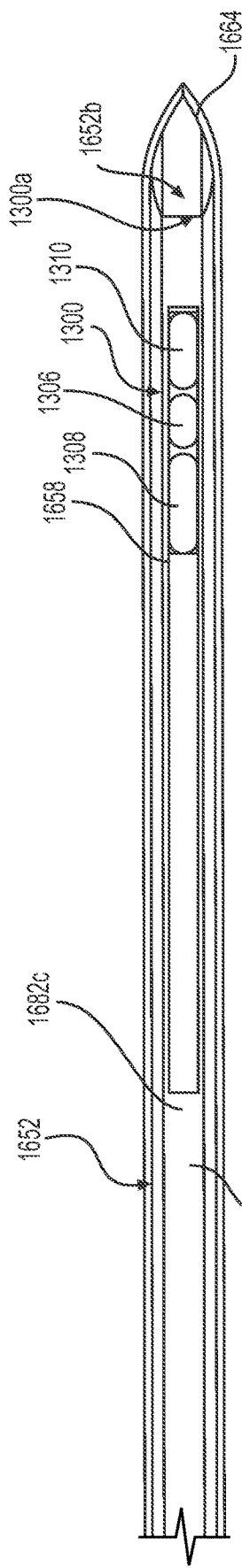
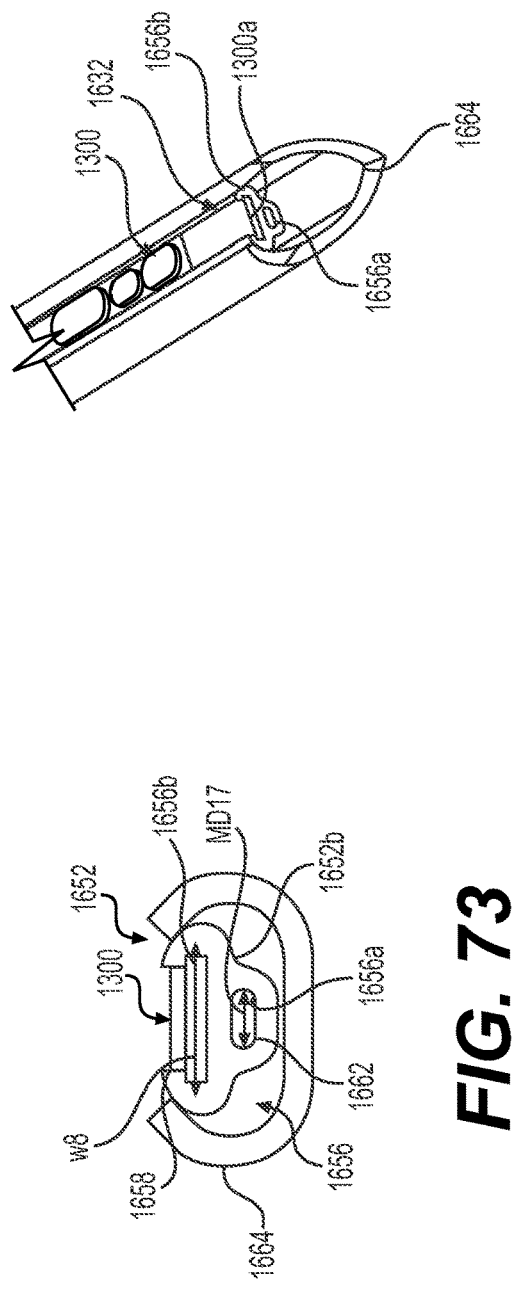
FIG. 72
FIG. 73
FIG. 74

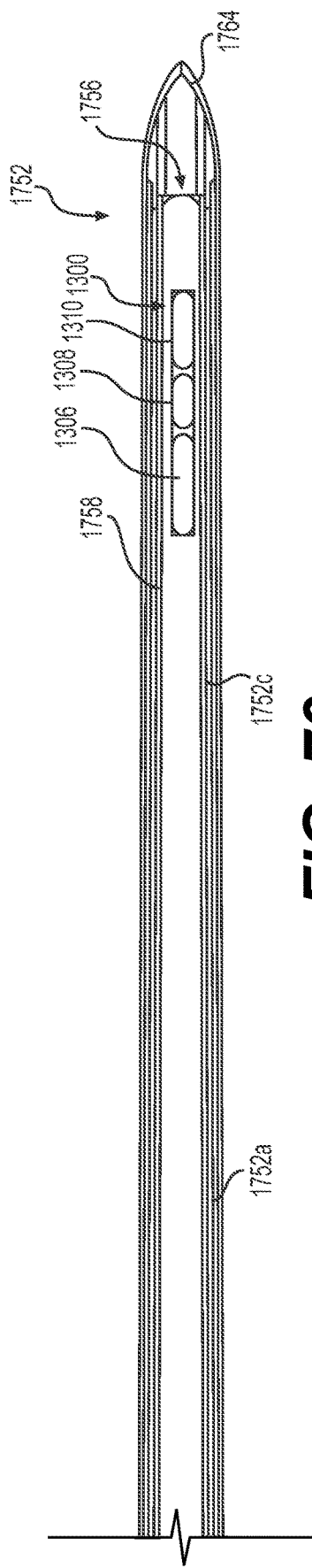
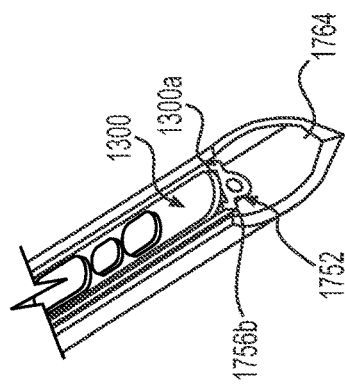
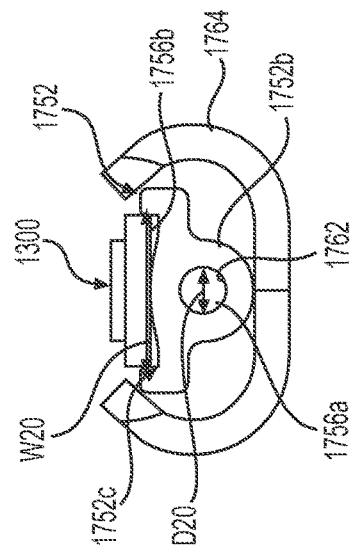
FIG. 79
FIG. 80
FIG. 81

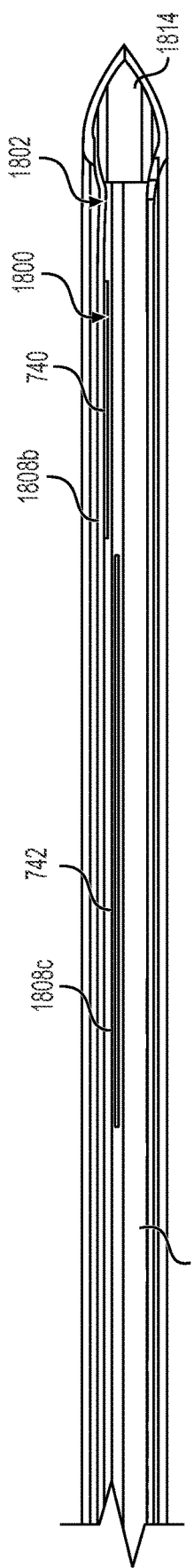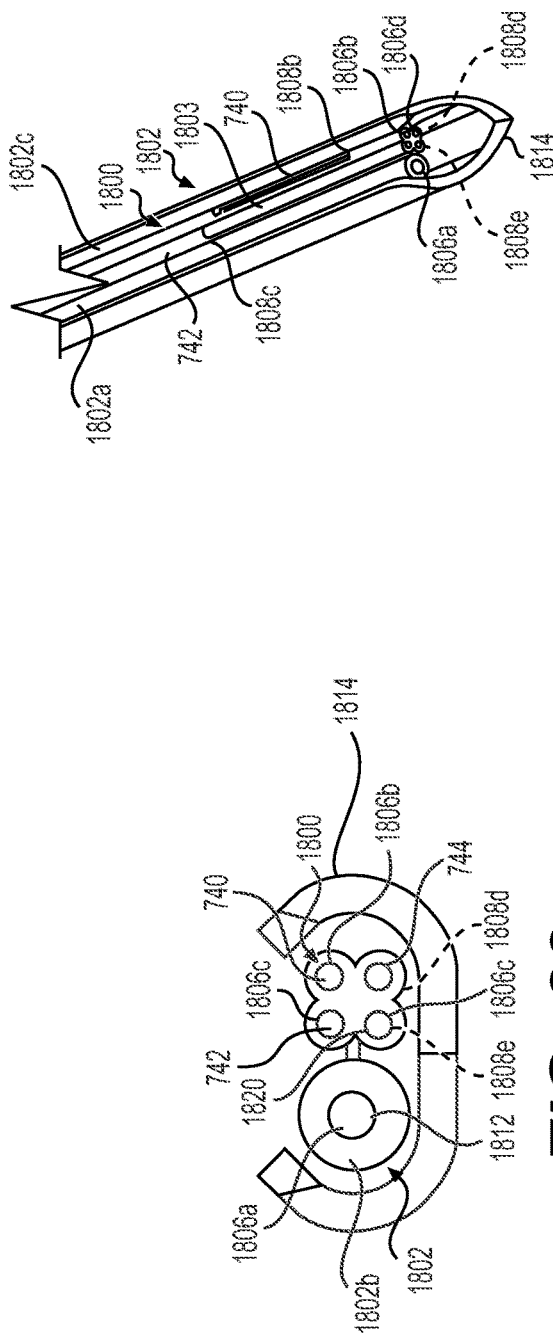
FIG. 82
FIG. 84
FIG. 83

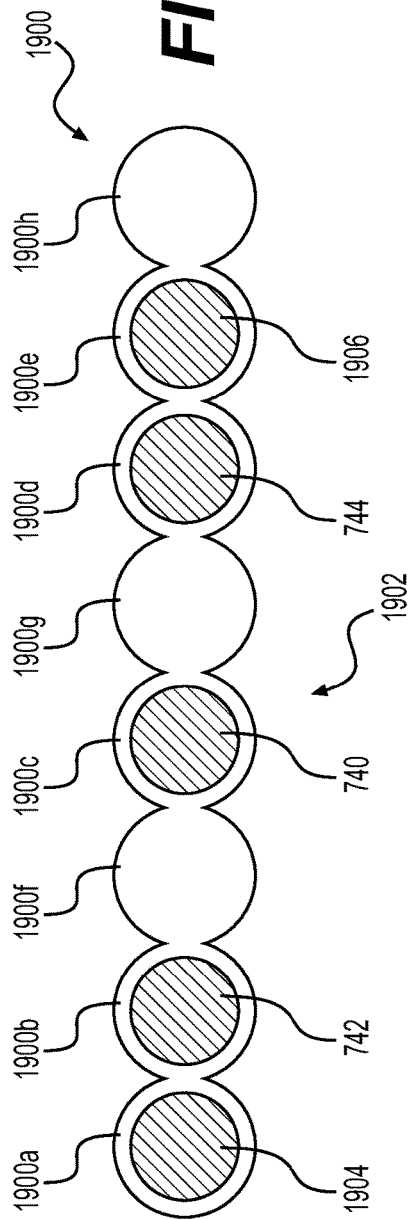
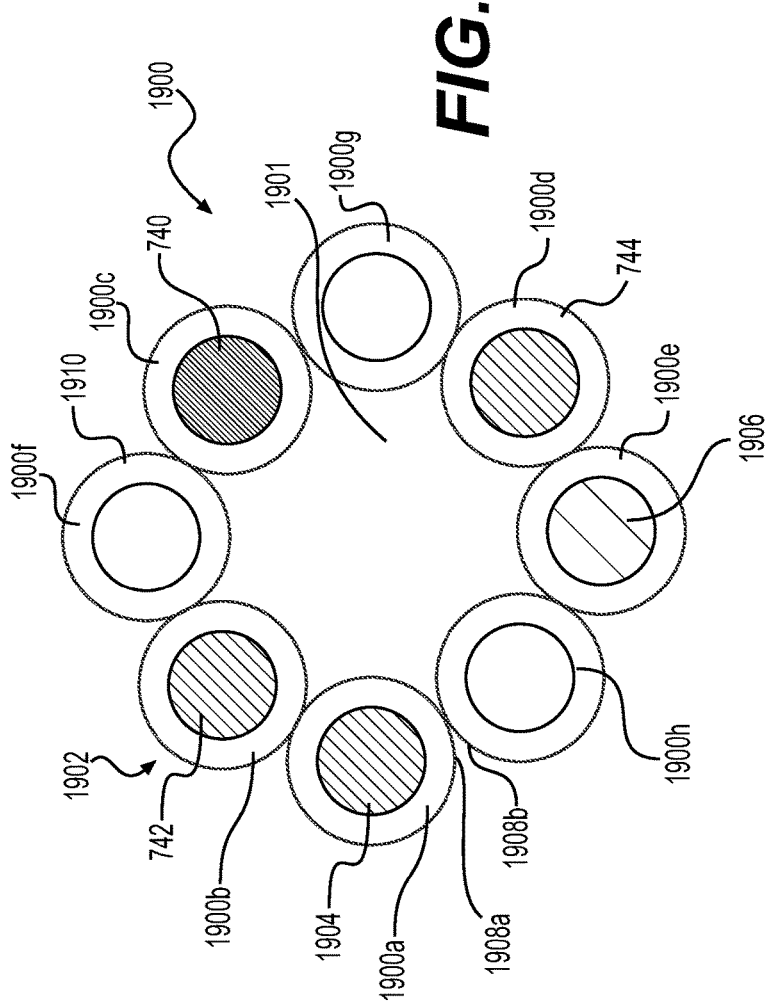
FIG. 87
FIG. 88

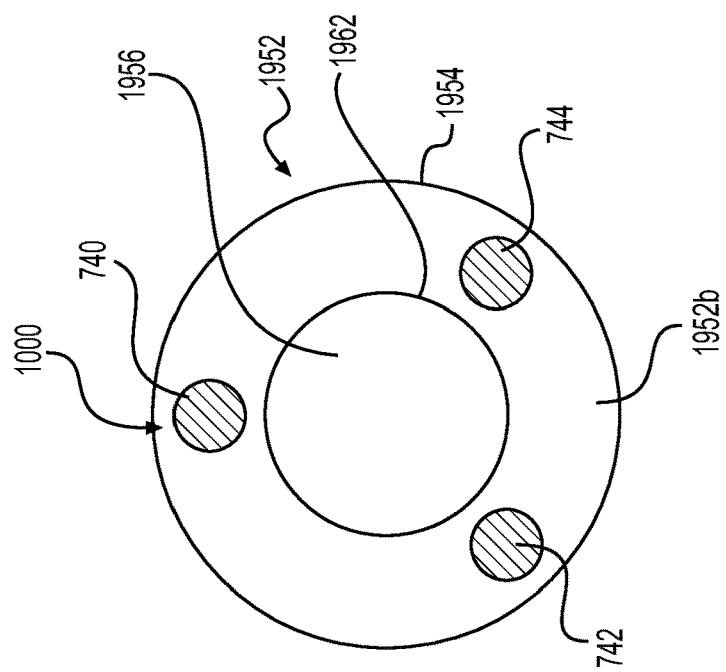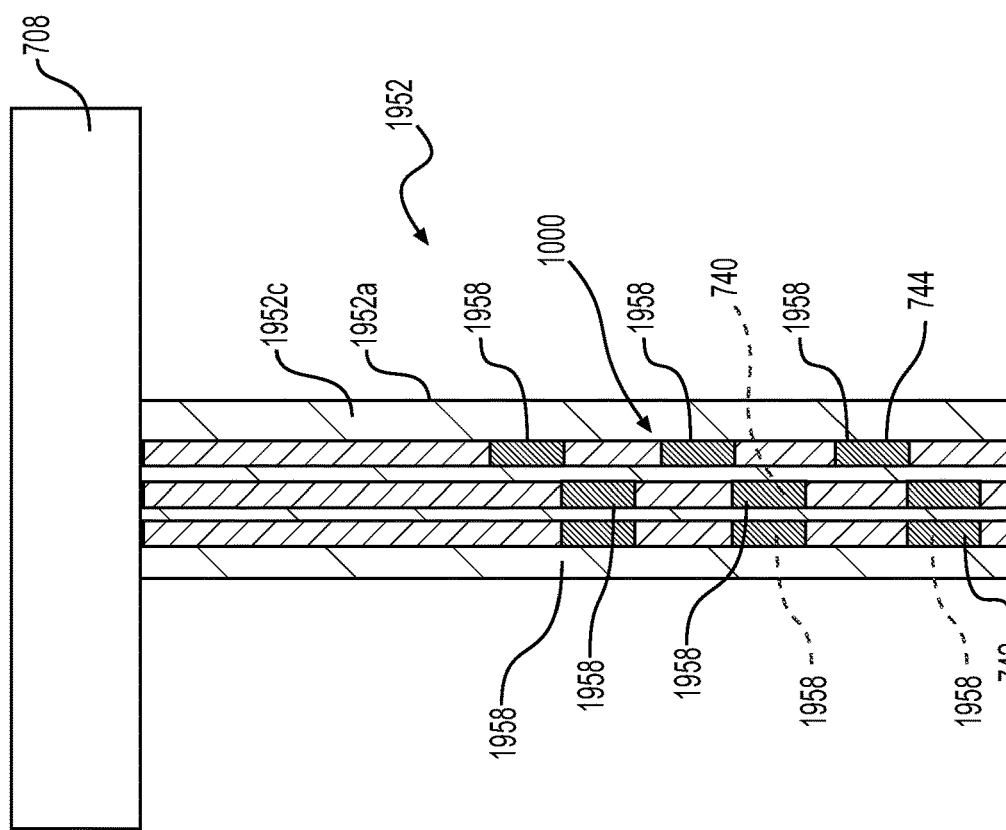

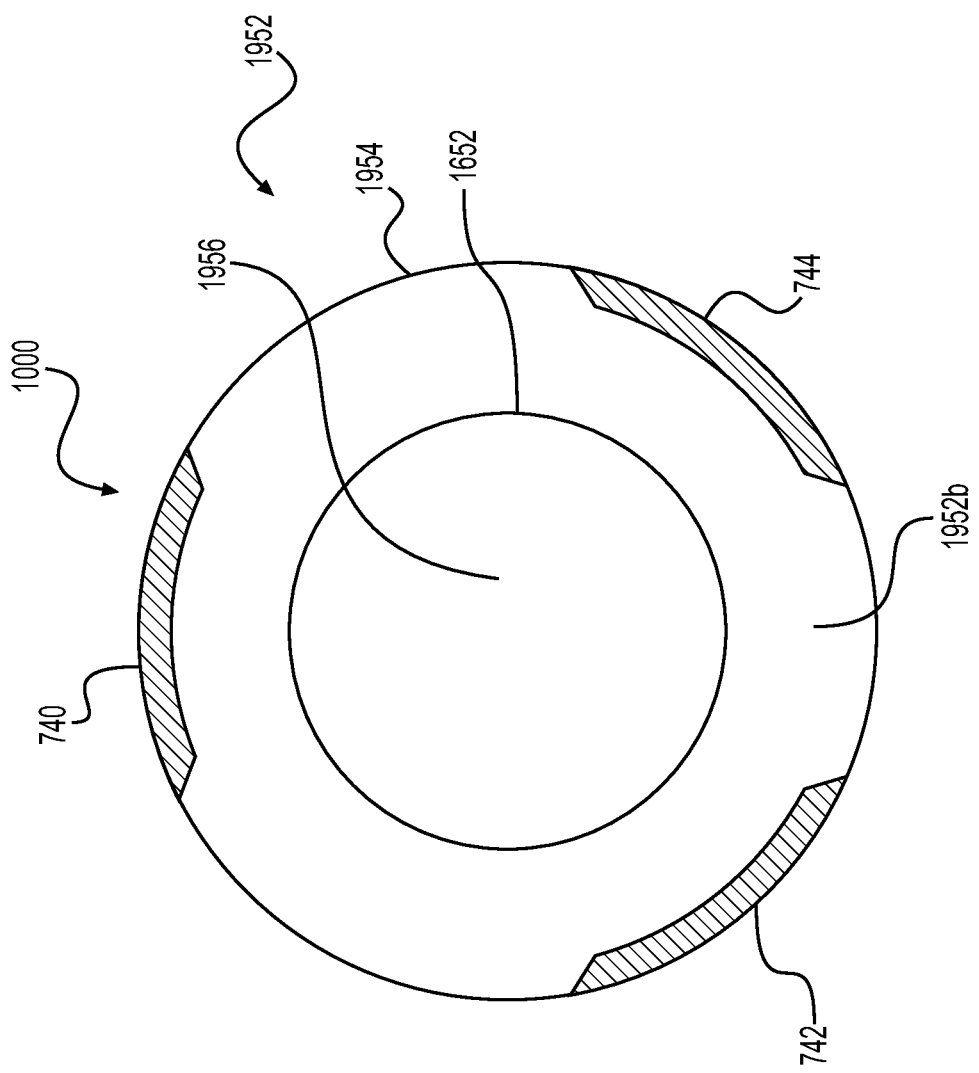

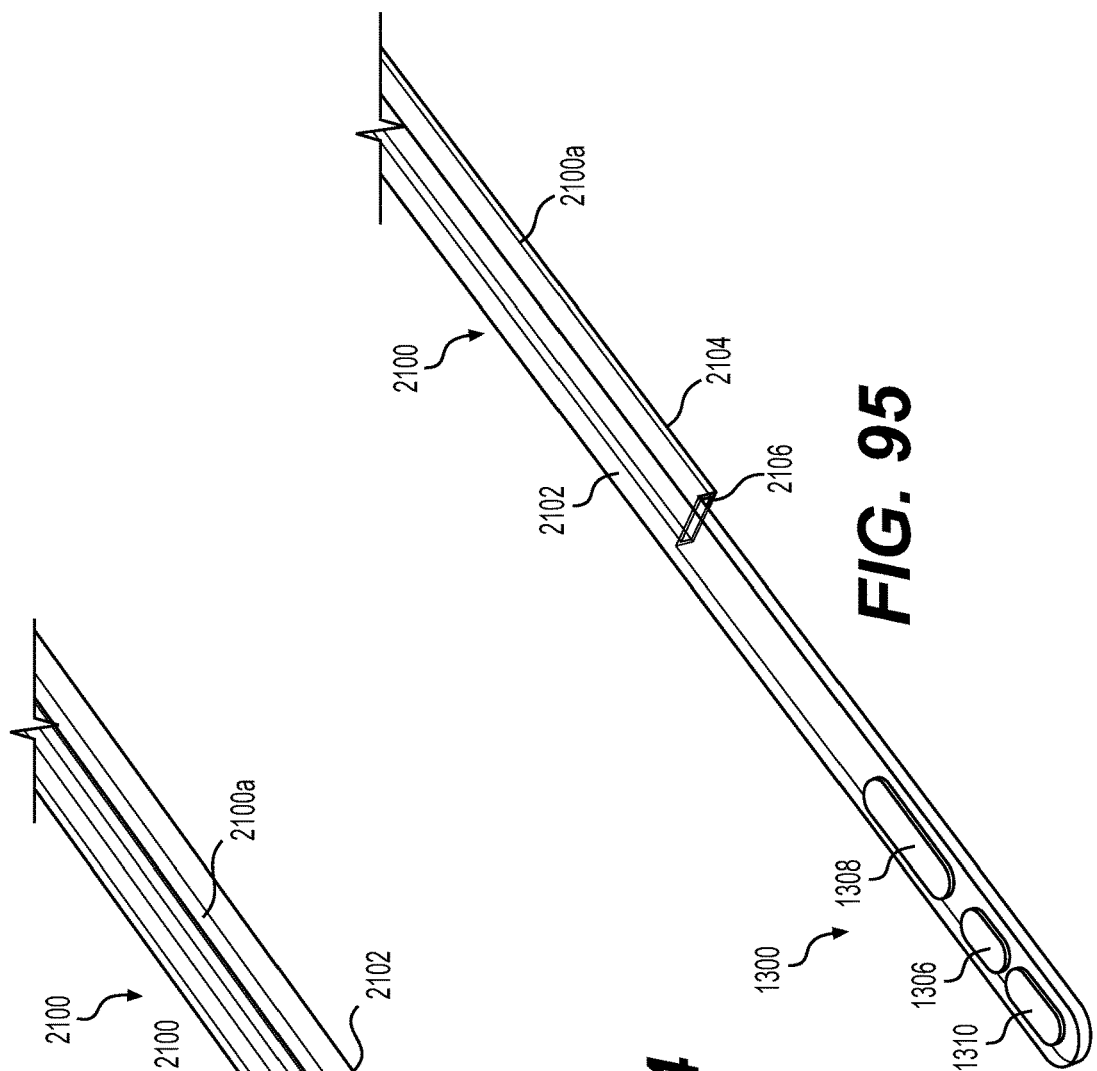
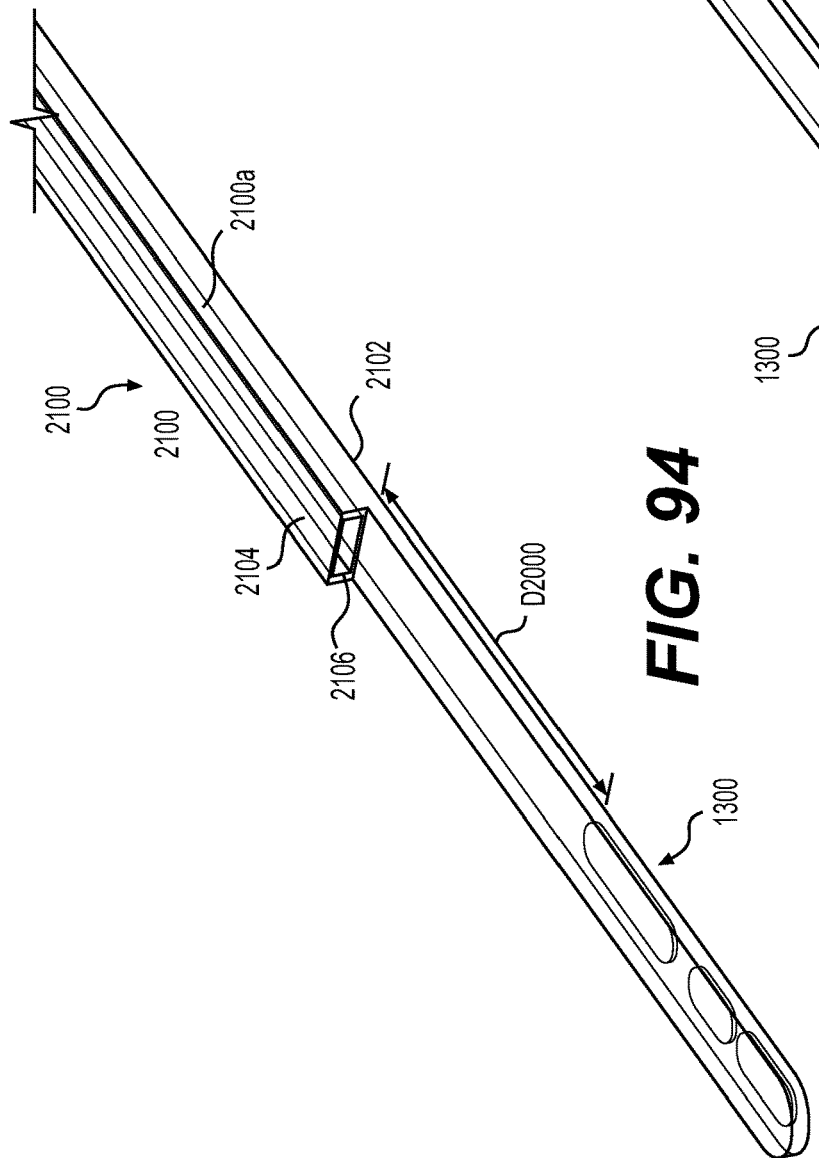

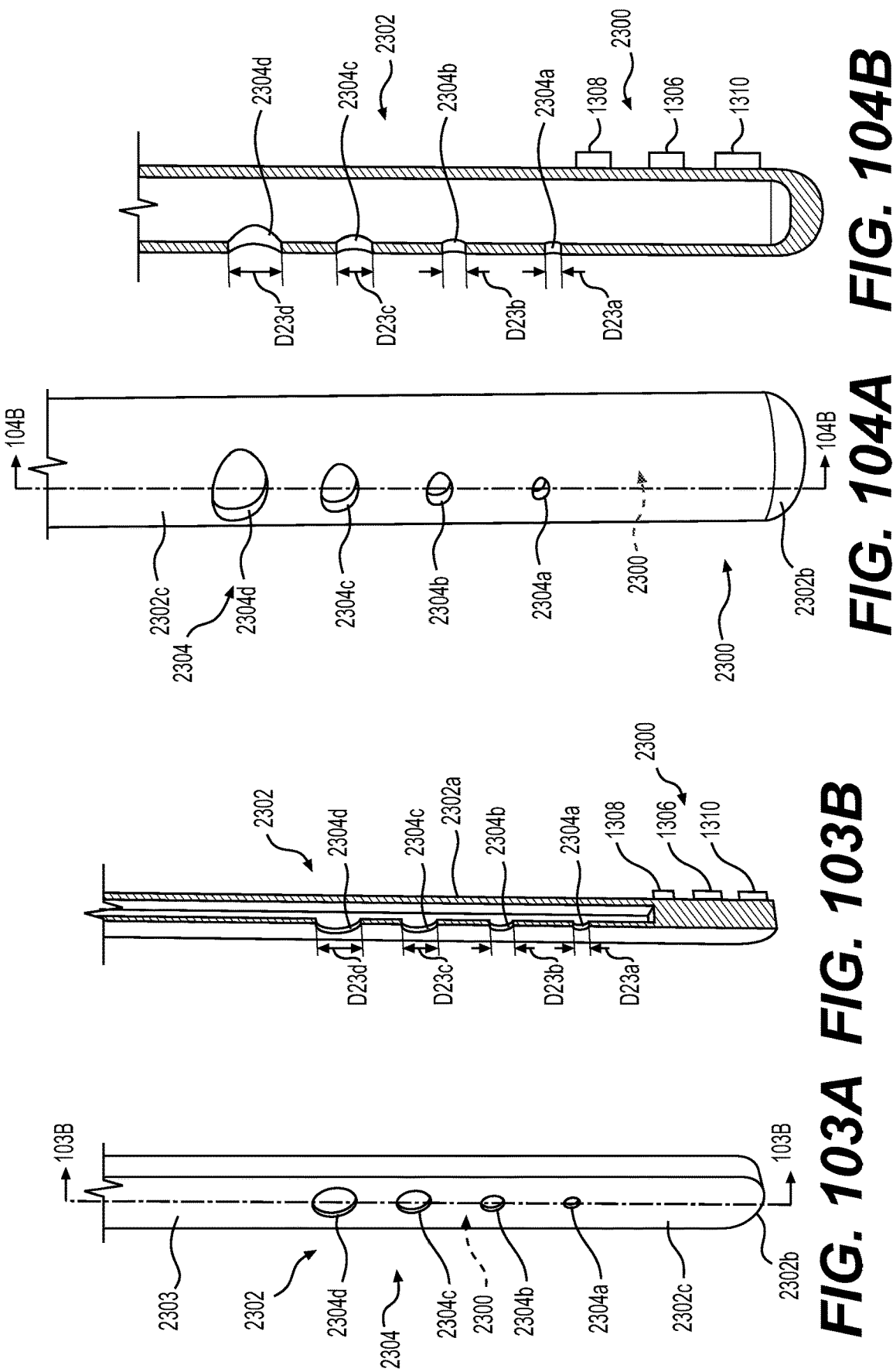

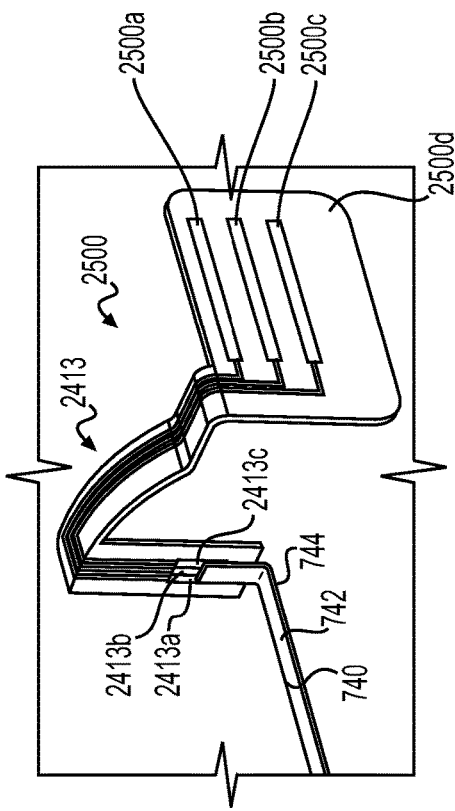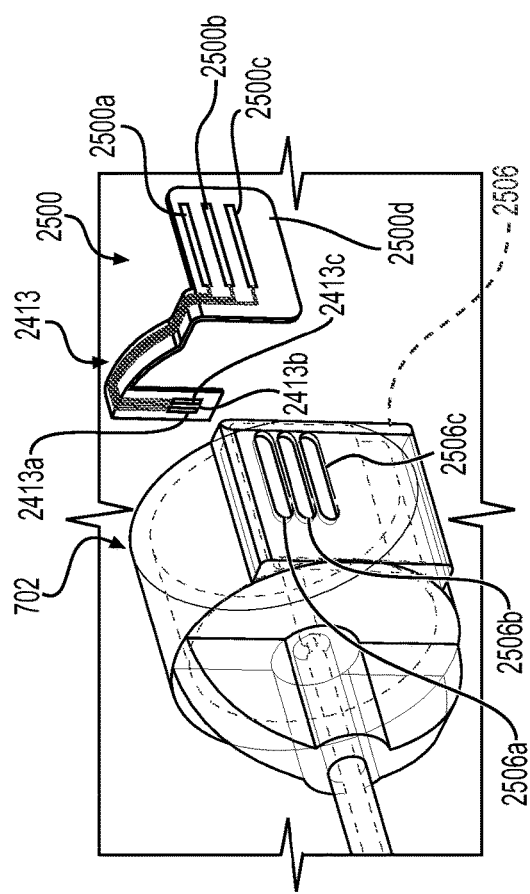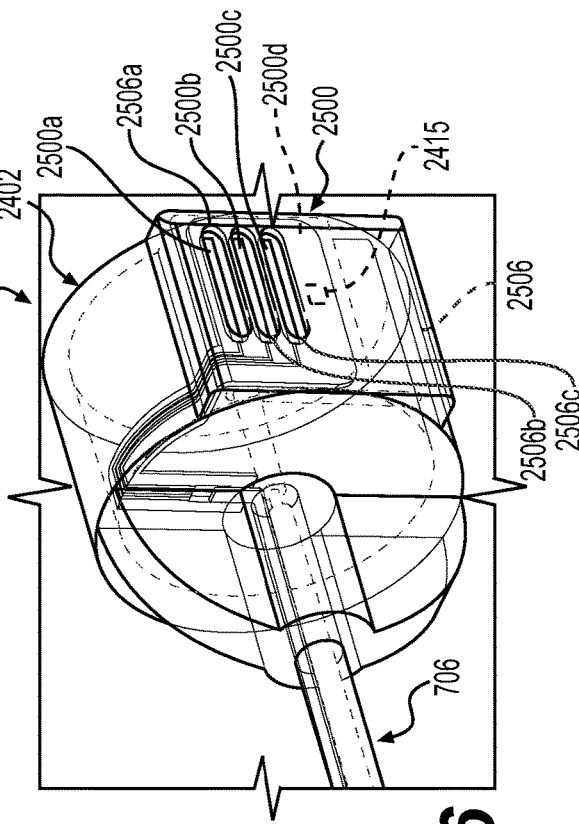
FIG. 115
FIG. 114
FIG. 116

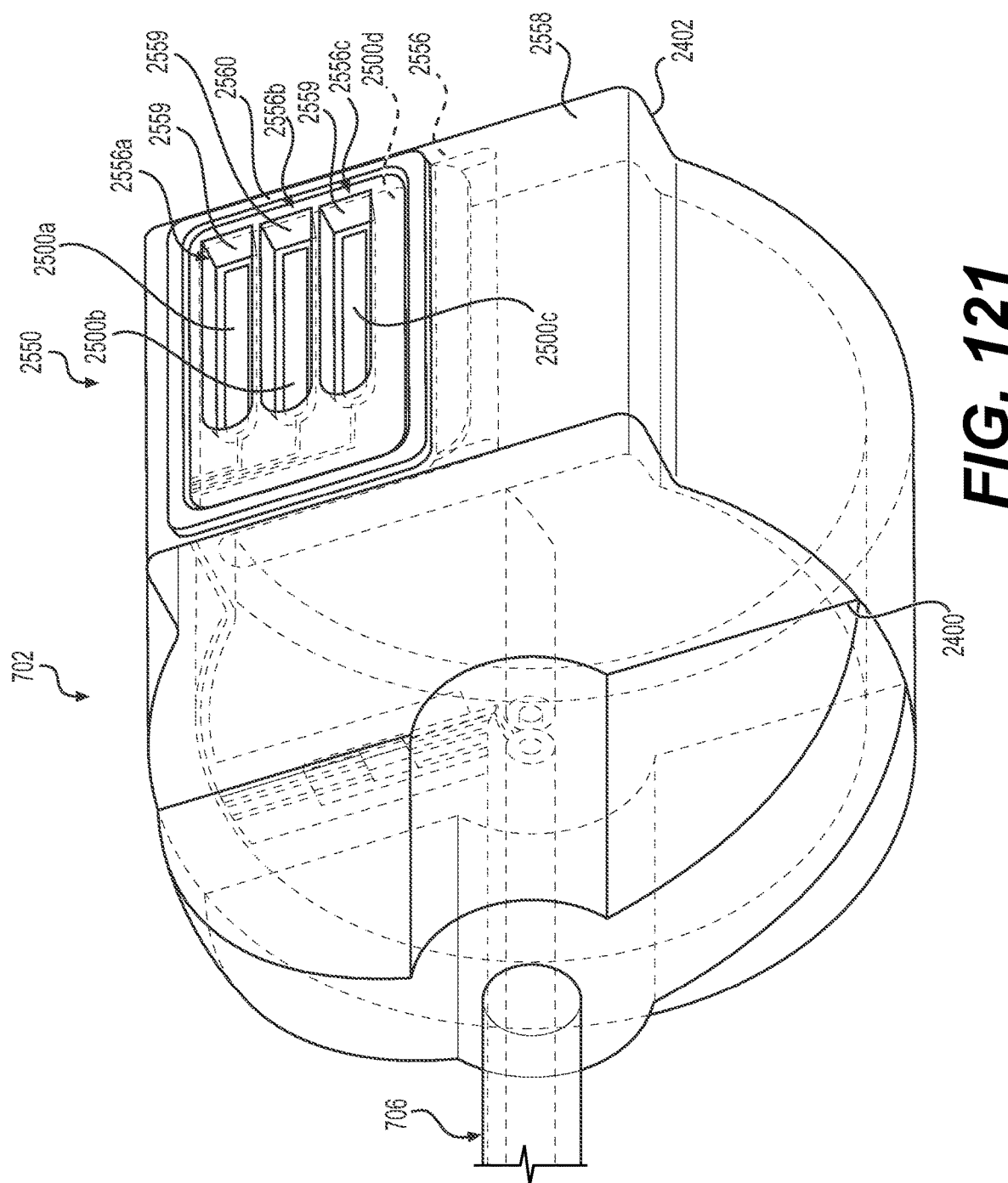

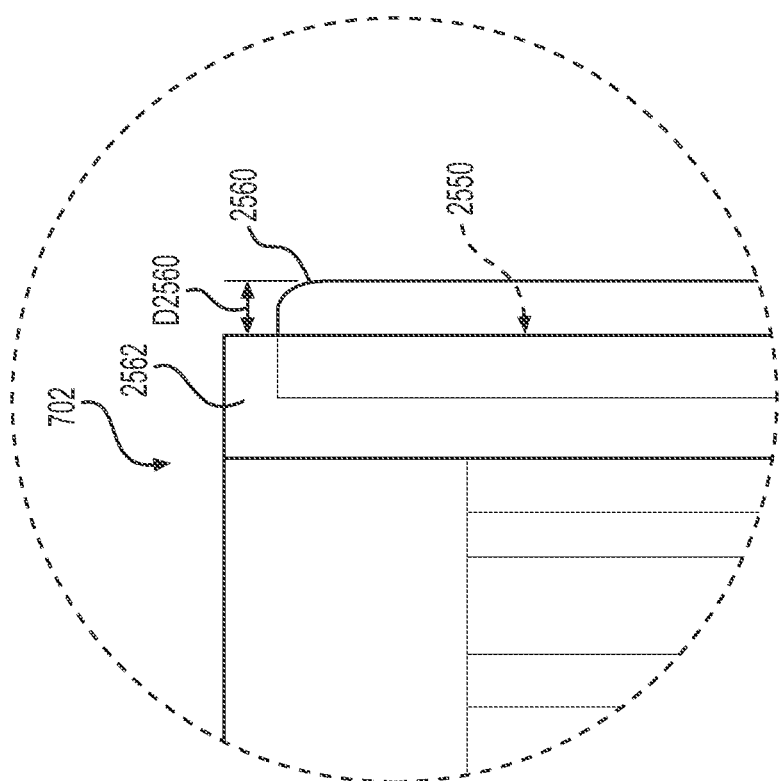
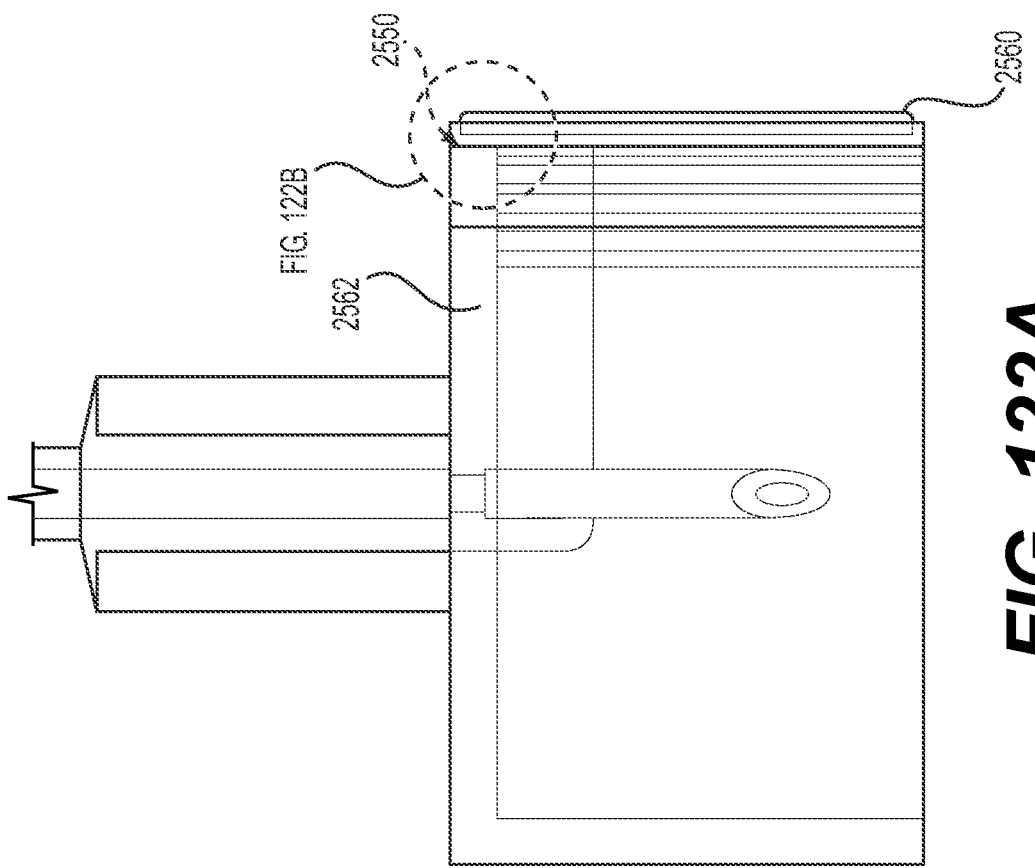
FIG. 122B
FIG. 122A

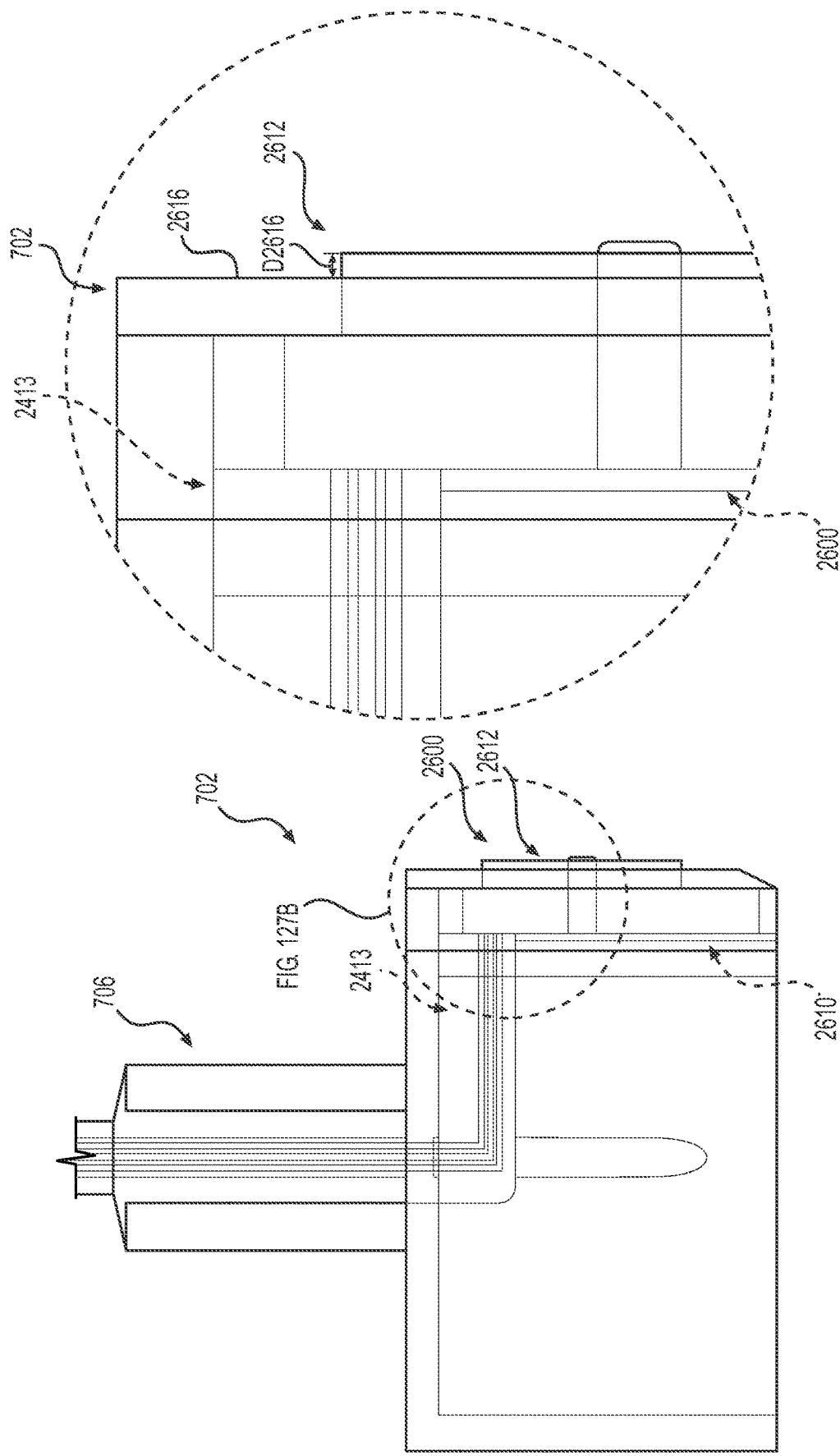

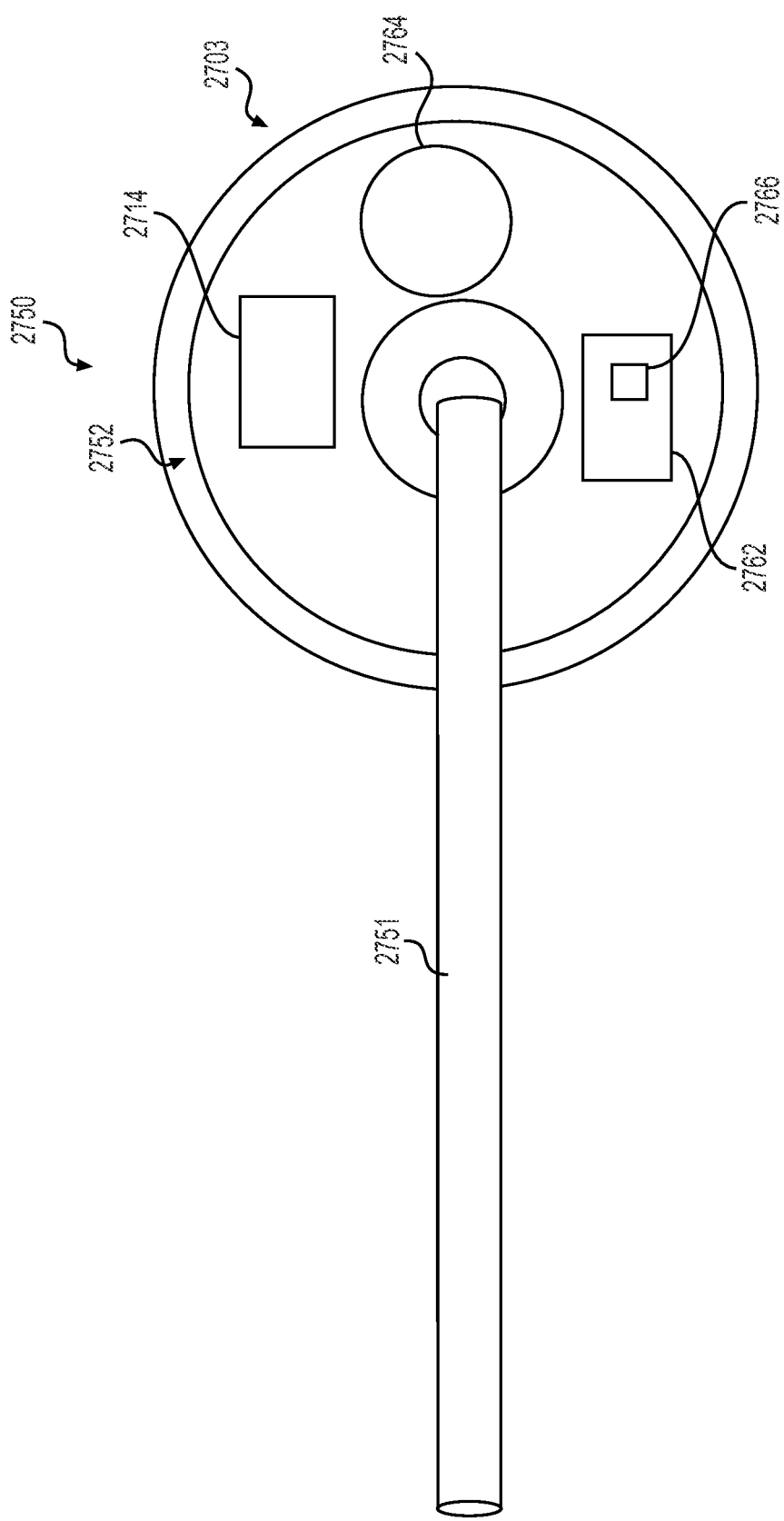

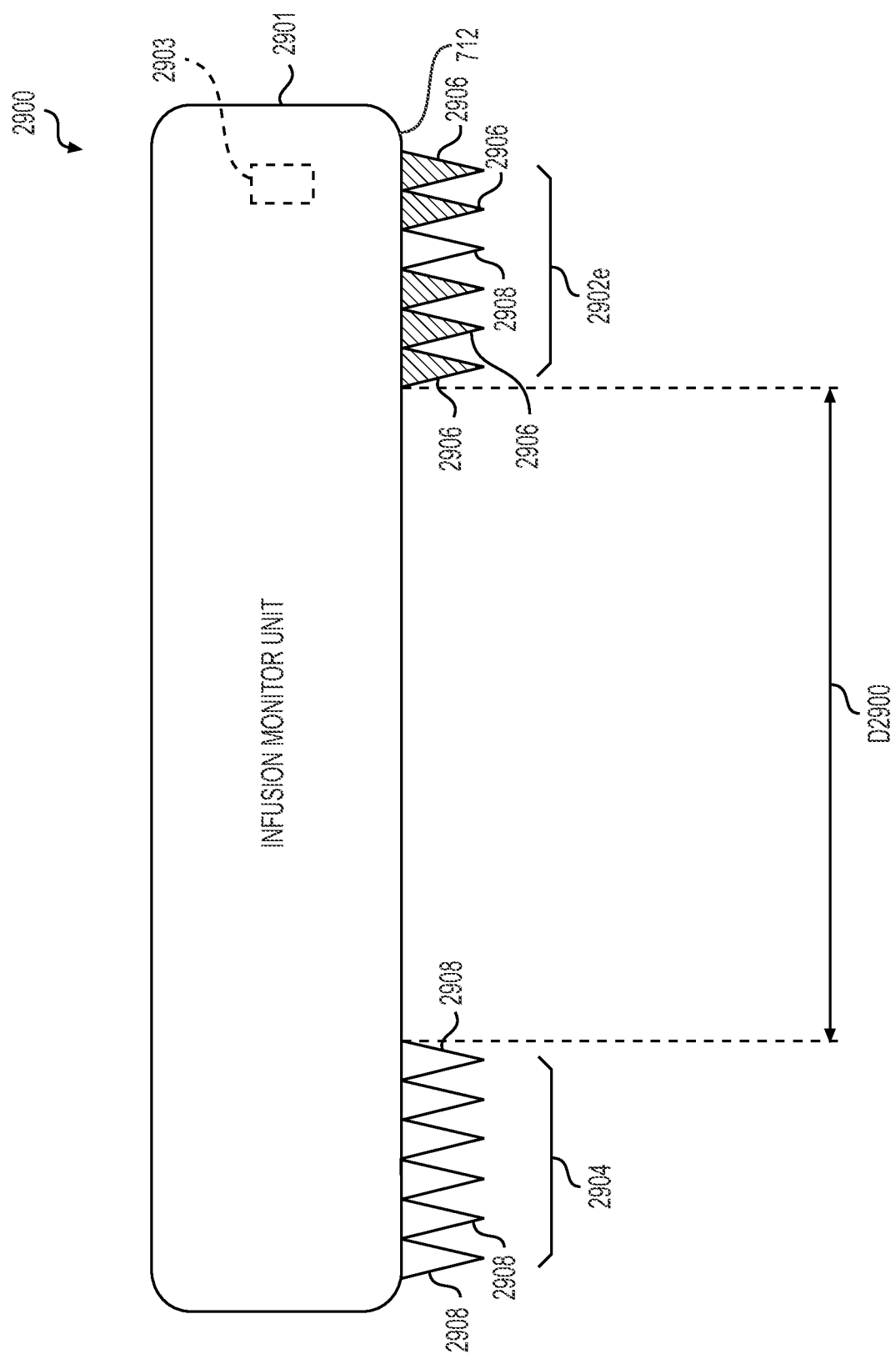

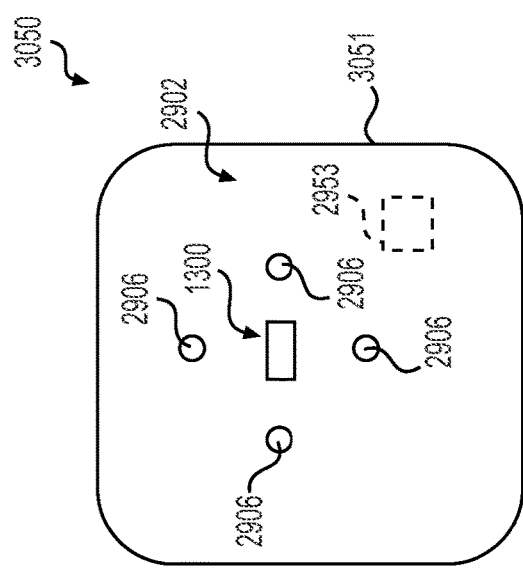
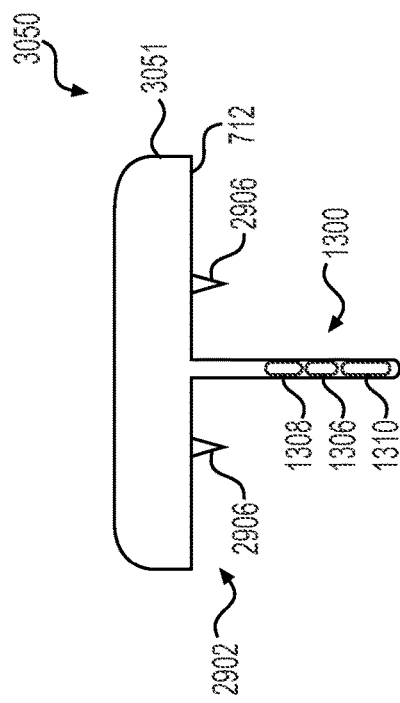
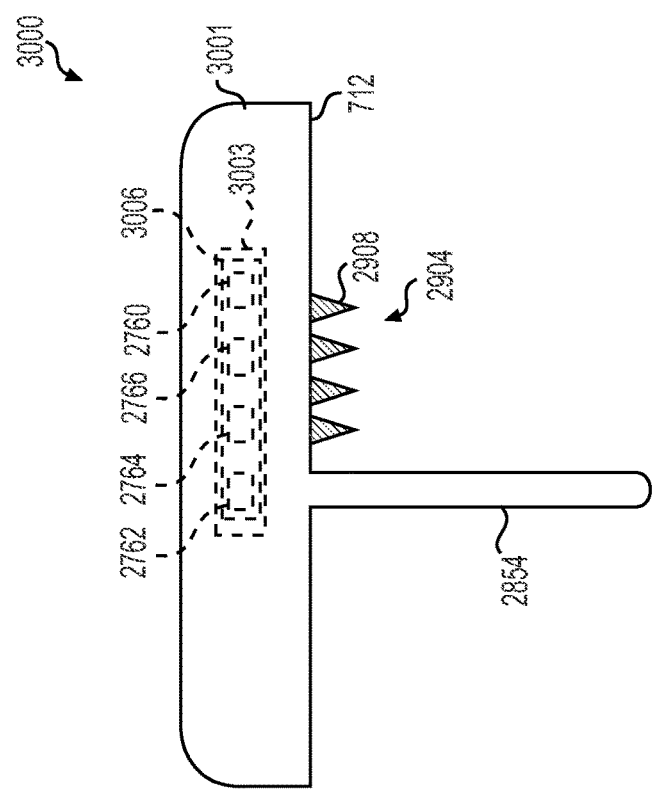

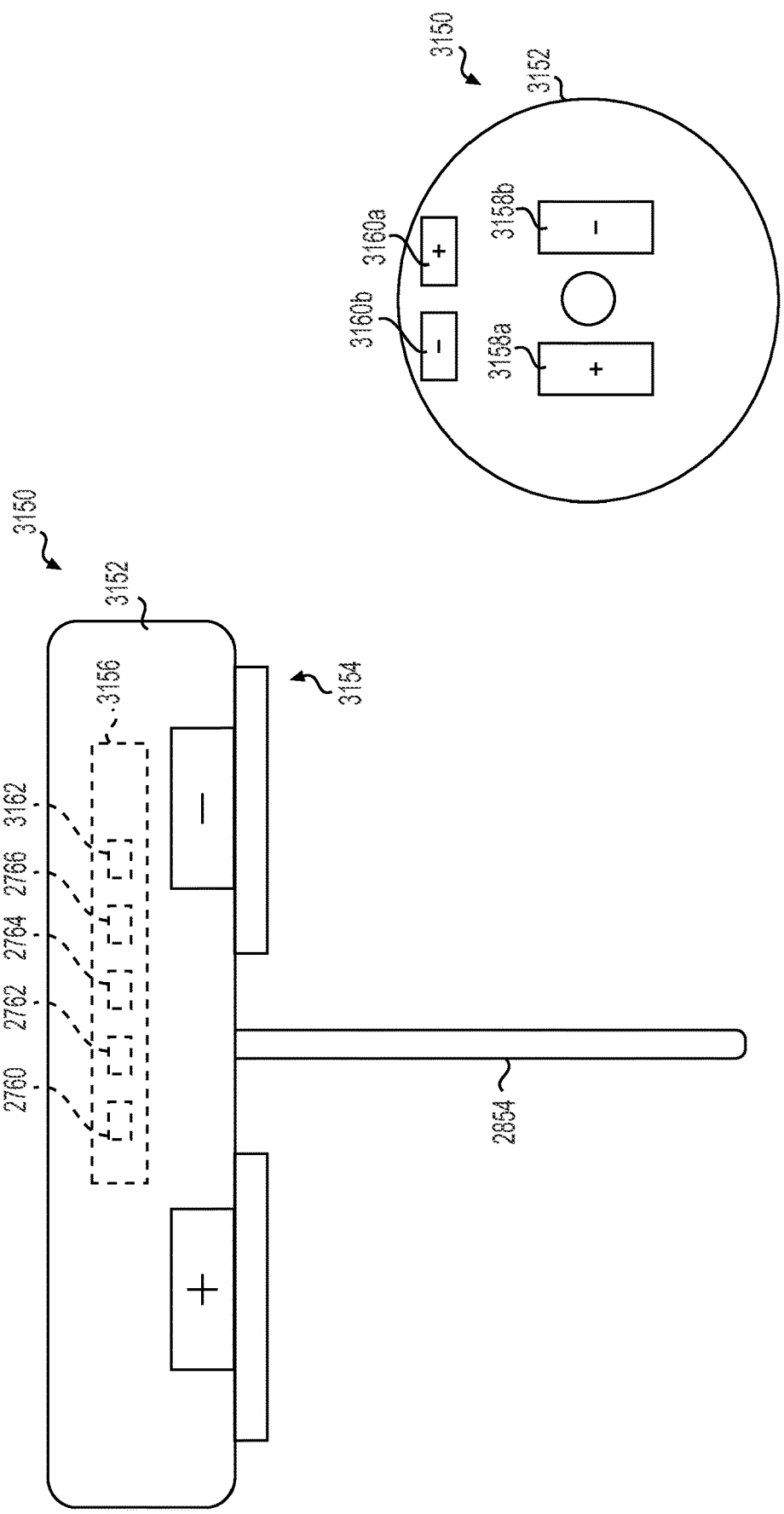

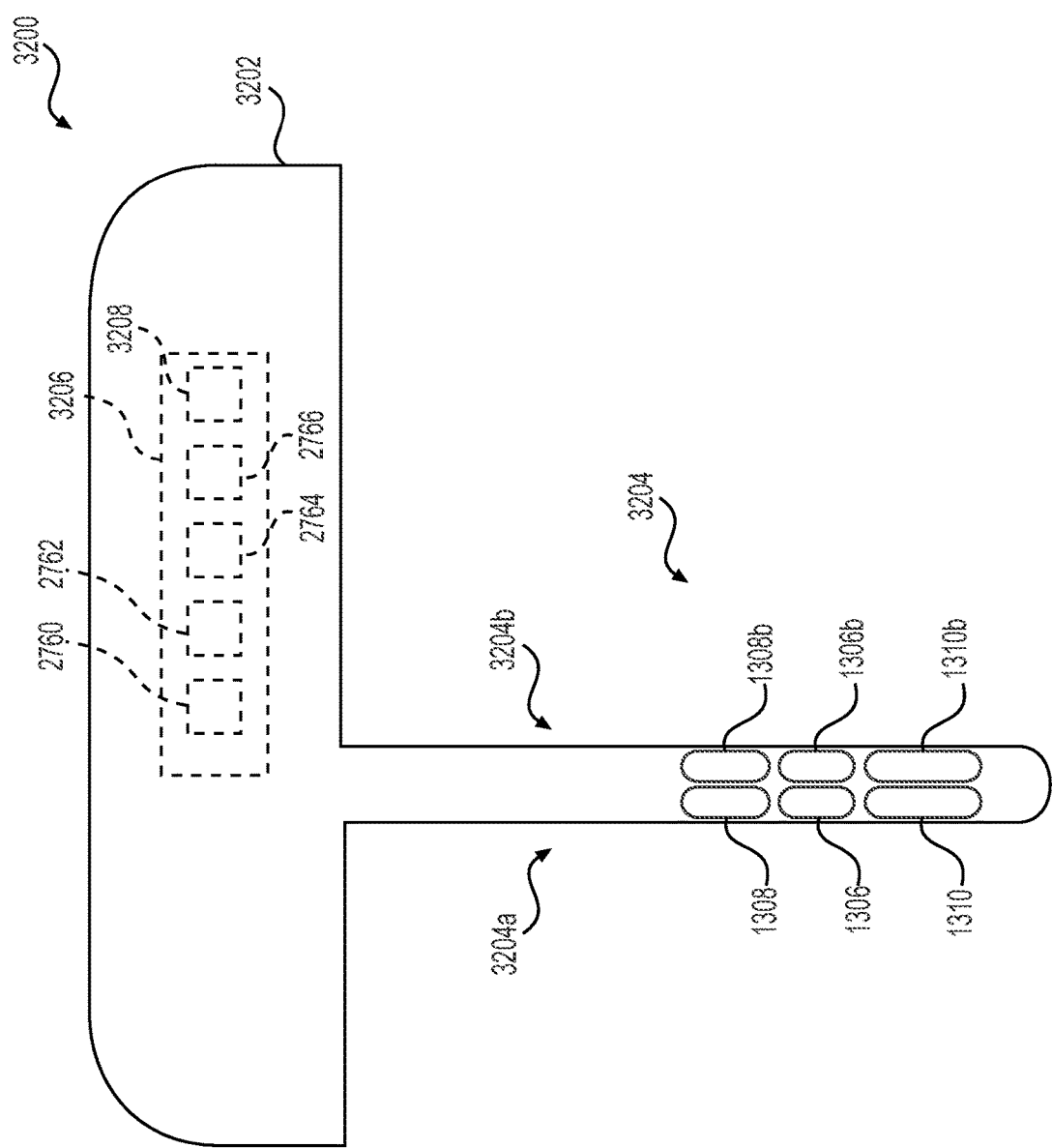

FLUID INFUSION SYSTEMS

CROSS-REFERENCE TO RELATED APPLICATION

This application claims the benefit of U.S. Provisional Application No. 62/858,304, filed on Jun. 6, 2019. The disclosure of the above referenced application is incorporated herein by reference.

FIELD

Embodiments of the subject matter described herein relate generally to medical devices, such as fluid infusion devices. More particularly, embodiments of the subject matter relate to devices for a fluid infusion, such as a fluid infusion device that is configurable for use as a fluid injection device, is configurable to be worn on a user's body and/or is configurable to be carried by a user. Embodiments of the subject matter also relate to devices for fluid infusion, such as an infusion set having an integrated physiological characteristic monitor for use with the fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some modes of providing insulin therapy to a user include delivery of insulin through manually operated syringes and insulin pens. Some other modes employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of a user. External fluid infusion devices include devices designed for use in a generally stationary location (for example, in a hospital or clinic), and devices configured for ambulatory or portable use (to be carried by a user). A fluid flow path may be established from a fluid reservoir of a fluid infusion device to the patient via, for example, a set connector of an infusion set, which is coupled to the fluid reservoir.

In certain instances, an external fluid infusion device may be cumbersome for the user to carry during the user's daily activities. In certain instances, an infusion device may include features that are complex for a particular user, or that a particular user may not desire. Certain fluid infusion devices, due to their complexity, may also have an increased cost. Moreover, in certain instances, it may be desirable for an infusion device to receive feedback from a physiological characteristic monitor, such as a continuous glucose monitor. In these instances, the physiological characteristic monitor and the infusion set are often separately coupled to the user's anatomy at different insertion sites.

Accordingly, it is desirable to provide an external fluid infusion device that is more convenient for a user to carry. In addition, it is desirable to provide a fluid infusion device that is easier to use and has a reduced cost. Further, it is desirable to provide a fluid infusion device that includes an infusion set integrated with a physiological characteristic sensor (e.g., a glucose sensor) so as to reduce the number of insertion sites. Furthermore, other desirable features and characteristics will become apparent from the subsequent detailed description and the appended claims, taken in conjunction with the accompanying drawings and the foregoing technical field and background.

BRIEF SUMMARY

The techniques of this disclosure generally relate to a fluid infusion device and infusion sets associated with a fluid infusion device, such as an insulin infusion pump for the treatment of diabetes.

According to various embodiments, provided is a portable fluid infusion device. The portable fluid infusion device includes a housing configured to accommodate a removable fluid reservoir. The housing has a largest dimension and a smallest dimension. The portable fluid infusion device includes a drive system configured to be serially coupled to the removable fluid reservoir such that a combined dimension of the drive system and the removable fluid reservoir is less than or equal to the largest dimension. The portable fluid infusion device includes a planar battery configured to supply power to the drive system. The planar battery has a plurality of faces comprising one or more faces having a largest area, and the planar battery being situated such that the one or more faces are parallel to the largest dimension and the smallest dimension.

Also provided is a portable fluid infusion device. The portable fluid infusion device includes a housing configured to accommodate a removable fluid reservoir, and a drive system configured to dispense fluid from the removable fluid reservoir. The portable fluid infusion device includes a battery configured to supply power to the drive system, and a user interface without a display. The user interface includes a button and a light emitting element.

Further provided according to various embodiments is a wearable fluid infusion device devoid of a user interface. The wearable fluid infusion device includes a housing configured to accommodate a removable fluid reservoir. The housing has a largest dimension and a smallest dimension. The wearable fluid infusion device includes a drive system configured to be serially coupled to the removable fluid reservoir such that a combined dimension of the drive system and the removable fluid reservoir is less than or equal to the largest dimension. The wearable fluid infusion device includes a planar battery configured to supply power to the drive system. The planar battery has a plurality of faces comprising one or more faces having a largest area, and the planar battery is situated such that the one or more faces are parallel to the largest dimension and the smallest dimension. The wearable fluid infusion device includes a means for coupling the housing with an adhesive plate configured to couple the wearable fluid infusion device to a user.

Also provided is a wearable fluid infusion device devoid of a user interface. The wearable fluid infusion device includes a housing configured to accommodate a removable fluid reservoir via a first opening in the housing and to accommodate a disposable battery via a second opening in the housing. The wearable fluid infusion device includes a drive system configured to dispense fluid the removable fluid reservoir. The wearable fluid infusion device includes a means for coupling the housing with an adhesive plate configured to couple the wearable fluid infusion device to a user.

Further provided according to various embodiments is a fluid infusion system. The fluid infusion system includes a housing configured to be adhesively coupled to an anatomy of a user, and a tube configured to extend from the housing for insertion into the anatomy of the user. The tube includes a plurality of conduits defined within the tube. The plurality of conduits include a fluid delivery conduit configured to facilitate a fluidic connection between a fluid source and the anatomy of the user, and one or more conduits configured to accommodate a plurality of electrodes for determining a physiological characteristic of the user.

Also provided is a fluid infusion system that includes a housing configured to be adhesively coupled to an anatomy of a user and one or more fluid delivery tubes configured to extend from the housing for insertion into the anatomy of the user, thereby facilitating a fluidic connection between a fluid source and the anatomy of the user. The fluid infusion system includes a plurality of electrodes configured to determine a physiological characteristic of the user. The plurality of electrodes are printed on the one or more fluid delivery tubes.

A fluid infusion system is also provided according to the various embodiments. The fluid infusion system includes a housing configured to be adhesively coupled to an anatomy of a user and a fluid delivery tube configured to extend from the housing for insertion into the anatomy of the user, thereby facilitating a fluidic connection between a fluid source and the anatomy of the user. The fluid infusion system includes a substrate comprising a plurality of electrodes configured to determine a physiological characteristic of the user, the substrate being coupled to the fluid delivery tube such that the plurality of electrodes is positioned below one or more fluid outlets defined in the fluid delivery tube.

Further provided according to various embodiments is a fluid infusion system. The fluid infusion system includes a means for determining a physiological characteristic of a user, and a housing configured to be adhesively coupled to an anatomy of the user. The housing includes a communication device configured to wirelessly communicate the physiological characteristic to a communication component of a fluid infusion device. The fluid infusion system includes a means for defining a fluid flow path from the fluid infusion device into the anatomy of the user, and the means for defining the fluid flow path is configured to extend from the housing for insertion into the anatomy of the user.

Also provided is fluid infusion system. The fluid infusion system includes a housing configured to be adhesively coupled to an anatomy of a user, and a means for determining a physiological characteristic of the user. The fluid infusion system includes a means for defining a fluid flow path from a fluid infusion device into the anatomy of the user. The means for defining the fluid flow path being configured to extend from the housing for insertion into the anatomy of the user, and a connector configured to secure the means for defining the fluid flow path to the fluid infusion device. The connector includes a communication device configured to communicate the physiological characteristic to a communication component of the fluid infusion device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 7 is a top view of the housing component of FIG. 6;

FIG. 8 is a side view of the housing component of FIG. 6;

FIG. 17A is a cross-sectional view of the fluid infusion device of FIG. 11, taken along line 17A-17A of FIG. 14;

FIG. 17B is a cross-sectional view of the fluid infusion device of FIG. 11, taken along line 17B-17B of FIG. 14;

FIG. 17C is a cross-sectional view of the fluid infusion device of FIG. 11, taken along line 17C-17C of FIG. 14;

FIG. 18 is a schematic illustration of an exemplary charging coil coupled to a printed circuit board associated with a fluid infusion device;

FIG. 19 is another schematic illustration of an exemplary charging coil coupled to a printed circuit board associated with a fluid infusion device;

FIG. 22A is a perspective view of an infusion set assembly for use with a fluid infusion device, in which the infusion set assembly is uncoupled from the fluid infusion device;

FIG. 22B is a perspective view of an infusion set assembly for use with a fluid infusion device, in which the infusion set assembly is coupled to the fluid infusion device;

FIG. 22C is a detail view of a connector of an infusion set assembly coupled to a housing of a fluid infusion device;

FIG. 22D is a cross-sectional view through the housing of the fluid infusion device, which shows the connection between the connector and the housing, and is taken along line 22D-22D of FIG. 22C;

FIG. 23A is a perspective view of an exemplary patch plate that is uncoupled from a fluid infusion device;

FIG. 23B is a perspective view of the patch plate and the fluid infusion device of FIG. 23A coupled together;

FIG. 24A is a perspective view of another exemplary patch plate that is uncoupled from a fluid infusion device;

FIG. 24B is a perspective view of the patch plate and the fluid infusion device of FIG. 24A coupled together;

FIG. 25 is a perspective view of an exemplary infusion set assembly for use with a fluid infusion device, in which the infusion set assembly is coupled to the fluid infusion device;

FIG. 26A is a perspective view of a needle connector that is uncoupled from a fluid infusion device;

FIG. 26B is a perspective view of the needle connector and the fluid infusion device of FIG. 26A coupled together;

FIG. 29 is a partially exploded view of the fluid infusion system of FIG. 27, in which a first housing portion is separated from a second housing portion;

FIG. 37A is a perspective view of an exemplary patch plate that is uncoupled from a fluid infusion device;

FIG. 37B is a perspective view of the patch plate and the fluid infusion device of FIG. 37A coupled together;

FIG. 38A is a perspective view of another exemplary patch plate that is uncoupled from a fluid infusion device;

FIG. 38B is a perspective view of the patch plate and the fluid infusion device of FIG. 38A coupled together;

FIG. 45 is a front perspective view of another exemplary implementation involving a tube integrated with a physiological characteristic sensor;

FIG. 46 is a cross-sectional view of the implementation of FIG. 45, taken along line 46-46 of FIG. 47;

FIG. 47 is a back perspective view of the implementation of FIG. 45;

FIG. 48 is a perspective view of another exemplary implementation involving a tube integrated with a physiological characteristic sensor;

FIGS. 49-52 depict an exemplary process for integrating a tube with a physiological characteristic sensor;

FIG. 53 is a side view of an exemplary implementation involving a tube and a physiological characteristic sensor;

FIG. 54 is a schematic view of the implementation of FIG. 53, in which the tube and the sensor are at least partially enveloped within a needle;

FIG. 55 is a perspective view of the implementation of FIG. 53;

FIG. 61 is a perspective view of an exemplary implementation involving a tube, a physiological characteristic sensor, and a hollow needle;

FIG. 62 is an end view of the implementation of FIG. 61;

FIG. 63 is a top view of the implementation of FIG. 61;

FIG. 64 is a perspective view of another exemplary implementation involving a tube, a physiological characteristic sensor, and a hollow needle;

FIG. 65 is an end view of the implementation of FIG. 64;

FIG. 66 is a top view of the implementation of FIG. 64;

FIG. 67 is a perspective view of another exemplary implementation involving a tube integrated with a physiological characteristic sensor;

FIG. 68 is an end view of the implementation of FIG. 67, in which the tube and the sensor are at least partially enveloped within a needle;

FIG. 69 is a top view of the implementation of FIG. 67, in which the tube and the sensor are at least partially enveloped within a needle;

FIG. 72 is a top view of another exemplary implementation involving a tube and a physiological characteristic sensor that are at least partially enveloped within a needle;

FIG. 73 is an end view of the implementation of FIG. 72;

FIG. 74 is a perspective view of the implementation of FIG. 72;

FIG. 79 is a top view of another exemplary implementation involving a tube and a physiological characteristic sensor that are at least partially enveloped within a needle;

FIG. 80 is an end view of the implementation of FIG. 79;

FIG. 81 is a perspective view of the implementation of FIG. 79;

FIG. 82 is a top view of another exemplary implementation involving a tube and a physiological characteristic sensor that are at least partially enveloped within a needle;

FIG. 83 is an end view of the implementation of FIG. 82;

FIG. 84 is a perspective view of the implementation of FIG. 82;

FIGS. 87-88 depict an exemplary process for forming a conduit using a ribbon cable comprising a physiological characteristic sensor;

FIG. 89 is a schematic illustration of an infusion monitor unit coupled to an exemplary implementation involving a tube integrated with a physiological characteristic sensor;

FIG. 90 is an end view of the implementation of FIG. 89;

FIG. 91 is an end view of another exemplary implementation involving a tube integrated with a physiological characteristic sensor;

FIG. 94 is a front perspective view of another exemplary implementation involving a tube integrated with a physiological characteristic sensor;

FIG. 95 is a rear perspective view of the implementation of FIG. 94;

FIG. 103A is a rear perspective view of another exemplary implementation involving a tube integrated with a physiological characteristic sensor;

FIG. 103B is a cross-sectional view of the implementation of FIG. 103A, taken along line 103B-103B of FIG. 103A;

FIG. 104A is a rear perspective view of another exemplary implementation involving a tube integrated with a physiological characteristic sensor;

FIG. 104B is a cross-sectional view of the implementation of FIG. 104A, taken along line 104B-104B of FIG. 104A;

FIG. 109 is a perspective view of the communication component;

FIG. 110 is a detail view of the connector, in which the communication component is coupled to the connector;

FIG. 111 is a partially exploded view of the fluid infusion device of FIG. 105, in which the connector is coupled to the fluid reservoir associated with the fluid infusion device;

FIG. 112 is a perspective view of a connector having another exemplary communication component for communicating with another exemplary device communication component associated with the fluid infusion device of FIG. 105, in which the connector is coupled to the fluid reservoir of the fluid infusion device;

FIG. 113 is a perspective view of the connector and fluid infusion device of FIG. 112, in which the connector is uncoupled from the fluid infusion device;

FIG. 114 is an exploded view of the connector and the communication component;

FIG. 115 is a perspective view of the communication component;

FIG. 116 is a detail view of the connector, in which the communication component is coupled to the connector;

FIG. 117 is a cross-sectional view of the fluid infusion device, taken along line 117-117 of FIG. 113, which illustrates the device communication component;

FIG. 118 is a detail view of the device communication component;

FIG. 119 is a perspective view of the connector coupled to the fluid infusion device, in which a portion of a housing of the fluid infusion device is removed to illustrate the electrical and mechanical coupling between the communication component and the device communication component;

FIG. 120 is a detail view of the electrical and mechanical coupling between the communication component and the device communication component;

Figure 11:
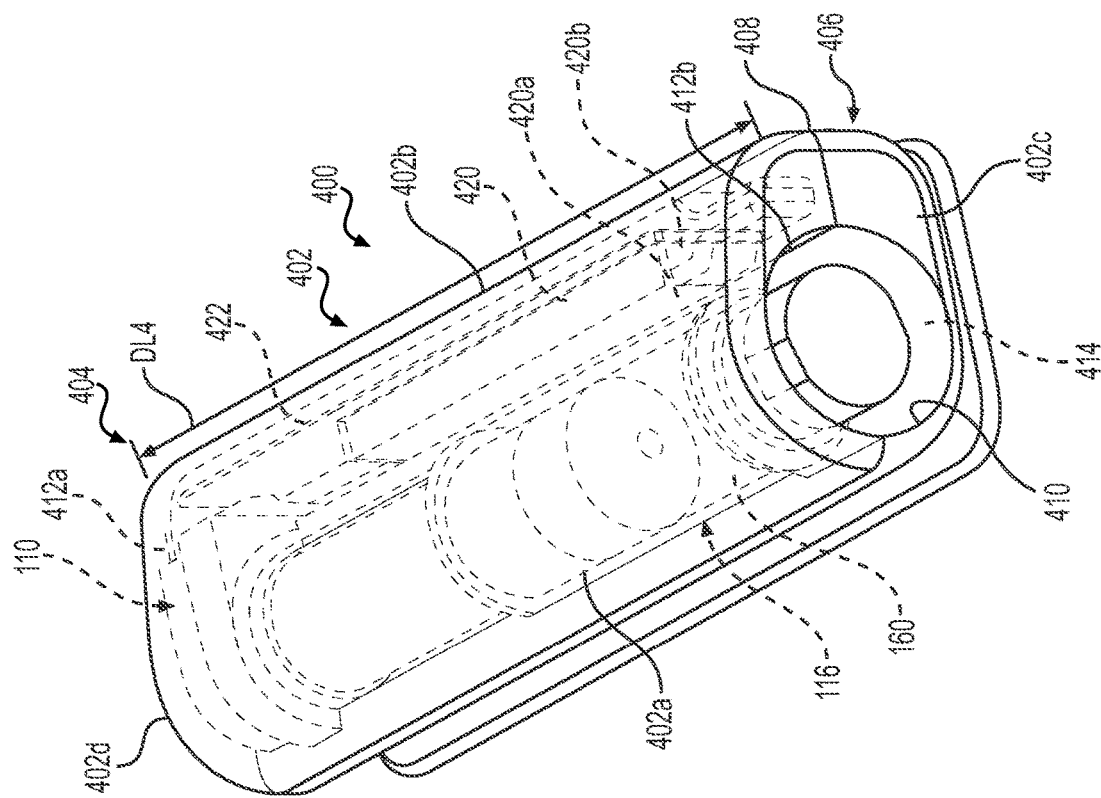
FIG. 11 is a perspective view of an implementation involving an exemplary fluid infusion device according to various teachings of the present disclosure.
Figure 105:
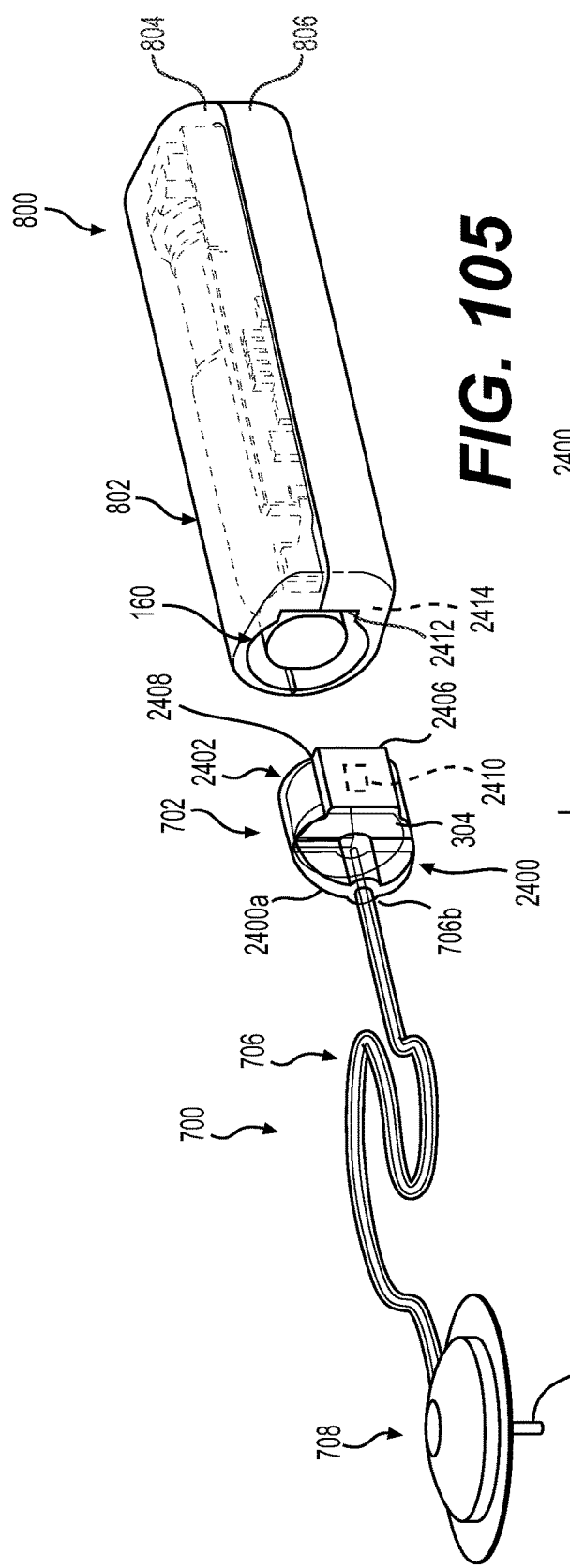
FIG. 105 is a perspective view of another exemplary fluid infusion device having a device communication component for communicating with an infusion set assembly that includes a communication component and an infusion monitor unit for measuring a physiological characteristic of a user, such as a blood glucose level, and for delivering a fluid to the user.
Figure 112:
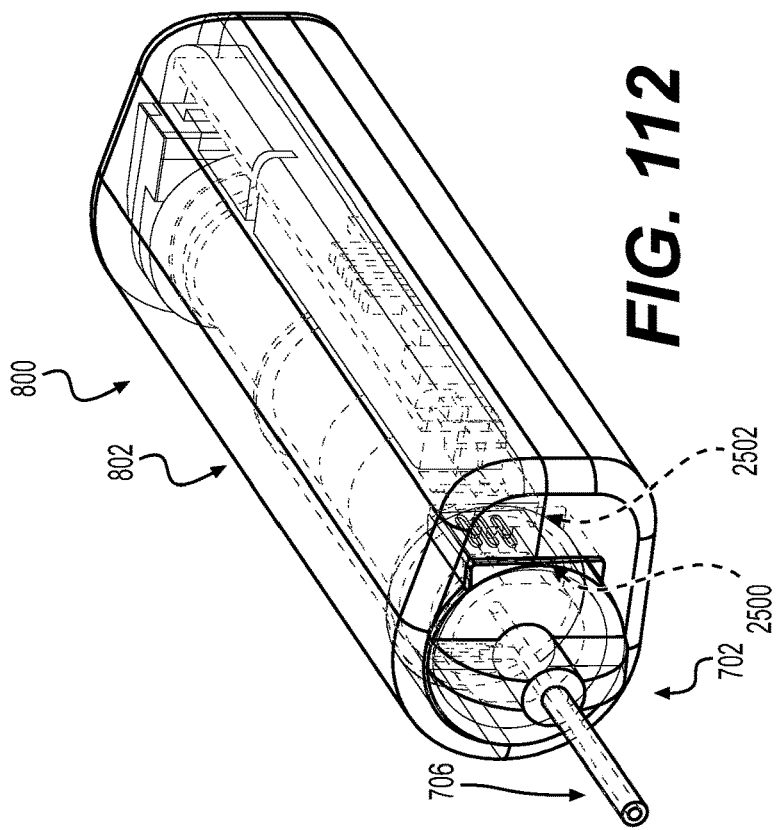
Figure 123:
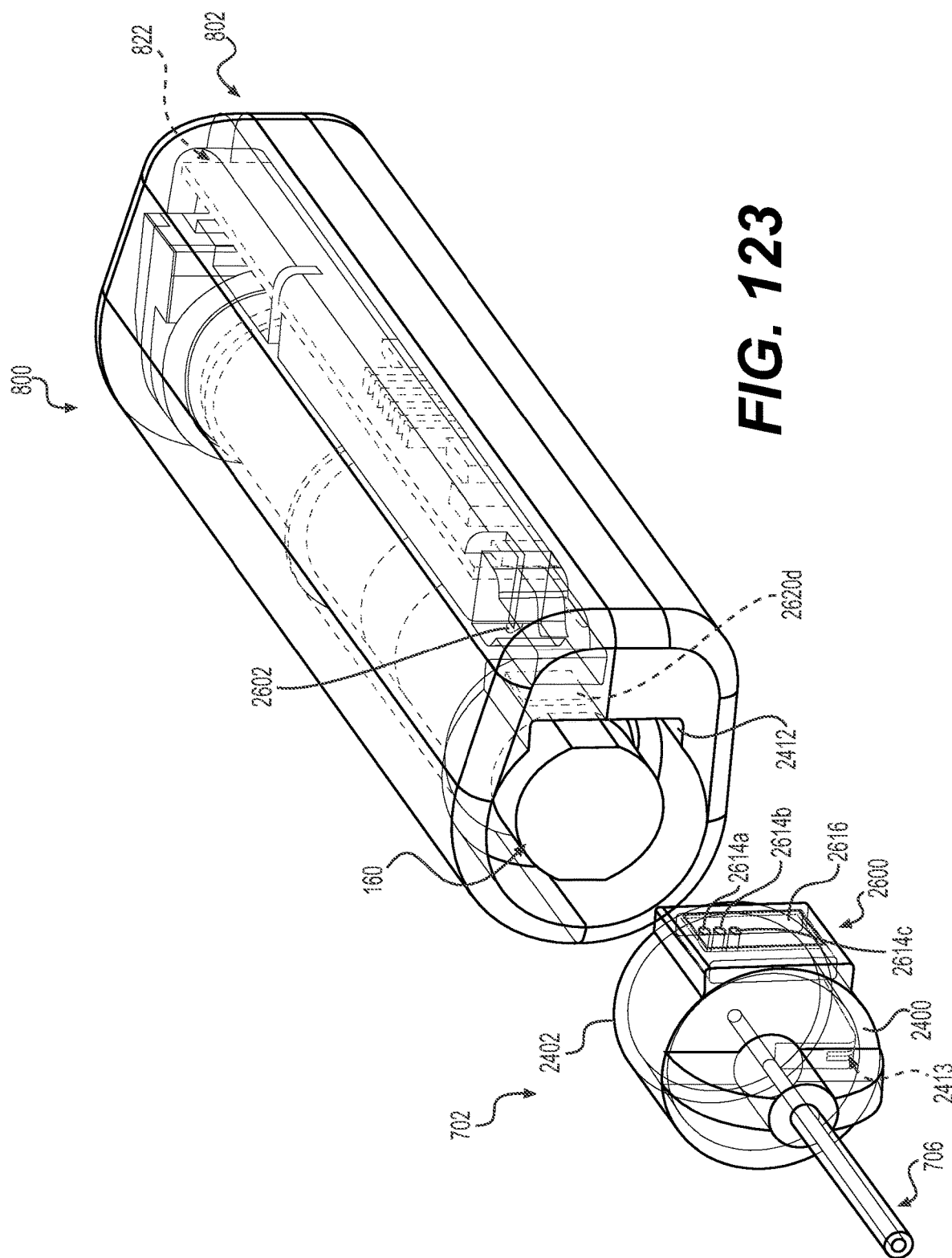
Figure 124:
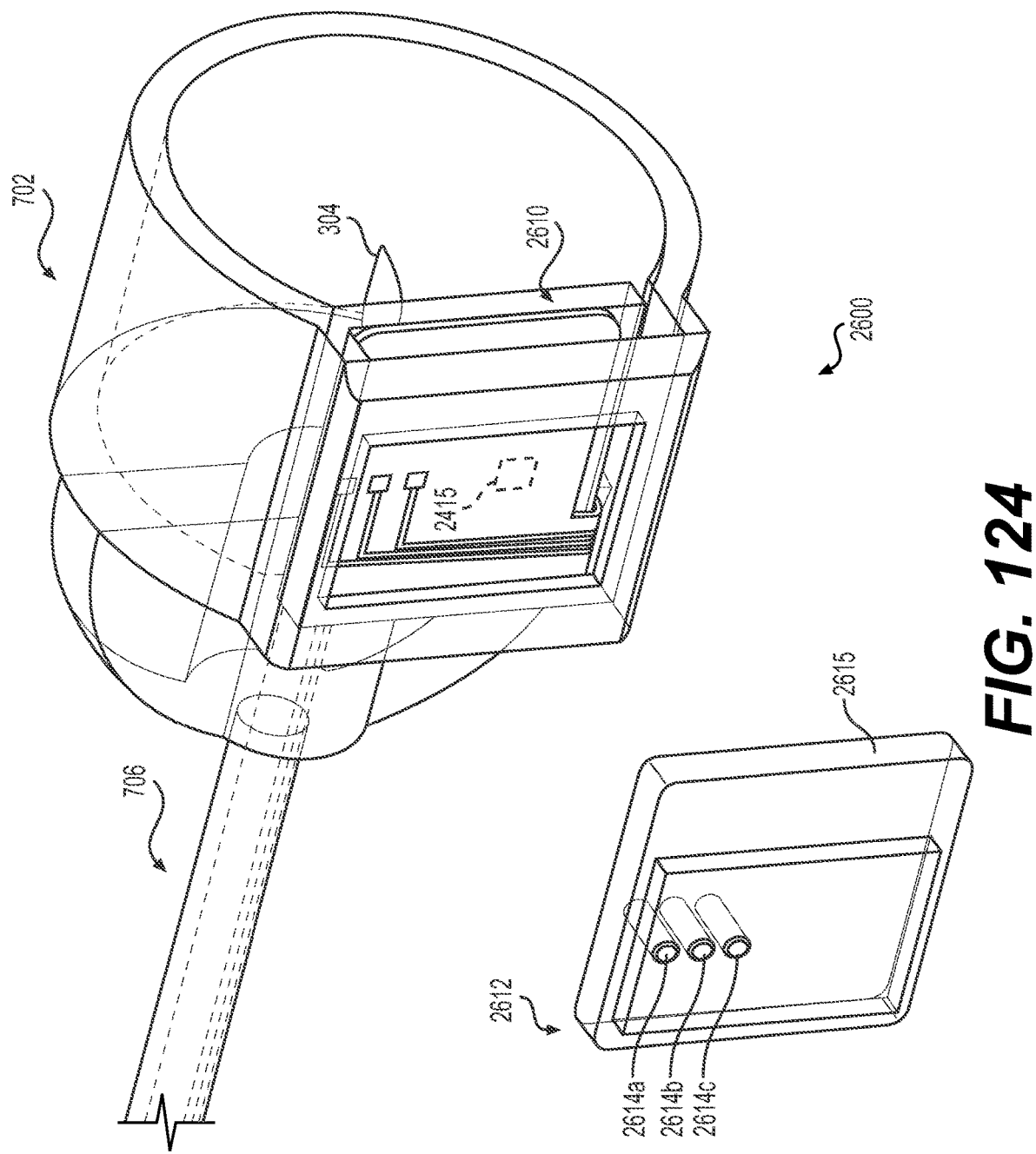
Figure 126:
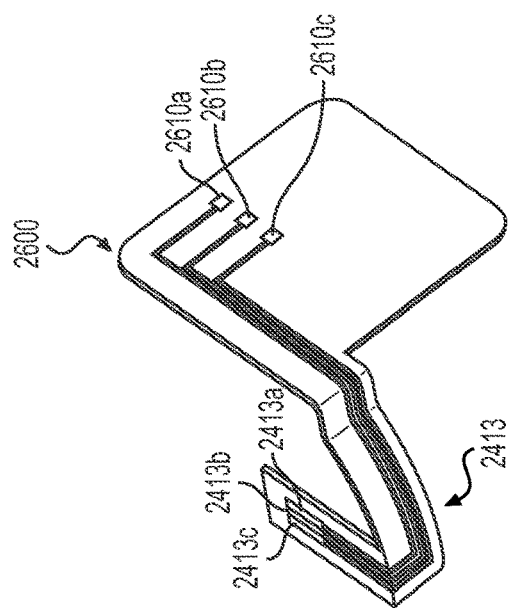
Figure 125:
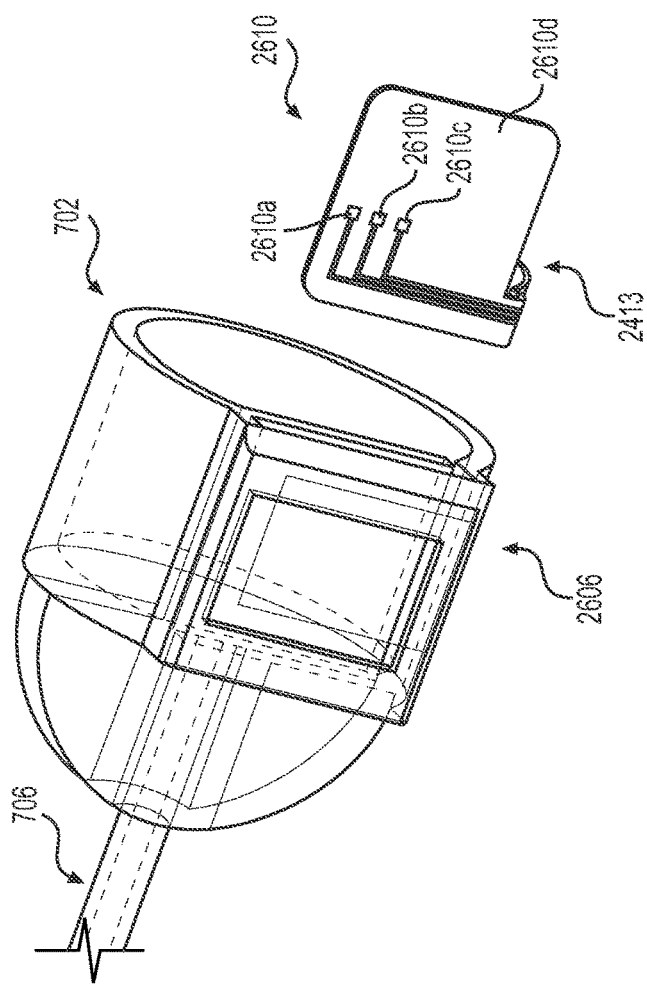
Figure 129:
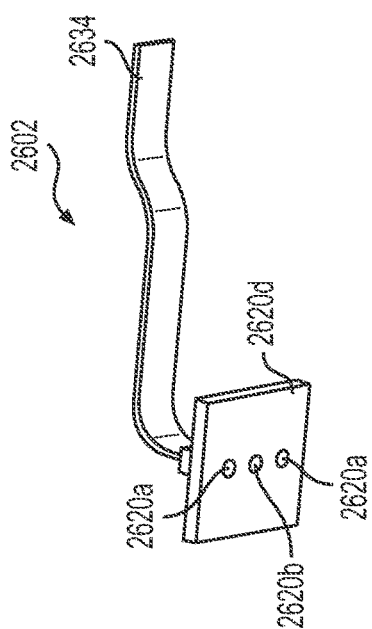
Figure 128:
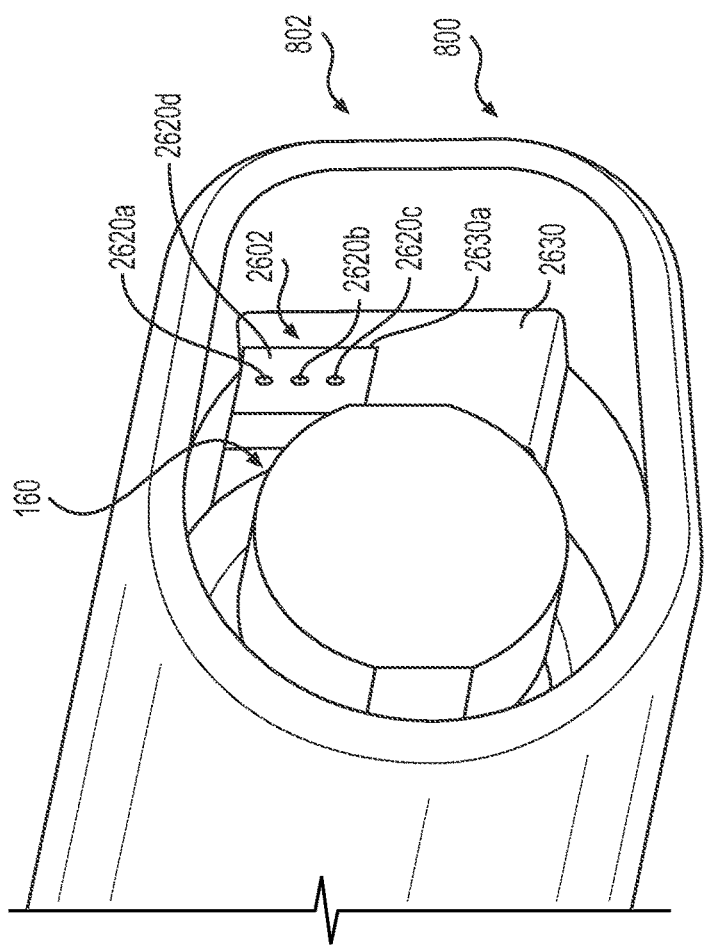
Figure 130:
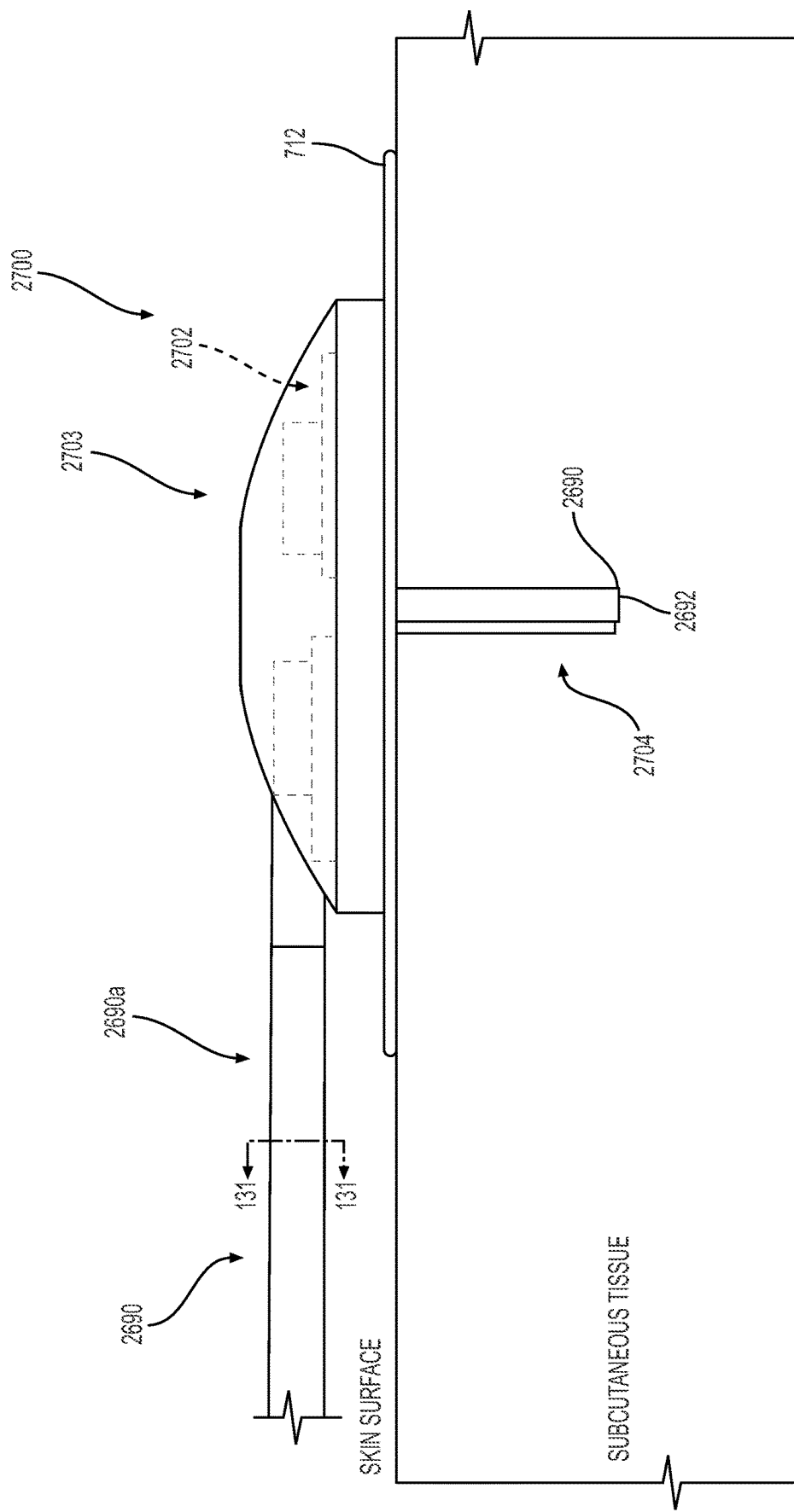
Figure 131:
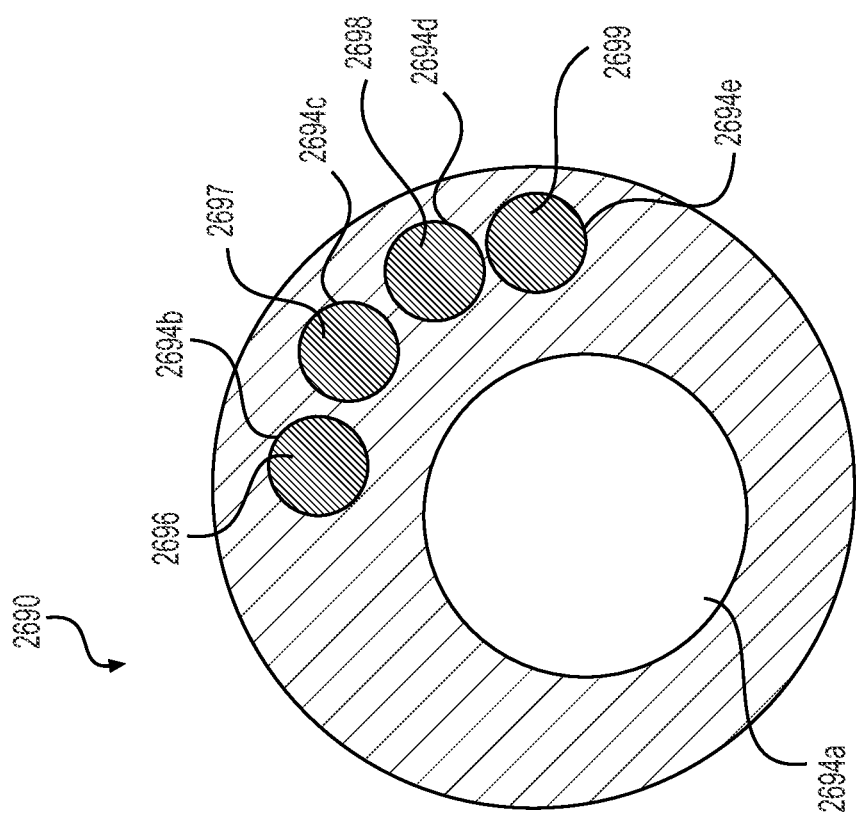
Figure 132:
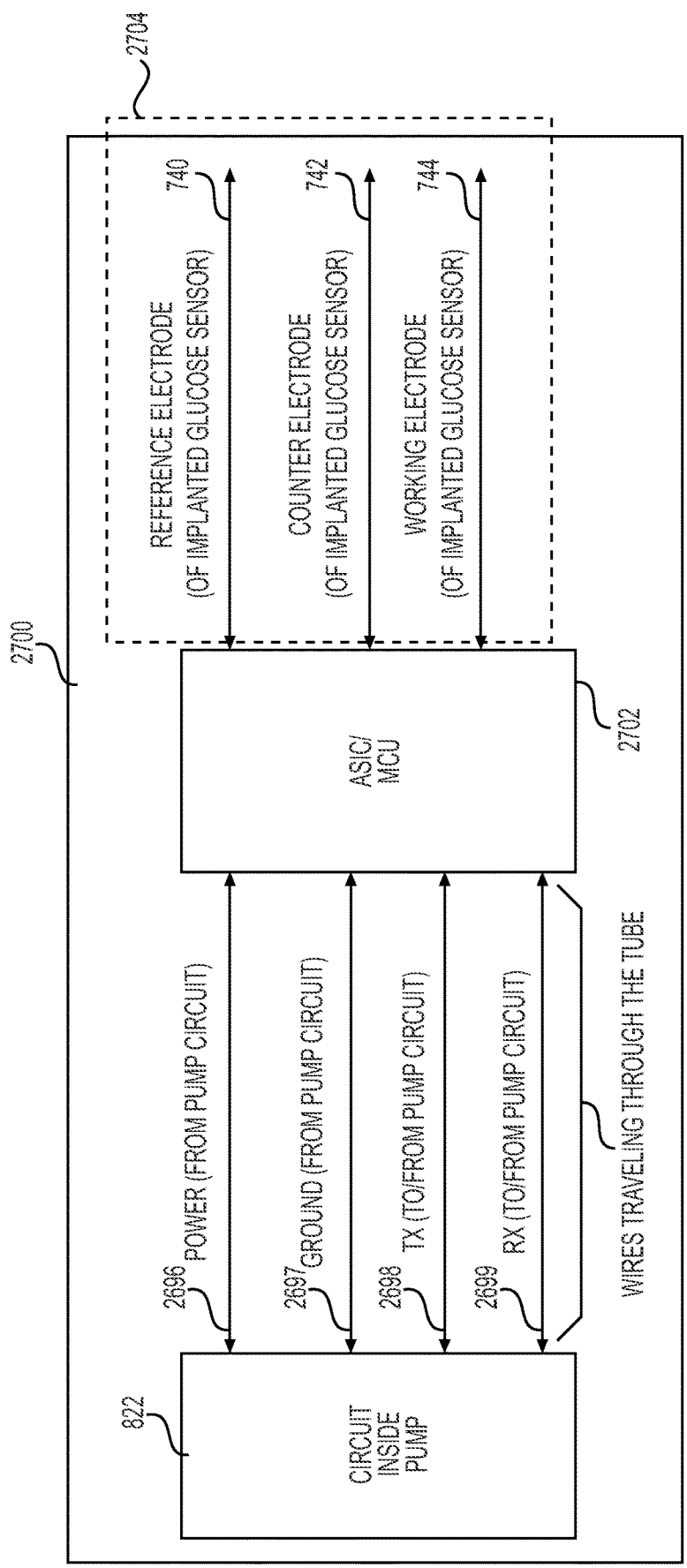
Figure 133:
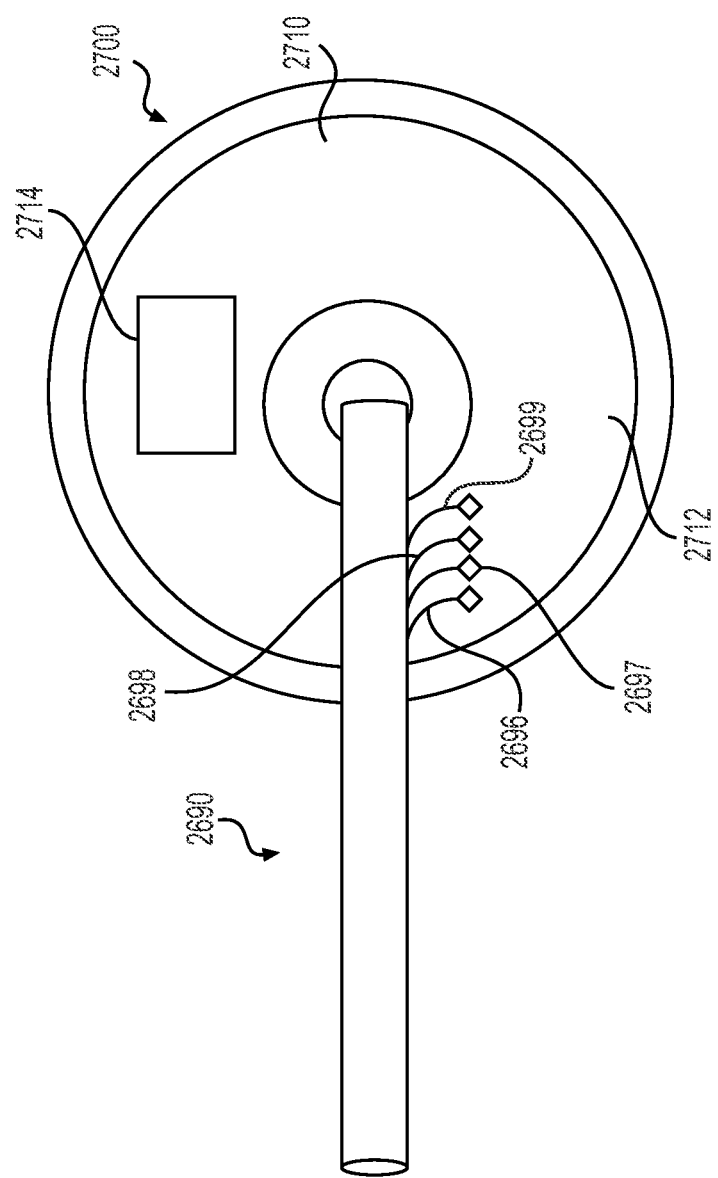
Figure 134:
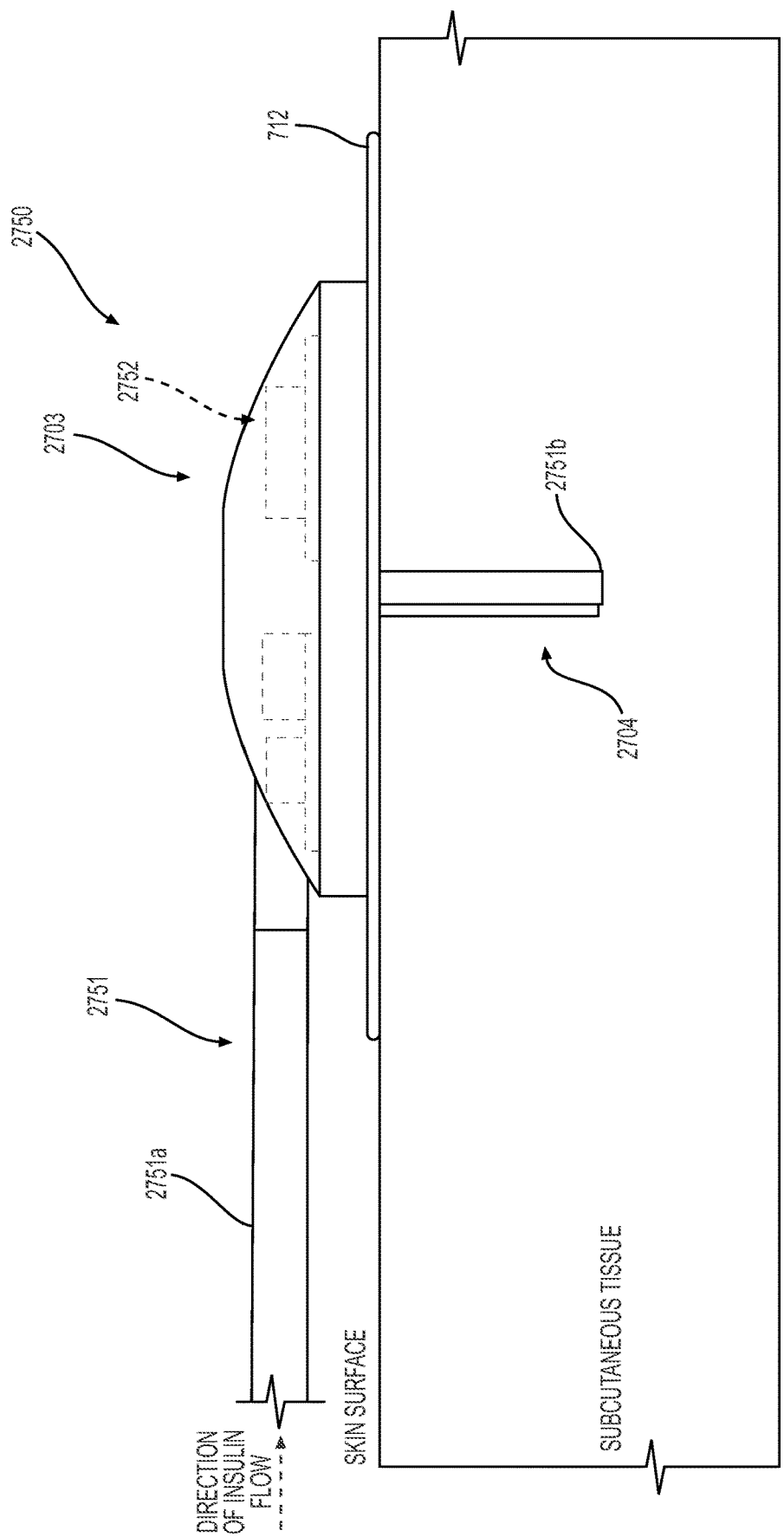
Figure 137:
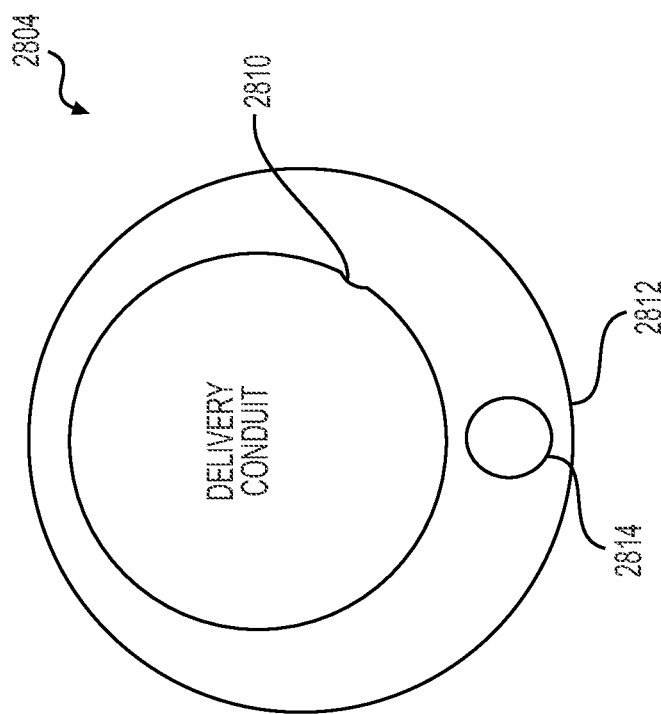
Figure 136:
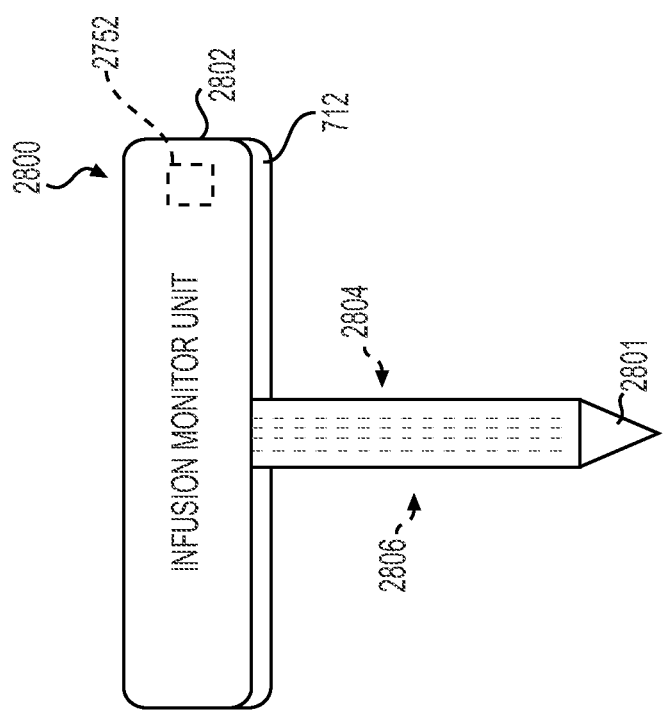
Figure 139:
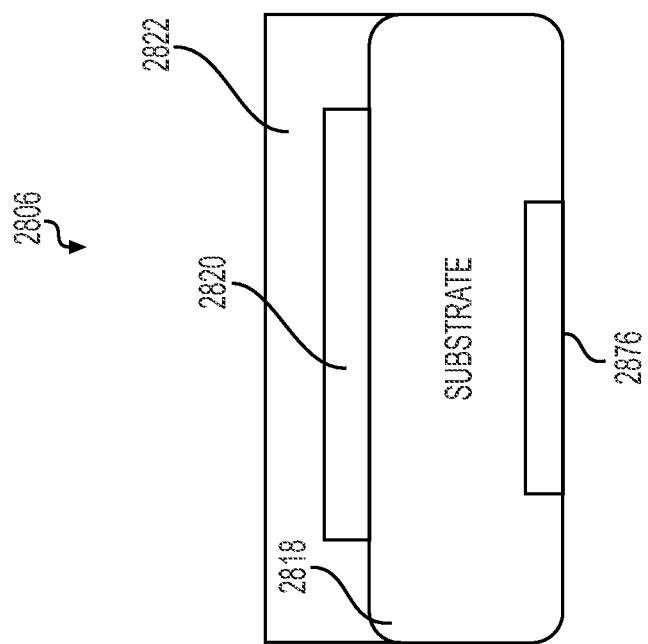
Figure 138:
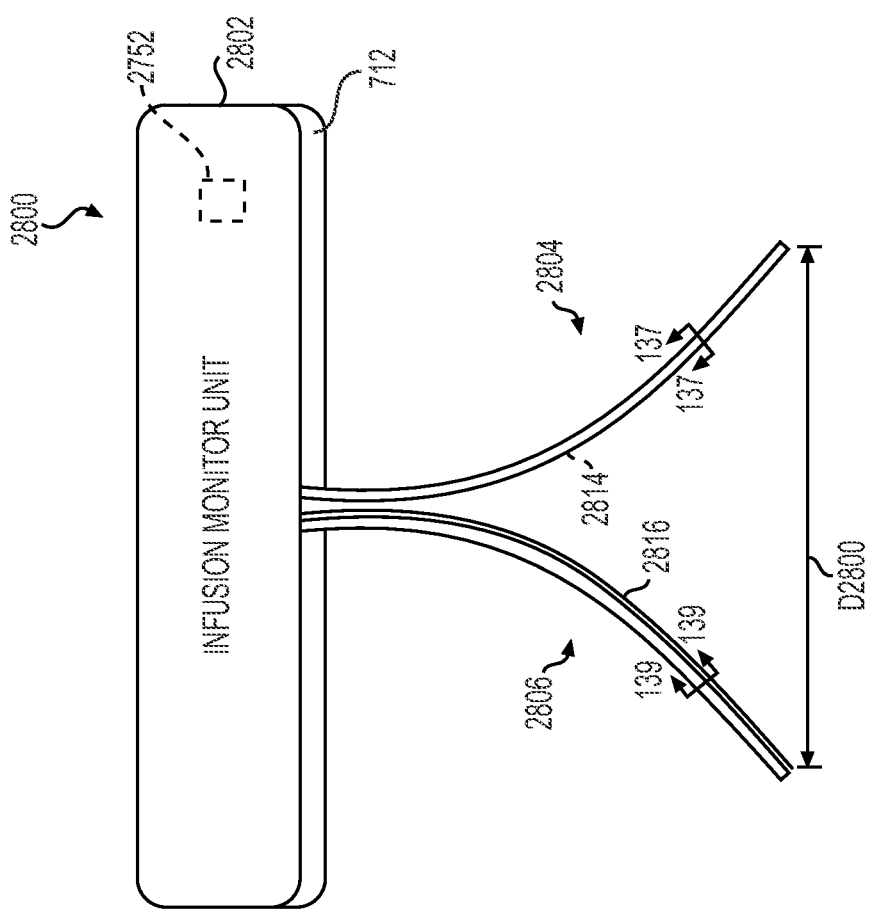
Figure 140:
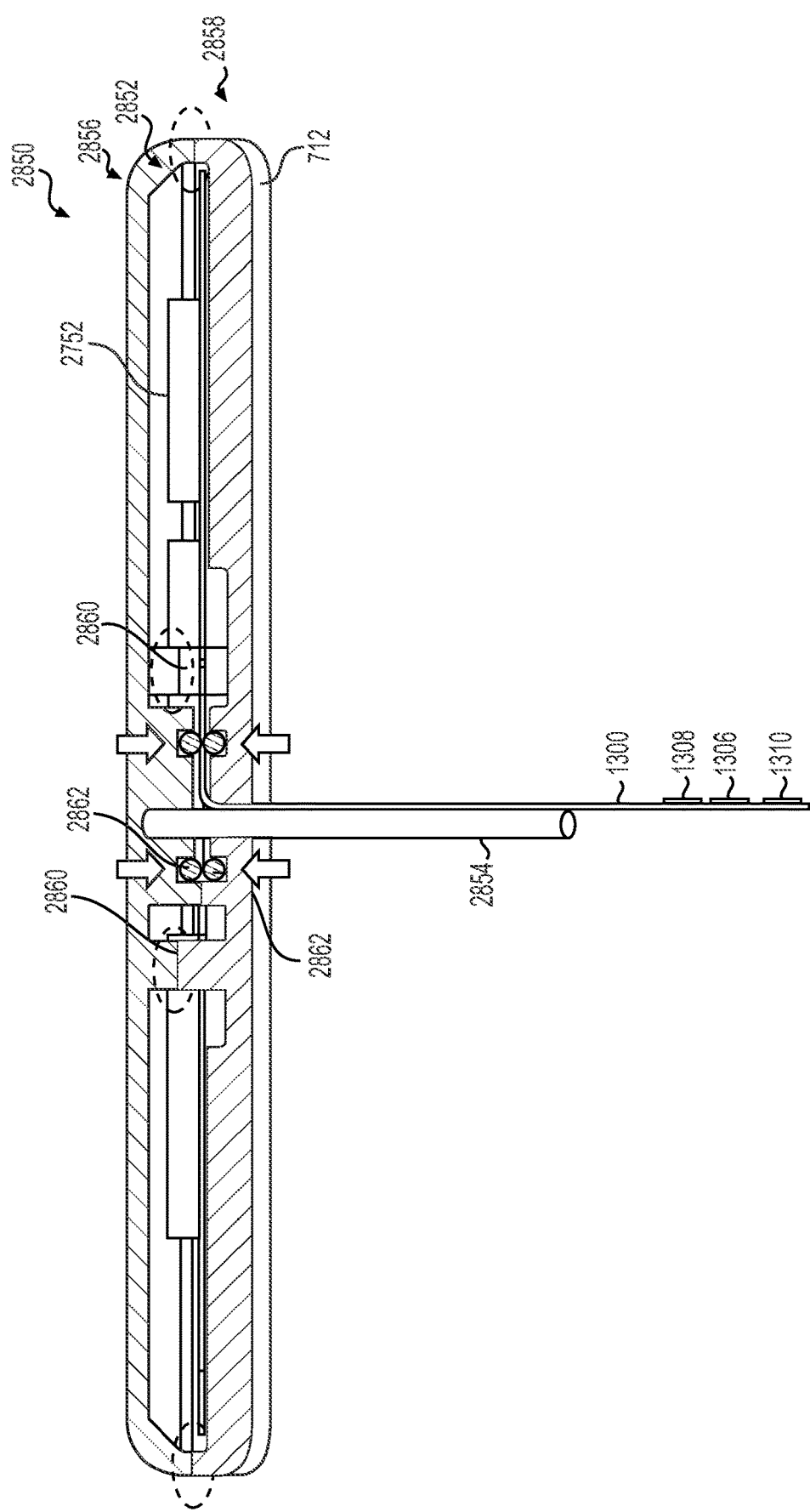
Figure 141:
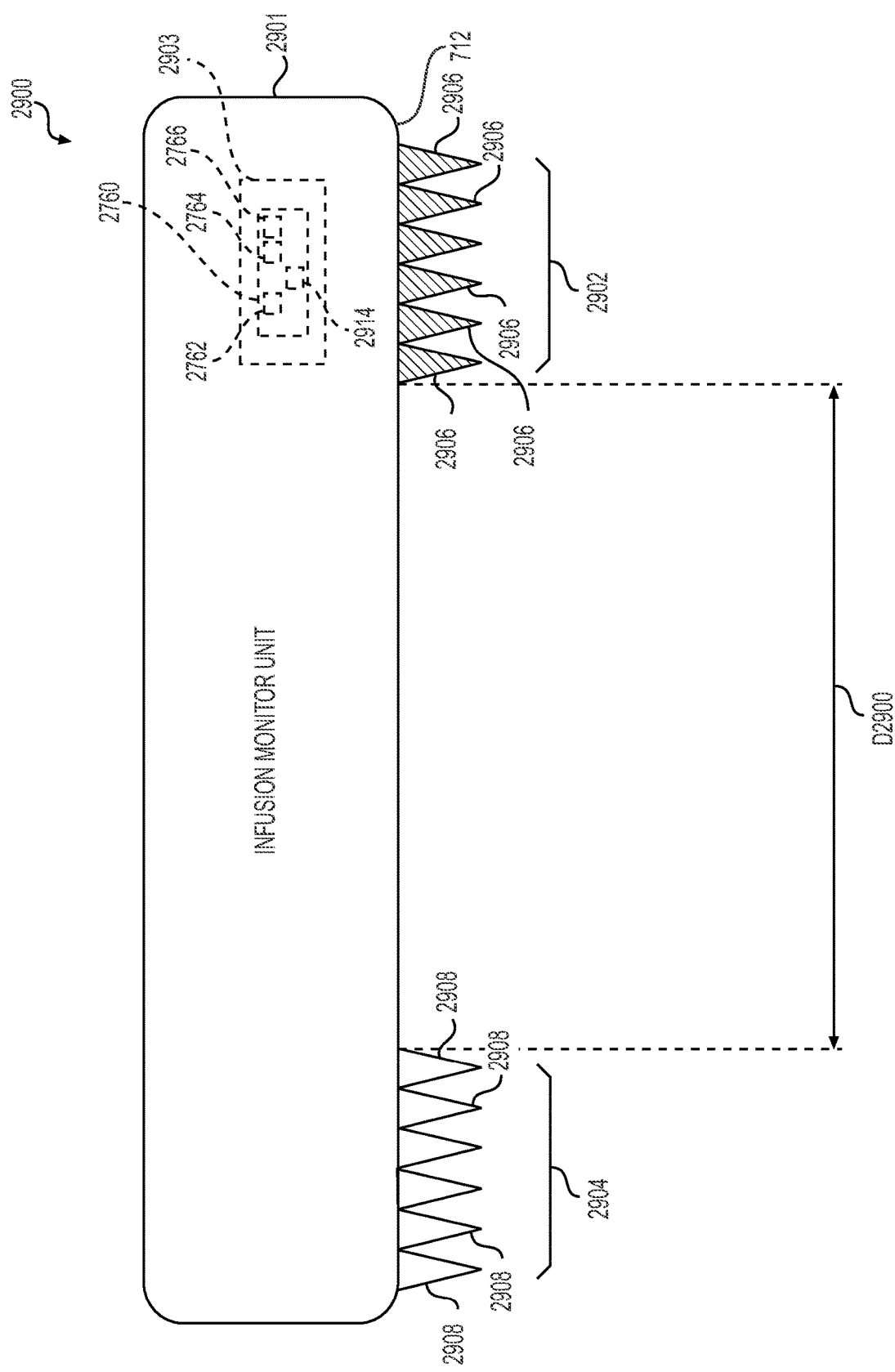
Figure 144:
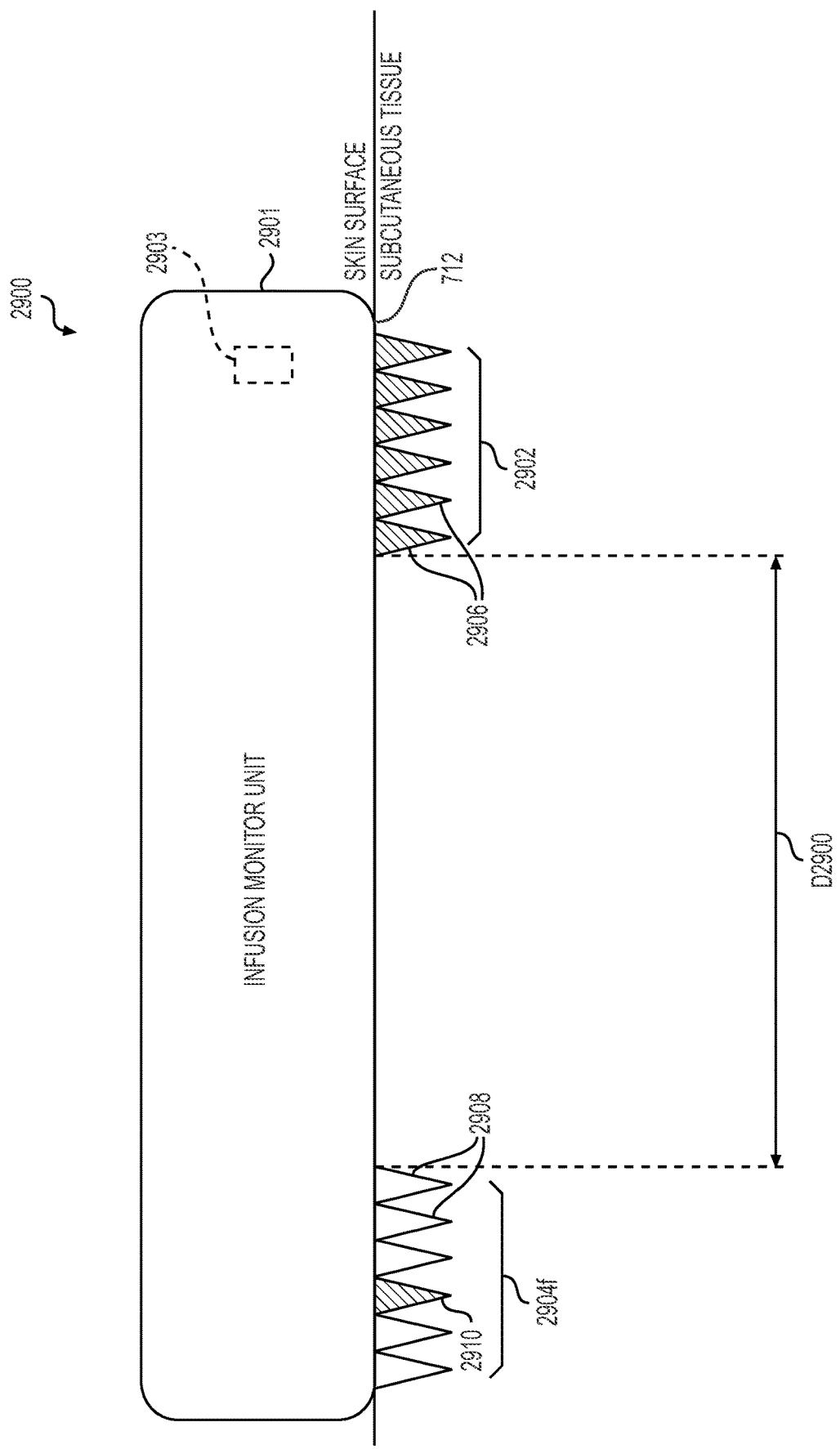
Figure 146:
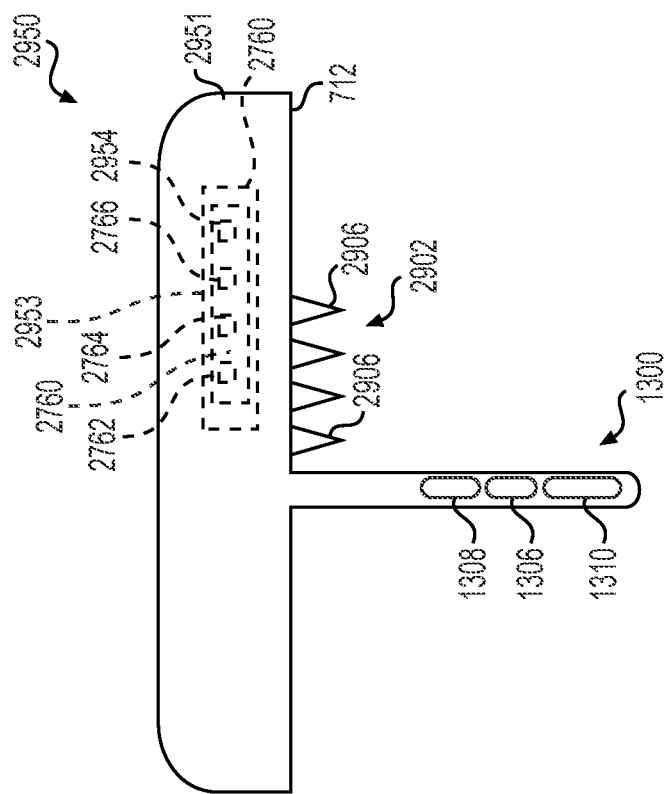
Figure 145A:
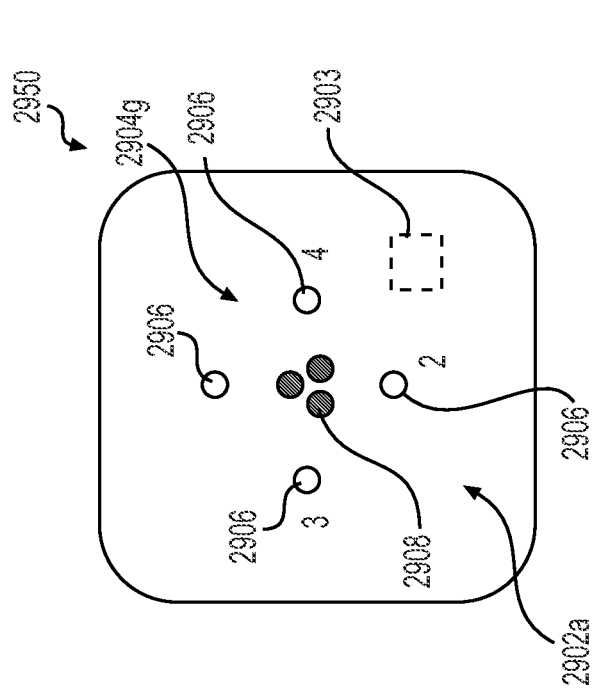
Figure 145B:
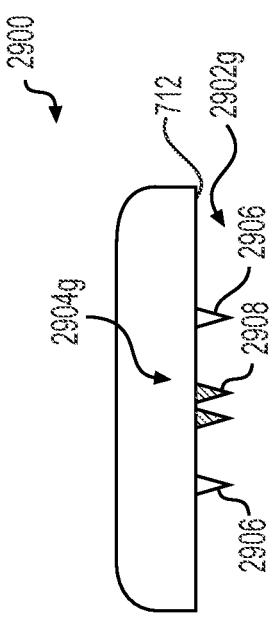
Figure 149:
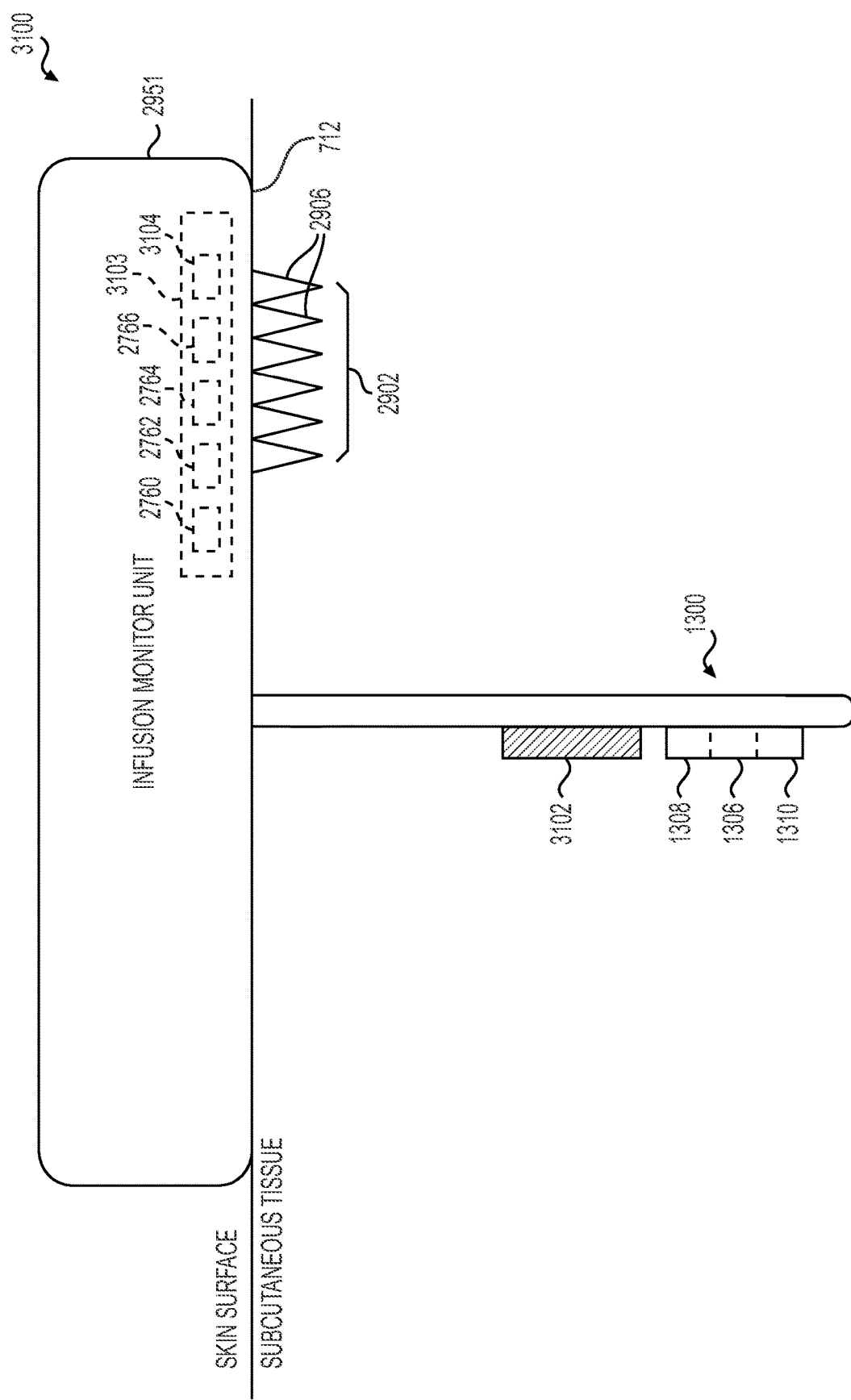

FIG. 121 is a detail view of another exemplary communication component coupled to a connector for communicating with the device communication component of the fluid infusion device of FIG. 112;

FIG. 122A is a side view of the connector of FIG. 121;

FIG. 122B is a detail side view of a portion of the connector of FIG. 121 taken from FIG. 122A;

FIG. 123 is a perspective view of a connector having another exemplary communication component for communicating with another exemplary device communication component associated with the fluid infusion device of FIG. 105, in which the connector is coupled to the fluid reservoir of the fluid infusion device;

FIG. 124 is a partially exploded view of the connector and the communication component;

FIG. 125 is an exploded view of a portion of the communication component and the connector;

FIG. 126 is a perspective view of the communication component;

FIG. 127A is a side view of the connector of FIG. 123;

FIG. 127B is a detail side view of a portion of the connector of FIG. 123 taken from FIG. 127A;

FIG. 128 is an end view of the fluid infusion device, which illustrates the device communication component;

FIG. 129 is a detail view of the device communication component;

FIG. 130 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 131 is a cross-sectional view of a tube associated with the infusion monitor unit of FIG. 130, taken along line 131-131 of FIG. 130;

FIG. 132 is an exemplary schematic circuit diagram for the infusion monitor unit of FIG. 130;

FIG. 133 is a top view of the infusion monitor unit of FIG. 130, in which a portion of the housing has been removed;

FIG. 134 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 135 is a top view of the infusion monitor unit of FIG. 134, in which a portion of the housing has been removed;

FIG. 136 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11 in a first state;

FIG. 137 is a cross-sectional view of a tube associated with the infusion monitor unit of FIG. 136, taken along line 137-137 of FIG. 138;

FIG. 138 is a schematic side view of the infusion monitor unit of FIG. 136 in a second state;

FIG. 139 is a cross-sectional view of a glucose sensor associated with the infusion monitor unit of FIG. 136, taken along line 139-139 of FIG. 138;

FIG. 140 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 141 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIGS. 142A-142D are each a top view of an alternative configuration for a delivery array and a sensing array associated with the infusion monitor unit of FIG. 141;

FIG. 143 is a schematic side view of another exemplary configuration for the delivery array and the sensing array associated with the infusion monitor unit of FIG. 141;

FIG. 144 is a schematic side view of another exemplary configuration for the delivery array and the sensing array associated with the infusion monitor unit of FIG. 141;

FIG. 145A is a top view of another exemplary configuration for the delivery array and the sensing array associated with the infusion monitor unit of FIG. 141;

FIG. 145B is a side view of the configuration of FIG. 145A;

FIG. 146 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 147 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 148A is a top view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 148B is a side view of the infusion monitor unit of FIG. 148A;

FIG. 149 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 150 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11;

FIG. 151 is a bottom view of the infusion monitor unit of FIG. 150; and

FIG. 152 is a schematic side view of another exemplary infusion monitor unit for measuring a physiological characteristic of a user, such as a blood glucose level, and for delivering a fluid to the user, which is associated with an infusion set assembly and is for use with a fluid infusion device, such as the fluid infusion device of FIG. 11.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of schematic, functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the fluid infusion device described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to various embodiments of a fluid infusion device, such as for the treatment of diabetes, and to various embodiments of an infusion set for coupling to the fluid infusion device to deliver fluid to an anatomy. The fluid infusion devices described herein provide a reduced form factor and/or a simplified user interface, which may reduce complexity and cost while making it easier for the user to carry the fluid infusion device. In addition, infusion sets described herein may reduce a number of insertion sites associated with the user by incorporating a continuous glucose sensor into the infusion set. The non-limiting examples described below relate to medical devices used to treat diabetes (such as an insulin pump and/or an infusion set), although embodiments of the disclosed subject matter are not so limited. Accordingly, the infused fluid is insulin in certain embodiments. In alternative embodiments, however, many other fluids may be administered through infusion such as, but not limited to, other disease treatments, drugs to treat pulmonary hypertension, iron chelation drugs, pain medications, anti-cancer treatments, other medications, vitamins, other hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein. In addition, conventional aspects and technology related to glucose sensors, glucose sensor fabrication and the determination of a glucose level or blood glucose level using a glucose sensor may not be described in detail here. In this regard, examples of glucose sensors and their manufacturing may be of the type described in, but not limited to: U.S. Pat. Nos. 5,391,250, 6,892,085, 7,468,033 and 9,295,786; and United States patent application number 2009/0299301 (which are each incorporated by reference herein).

Figure 1:
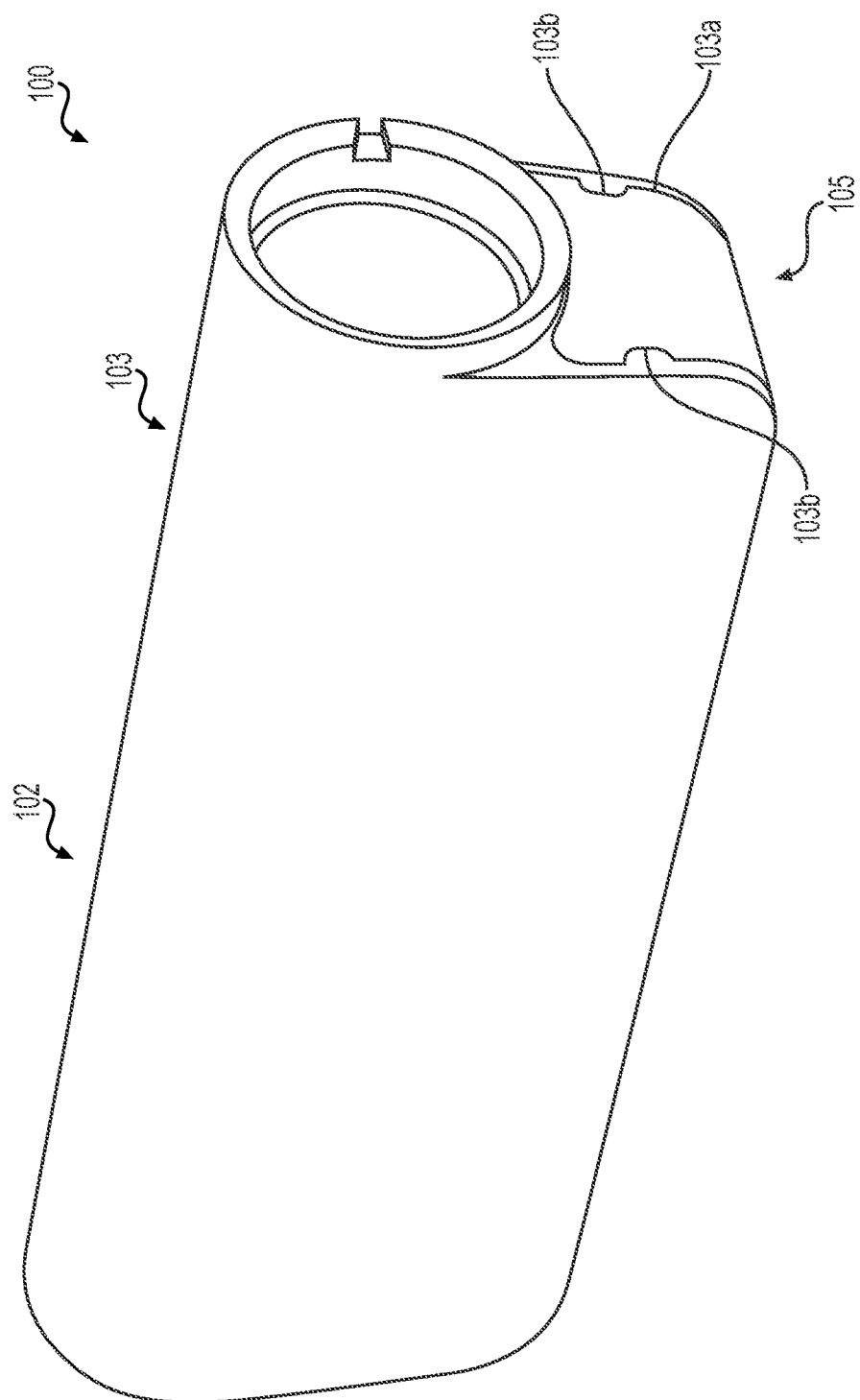
FIG. 1 is a perspective view of an exemplary fluid infusion device according to various teachings of the present disclosure.

With reference to FIG. 1, FIG. 1 is a perspective view of a fluid infusion device 100. In this example, the fluid infusion device 100 includes a housing 102. Generally, the housing 102 has a small form factor for portability, and is about 3 inches (in.) to about 4 inches (in.) long, about 1 inch (in.) to about 2 inches (in.) wide and is about 0.5 inches (in.) to about 1.5 inches (in.) thick. The fluid infusion device 100 also generally weights less than about 80 grams (g). In some examples, the housing 102 includes a first housing portion 103 and a second housing portion 105, which are coupled together to form the housing 102. In some examples, the first housing portion 103 of the housing 102 is composed of a metal or metal alloy, such as aluminum, titanium, stainless steel, etc., and is formed via casting, stamping, additive manufacturing, etc. By forming the first housing portion 103 of the housing 102 using a metal or metal alloy, the first housing portion 103 of the housing 102, which is larger than the second housing portion 105, is resistant to environmental factors and chemical exposure, such as water, sunscreen, etc. The use of a metal or metal alloy also protects the fluid infusion device 100 from accidental drops, vibrations and static loads during use, which improves reliability. Moreover, the size and configuration of the housing 102 enables the fluid infusion device 100 to be carried more easily, and to be attached in different orientations, such as lengthwise, via a clip, for example. Thus, the fluid infusion device 100 is sized and shaped to enable ease of use, which increases user satisfaction and convenience. In some examples, the housing 102 has a largest dimension Dl and a smallest dimension Ds (FIG. 3).

As shown in FIG. 1, the second housing portion 105 of the housing 102 is received within a channel 103a of the first housing portion 103 such that the first housing portion 103 surrounds a majority of the second housing portion 105. The channel 103a may include tabs 103b, notches or other guidance features to assist in coupling the first housing portion 103 to the second housing portion 105. The first housing portion 103 may be coupled to the second housing portion 105 via laser welding, adhesives, mechanical fasteners, etc. In some examples, the first housing portion 103 defines a case, while the second housing portion 105 forms a cover subassembly, which will be discussed in greater detail below.

Figure 2:
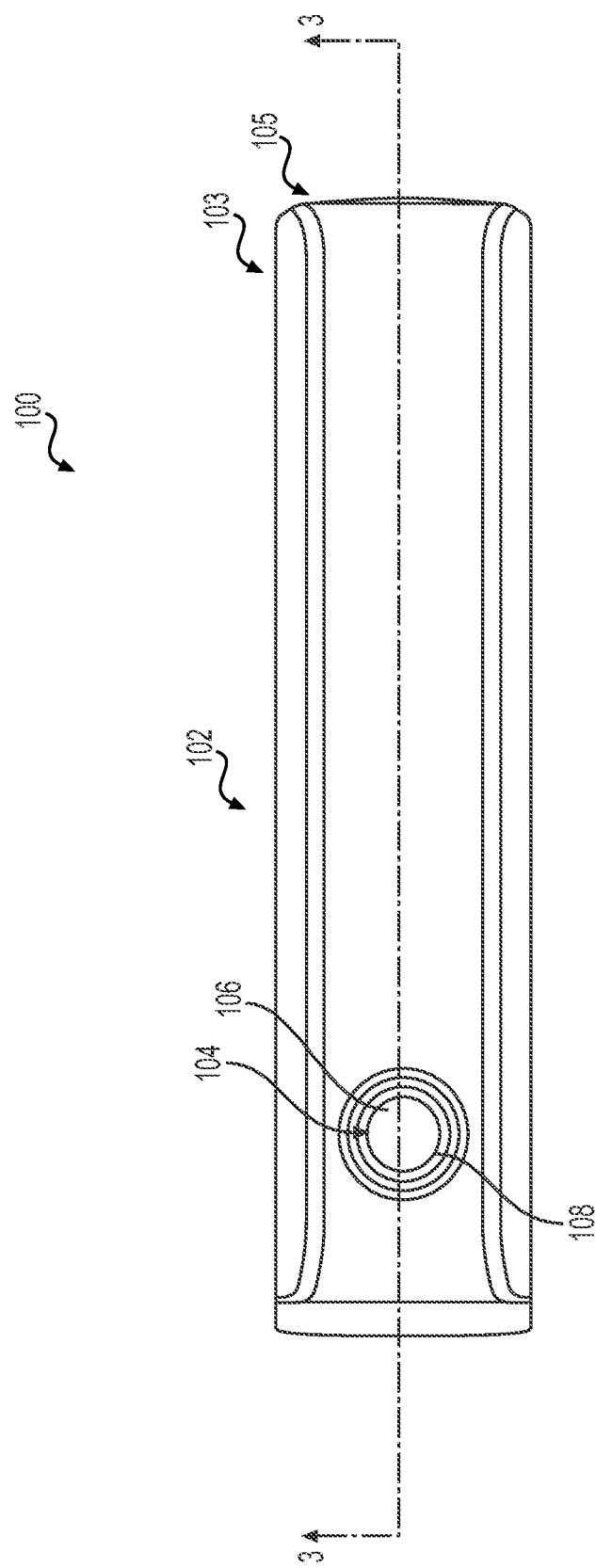
FIG. 2 is a bottom view of the fluid infusion device of FIG. 1.

With reference to FIG. 2, a bottom view including a user interface 104 is shown. In this example, the user interface 104 includes a button 106 and a light emitting element 108, such as a light emitting diode (LED). Notably, the user interface 104 is devoid of a display, which enables a reduction in size and cost of the fluid infusion device 100. The button 106 enables the user to turn the fluid infusion device 100 "off" or "on," and also enables the user to clear alarms or alerts generated by the fluid infusion device 100, reset or reboot the fluid infusion device 100, provide a quick bolus, and to pair the fluid infusion device 100 with a remote device or portable electronic device associated with the user, such as the user's smart phone, tablet, smart watch, computer, continuous glucose monitor, etc. In this example, the light emitting element 108 surrounds the button 106, however, the light emitting element 108 may be positioned at other locations on the housing 102. The light emitting element 108 may be integrated with the button 106, or may be coupled to the button 106 through any suitable technique, such as press-fitting, adhesives, in-mold electronics, etc. In addition, in certain embodiments, the button 106 may be a cosmetic surface coupled to a force sensitive resistor (FSR) or a pressure sensor with a linear resonant actuator (LRA) that is programmed to vibrate and simulate the effect of button presses. The light emitting element 108 provides a visual indicator of a status associated with the fluid infusion device 100. For example, the light emitting element 108 may comprise a multicolor LED, which is controlled to illuminate in different colors based on a status of the fluid infusion device 100. For example, the light emitting element 108 may be illuminated in green when the fluid infusion device 100 is operating properly, may be illuminated in red when there is an alarm or alert associated with the fluid infusion device 100, may be illuminated in blue when pairing the fluid infusion device 100 with the user's portable electronic device, etc.

Figure 3:
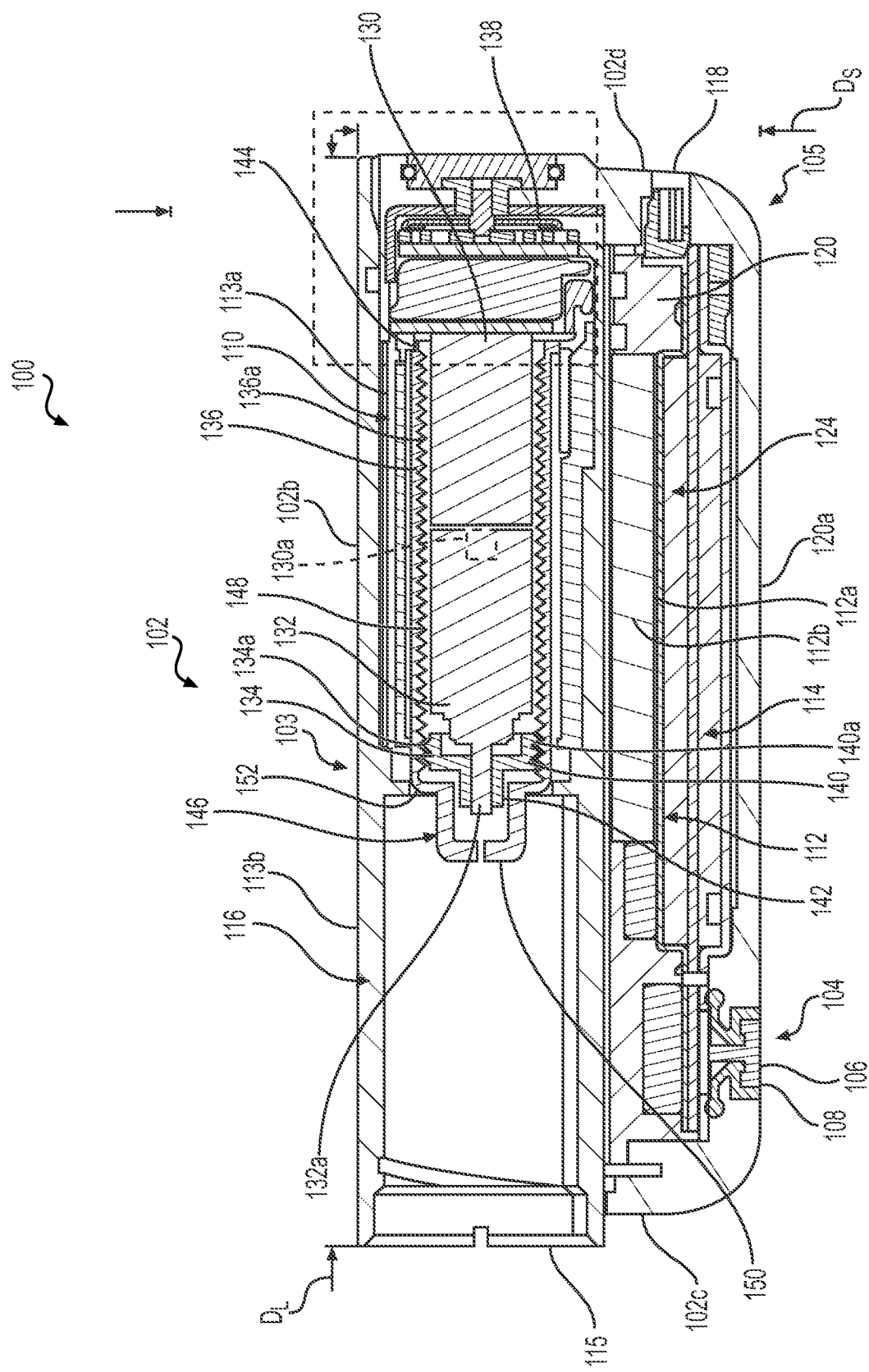
FIG. 3 is a cross-sectional view of the fluid infusion device of FIG. 1, taken along line 3-3 of FIG. 2, in which a fluid delivery system associated with the fluid infusion device is removed.

With reference to FIG. 3, the user interface 104 is generally disposed on one end 102a of the housing 102, which is opposite an end 102b of the housing 102 that encloses a drive system 110. The housing 102 also includes opposed sides 102c, 102d, which cooperate with ends 102a, 102b to enclose a power supply 112, a controller or control module 114, the drive system 110 and a fluid reservoir system 116. Generally, the side 102c includes an opening 115 to receive a fluid reservoir (not shown). In this example, the power supply 112, the control module 114 and the drive system 110 are accommodated in a pump chamber 113a enclosed by the housing 102, and the fluid reservoir system 116 is accommodated in a reservoir chamber 113b enclosed by the housing 102.

Figure 4:
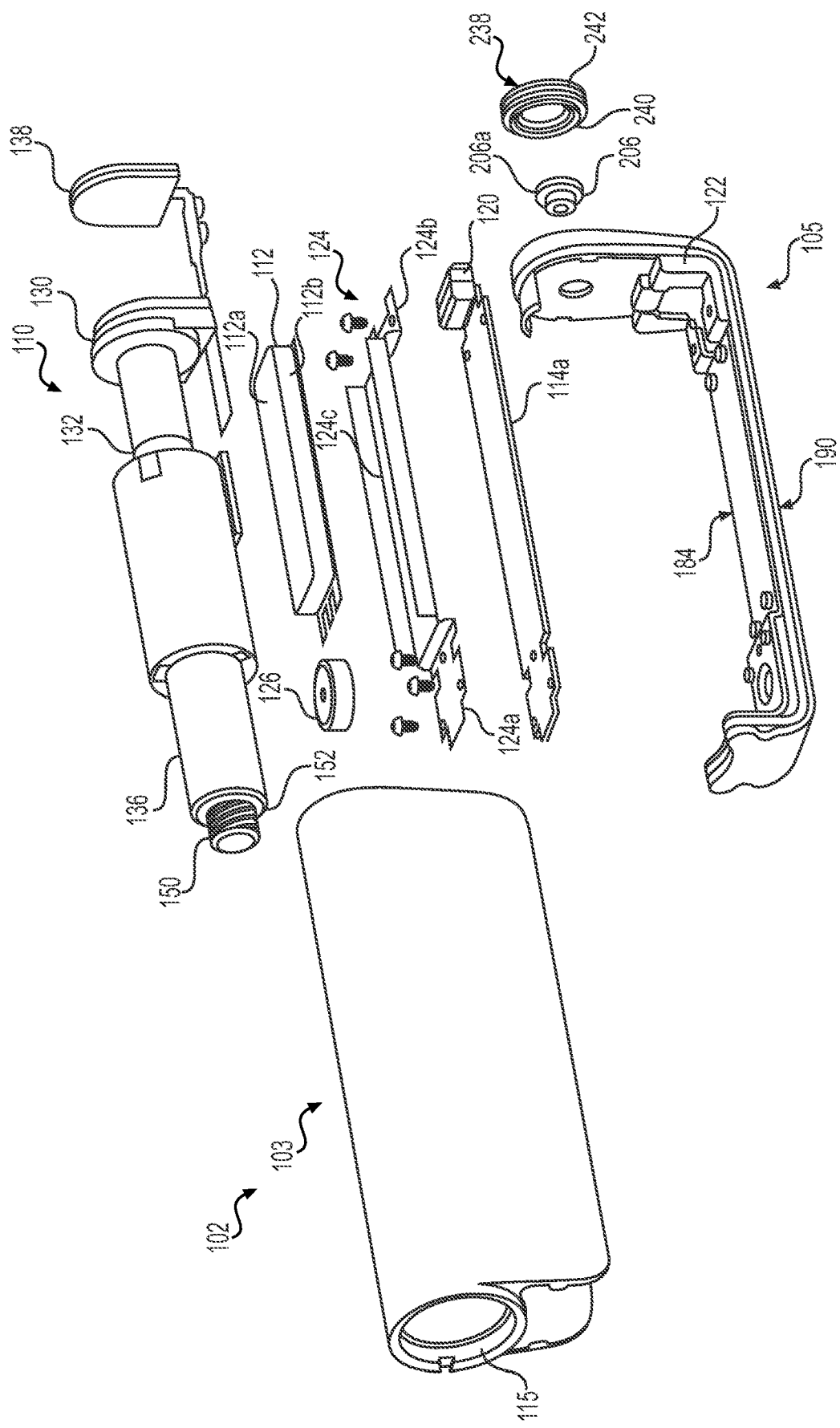
FIG. 4 is an exploded view of the fluid infusion device of FIG. 1.

The power supply 112 is any suitable device for supplying the fluid infusion device 100 with power, including, but not limited to, a battery. In some examples, the power supply 112 is a rechargeable battery, which is fixed within the housing 102. In this example, the power supply 112 is a planar battery configured to supply power to the drive system 110 that has a plurality of faces comprising one or more faces 112a having a largest area, and the planar battery is situated such that the one or more faces 112a, 112b are parallel to the largest dimension Dl of the housing 102 (face 112a) and the smallest dimension Ds of the housing 102 (face 112b) (FIG. 4). The power supply 112 may comprise a planar rectangular battery or a planar cylindrical battery. In such examples, the power supply 112 is rechargeable via USB, wireless charging, etc. In the example of USB charging, the housing 102 may enclose a first charging device or USB port 118 to enable an electrical connection between a USB receptacle 120 coupled to the control module 114 of the fluid infusion device 100 and a remote charging source. Generally, the power supply 112 is chargeable for at least a 7-day use.

The control module 114 is in communication with the user interface 104, the power supply 112 and drive system 110. The control module 114 is also in communication with the USB receptacle 120 to supply power received to the power supply 112. The control module 114 controls the operation of the fluid infusion device 100 based on user specific operating parameters. For example, the control module 114 controls the supply of power from the power supply 112 to the drive system 110 to activate the drive system 110 to dispense fluid from the fluid reservoir system 116. Further detail regarding the control of the fluid infusion device 100 can be found in U.S. Pat. Nos. 6,485,465 and 7,621,893, the relevant content of which was previously incorporated herein by reference.

Briefly, the control module 114 includes at least one processor and a computer readable storage device or media, which are mounted to a printed circuit board 114a like the one depicted in FIG. 4. The printed circuit board 114a is a rigid-flex printed circuit board that allows the flexible connections among the user interface 104, the power supply 112, drive system 110, and the other components associated with the fluid infusion device 100 (such as the control module 114) and the printed circuit board 114a. The processor can be any custom made or commercially available processor, a central processing unit (CPU), a graphics processing unit (GPU), an auxiliary processor among several processors associated with the control module 114, a semiconductor based microprocessor (in the form of a microchip or chip set), a macroprocessor, any combination thereof, or generally any device for executing instructions. In certain embodiments, the fluid infusion device 100 includes more than one processor, and includes a processor dedicated to the drive system 110 to manage delivery of the fluid and movement of the drive system 110. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electrical, magnetic, and/or optical memory devices capable of storing data, some of which represent executable instructions, used by the control module 114 in controlling components associated with the fluid infusion device 100.

The instructions may include one or more separate programs, each of which comprises an ordered listing of executable instructions for implementing logical functions. The instructions, when executed by the processor, may receive and process input signals; perform logic, calculations, methods and/or algorithms for controlling the components of the fluid infusion device 100; and generate signals to components of the fluid infusion device 100 to control the drive system 110 and/or the light emitting element 108 based on the logic, calculations, methods, and/or algorithms. Although only one control module 114 is shown, embodiments of the fluid infusion device 100 can include any number of control modules that communicate over any suitable communication medium or a combination of communication mediums and that cooperate to process the signals from the user interface 104; process signals received from the portable electronic device, perform logic, calculations, methods, and/or algorithms; and/or generate control signals to control features of the fluid infusion device 100.

In various embodiments, one or more instructions of the control module 114, when executed by the processor, enable receiving and processing signals from the user interface 104 to generate one or more control signals to the power supply 112 to supply power to the drive system 110, for example. Additionally, or alternatively, the one or more instructions of the control module 114, when executed by the processor, may enable receiving and processing signals from the user interface 104 to generate one or more control signals to clear an alarm or alert associated with the fluid infusion device 100. Additionally, or alternatively, the one or more instructions of the control module 114, when executed by the processor, may enable receiving and processing signals from the user interface 104 to generate one or more control signals to wirelessly pair the portable electronic device associated with the user with the fluid infusion device 100. Additionally, or alternatively, the one or more instructions of the control module 114, when executed by the processor, enable receiving and processing signals received from the portable electronic device, to generate one or more control signals to the power supply 112 to supply power to the drive system 110.

In certain instances, the control module 114 is in communication with an antenna 122 like the one depicted in FIG. 4. In some examples, the antenna 122 is a laser direction structure antenna, which is electrically and mechanically coupled to the printed circuit board 114a of the control module 114. It should be noted, however, that the antenna 122 may comprise any suitable antenna 122 that enables bi-directional communication between the fluid infusion device 100 and the portable electronic device of the user. Thus, generally, the antenna 122 enables wireless communication between the fluid infusion device 100 and another device, including, but not limited to, an infusion pump, handheld device (tablet, smart phone, etc.) and/or a monitoring device. In some examples, the antenna 122 may include, but is not limited to, a near-field communication (NFC) antenna, a radio frequency (RF) communication antenna, a far-field communication antenna, a wireless communication system configured to communicate via a wireless local area network (WLAN) using Institute of Electrical and Electronics Engineers (IEEE) 802.11 standards or by using cellular data communication, a BLUETOOTH antenna, etc. In certain embodiments, the antenna 122 of the fluid infusion device 100 may include more than one communication device, such as a near-field communication (NFC) antenna and a BLUETOOTH low energy (BLE) trace antenna.

In some examples, a bracket 124 is positioned between the power supply 112 and the printed circuit board 114a of the control module 114. The bracket 124 provides a mounting location for the power supply 112, and assists in securing the printed circuit board 114a to the second housing portion 105 of the housing 102. The bracket 124 may be composed of a polymeric material, and may be molded, additive manufactured, etc. With reference to FIG. 4, the bracket 124 includes a first mounting end 124a, a second mounting end 124b opposite the first mounting end 124a and includes or defines a slot 124c.

The first mounting end 124a is coupled to the printed circuit board 114a. The first mounting end 124a is also coupled to a vibration motor 126. The vibration motor 126 is electrically coupled to the printed circuit board 114a to be in communication with the control module 114. The vibration motor 126 is responsive to one or more signals from the control module 114 to vibrate, which causes a vibration of the housing 102. The vibration of the housing 102 provides a tactile alert, alarm or notification to the user. The vibration motor 126 may be a rotary or linear resonant actuator. The use of a linear resonant actuators may also provide qualitative haptics as additional feedback mechanisms to the user.

The second mounting end 124b is coupled to the printed circuit board 114a and at least partially surrounds the USB receptacle 120. The slot 124c is sized to accommodate the power supply 112 and to retain the power supply 112 within the housing 102. The first mounting end 124a and the second mounting end 124b may be coupled to the printed circuit board 114a via one or more mechanical fasteners, which extend through the printed circuit board 114a and engage with the second housing portion 105 of the housing 102, as will be discussed below.

Referring back to FIG. 3, the drive system 110 cooperates with the fluid reservoir system 116 to dispense the fluid from the fluid reservoir system 116. In some examples, the drive system 110 includes a motor 130, a gear box 132, a drive screw 134, a slide 136 and a force sensor 138. The motor 130 receives power from the power supply 112 as controlled by the control module 114. In some examples, the motor 130 is an electric motor. The motor 130 includes an output shaft 130a. The output shaft 130a is coupled to the gear box 132. In some embodiments, the gear box 132 is a reduction gear box. The gear box 132 enables the fluid infusion device 100 to be controlled to deliver different concentrations of fluid.

The gear box 132 includes an output shaft 132a, which is coupled to the drive screw 134.

The drive screw 134 includes a generally cylindrical distal portion 140 and a generally cylindrical proximal portion 142. The distal portion 140 has a diameter, which is larger than a diameter of the proximal portion 142. The distal portion 140 includes a plurality of threads 140a. The plurality of threads 140a are generally formed about an exterior circumference of the distal portion 140. The proximal portion 142 is generally unthreaded and can be sized to be received within a portion of the slide 136. The proximal portion 142 can serve to align the drive screw 134 within the slide 136 during assembly, for example.

With continued reference to FIG. 3, the slide 136 is substantially cylindrical and includes a distal slide end 144, a proximal slide end 146 and a plurality of threads 148. The distal slide end 144 is adjacent to the motor 130 when the slide 136 is in a first, fully retracted position and the proximal slide end 146 is adjacent to the drive screw 134 when the slide 136 is in the first, fully retracted position. The proximal slide end 146 includes a projection 150 and a shoulder 152, which cooperate with the fluid reservoir system 116 to dispense the fluid from the fluid reservoir system 116. The shoulder 152 is defined adjacent to the projection 150 and contacts a portion of the fluid reservoir system 116 to dispense fluid from the fluid reservoir system 116.

The plurality of threads 148 of the slide 136 are formed along an interior surface 136a of the slide 136 between the distal slide end 144 and the proximal slide end 146. The plurality of threads 148 are formed so as to threadably engage the threads 140a of the drive screw 134. Thus, the rotation of the drive screw 134 causes the linear translation of the slide 136.

In this regard, the slide 136 is generally sized such that in a first, retracted position, the motor 130, the gear box 132 and the drive screw 134 are substantially surrounded by the slide 136 as shown in FIG. 3. The slide 136 is movable to a second, fully extended position through the operation of the motor 130. The slide 136 is also movable to a plurality of positions between the first, retracted position and the second, fully extended position via the operation of the motor 130. Generally, the operation of the motor 130 rotates the output shaft 130a, which is coupled to the gear box 132. The gear box 132 reduces the speed and increases the torque output by the motor 130, and the output shaft 132a of the gear box 132 rotates the drive screw 134, which moves along the threads 148 formed within the slide 136. The movement or rotation of the drive screw 134 relative to the slide 136 causes the movement or linear translation of the slide 136 within the housing 102. The forward advancement of the slide 136 (i.e., the movement of the slide 136 toward the fluid reservoir system 116) causes the fluid reservoir system 116 to dispense fluid.

The force sensor 138 is operatively associated with the drive system 110 and is in communication with the control module 114. In some examples, with reference to FIG. 5, the force sensor 138 is coupled to the drive system 110, and it is located between the motor 130 and the second housing portion 105 of the housing 102. In some configurations, the force sensor 138 is affixed to the second housing portion 105 such that the force sensor 138 reacts when the motor 130 bears against the force sensor 138. This configuration and arrangement of the motor 130 and the force sensor 138 allows the force sensor 138 to react to forces imparted thereto by the drive system 110 and/or forces imparted to the drive system 110 via a fluid pressure associated with the fluid reservoir system 116. In some other configurations, the force sensor 138 may be affixed to the motor 130 such that the force sensor 138 reacts when it bears against the second housing portion 105.

Further details regarding the features and operation of the force sensor 138 are found in commonly assigned U.S. Pat. No. 8,628,510, the relevant portion of which is incorporated by reference. Generally, the force sensor 138 is used to detect when the slide 136 contacts a portion of the fluid reservoir system 116, to detect when the force sensor 138 needs calibration, to detect when the force sensor 138 is not operating within a normal operating range, to detect when an occlusion is present in a fluid flow path defined by the fluid reservoir system 116 and/or to determine whether a fluid reservoir 160 associated with the fluid reservoir system 116 may be properly seated and installed. As will be discussed further herein, the force sensor 138 is coupled to the second housing portion 105 such that the force sensor 138 is not pre-loaded or is minimally preloaded to a preset value.

Figure 5:
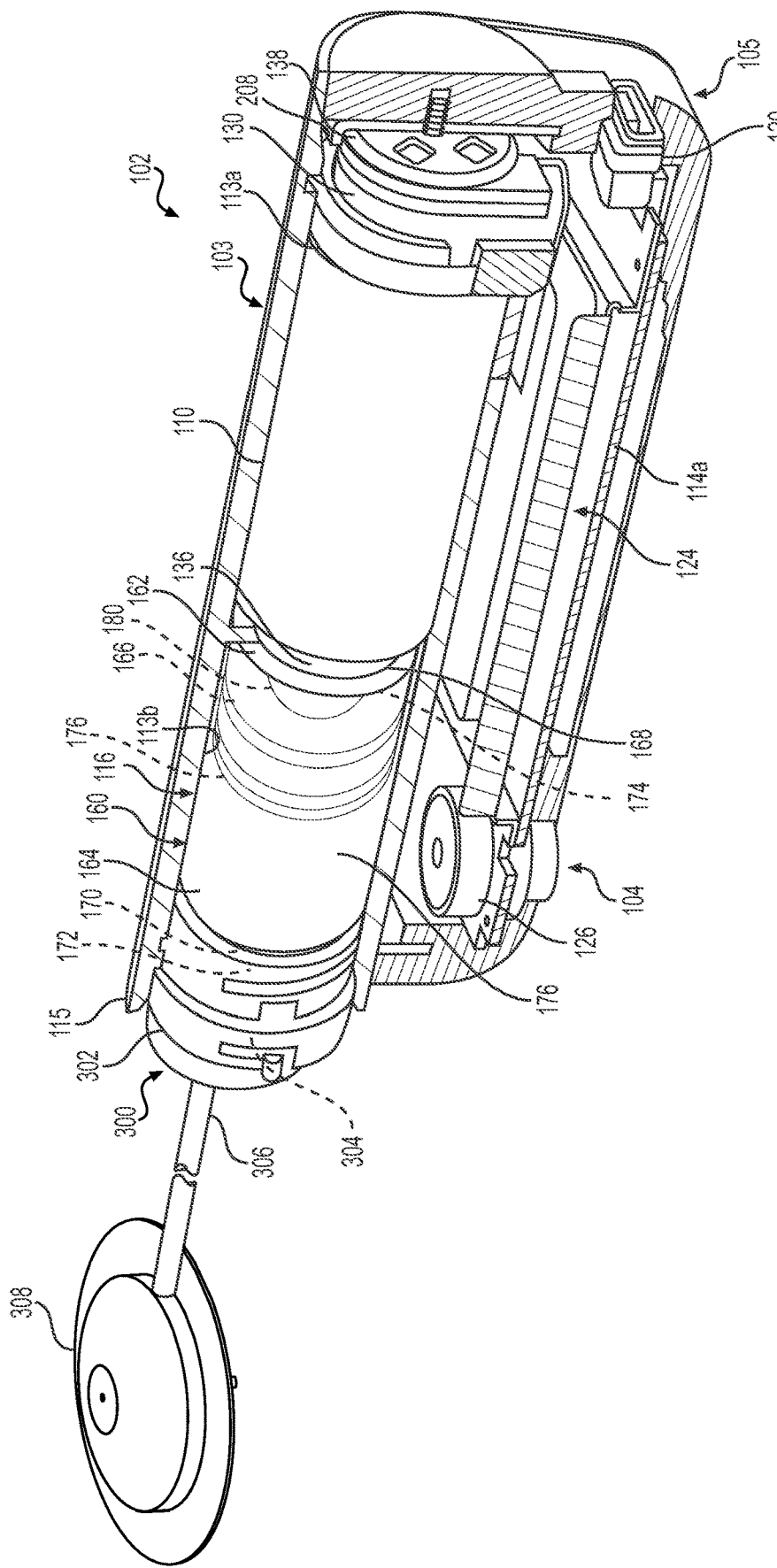
FIG. 5 is a cross-sectional view of the fluid infusion device of FIG. 1, taken along line 3-3 of FIG. 2, in which a fluid delivery system associated with the fluid infusion device is coupled to the fluid infusion device.

With continued reference to FIG. 5, the fluid reservoir system 116 includes the fluid reservoir 160 and a sealing member 162. The sealing member 162 is situated between the fluid reservoir 160 and the drive system 110 to prevent the ingress of fluids into the pump chamber 113a of the housing 102. In some examples, the sealing member 162 comprises an O-ring; however, any suitable device can be used to prevent the ingress of fluids, as known to one skilled in the art.

The fluid reservoir 160 can be inserted into the opening 115 defined in the housing 102. The fluid reservoir 160 is removable from the housing 102 to enable replacement as needed. Thus, the housing 102 is configured to accommodate the fluid reservoir 160, which is removable. The fluid reservoir 160 includes a body or barrel 164 and a stopper 166. The barrel 164 has a first or distal barrel end 168 and a second or proximal barrel end 170. Fluid is retained within the barrel 164 between the distal barrel end 168 and the proximal barrel end 170. The distal barrel end 168 is positioned adjacent to the slide 136 when the fluid reservoir 160 is inserted into the opening 115 of the housing 102. Generally, the distal barrel end 168 has a substantially open perimeter or is substantially circumferentially open such that the slide 136 is receivable within the barrel 164 through the distal barrel end 168. Generally, the slide 136 is interoperable with the fluid reservoir 160 at the distal barrel end 168 (e.g., the distal barrel end 168 may include an opening that can accommodate at least part of the slide 136 within the barrel 164).

The proximal barrel end 170 can have any suitable size and shape for mating with at least a portion of an infusion set assembly 300, as will be discussed in further detail herein. In some examples, the proximal barrel end 170 defines a passageway 172 through which the fluid flows out of the fluid reservoir 160. The passageway 172 may be closed by a septum (not shown). The septum may be positioned within a portion of the proximal barrel end 170, and is coupled to the proximal barrel end 170 through any suitable technique, such as ultrasonic welding, press-fit, etc. The septum serves as a barrier to prevent the ingress of fluids into the fluid reservoir 160, and prevents the egress of fluids from the fluid reservoir 160. The septum is pierceable by the infusion set assembly 300 to define a fluid flow path out of the fluid reservoir 160. In some examples, the infusion set assembly 300 includes a connector 302, a hollow instrument or needle 304 and the tube 306. The connector 302 couples the needle 304 and the tube 306 to the fluid reservoir 160, and locks into place once coupled to the fluid reservoir 160 to maintain the fluid flow path between the fluid reservoir 160 and an infusion unit 308. The connector 302 may be a removable reservoir cap (or fitting) that is suitably sized and configured such that the connector 302 can be separated from the fluid reservoir 160 when the fluid reservoir 160 (which is typically disposable) is to be replaced. The needle 304 defines a flow path for the fluid out of the fluid reservoir 160, through the connector 302 and into the tube 306.

With reference to FIG. 3, the stopper 166 is disposed within the barrel 164. The stopper 166 is movable within and relative to the barrel 164 to dispense fluid from the fluid reservoir 160. When the barrel 164 is full of fluid, the stopper 166 is adjacent to the distal barrel end 168, and the stopper 166 is movable to a position adjacent to the proximal barrel end 170 to empty the fluid from the fluid reservoir 160. In some examples, the stopper 166 is substantially cylindrical, and includes a first stopper end 174, a second stopper end 176, at least one friction element and a counterbore 180 defined from the first stopper end 174 to the second stopper end 176.

The first stopper end 174 is open about a perimeter of the first stopper end 174, and thus, is generally circumferentially open. The second stopper end 176 is closed about a perimeter of the second stopper end 176, and thus, is generally circumferentially closed. The second stopper end 176 includes a slightly conical external surface, however, the second stopper end 176 can be flat, convex, etc. The at least one friction element is coupled to the stopper 166 about an exterior surface of the stopper 166. In some examples, the at least one friction element comprises two friction elements, which include, but are not limited to, O-rings. The friction elements are coupled to circumferential grooves defined in the exterior surface of the stopper 166. The counterbore 180 receives the projection 150 of the slide 136 and the movement of the slide 136 causes the shoulder 152 of the slide 136 to contact and move the stopper 166. Generally, the drive system 110 is configured to be serially coupled to the removable fluid reservoir 160 such that a combined dimension of the drive system 110 and the removable fluid reservoir 160 is less than or equal to the largest dimension Dl (FIG. 3).

Figure 6:
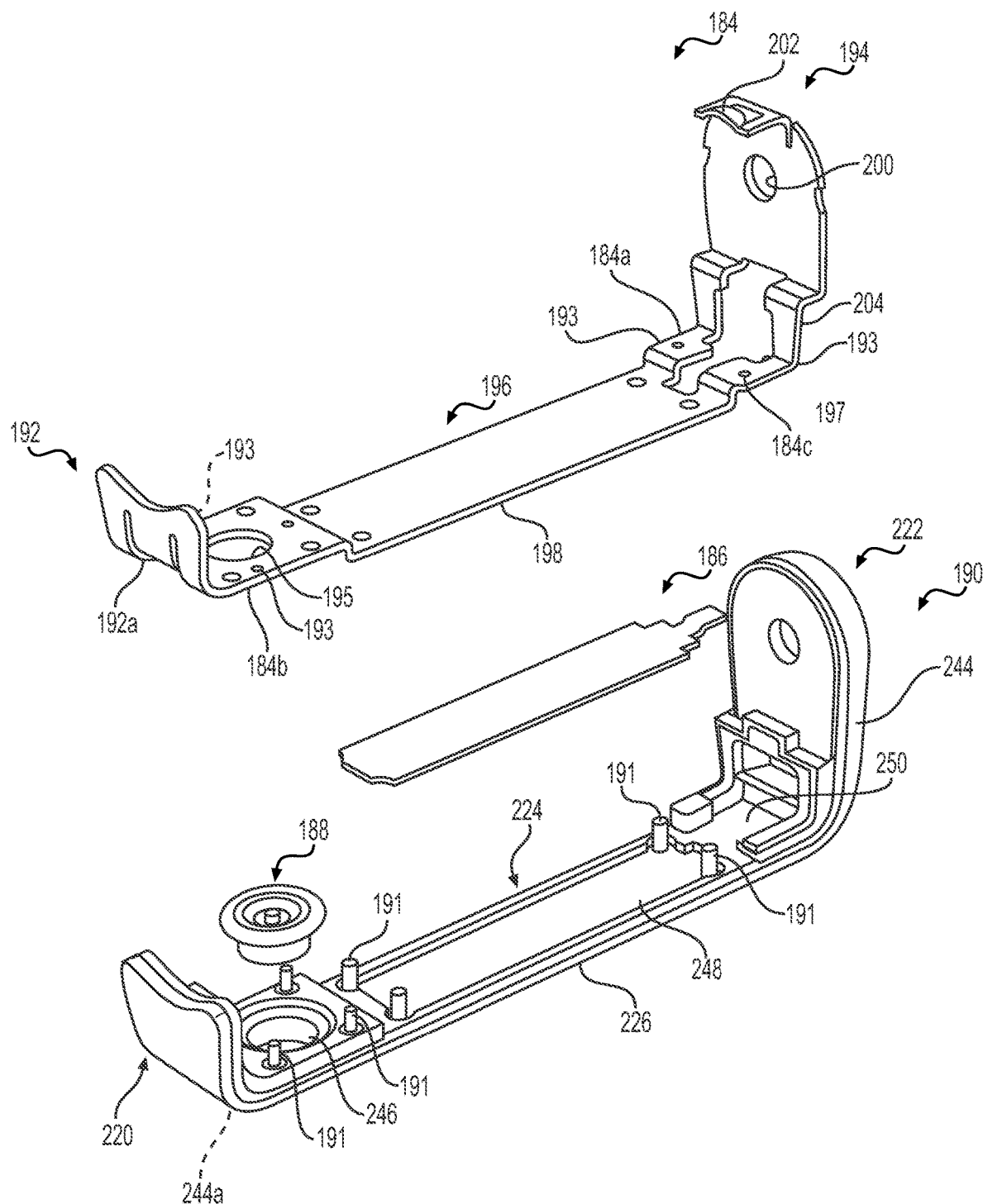
FIG. 6 is an exploded view of a housing component of a housing of the fluid infusion device of FIG. 1.

As discussed, the second housing portion 105 forms a cover subassembly and cooperates with the first housing portion 103 to enclose the fluid infusion device 100. With reference to FIG. 6, the second housing portion 105 is shown in greater detail. FIG. 6 is an exploded view of the second housing portion 105. The second housing portion 105 includes a frame 184, a second charging device or charging coil 186, a sealing member 188 and a cover 190. The frame 184 is composed of a metal or metal alloy, such as aluminum, stainless steel, titanium, and is stamped, cast, additive manufactured, etc. By forming the frame 184 of a metal or metal alloy, the frame 184 provides strength for the second housing portion 105. The frame 184 includes a first frame end 192 opposite a second frame end 194, and a first frame side 196 opposite a second frame side 198. The first frame end 192 is coupled to the cover 190, and assists in absorbing shocks and loads when the fluid infusion device 100 is mishandled, for example. As will be discussed, the first frame end 192 includes a tab 192a. The tab 192a projects into a recess defined along the first frame end 192 to enable the tab 192a to engage the cover 190. The tab 192a forms a mechanical interlock with the cover 190, which immobilizes the frame 184 on the cover 190. The second frame end 194 may be coupled to the cover 190, and may extend for a distance from the first frame side 196 that is greater than the first frame end 192. The second frame end 194 includes a bore 200, a lip 202 and a relief 204. As will be discussed, the bore 200 receives a force sensor nut 206 (FIG. 4) for coupling the force sensor 138 to the frame 184. The lip 202 cooperates with an undercut 208 (FIG. 5) on the first housing portion 103 to assist in coupling the first housing portion 103 to the second housing portion 105, as will also be discussed. The relief 204 enables the frame 184 to be positioned about the antenna 122. Generally, the frame 184 enables ease of manufacturing. In this regard, components can be assembled onto the frame 184 in a relatively open construct which allows easy access and limits compromise or damage of the user-facing outside surfaces with inadvertent nicks, scratches, etc. during manufacturing.

The first frame side 196 is positioned adjacent to the printed circuit board 114a (FIG. 5) and the second frame side 198 is positioned adjacent to the cover 190. In some examples, the frame 184 is coupled to the cover 190 via at least one or a plurality of heat stakes 191; however, any suitable technique may be employed to couple the frame 184 to the cover 190, such as adhesives, mechanical fasteners, etc. A bore 195 is defined through the first frame side 196 and the second frame side 198 to enable electrical communication between the user interface 104 and the printed circuit board 114a. A slit 184a is defined between the first frame side 196 and the second frame side 198 to enable electrical communication between the charging coil 186 and the printed circuit board 114a. The slit 184a is in communication with or adjacent to a slot 197 defined through first frame side 196 and the second frame side 198. The slot 197 receives the USB receptacle 120 (FIG. 5). The frame 184 may also include raised portions 184b, 184c, which cooperate with the cover 190. In some examples, the raised portion 184b interfaces with the cover 190 to accommodate the sealing member 188 and the user interface 104; and the raised portion 184c cooperates with the cover 190 to enable electrical communication between the charging coil 186 and the printed circuit board 114a. The frame 184 also includes a plurality of threaded bores 193, which receive a respective mechanical fastener, such as a screw, to couple the bracket 124 to the frame 184 (FIG. 4).

The charging coil 186 is positioned between the frame 184 and the cover 190. The charging coil 186 is electrically coupled to the printed circuit board 114a via the slit 184a defined in the frame 184, and the charging coil 186 is in communication with the control module 114. The charging coil 186 enables a user to wirelessly charge the fluid infusion device 100. The charging coil 186 may comprise any suitable charging coil that enables the charging of the power supply 112. The charging coil 186 is configured and oriented in such a way that it charges with the greatest efficiency, thereby reducing the time to charge. The orientation of the charging coil 186 within the frame 184 is such that the fluid infusion device 100 may be set down onto a charging pad for general charging, or may be set into a form-fitting wireless charging receptacle with predetermined positioning. This charging receptacle may, itself, be battery powered and can slip over the fluid infusion device 100 for charging while on the go such that the fluid infusion device 100 remains functional during charging.

The sealing member 188 surrounds the user interface 104 and forms a seal between the user interface 104 and the cover 190. In some examples, the sealing member 188 is composed of an elastomeric, semi-solid, or similarly compliant material, including, but not limited to silicone, ethylene propylene diene terpolymer (EPDM), Polytetrafluoroethylene (PTFE), synthetic or natural rubbers, or fluoropolymer. Alternatively, sealing may be accomplished by means of a material exhibiting or comprising a high surface tension in combination with a gap between components that in combination do not allow the ingress of water or dust up to the levels anticipated with the fluid infusion device 100, for example, about 8 to about 12 feet for water and dust, such as that associated with an IP58 rating. Generally, the sealing member 188 is clear, however, the sealing member 188 may have any desired color. In some examples, the sealing member 188 is overmolded around the user interface 104. With reference to FIG. 7, an end view of the second housing portion 105 is shown. As shown, the frame 184 is coupled to the cover 190 so as to sandwich the sealing member 188 and the charging coil 186 between the frame 184 and the cover 190. With reference to FIG. 8, a side view of the second housing portion 105 is shown. As shown in FIG. 8, the sealing member 188 includes a first member end 210 opposite a second member end 212 and a central bore 188a. The central bore 188a enables receipt of the user interface 104 and electrical connection to the printed circuit board 114a to place the user interface 104 in communication with the control module 114. The first member end 210 extends outwardly from the central bore 188a, and the first member end 210 is coupled to the frame 184 and the cover 190 such that the second member end 212 is movable or compressible relative to the first member end 210 to enable the user to depress the button 106. In this example, material is removed between the first member end 210 and the second member end 212 to define a gap 213 (FIG. 9) between the first member end 210 and the second member end 212, which enables the movement of the button 106 relative to the second housing portion 105 of the housing 102.

Figure 9:
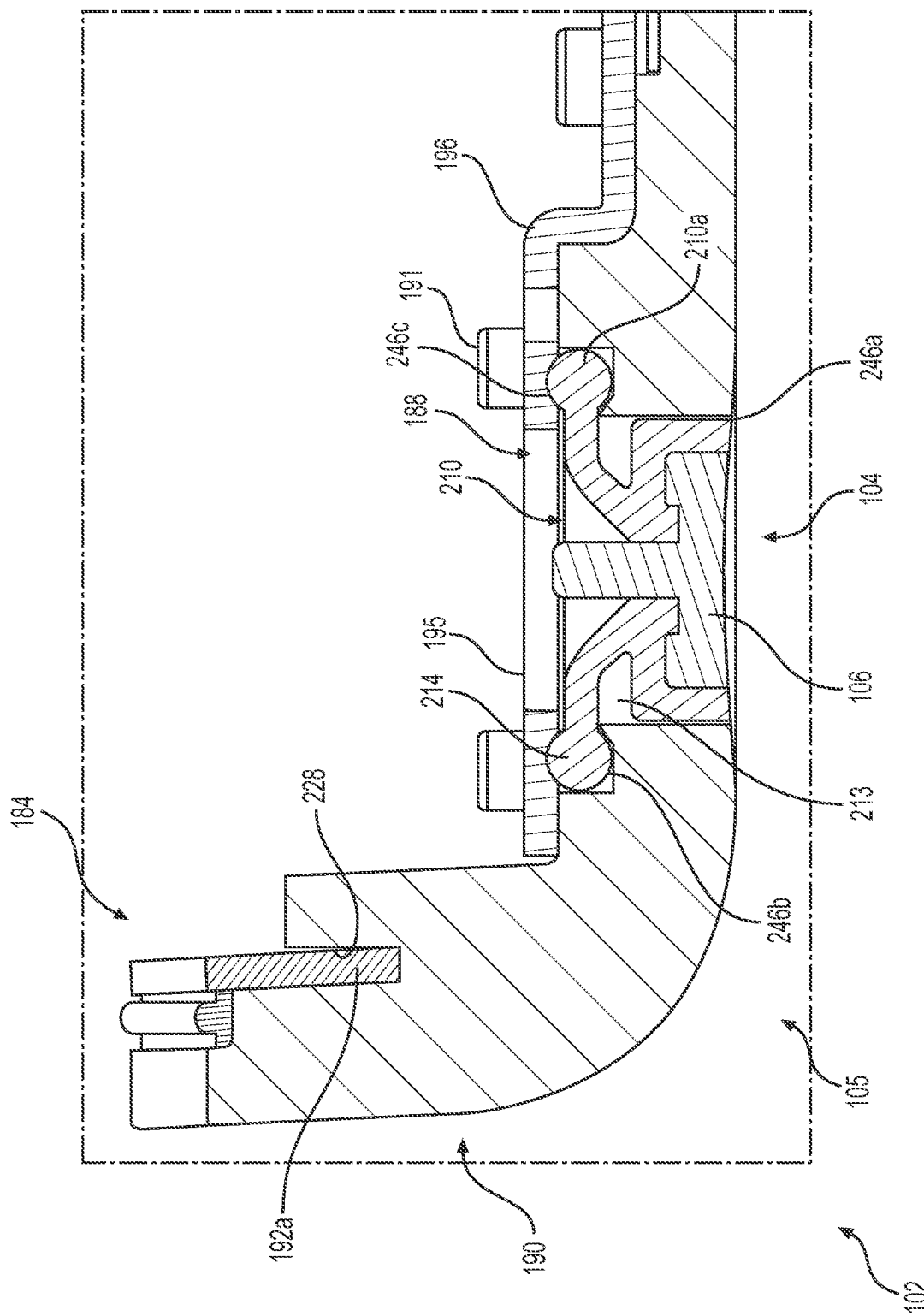
FIG. 9 is a detail view of the housing component of FIG. 8, taken at Section 9 of FIG. 8.

The second member end 212 is annular, and is sized to receive and surround the user interface 104. The first member end 210 includes an annular sealing flange 214, which extends outwardly from the central bore 188a. The annular sealing flange 214 may be bulbous at a terminal end 210a to assist in forming the seal between the frame 184 and the cover 190. With reference to FIG. 9, FIG. 9 is a detail view of FIG. 8. As shown in FIG. 9, the coupling of the frame 184 to the cover 190 compresses the sealing member 188 to form a hermetic seal between the housing 102 and the user interface 104. The hermetic seal inhibits the flow of fluids or other debris into the housing 102, which protects the internal components of the housing 102.

With reference back to FIG. 6, the cover 190 forms part of an exterior surface of the housing 102. The cover 190 is composed of a polymeric material, such as polycarbonate (PC), polybutylene succinate (PBS), acrylonitrile butadiene styrene (ABS), polypropylene (PP), nylon, polyethylene (PE), polyethylene terephthalate (PET, PETG), polyvinyl chloride (PVC), or blends thereof, and is molded, cast, additive manufactured, etc. By composing the cover 190 of a polymeric material, the cover 190 enables radio frequencies to pass through the housing 102 and also allows a magnetic field to pass through the housing 102. Alternatively, it should be noted that the first housing portion 103 and the cover 190 may be composed of the same metal or metal alloy, and are coupled together via welding, adhesives, etc. The cover 190 includes a first cover end 220 opposite a second cover end 222, and a first cover side 224 opposite a second cover side 226. The first cover end 220 is coupled to the first frame end 192. In some examples, with reference to FIG. 9, the first cover end 220 includes or defines a slot 228. The slot 228 receives the tab 192a of the frame 184 to mechanically couple the frame 184 to the cover 190.

Figure 10:
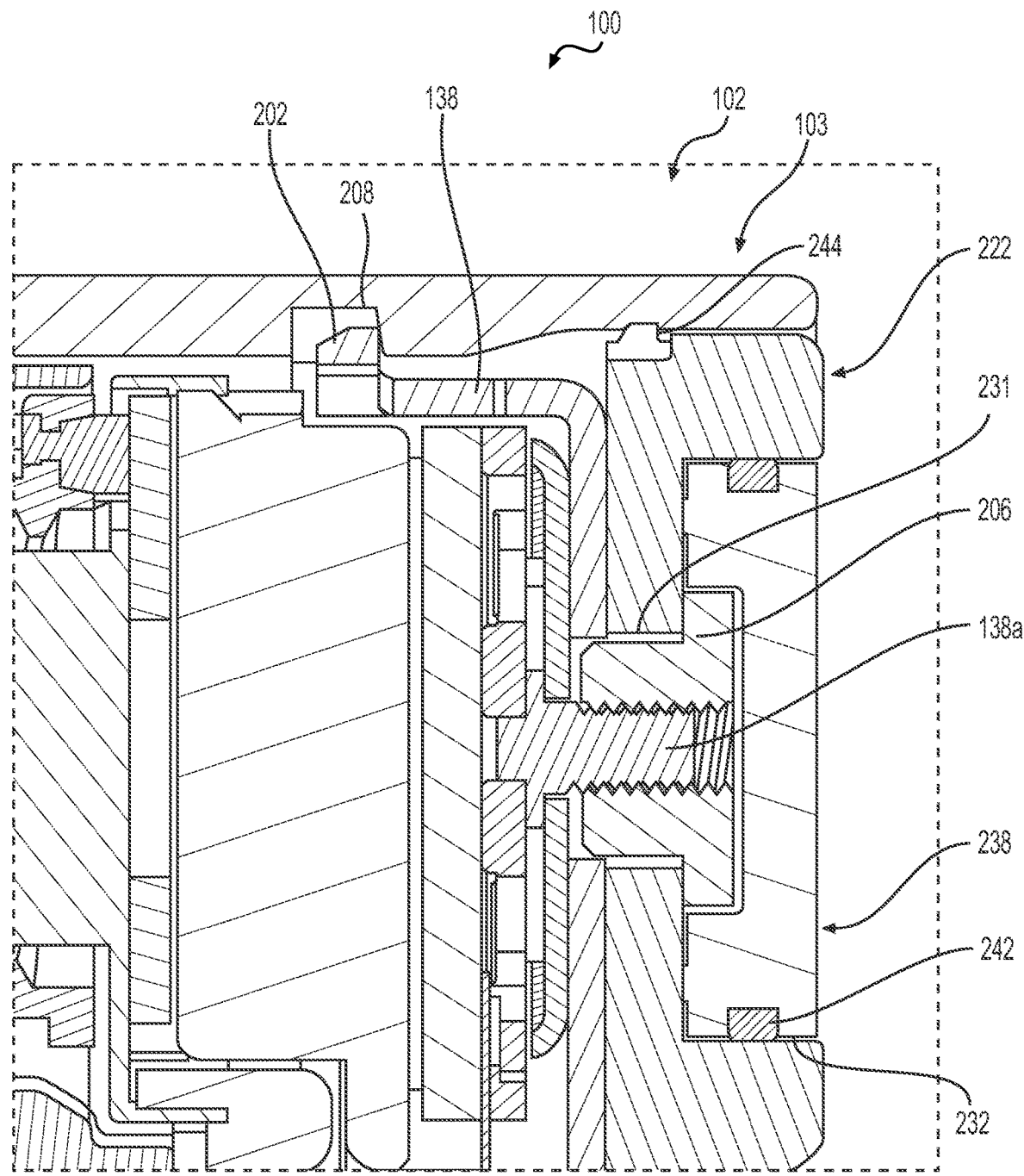
FIG. 10 is a detail view of the fluid infusion device of FIG. 1, taken at Section 10 of FIG. 3.

With reference to FIG. 8, the second cover end 222 includes or defines a first bore 230 and a second bore 232, which circumscribes the first bore 230. The second cover end 222 is also overmolded over the antenna 122. The first bore 230 is sized to receive the force sensor nut 206, and the second bore 232 is sized to receive an end plate 238. The first bore 230 generally has a diameter, which is different and smaller than the second bore 232. With reference to FIG. 10, a detail view of the second cover end 222 is shown. As shown, the force sensor nut 206 is received through the first bore 230 and the bore 200 of the frame 184 and is threadably coupled to the force sensor 138. In this example, the force sensor nut 206 is threaded onto a pin 138a of the force sensor 138. The threaded connection between the force sensor nut 206 and pin 138a of the force sensor 138 may eliminate any clearance at the interface between the force sensor 138 and the second housing portion 105 without introducing any preload on force sensor 138.

The end plate 238 is composed of a polymeric material, including, but not limited to polycarbonate (PC), polybutylene succinate (PBS), acrylonitrile butadiene styrene (ABS), polypropylene (PP), nylon, polyethylene (PE), polyethylene terephthalate (PET, PETG), polyvinyl chloride (PVC), or blends thereof. The end plate 238 is coupled to the force sensor nut 206 to inhibit the force sensor nut 206 from backing out during the use of the fluid infusion device 100. The end plate 238 is circular, however, the end plate 238 may have any desired shape. In some examples, with reference to FIG. 4, the end plate 238 includes an inner bore 240 and a plate sealing member 242. The inner bore 240 defines a shape about a circumference of the inner bore 240 that corresponds with a shape of a perimeter or circumference of the force sensor nut 206. In this example, the inner bore 240 defines a hexagonal shape, which corresponds with a hexagonal head 206a of the force sensor nut 206. By providing the inner bore 240 with a shape that matches a shape of the head 206a of the force sensor nut 206, relative rotation between the force sensor nut 206 and the end plate 238 is inhibited. The plate sealing member 242 may be composed of a polymeric material, such as an elastomeric material, which is overmolded about an outer perimeter or circumference of the end plate 238. The plate sealing member 242 provides a hermetic seal between the force sensor nut 206 and the cover 190.

With reference back to FIG. 6, the cover 190 may also include a sealing member 244, which extends about a perimeter of the cover 190. The sealing member 244 may contact the first housing portion 103 and may form a seal between the first housing portion 103 and the second housing portion 105. The sealing member 244 may be composed of a suitable polymeric material, such as an elastomeric material, which may be overmolded on the cover 190 or coupled to the cover 190 via ultrasonic welding, adhesives, press-fit into a groove 244a defined about the perimeter of the cover 190, etc.

With reference back to FIG. 6, the first cover side 224 defines a user interface receptacle 246, a charging coil slot 248 and a port receptacle 250. The user interface receptacle 246 includes a bore 246a (FIG. 9), which is defined through the cover 190 from the first cover side 224 to the second cover side 226. The user interface receptacle 246 includes a circumferential recess 246b, which is defined about the bore 246a. With reference to FIG. 9, the circumferential recess 246b receives the annular sealing flange 214 of the sealing member 188. In this example, the circumferential recess 246b is defined so as to be spaced apart from the bore 246a to form a lip 246c about a perimeter of the bore 246a. The lip 246c assists in assembly of the sealing member 188 to the cover 190.

With reference back to FIG. 6, the charging coil slot 248 is recessed within the first cover side 224 and is sized to receive the charging coil 186. The port receptacle 250 is defined between adjacent sidewalls 224a of the first cover side 224, and is sized to receive and support the USB receptacle 120 (FIG. 5) within the cover 190. The second cover side 226 is generally smooth, as shown in FIG. 3.

With continued reference to FIG. 3, in some examples, with the slide 136, the drive screw 134, the gear box 132 and the motor 130 formed, the motor 130 is coupled to the gear box 132 and the drive screw 134 is coupled to the gear box 132. The slide 136 is positioned over the drive screw 134 and the threads 134a of the drive screw 134 threadably engage the threads 140a of the slide 136. With the first housing portion 103 of the housing 102 formed, the sealing member 162 is positioned in the first housing portion 103 and the assembled drive system 110 is coupled to the first housing portion 103 of the housing 102. The force sensor 138 is positioned within the first housing portion 103 and electrically connected to the printed circuit board 114a to be in communication with the control module 114. With reference to FIG. 6, with the cover 190 formed, the charging coil 186 is coupled to the cover 190. The sealing member 188 is overmolded onto the user interface 104, and the sealing member 188, with the user interface 104, is positioned within the user interface receptacle 246. The frame 184 is coupled to the cover 190 such that the tab 192a engages the slot 228 and the frame 184 compresses the terminal end 210a of the sealing member 188. The frame 184 is then coupled to the cover 190 via one or more heat stakes 191, for example.

With reference to FIG. 4, with the control module 114 and the USB receptacle 120 coupled to and in communication with the printed circuit board 114a, the printed circuit board 114a is coupled to the second housing portion 105. The user interface 104 and the charging coil 186 are electrically coupled to the printed circuit board 114a and placed in communication with the control module 114. The bracket 124 is positioned over the printed circuit board 114a and coupled to the frame 184 via one or more mechanical fasteners received in the bores 193, for example. The power supply 112 is positioned on the bracket 124 and electrically coupled to the printed circuit board 114a to be in communication with the control module 114. The vibration motor 126 is coupled to the bracket 124, and the vibration motor 126 is electrically coupled to the printed circuit board 114a to be in communication with the control module 114. The second housing portion 105 is coupled to the first housing portion 103.

In some examples, with reference to FIG. 10, the second housing portion 105 of the housing 102 is positioned such that the lip 202 of the frame 184 engages with the undercut 208 of the first housing portion 103. The contact between the lip 202 and the undercut 208 forms a snap-fit. As the engagement between the lip 202 and the undercut 208 is spring loaded, the lip 202 maintains contact with the undercut 208 of the first housing portion 103 to couple the second housing portion 105 with the first housing portion 103. Generally, the undercut 208 is defined such that an angle on the surface of the undercut 208 is smaller than a friction angle between the lip 202 and the first housing portion 103. The lip 202 and the undercut 208 cooperate to eliminate clearance between the first housing portion 103 and the second housing portion 105 during assembly. With the second housing portion 105 coupled to the first housing portion 103, the force sensor nut 206 is coupled to the pin 138a of the force sensor 138. The end plate 238 is coupled to the force sensor nut 206 to surround the force sensor nut 206 and is received within the second bore 232 of the cover 190.

With the fluid infusion device 100 assembled, the fluid infusion device 100 may be packaged and shipped to an end user. Once received, the end user may remove the packaging and with reference to FIG. 5, the user may couple the fluid reservoir 160 to the housing 102 by positioning the fluid reservoir 160 within the opening 115 defined in the housing 102. Generally, the fluid reservoir 160 is prefilled with fluid, in this example, insulin, such that the stopper 166 is positioned at the distal barrel end 168. The connector 302 is coupled to the fluid reservoir 160 prior to insertion of the fluid reservoir 160 into the housing 102 for ease of handling by the user. With the infusion set assembly 300 fixedly coupled or secured to the housing 102, the needle 304 pierces the septum, thereby defining a fluid flow path for the fluid out of the fluid reservoir 160. With the infusion set assembly 300 coupled to the fluid reservoir 160 and the infusion unit 308 coupled to the anatomy of the user, one or more control signals from the control module 114 can drive the motor 130, thereby rotating the drive screw 134, which results in the linear translation of the slide 136. The advancement of the slide 136 into the fluid reservoir 160 moves the stopper 166, causing the fluid to flow from the fluid reservoir 160 through the fluid flow path defined by the infusion set assembly 300.

It should be noted that the fluid infusion device 100 may also be configured to draw fluid, such as insulin, from a vial into the fluid reservoir 160 autonomously instead of from pre-filled fluid reservoirs 160. It should be noted that the shape of the fluid reservoir 160 for use with the fluid infusion device 100 allows for a very even seal pressure within the fluid reservoir 160, thereby reducing leaks in the fluid reservoir system 116. The cylindrical shape of the fluid reservoir 160 is also easier to manufacture at high volumes for a reduced cost due to the inherent symmetry in the design.

In addition, the fluid infusion device 100 may include accelerometers in communication with the control module 114 to track movement of the fluid infusion device 100 to measure and confirm gestures for functions of the fluid infusion device 100. For example, a particular movement of the fluid infusion device 100 may be observed/measured by the accelerometer, and the control module 114 may output one or more control signals to trigger pairing, quick bolus, confirm bolus, query pump status, etc. based on a detected movement with notifications output to the user via one or more control signals to the vibration motor 126. In addition, the fluid infusion device 100 may include a sensor that detects a presence of a magnetic field, which is in communication with the control module 114, and the control module 114 may determine whether an infusion set is coupled to the fluid infusion device 100 based on the sensor signals from the sensor. The fluid infusion device 100 may also include other communication devices to enable the fluid infusion device 100 to communicate with infusion sets or other devices to enable the fluid infusion device 100 to automate priming, fill tubing and fill a cannula based on received communications and sensor signals from the force sensor 138. For example, the fluid infusion device 100 may include a magnetic field sensor in communication with the control module 114, which observes a magnetic field generated by a magnet coupled to the infusion set assembly 300, such as the connector 302, to determine the type of infusion set assembly 300 coupled to the fluid infusion device 100. For example, an infusion set assembly may include a tube 306 that is longer or shorter than another infusion set assembly, and the control module 114 may process the signals from the magnetic field sensor and determine which infusion set assembly (long tube, short tube) is coupled to the fluid infusion device 100.

Figure 12:
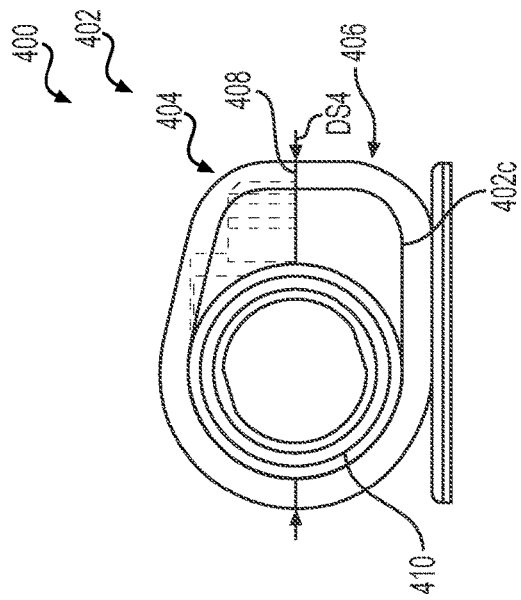
FIG. 12 is an end view of the fluid infusion device of FIG. 11.

It should be noted that configurations of, the fluid infusion device 100 may vary from implementation to implementation. For example, with reference to FIG. 11, a portable fluid infusion device 400 is shown. As the fluid infusion device 400 includes the same or similar components as the fluid infusion device 100 discussed with regard to FIGS. 1-10, the same reference numerals will be used to denote the same or similar components. FIG. 11 is a perspective view of the fluid infusion device 400, and FIG. 12 is an end view. The fluid infusion device 400 may be used with the infusion set assembly 300 or other devices, as will be discussed in further detail below.

In the examples of FIGS. 11 and 12, the fluid infusion device 400 includes a housing 402. Generally, the housing 402 has a small form factor for portability, and is about 10 millimeters (mm.) to about 20 millimeters (mm.) thick, about 20 millimeters (mm.) to about 30 millimeters (mm.) wide and is about 75 millimeters (mm.) to about 85 millimeters (mm.) long. Thus, the housing 402 has a largest dimension DL4 (FIG. 11) and a smallest dimension DS4 (FIG. 12). In some examples, the housing 402 includes a first housing portion 404 and a second housing portion 406, which are coupled together to form the housing 402. The first housing portion 404 and the second housing portion 406 are each composed of a polymeric material, including, but not limited to polycarbonate, and may be molded, additively manufactured, etc. Generally, with reference to the example of FIG. 13, the first housing portion 404 and the second housing portion 406 cooperate to enclose a power supply 420, a controller or control module 422, the drive system 110 and the fluid reservoir system 116. In this example, the fluid infusion device 400 is devoid of a user interface.

In some examples, with reference back to FIGS. 11 and 12, the first housing portion 404 and the second housing portion 406 are coupled together in a manner that forms a seal at an interface 408 between the first housing portion 404 and the second housing portion 406. In these examples, the first housing portion 404 and the second housing portion 406 are coupled together via welding, including, but not limited to laser welding, ultrasonic welding, radiofrequency welding, etc. In certain embodiments, the first housing portion 404 and the second housing portion 406 may each have alignment features defined along the interface 408, which assist in coupling the first housing portion 404 to the second housing portion 406. For example, one of the first housing portion 404 and the second housing portion 406 may include male posts at the interface, and the other of the first housing portion 404 and the second housing portion 406 may include corresponding female posts so that the first housing portion 404 and the second housing portion 406 are aligned prior to welding.

In certain instances, such as in the instance of coupling the first housing portion 404 and the second housing portion 406 together via laser welding, the second housing portion 406 is made of transparent polymeric material, while the first housing portion 404 is made of opaque polymeric material (or vice versa). This allows the laser beam to pass through the transparent polymeric material and heat up the opaque polymeric material at the interface 408 with the transparent polymeric material, and thus, melt/weld the two materials together at the interface 408. Additionally, or alternatively, the first housing portion 404 and the second housing portion 406 may be coupled together via an adhesive applied at the interface 408. Additionally, or alternatively, the first housing portion 404 and the second housing portion 406 may be coupled together via a snap fit, with snap fit engagement features defined along the interface 408. Additionally, or alternatively, the first housing portion 404 and the second housing portion 406 may be coupled together via one or more mechanical fasteners, such as screws. As will be discussed, in some examples, the second housing portion 406 defines a coupling slot 414, which enables the fluid infusion device 400 to be coupled to an anatomy.

Figures 14, 15:
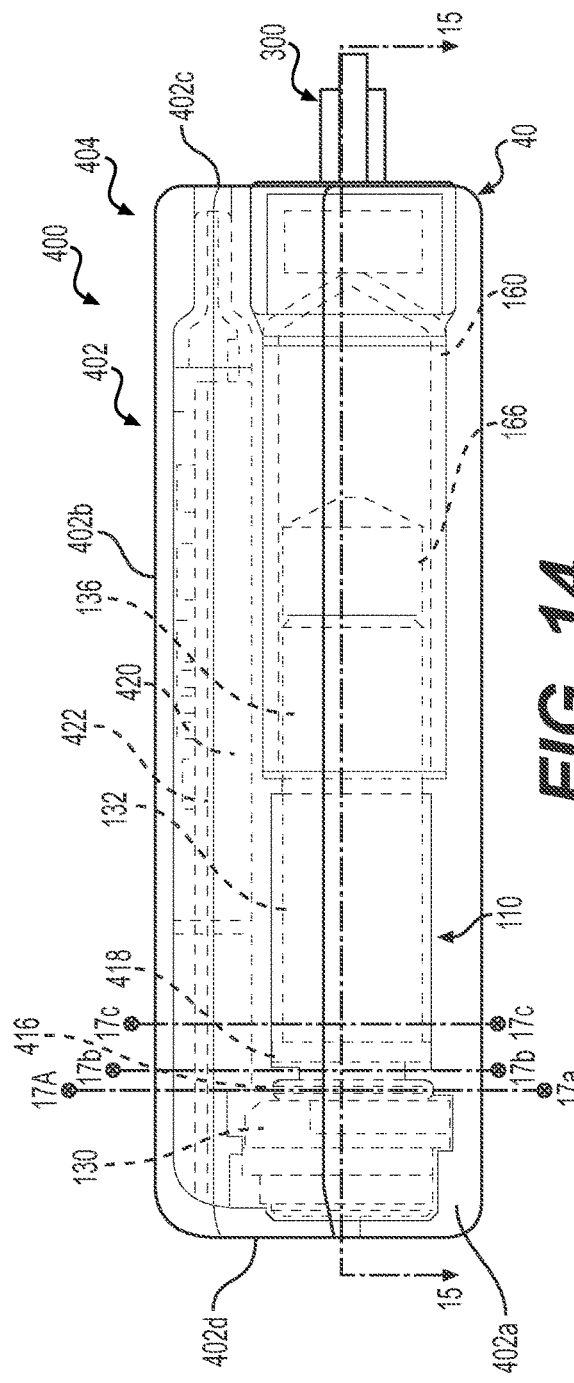
FIG. 14 is a top view of the fluid infusion device of FIG. 11.
FIG. 15 is a cross-sectional view of the fluid infusion device of FIG. 11, taken along line 15-15 of FIG. 14.

The housing 402, when assembled, includes opposed sides 402a, 402b, and opposed ends 402c, 402d. Generally, the end 402c defines an opening 410 to receive the fluid reservoir 160. Generally, the power supply 420, the control module 422 and the drive system 110 are accommodated in a pump chamber 412a defined by the housing 402, and the fluid reservoir system 116 is accommodated in a reservoir chamber 412b defined by the housing 402. With reference to FIG. 14, a top view of the fluid infusion device 400 is shown. With reference to FIG. 15, in order to provide waterproofing or to inhibit fluids from flowing from the reservoir chamber 412b to the pump chamber 412a, a sealing member 416 may be situated between the pump chamber 412a and the reservoir chamber 412b. The sealing member 416, in some examples, is an O-ring, which is composed of an elastomeric material, including, but not limited to rubber, nitrile, silicone, polyurethane, synthetic or natural rubbers, etc. The sealing member 416 is positioned about the motor 130. By positioning the sealing member 416 about the motor 130, a fluid path from an external environment is blocked by the sealing member 416, which inhibits fluid from reaching the pump chamber 412a including the components contained in the pump chamber 412a, such as the control module 422, power supply 420, etc.

Figure 16:
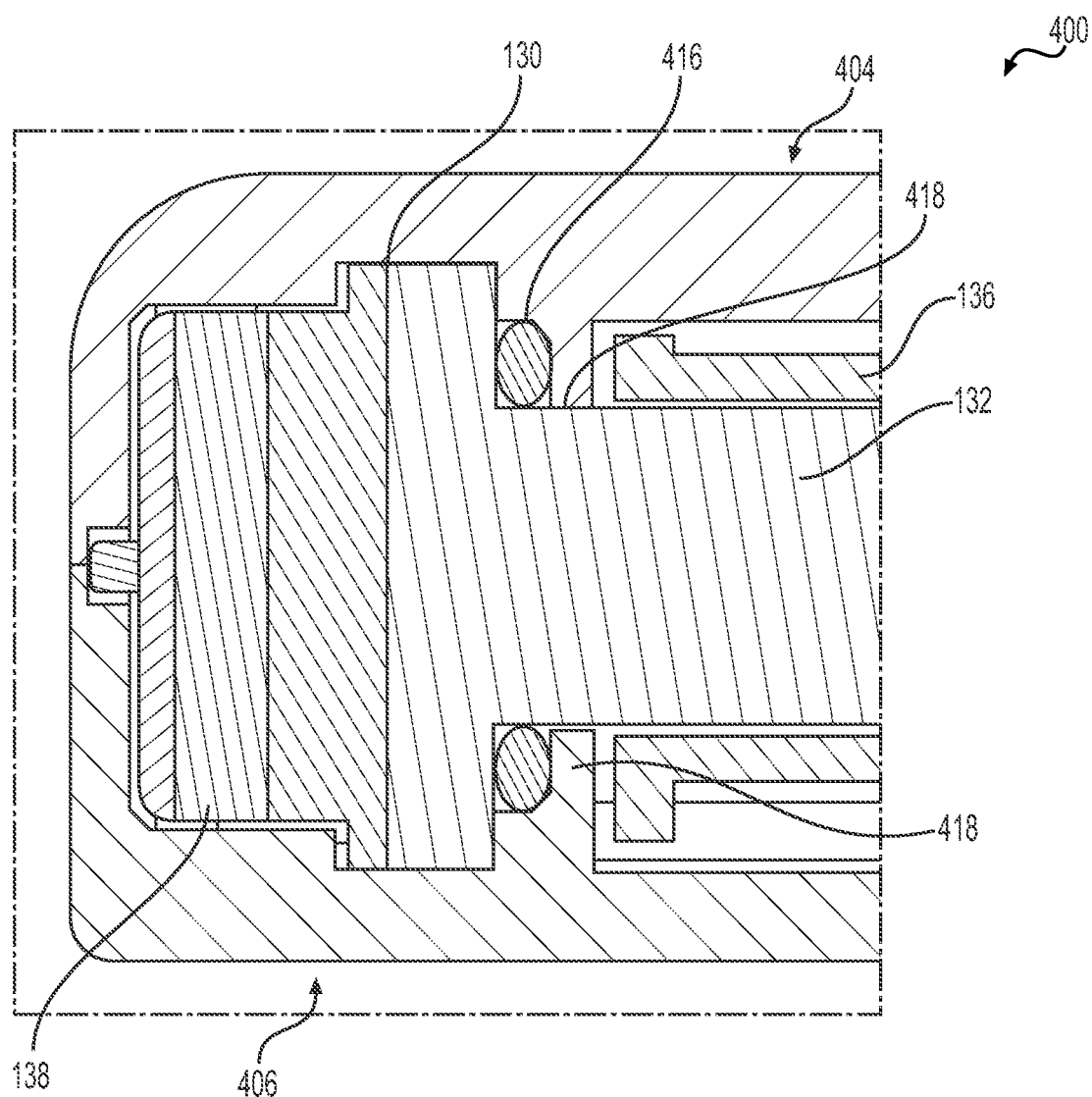
FIG. 16 is a detail cross-sectional view, taken at Section 16 of FIG. 15.

Generally, with reference to FIG. 16, the sealing member 416 is compressed by the first housing portion 404 on one side and by the second housing portion 406 on the other side. With reference to FIG. 17A, this causes the sealing member 416, which is elastic, to expand outward and fill an area defined between the first housing portion 404 and the second housing portion 406. As the interface 408 between the first housing portion 404 and the second housing portion 406 is welded, the sealing member 416 inhibits fluid from the external environment from entering the pump chamber 412a, thereby waterproofing the fluid infusion device 400. The first housing portion 404 and the second housing portion 406 each include an internal flange 418 (FIGS. 16 and 17B), which extends outward from the respective one of the first housing portion 404 and the second housing portion 406. The flange 418 ensures that the sealing member 416 is retained adjacent to the motor 130 when compressed by the first housing portion 404 and the second housing portion 406, as shown in FIG. 17B. With reference to FIG. 17C, the slide 136 also cooperates with the first housing portion 404 and the second housing portion 406 to inhibit a flow of fluid toward the sealing member 416.

With reference back to FIG. 13, the power supply 420 is any suitable device for supplying the fluid infusion device 400 with power, including, but not limited to, a battery. In some examples, the power supply 420 is a rechargeable battery, which is fixed within the housing 402 (FIG. 14). In some embodiments, the power supply 420 is rechargeable via wireless charging, etc. The power supply 420 is a planar battery configured to supply power to the fluid infusion device 400 that has a plurality of faces comprising one or more faces 420a having a largest area, and the planar battery is situated such that the one or more faces 420*a*, 420*b* are parallel to the largest dimension Dl4 of the housing 402 (face 420*a*) and the smallest dimension Ds4 (face 420*b*) (FIG. 11). The one or more faces 420*b* may have the smallest area. The power supply 420 may comprise a planar rectangular battery or a planar cylindrical battery. In some embodiments, the power supply 420 is chargeable for at least a 7-day use. It should be noted that in some embodiments, the fluid infusion device 400 may also include a buck boost converter to boost the voltage of the power supply 420 supplied to the control module 422.

The control module 422 may be in communication with the power supply 420 and drive system 110. As depicted in FIG. 18, the control module 422 may be in communication with a charging coil 424 to supply power to the power supply 420. The control module 422 may control the operation of the fluid infusion device 400 based on patient specific operating parameters. In some embodiments, the control module 422 may control the supply of power from the power supply 420 to the drive system 110 to activate the drive system 110 to dispense fluid from the fluid reservoir system 116. Further detail regarding the control of the fluid infusion device 400 can be found in U.S. Pat. Nos. 6,485,465 and 7,621,893, the relevant content of which was previously incorporated herein by reference.

Briefly, the control module 422 may include at least one processor and a computer readable storage device or media, which are mounted to a printed circuit board 422*a*. In some embodiments, the printed circuit board 422*a* is a rigid printed circuit board that enables communication between the power supply 420, drive system 110, the charging coil 424, 424', the other components associated with the fluid infusion device 400 and the control module 422. The processor can be any custom made or commercially available processor, a central processing unit (CPU), an auxiliary processor among several processors associated with the control module 422, a semiconductor based microprocessor (in the form of a microchip or chip set), a macroprocessor, any combination thereof, or generally any device for executing instructions. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electrical, magnetic, and/or optical memory devices capable of storing data, some of which represent executable instructions, used by the control module 422 in controlling components associated with the fluid infusion device 400.

The instructions may include one or more separate programs, each of which comprises an ordered listing of executable instructions for implementing logical functions. The instructions, when executed by the processor, receive and process input signals, perform logic, calculations, methods and/or algorithms for controlling the components of the fluid infusion device 400, and generate signals to components of the fluid infusion device 400 to control the drive system 110 based on the logic, calculations, methods, and/or algorithms. Although only one control module 422 is shown, embodiments of the fluid infusion device 400 can include any number of control modules that communicate over any suitable communication medium or a combination of communication mediums and that cooperate to process signals received from the portable electronic device, perform logic, calculations, methods, and/or algorithms, and generate control signals to control features of the fluid infusion device 400. In various embodiments, one or more instructions of the control module 422, when executed by the processor, receive and process signals from the portable electronic device associated with a user to generate one or more control signals to the power supply 420 to supply power to the drive system 110, for example.

With reference to the example of FIG. 18, the charging coil 424 comprises a plurality of concentric signal trace coils 424*a* embedded in two layers on a flexible printed circuit board 425. The flexible printed circuit board 425 is electrically and physically coupled to the printed circuit board 422*a* to enable communication between the charging coil 424 and the control module 422. In this example, the use of the flexible printed circuit board 425 allows the charging coil 424 to be contained within the housing 402 (FIG. 13) without taking up space on the printed circuit board 422*a*, and enables the charging coil 424 to be placed within the housing 402 wherever it is mechanically feasible. The charging coil 424 enables the ability for a user to wirelessly charge the fluid infusion device 400 via inductive charging. In some examples, magnetic coupling between a wireless charging dongle 434 and the fluid infusion device 400 is provided via a magnet positioned within the wireless charging dongle 434 of FIG. 20B, which is magnetically attracted to a ferrous material that is placed inside the fluid infusion device 400. Alternatively, the flexible printed circuit board 425 may include a coupler 428. In some examples, the coupler 428 is a disk composed of a ferrous material, which acts as a magnetic shield while improving magnetic coupling between the fluid infusion device 400 and a remote charging source, such as the wireless charging dongle 434 and/or charging mat 432. It should be noted that the coupler 428 may have any desired size and shape. In this example, the coupler 428 is coupled to the backside of the flexible printed circuit board 425.

It should be noted, however, that various other configurations of the charging coil 424 relative to the printed circuit board 422*a* are also contemplated. For example, FIG. 19 depicts a charging coil 424'. The charging coil 424' comprises a plurality of concentric signal trace coils 424*a'* embedded on the printed circuit board 422*a*. The trace coils 424*a'* are electrically and physically coupled to the printed circuit board 422*a* to enable communication between the charging coil 424' and the control module 422. The charging coil 424' also enables the ability for a user to wirelessly charge the fluid infusion device 400. In some examples, the printed circuit board 422*a* for use with the charging coil 424' may also include the coupler 428, which may be coupled to the backside of the printed circuit board 422*a*. Alternatively, the charging coil 424 may be formed on a separate circuit board, and communicatively coupled to the printed circuit board 422*a*.

Figure 20A:
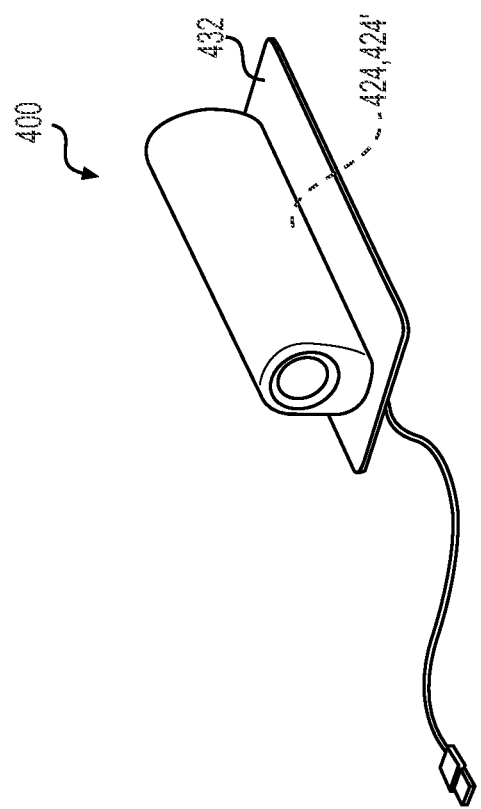
FIG. 20A is an environmental view of a charging mat for use with a charging coil to charge a power supply associated with a fluid infusion device.

With reference to the example of FIG. 20A, an exemplary method for charging the fluid infusion device 400 utilizing the charging coil 424 or charging coil 424' is shown. In this example, the fluid infusion device 400 is positioned upon a charging mat 432, and the charging mat 432 cooperates with the charging coil 424, 424' to charge the fluid infusion device 400 wirelessly via induction. The charging mat 432 may comprise any suitable charging mat capable of inductively charging the fluid infusion device 400, and may be connected to a power source via a USB connection, for example. Generally, charging mat 432 may include an induction coil, which cooperates with the charging coil 424, 424' (that acts as a receiver coil) to charge the fluid infusion device 400.

Figure 20B:
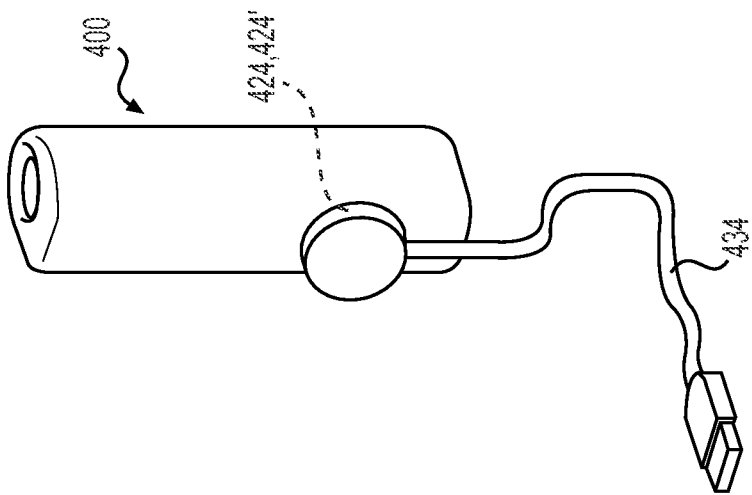
FIG. 20B is an environmental view of a charging dongle for use with a charging coil to charge a power supply associated with a fluid infusion device.

Alternatively, with reference to the example of FIG. 20B, another exemplary method for charging the fluid infusion device 400 utilizing the charging coil 424 or charging coil 424' is shown. In this example, the wireless charging dongle 434 is coupled to the fluid infusion device 400, and the wireless charging dongle 434 cooperates with the charging coil 424, 424' to charge the fluid infusion device 400 wirelessly via induction. In one example, the wireless charging dongle 434 is coupled to the fluid infusion device 400 magnetically, via the magnet contained within the wireless charging dongle 434 and the coupler 428. The wireless charging dongle 434 may comprise any suitable charging dongle capable of inductively charging the fluid infusion device 400, and may be connected to a power source via a USB connection, for example. The wireless charging dongle 434 may include an induction coil, which cooperates with the charging coil 424, 424' (that acts as a receiver coil) to charge the fluid infusion device 400. The use of the wireless charging dongle 434 allows the fluid infusion device 400 to be charged either while worn on the body or when carried in a pocket. The coupling of the wireless charging dongle 434 to the fluid infusion device 400 is permissible through clothing, which allows the fluid infusion device 400 to be charged without being taken off or disconnected from the user. Also, if the user forgets he/she is charging the fluid infusion device 400 and walks away from the wireless charging dongle 434, the wireless charging dongle 434 harmlessly detaches from the fluid infusion device 400. In this regard, the magnetic coupling of the wireless charging dongle 434 and the fluid infusion device 400 enables the wireless charging dongle 434 to be attached to the user through clothing, while also enabling the inductive charging of the fluid infusion device 400. It should be noted in other implementations, the wireless charging dongle 434 may not include a magnet for magnetically coupling to the fluid infusion device 400, and may be positioned onto or in proximity to the fluid infusion device 400 to perform the inductive charging. In other implementations, the fluid infusion device 400 may also send a notification to a remote portable device associated with the user based on the alignment of the wireless charging dongle 434 relative to the fluid infusion device 400 to instruct the user to modify the alignment to improve charging. It should be noted that the shape and configuration of the wireless charging dongle 434 in FIG. 20B is merely exemplary, as the wireless charging dongle 434 may have any desired size or shape that facilitates the inductive charging of the fluid infusion device 400. It should be understood that the methods depicted in FIGS. 20A, 20B are shown independently, the charging coils 424, 424' are capable of wirelessly charging the fluid infusion device 400 using either one of the charging mat 432 or wireless charging dongle 434, and thus, the fluid infusion device 400 may be packaged for a consumer with the charging mat 432, the wireless charging dongle 434 or both the charging mat 432 and the wireless charging dongle 434, if desired.

Figure 20C:
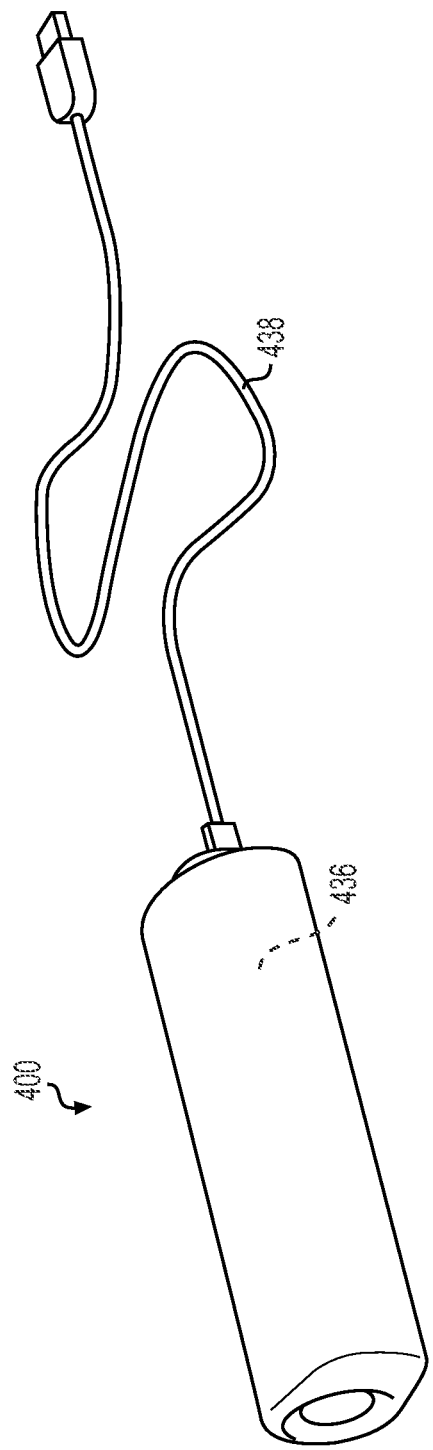
FIG. 20C is an environmental view of a charging cable that is used to charge a power supply associated with a fluid infusion device.

Alternatively, with reference to FIG. 20C, the power supply 420 may also be rechargeable via USB charging. In the example of USB charging, the housing 402 may define a micro-USB port to enable an electrical connection between a USB cable 438 and a micro-USB receptacle 436 electrically coupled to and in communication with the control module 422 of the fluid infusion device 400 and a remote charging source. The control module 422 is in communication with the USB receptacle 436 to supply power received to the power supply 420.

In certain instances, the control module 422 is in communication with an antenna 426. In some examples, the antenna 426 is an RF transceiver, which is electrically and physically coupled to the printed circuit board 422a of the control module 422. It should be noted, however, that the antenna 426 may comprise any suitable antenna 426 that enables bi-directional communication between the fluid infusion device 400 and another portable electronic device of the user. Thus, generally, the antenna 426 enables wireless communication between the fluid infusion device 400 and another device, including, but not limited to, an infusion pump, continuous glucose monitor, infusion monitor unit, portable electronic device (tablet, smart phone, etc.) and/or another monitoring device. In some examples, the antenna 426 may include, but is not limited to, a near-field communication (NFC) antenna, a radio frequency (RF) communication antenna, a far-field communication antenna, a wireless communication system configured to communicate via a wireless local area network (WLAN) using Institute of Electrical and Electronics Engineers (IEEE) 802.11 standards or by using cellular data communication, a BLUETOOTH antenna, etc. In certain embodiments, the antenna 426 of the fluid infusion device 400 may include more than one communication device, such as an NFC transceiver and a BLUETOOTH low energy (BLE) antenna.

In some examples, the fluid infusion device 400 includes an NFC transceiver and a BLUETOOTH low energy (BLE) antenna. In the example, with reference to FIG. 21, the fluid infusion device 400 is capable of communicating with one or more remote portable electronic devices, including, but not limited to, a portable electronic device such as a smartphone 440 and a continuous glucose monitor 442. It should be noted that the smartphone 440 and the continuous glucose monitor 442 are merely examples, as the fluid infusion device 400 may communicate wirelessly with any suitable user device, such as a computer, smart watch, tablet, infusion monitor unit as discussed herein, etc. In some examples, the fluid infusion device 400, the smartphone 440 and the continuous glucose monitor 442 are part of a mesh network, which enables communication between any two devices of the fluid infusion device 400, the smartphone 440 and the continuous glucose monitor 442. In some other examples, the fluid infusion device 400, the smartphone 440 and the continuous glucose monitor 442 are part of a star network. In such examples, the fluid infusion device 400 is the center of the star network such that the continuous glucose monitor 442 and the smartphone 440 never directly communicate. Rather, information from the continuous glucose monitor 442 must travel through the fluid infusion device 400 to reach the smartphone 440 and vice versa.

Figure 21:
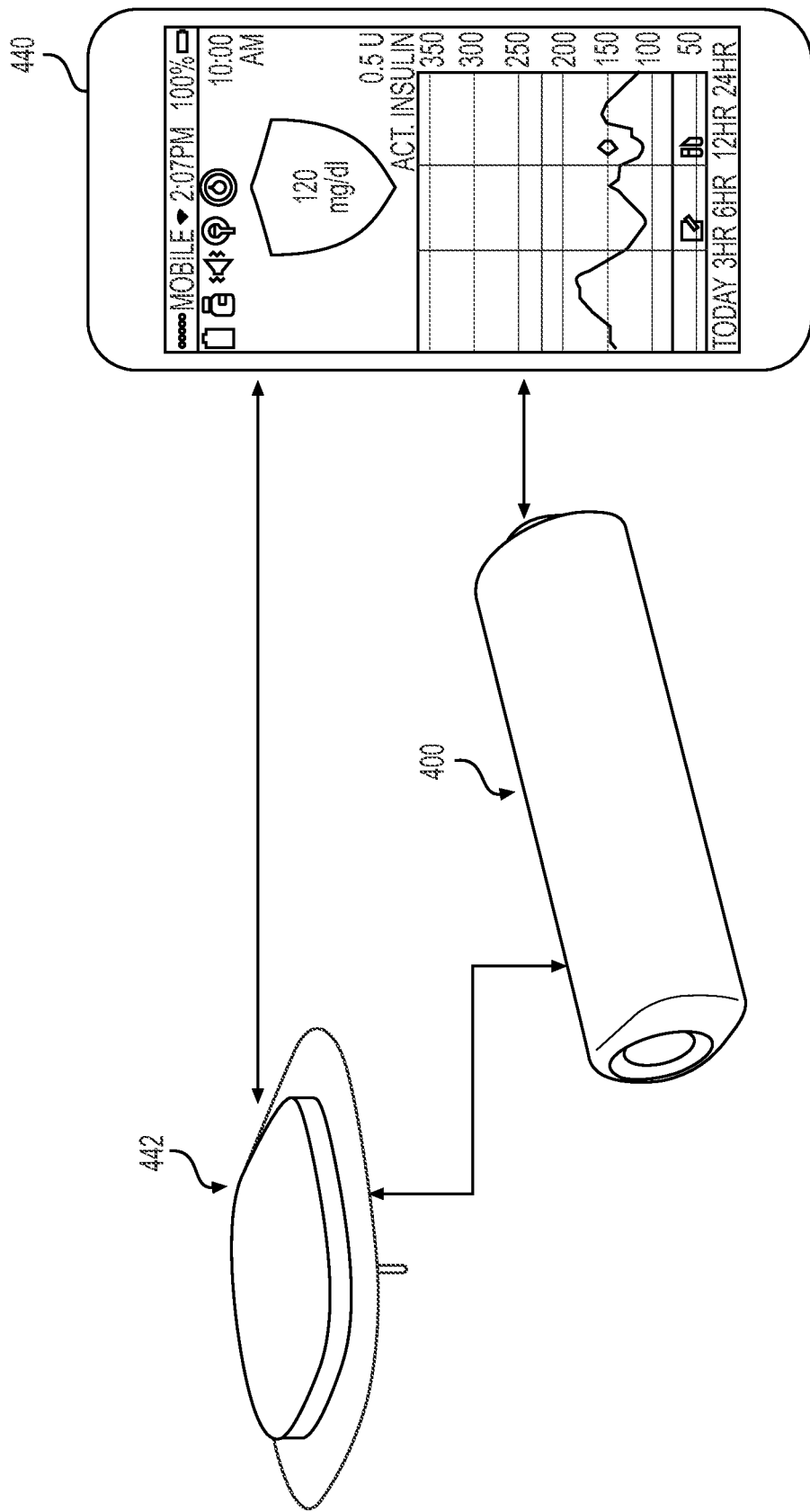
FIG. 21 is a schematic illustration of a communication network associated with a fluid infusion device.

In the example of FIG. 21, the fluid infusion device 400 does not include a user interface, and the smartphone 440 is used to interface with the fluid infusion device 400. Thus, data associated with the fluid infusion device 400 is displayed to the user via the smartphone 440, not on the fluid infusion device 400. In addition, the user inputs (e.g. user-controlled settings) are provided to the fluid infusion device 400 via input on the smartphone 440. It should be noted that in some embodiments, the fluid infusion device 400 may have a reset button or one or several indicator light emitting diodes (LEDs) which shine through the housing of the fluid infusion device 400. The LEDs may indicate various data such as data indicating that the fluid infusion device 400 is "on," the fluid infusion device 400 is undergoing wireless charging, the fluid infusion device 400 is done with wireless charging, etc. It should be noted that while the smartphone 440 is shown and illustrated herein as comprising the portable electronic device, a smart watch, tablet, computer, etc. may be used in addition to or instead of the smartphone 440 to communicate with the fluid infusion device 400.

Figure 13:
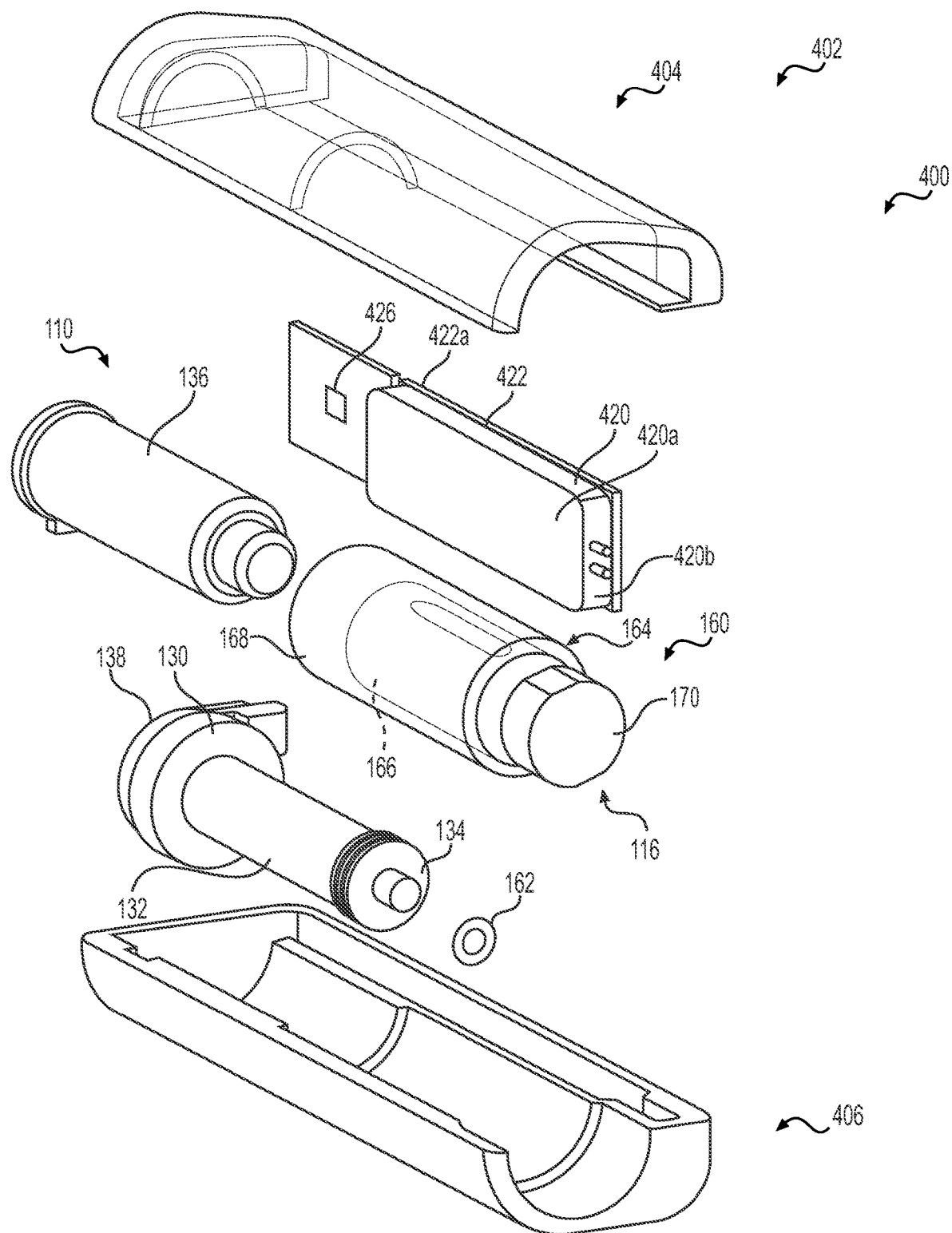
FIG. 13 is an exploded view of the fluid infusion device of FIG. 11.

As discussed previously, with reference back to FIG. 13, the drive system 110 cooperates with the fluid reservoir system 116 to dispense the fluid from the fluid reservoir system 116. Generally, the drive system 110 is configured to be serially coupled to the removable fluid reservoir 160 such that a combined dimension of the drive system 110 and the removable fluid reservoir 160 is less than or equal to the largest dimension DL4 of the housing 402 (FIG. 13). The drive system 110 includes the motor 130, the gear box 132, the drive screw 134, the slide 136 and the force sensor 138. The motor 130 receives power from the power supply 420 as controlled by the control module 422. As discussed, the rotation of the drive screw 134 causes the linear translation of the slide 136. The slide 136 is also movable to a plurality of positions between the first, retracted position and the second, fully extended position via the operation of the motor 130. The forward advancement of the slide 136 (i.e. the movement of the slide 136 toward the fluid reservoir system 116) causes the fluid reservoir system 116 to dispense fluid. The force sensor 138 is operatively associated with the drive system 110, and is in communication with the control module 422. The fluid reservoir system 116 includes the fluid reservoir 160 and the sealing member 162. The fluid reservoir 160 is received within the opening 410 (FIG. 11) defined by the housing 402. The fluid reservoir 160 is removable from the housing 402 to enable replacement as needed. The fluid reservoir 160 includes the body or barrel 164 and the stopper 166. The barrel 164 has the first or distal barrel end 168 and the second or proximal barrel end 170. Fluid is retained within the barrel 164 between the distal barrel end 168 and the proximal barrel end 170. The proximal barrel end 170 can have any desirable size and shape configured to mate with at least a portion of an infusion set assembly 300, as will be discussed in further detail herein. In some examples, the proximal barrel end 170 defines a passageway 172 through which the fluid flows out of the fluid reservoir 160. The passageway 172 is closed by the septum (not shown). The septum is pierceable by the infusion set assembly 300 to define a fluid flow path out of the fluid reservoir 160.

In some examples, with reference to FIG. 22A, the infusion set assembly 300 includes the connector 302, the hollow instrument or needle 304 and the tube 306. The connector 302 couples the needle 304 and the tube 306 to the fluid reservoir 160, and locks into place once coupled to the fluid reservoir 160 to maintain the fluid flow path between the fluid reservoir 160 and an infusion unit 308, as shown in FIG. 22B. The connector 302 is a removable reservoir cap (or fitting) that is suitably sized and configured to accommodate replacement of the fluid reservoir 160 (which are typically disposable) as needed. The needle 304 defines a flow path for the fluid out of the fluid reservoir 160, through the connector 302 and into the tube 306.

In some examples, with reference to FIG. 22C, the first housing portion 404 and the second housing portion 406 include opposing slots 444. With reference to FIG. 22D, each slot 444 may define a pocket 444a. The opposing slots 444 are sized to receive corresponding tabs 446 defined on the connector 302, and the pocket 444a cooperates with the tabs 446 to secure the connector 302 to the fluid infusion device 400. The tabs 446 are cantilevered, and are movable to lock into place in the respective pocket 444a. The cooperation between the opposing slots 444 and the tabs 446 enables the user to rotate the connector 302 onto the fluid reservoir 160 until the tab 446 expands into the pocket 444a. Once the tab 446 is disposed in the pocket 444a, the connector 302 is coupled to the fluid infusion device 400 and the tube 306 facilitates a fluidic connection between the fluid reservoir 160 and the infusion unit 308.

As discussed, the fluid infusion device 400 may be carried by the user, in a pocket of the user's clothing, for example. Alternatively, with reference to the example of FIG. 23A, the fluid infusion device 400 may be coupled or adhered to a body of the user. In this regard, the coupling slot 414 (FIGS. 17A-17C) of the second housing portion 406 may be used to couple the fluid infusion device 400 to a patch plate 450. The patch plate 450 in this example, is rigid, and is composed of a polymeric material, including, but not limited to acrylonitrile butadiene styrene (ABS), nylon, an acrylonitrile butadiene styrene polycarbonate blend, polyvinyl chloride, polytetrafluoroethylene (PTFE), polypropylene, polyether ether ketone (PEEK), polycarbonate or the like. The patch plate 450 may be molded, additively manufactured, etc. The patch plate 450 includes a top plate side 452 and an opposite second plate side 454. The top plate side 452 defines a rail 456. The rail 456 is shaped and configured to be received within the coupling slot 414. The coupling slot 414 may extend only over a portion of the second housing portion 406, or may extend over an entirety of the second housing portion 406. Generally, the fluid infusion device 400 may be moved or slid over the patch plate 450 such that the rail 456 is received within the coupling slot 414 to couple the fluid infusion device 400 to the patch plate 450 as shown in FIG. 23B. The second plate side 454 includes a biocompatible adhesive 458 for coupling the patch plate 450 to an anatomy of the user. In some examples, the adhesive 458 is provided on an adhesive patch, which is coupled to the second plate side 454 during manufacturing of the patch plate 450, via a double sided pressure sensitive adhesive, for example. The adhesive 458 may comprise a hydrogel based, silicone-based, or acrylic-based adhesive, which is capable of coupling the patch plate 450 to the anatomy. The adhesive 458 may be covered with a liner (not shown) to protect the adhesive 458 during shipping of the patch plate 450, for example.

With reference to the example of FIG. 24A, the fluid infusion device 400 may be coupled or adhered to a body of the user with an alternative patch plate 460. The coupling slot 414 (FIGS. 17A-17C) of the second housing portion 406 may be used to couple the fluid infusion device 400 to the patch plate 460. The patch plate 460 in this example, is flexible, and is composed of a polymeric material, including, but not limited to thermoplastic elastomers (TPE), thermoplastic polyurethane (TPU), silicone etc. In some examples, long edges of the patch plate 460 are capable of being displaced by about 1.0 millimeter or more from a plane upon which the patch plate 460 rests to provide increased comfort to the user. The patch plate 460 may be molded, additively manufactured, etc. The patch plate 460 includes a top plate side 462 and an opposite second plate side 464. The top plate side 462 defines a rail 466. The rail 466 is shaped and configured to be received within the coupling slot 414. The coupling slot 414 may extend only over a portion of the second housing portion 406, or may extend over an entirety of the second housing portion 406. Generally, the fluid infusion device 400 may be moved or slid over the patch plate 460 such that the rail 466 is received within the coupling slot 414 to couple the fluid infusion device 400 to the patch plate 460 as shown in FIG. 24B. The second plate side 464 includes a biocompatible adhesive 468 for coupling the patch plate 460 to an anatomy of the user. In some examples, the adhesive 468 is provided on an adhesive patch, which is coupled to the second plate side 464 during manufacturing of the patch plate 460, via a double sided pressure sensitive adhesive, for example. In other embodiments, the adhesive 468 may be formed on the second plate side 464, if desired. The adhesive 468 may comprise a hydrogel based, silicone-based, or acrylic-based adhesive, which is capable of coupling the patch plate 460 to the anatomy. The adhesive 468 may be covered with a liner (not shown) to protect the adhesive 468 during shipping of the patch plate 460, for example.

It should be noted that while the fluid infusion device 400 is described above as being coupled to the patch plates 450, 460 via sliding along the rail 456, 466, which mates with the coupling slot 414, the fluid infusion device 400 may be coupled to the patch plate 450, 460 by various other techniques. In some examples, the fluid infusion device 400 may be coupled to the patch plate 450, 460 via magnetic coupling. In this regard, the patch plate 450, 460 may include a magnet, which couples with the coupler 428 of the fluid infusion device 400 to provide a holding force that couples the fluid infusion device 400 to the patch plate 450, 460. In some examples, the patch plate 450, 460 may include a sleeve, which extends outwardly from the patch plate 450, 460 and defines a receptacle that is shaped to receive the fluid infusion device 400. In these examples, the fluid infusion device 400 may be slid into the sleeve and retained on the patch plate 450, 460 via friction. In some examples, the patch plate 450, 460 may include one or more mechanical fasteners, such as plastic screws, which are used to mechanically couple the housing 402 of the fluid infusion device 400 to the patch plate 450, 460. The mechanical fasteners, such as the plastic screws, may engage with threaded bores defined within the second housing portion 406 of the housing 402, for example. It should be noted that any combination of these methods may be employed to couple the fluid infusion device 400 to the patch plate 450, 460.

Although the fluid infusion device 400 is shown in FIGS. 22A and 22B for use with the infusion set assembly 300, which includes an elongated or long tube 306, it should be noted that the fluid infusion device 400 in combination with the patch plate 450, 460 may be used with alternative devices to enable a fluid flow path from the fluid reservoir 160 to an anatomy of a user. For example, with reference to FIG. 25, an infusion set assembly 300' includes the connector 302, the hollow instrument or needle 304 and a tube 306'. The connector 302 couples the needle 304 and the tube 306' to the fluid reservoir 160, and locks into place once coupled to the fluid reservoir 160 to maintain the fluid flow path between the fluid reservoir 160 and the infusion unit 308. In this example, the tube 306' has a length, which is different, and in this example, less than a length of the tube 306 (FIGS. 22A and 22B). In some examples, the tube 306' may have a length of about 3.0 millimeters (mm) to about 5 inches (in.), while the tube 306 (FIGS. 22A and 22B) may have a length of greater than 5 inches (in.) to 4 feet (ft.) The infusion set assembly 300' in combination with the patch plate 450, 460 enables the fluid infusion device 400 to be used as a patch pump.

Although the fluid infusion device 400 is shown in FIGS. 22A, 22B and 25 for use with the infusion set assembly 300, 300', it should be noted that the fluid infusion device 400 may be used with alternative devices to enable a fluid flow path from the fluid reservoir 160 to an anatomy of a user. For example, with reference to FIG. 26A, a needle connector 470 is shown. The needle connector 470 includes a cap 472 and a hollow instrument or needle 474. The needle connector 470 may be composed of a suitable biocompatible material, including, but not limited to a biocompatible polymer, which may be molded, additively manufactured, etc. The cap 472 couples the needle 474 to the fluid reservoir 160, as shown in the example of FIG. 26B, and locks into place once coupled to the fluid reservoir 160 to maintain the fluid flow path between the fluid reservoir 160 and the needle 474. The cap 472 is a removable reservoir cap (or fitting) that is suitably sized and configured to accommodate replacement of the fluid reservoir 160 (which are typically disposable) as needed. The needle 474 defines a flow path for the fluid out of the fluid reservoir 160, through the cap 472. The needle 474 includes opposed ends, one end of which is to pierce the septum associated with the fluid reservoir 160, while the other exposed end is for piercing a skin of the user to deliver the fluid into the anatomy of the user. Thus, in this example, the needle connector 470 enables the fluid infusion device 400 to be used as a pen to inject the fluid directly into the anatomy of the user. Alternatively, the user may use the fluid infusion device 400, with the needle connector 470 coupled to the fluid reservoir 160 to inject the fluid into an injection port 476 coupled to the anatomy of the user, such as an i-Port Advance™ commercially available from Medtronic MiniMed, Inc. of Northridge, California, USA. Thus, the needle connector 470 defines the fluid flow path from the fluid reservoir 160 to an injection site, such as the anatomy of the user or the injection port 476.

It should be noted that in certain embodiments, the needle connector 470 may include a magnet, and the fluid infusion device 400 may include a magnetic field sensor in communication with the control module 422. In such embodiments, the fluid infusion device 400 may determine, based on a detected magnetic field by the magnetic field sensor, that the needle connector 470 is coupled to the fluid infusion device 400 prior to dispensing the fluid. In addition, the magnetic field sensor may observe a magnetic field generated by a magnet coupled to the infusion set assembly 300, such as the connector 302, to determine the type of infusion set assembly 300 coupled to the fluid infusion device 400. For example, the infusion set assembly 300, 300' (or any of the infusion set assemblies discussed herein) may include the tube 306, 306' that is longer or shorter than another infusion set assembly, and the control module 422 may process the signals from the magnetic field sensor and determine which infusion set assembly (long tube 306, short tube 306', etc.) is coupled to the fluid infusion device 400. For example, the control module 422 of the fluid infusion device 400 is able to determine if a longer infusion set assembly or a smaller infusion set assembly is connected based on the orientation of the magnet placed in each of the respective connectors 302 (i.e. the magnet in the connector 302 of the longer infusion set assembly 300 may be oriented 90 degrees as compared to the connector 302 for the shorter infusion set assembly 306'), which is observed by the magnetic field sensor and processed by the control module 422. In some examples, the control module 422 of the fluid infusion device 400 is able to determine if the infusion set assembly 300 or the needle connector 470 is connected based on the orientation of the magnet placed in each of the respective connectors (i.e. the magnet in the needle connector 470 may be oriented 90 degrees as compared to the connector 302, for example, for the infusion set assembly 300), which is observed by the magnetic field sensor and processed by the control module 422. Further, the control module 422 of the fluid infusion device 400 is able to determine if a longer infusion set assembly 300, a smaller infusion set assembly 300' or the needle connector 470 is connected based on the orientation of a magnet placed in each of the respective connectors, which is offset by a pre-determined amount (e.g. increments of 30 degrees) that is observed by the magnetic field sensor and processed by the control module 422. Further, the control module 422 may be able to distinguish between infusion set assemblies of different lengths without a glucose sensor, and infusion set assemblies of different lengths that include a glucose sensor, based on an orientation of a magnet coupled to each of the respective infusion set assemblies and observed by the magnetic field sensor. The control module 422 may access a look-up table, for example, to determine the infusion set assembly based on the sensor signals received by the magnetic field sensor.

Referring back to FIG. 13, in some examples, with the slide 136, the drive screw 134, the gear box 132 and the motor 130 provided, the motor 130 is coupled to the gear box 132 and the drive screw 134 is coupled to the gear box 132. The slide 136 is positioned over the drive screw 134 and the threads 134a of the drive screw 134 threadably engage the threads 142a of the slide 136. With the second housing portion 406 formed, the assembled drive system 110 is coupled to the second housing portion 406. The control module 422 is coupled to the power supply 420 to be in communication with the power supply 420, and with the charging coil 424, 424' and the antenna 426 coupled and in communication with the control module 422, the control module 422 and the power supply 420 are coupled to the second housing portion 406. The motor 130 is coupled to the control module 422 to receive the one or more control signals to drive the motor 130. The force sensor 138 is positioned within the second housing portion 406 and electrically connected to the printed circuit board 422a to be in communication with the control module 422. The sealing members 162, 416 are coupled to the second housing portion 406. With the first housing portion 404 formed, the first housing portion 404 is coupled to the second housing portion 406, via welding, for example.

With the fluid infusion device 400 assembled, the fluid infusion device 400 may be packaged and shipped to an end user. Once received, the end user may remove the packaging and with reference to FIGS. 22A and 22B, the user may couple the fluid reservoir 160 to the housing 402 by positioning the fluid reservoir 160 within the opening 410 (FIG. 12) defined in the housing 402. In some embodiments, the fluid reservoir 160 is prefilled with fluid (for example, insulin) such that the stopper 166 is positioned at the distal barrel end 168 (FIG. 13). In some examples, the connector 302 is coupled to the fluid reservoir 160 prior to insertion of the fluid reservoir 160 into the housing 402 for ease of handling by the user. With the infusion set assembly 300 fixedly coupled or secured to the housing 402, the needle 304 pierces the septum, thereby defining a fluid flow path for the fluid out of the fluid reservoir 160. With the infusion set assembly 300 coupled to the fluid reservoir 160 and the infusion unit 308 coupled to the anatomy of the user, one or more control signals from the control module 422 can drive the motor 130, thereby rotating the drive screw 134, which results in the linear translation of the slide 136. The advancement of the slide 136 into the fluid reservoir 160 moves the stopper 166, causing the fluid to flow from the fluid reservoir 160 through the fluid flow path defined by the infusion set assembly 300.

Alternatively, in the case of the needle connector 470, with the needle connector 470 coupled to the fluid reservoir 160 such that the needle 474 pierces the septum to define a fluid flow path from the fluid reservoir 160, the exposed end of the needle 474 is inserted into the injection site. One or more control signals from the control module 422 drives the motor 130, thereby rotating the drive screw 134, which results in the linear translation of the slide 136. The advancement of the slide 136 into the fluid reservoir 160 moves the stopper 166, causing the fluid to flow from the fluid reservoir 160 through the fluid flow path defined by the needle 474 and into the injection site.

With reference to FIGS. 23A-24B, it should be noted that the end user may also take one of the patch plates 450, 460 and may slidably couple the coupling slot 414 of fluid infusion device 400 (FIG. 17A) to the respective rail 456, 466 of the patch plate 450, 460. The user may remove the backing from the adhesive 458, 468 of the respective patch plate 450, 460, and couple the adhesive 458, 468, and thus, the fluid infusion device 400, to the anatomy of the user.

Figure 27:
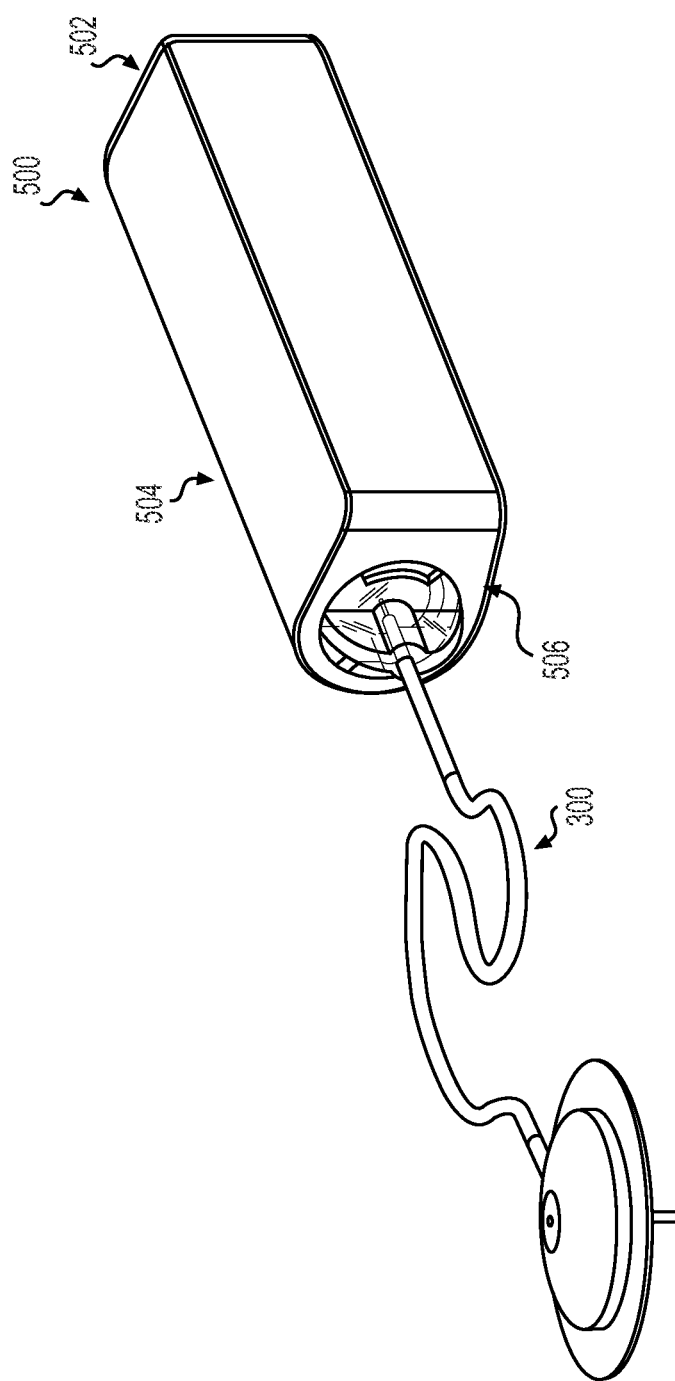
FIG. 27 is a perspective view of an exemplary fluid infusion system according to various teachings of the present disclosure.
Figure 28:
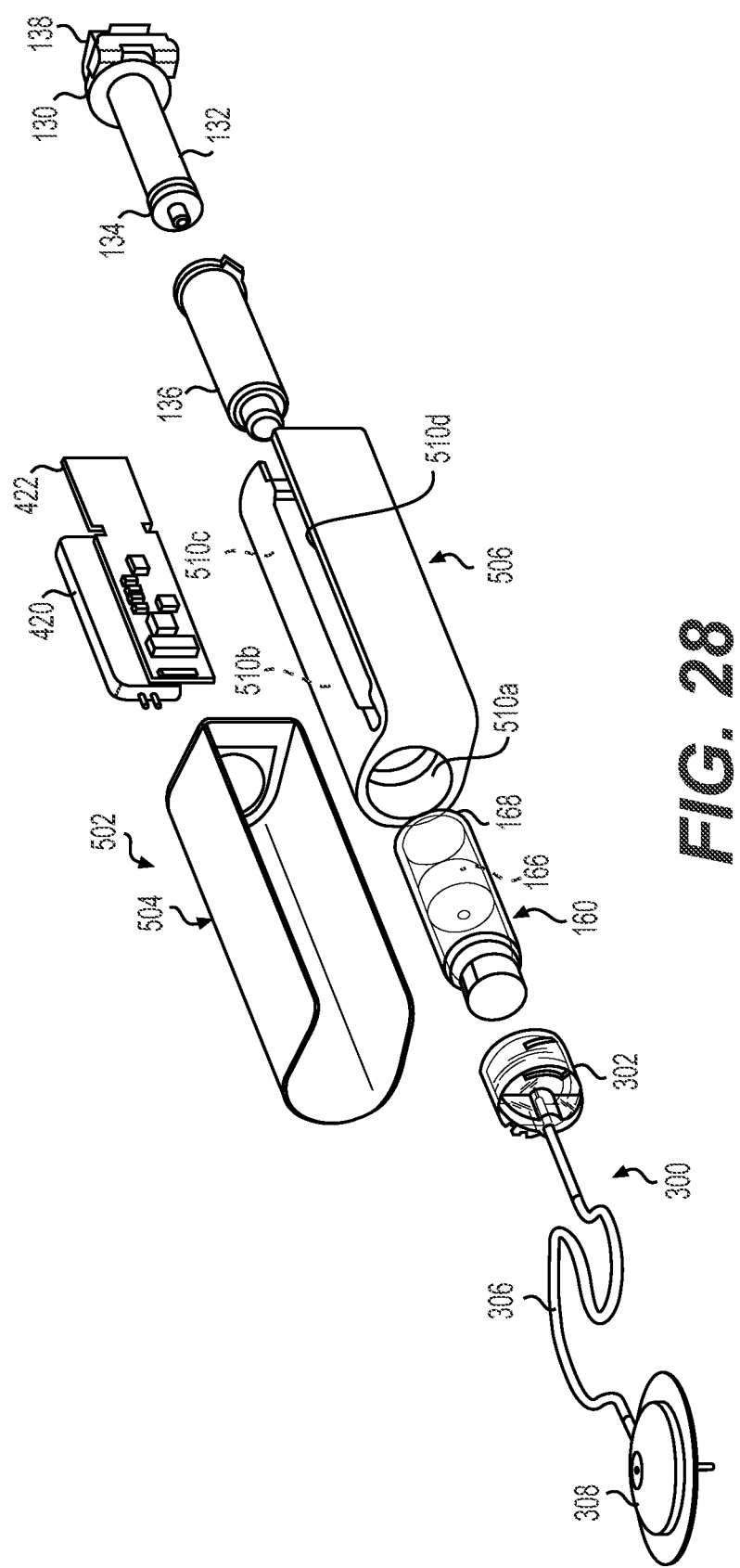
FIG. 28 is an exploded view of the fluid infusion system of FIG. 27.

It should be noted that configurations of the fluid infusion device 400 may vary from implementation to implementation. For example, with reference to FIG. 27, a portable fluid infusion device 500 is shown. As the fluid infusion device 500 includes the same or similar components as the fluid infusion device 400 discussed with regard to FIGS. 11-26B, the same reference numerals will be used to denote the same or similar components. FIG. 27 is a perspective view of the fluid infusion device 500, and FIG. 28 is an exploded view. The fluid infusion device 500 may be used with the infusion set assembly 300 or other devices, such as the infusion set assembly 300' or the needle connector 470. In the examples of FIGS. 27 and 28, the fluid infusion device 500 is shown with the infusion set assembly 300.

In these examples, the fluid infusion device 500 includes a housing 502. Generally, the housing 502 has a small form factor for portability and is about 15 millimeters (mm.) to about 25 millimeters (mm.) thick, about 20 millimeters (mm.) to about 30 millimeters (mm.) wide and is about 75 millimeters (mm.) to about 85 millimeters (mm.) long. In some examples, the housing 502 includes a first housing portion 504 and a second housing portion 506, which are coupled together to form the housing 502. The first housing portion 504 and the second housing portion 506 may each be composed of a polymeric material, including, but not limited to polycarbonate, and may be molded, additive manufactured, etc. Generally, with reference to FIG. 28, the first housing portion 504 and the second housing portion 506 cooperate to enclose the power supply 420, the controller or control module 422, the drive system 110 and the fluid reservoir system 116. In this example, the fluid infusion device 500 is devoid of a user interface.

In some examples, the first housing portion 504 is slid over the second housing portion 506, and the first housing portion 504 and the second housing portion 506 are coupled together via welding, including, but not limited to laser welding, ultrasonic welding, radiofrequency welding, etc. In certain embodiments, the first housing portion 504 and the second housing portion 506 may each have alignment features, which assist in coupling the first housing portion 504 to the second housing portion 506. In the examples of FIGS. 27 and 28, the first housing portion 504 is substantially C-shaped, and is sized to substantially surround the second housing portion 506. The second housing portion 506 includes a plurality of chambers 510. In some examples, with reference to FIG. 29, the second housing portion 506 includes a connector chamber 510a, a reservoir chamber 510*b*, a drive chamber 510*c* and an electronics chamber 510*d*. The chambers 510*a*-510*d* cooperate to contain the respective components for ease of assembly of the fluid infusion device 500. The connector chamber 510*a* is in communication with the reservoir chamber 510*b*. The connector chamber 510*a* receives the connector 302 or needle connector 470 (FIG. 26A), and defines an opening 512 into the second housing portion 506 that receives the fluid reservoir 160 and the connector 302. The reservoir chamber 510*b* receives the fluid reservoir 160. The drive chamber 510*c* is in communication with the electronics chamber 510*d*. The drive chamber 510*c* receives the drive system 110, and the electronics chamber 510*d* receives the control module 422 and the power supply 420.

With reference to the example of FIG. 28, with the slide 136, the drive screw 134, the gear box 132 and the motor 130 provided, the motor 130 is coupled to the gear box 132 and the drive screw 134 is coupled to the gear box 132. The slide 136 is positioned over the drive screw 134 and the threads 134*a* of the drive screw 134 threadably engage the threads 142*a* of the slide 136. With the second housing portion 506 formed, the assembled drive system 110 is coupled to the drive chamber 510*c* of the second housing portion 506. The control module 422 is coupled to the power supply 420 to be in communication with the power supply 420, and with the charging coil 424, 424' and the antenna 426 coupled and in communication with the control module 422, the control module 422 and the power supply 420 are coupled to the electronics chamber 510*d* of the second housing portion 506. The motor 130 is coupled to the control module 422 to receive the one or more control signals to drive the motor 130. The force sensor 138 is positioned within the drive chamber 510*c* of the second housing portion 506 and electrically connected to the printed circuit board 422*a* to be in communication with the control module 422. With the first housing portion 504 formed, the first housing portion 504 is coupled to the second housing portion 506.

With the fluid infusion device 500 assembled, the fluid infusion device 500 may be packaged and shipped to an end user. Once received, the end user may remove the packaging and the user may couple the fluid reservoir 160 to the housing 502 by positioning the fluid reservoir 160 within the reservoir chamber 510*b* defined in the housing 502. In some embodiments, the fluid reservoir 160 is prefilled with fluid (for example, insulin) such that the stopper 166 is positioned at the distal barrel end 168. In some examples, the connector 302 is coupled to the fluid reservoir 160 prior to insertion of the fluid reservoir 160 into the housing 502 for ease of handling by the user. With the infusion set assembly 300 fixedly coupled or secured to the connector chamber 510*a* of the housing 502, the needle 304 pierces the septum, thereby defining a fluid flow path for the fluid out of the fluid reservoir 160. With the infusion set assembly 300 coupled to the fluid reservoir 160 and the infusion unit 308 coupled to the anatomy of the user, one or more control signals from the control module 422 can drive the motor 130, thereby rotating the drive screw 134, which results in the linear translation of the slide 136. The advancement of the slide 136 into the fluid reservoir 160 moves the stopper 166, causing fluid to flow from the fluid reservoir 160 through the fluid flow path defined by the infusion set assembly 300.

Alternatively, in the case of the needle connector 470, with the needle connector 470 positioned within the connector chamber 510*a* coupled to the fluid reservoir 160 such that the needle 474 pierces the septum to define a fluid flow path from the fluid reservoir 160, the exposed end of the needle 474 is inserted into the injection site. One or more control signals from the control module 422 drives the motor 130, thereby rotating the drive screw 134, which results in the linear translation of the slide 136. The advancement of the slide 136 into the fluid reservoir 160 moves the stopper 166, causing the fluid to flow from the fluid reservoir 160 through the fluid flow path defined by the needle 474 and into the injection site.

It should be noted that the fluid infusion device 500 may include the coupling slot 414 defined in the second housing portion 506, for example, to couple the fluid infusion device 500 to the patch plates 450, 460. In this example, the fluid infusion device 500 may be coupled to the patch plates 450, 460 via sliding along the rail 456, 466 that mates with the coupling slot 414. It should be noted that the fluid infusion device 500 may be coupled to the patch plate 450, 460 by various other techniques. In some examples, the fluid infusion device 500 may be coupled to the patch plate 450, 460 via magnetic coupling; the patch plate 450, 460 may include a sleeve, which extends outwardly from the patch plate 450, 460 and defines a receptacle that is shaped to receive the fluid infusion device 500; and/or the patch plate 450, 460 may include one or more mechanical fasteners, such as plastic screws, which are used to mechanically couple the housing 502 of the fluid infusion device 500 to the patch plate 450, 460 as discussed with regard to the fluid infusion device 400. It should be noted that any combination of these methods may be employed to couple the fluid infusion device 500 to the patch plate 450, 460.

Figure 31:
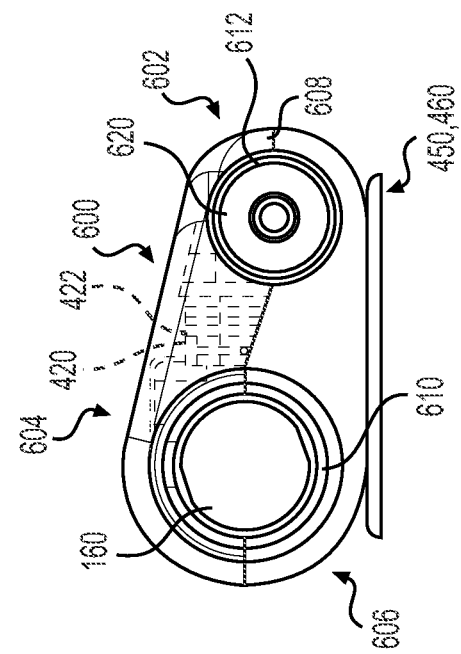
FIG. 31 is an end view of the fluid infusion device of FIG. 30.
Figure 30:
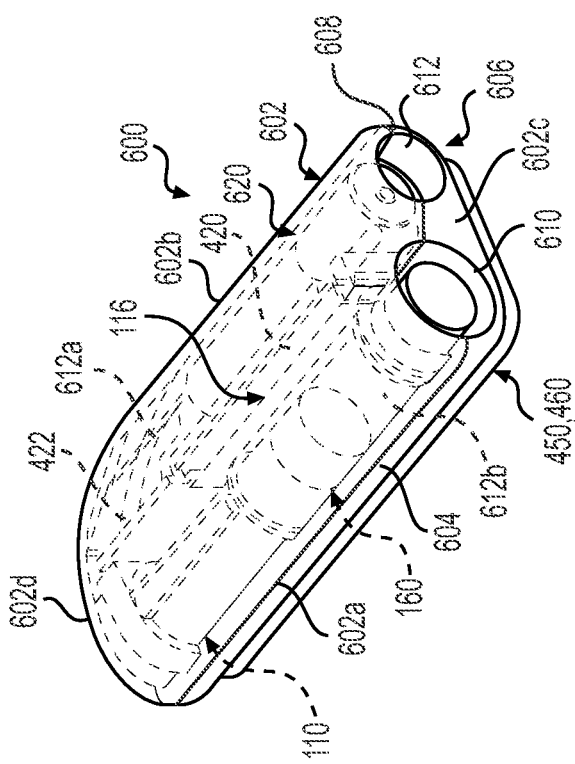
FIG. 30 is a perspective view of an implementation involving an exemplary fluid infusion device according to various teachings of the present disclosure.
Figure 32:
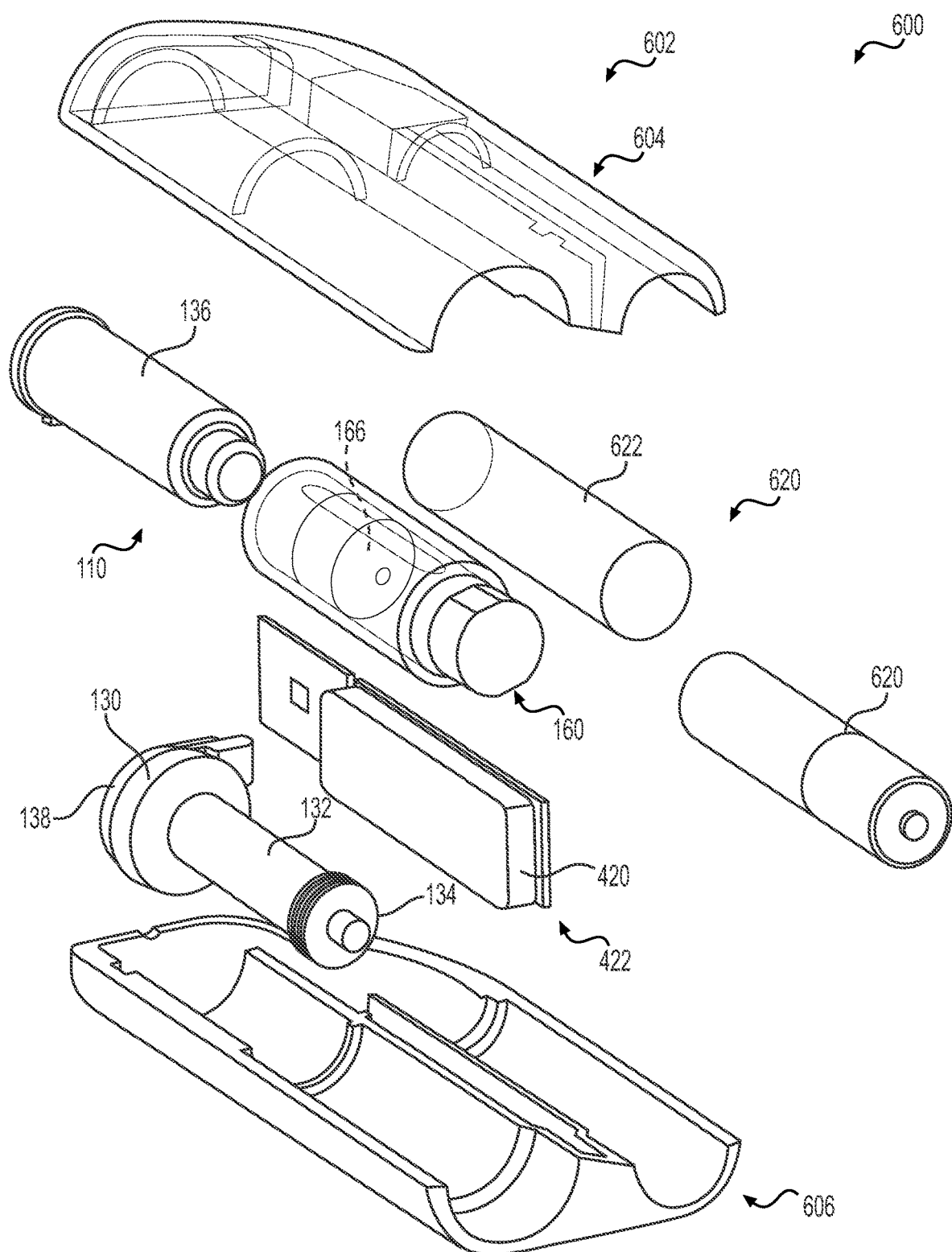
FIG. 32 is an exploded view of the fluid infusion device of FIG. 30.

It should be noted that in some embodiments, the fluid infusion device 400 may be configured differently. For example, with reference to FIG. 30, a portable fluid infusion device 600 is shown. As the fluid infusion device 600 includes the same or similar components as the fluid infusion device 400 discussed with regard to FIGS. 11-26B, the same reference numerals will be used to denote the same or similar components. FIG. 30 is a perspective view of the fluid infusion device 500, FIG. 31 is an end view and FIG. 32 is an exploded view. The fluid infusion device 600 may be used with the infusion set assembly 300 or other devices, such as the infusion set assembly 300' or the needle connector 470.

In the examples of FIGS. 30-32, the fluid infusion device 600 includes a housing 602. Generally, the housing 602 has a small form factor for portability and is about 15 millimeters (mm.) to about 25 millimeters (mm.) thick, about 33 millimeters (mm.) to about 42 millimeters (mm.) wide and is about 79 millimeters (mm.) to about 89 millimeters (mm.) long. In some examples, the housing 602 includes a first housing portion 604 and a second housing portion 606, which are coupled together to form the housing 602. The first housing portion 604 and the second housing portion 606 may each be composed of a polymeric material, including, but not limited to polycarbonate, and may be molded, additive manufactured, etc. Generally, with reference to the example of FIG. 32, the first housing portion 604 and the second housing portion 606 cooperate to enclose a power supply 620, the power supply 420, the controller or control module 422, the drive system 110 and the fluid reservoir system 116. In this example, the fluid infusion device 600 is devoid of a user interface.

Figure 34:
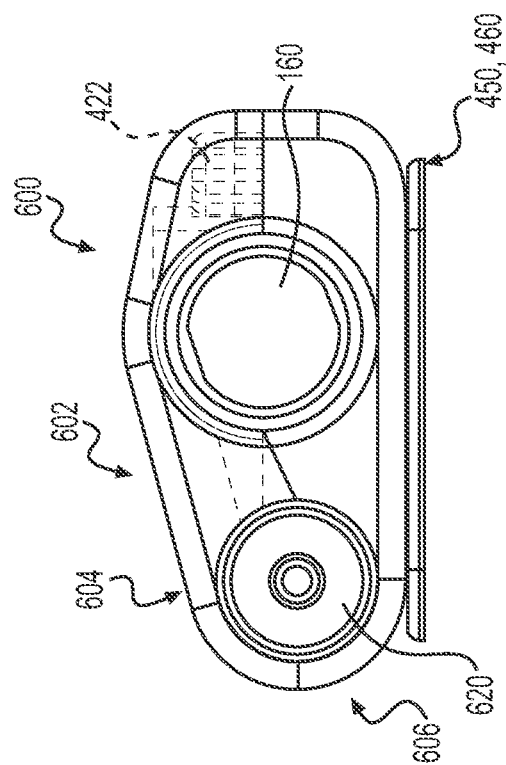
FIG. 34 is an end view of the fluid infusion device of FIG. 33.
Figure 33:
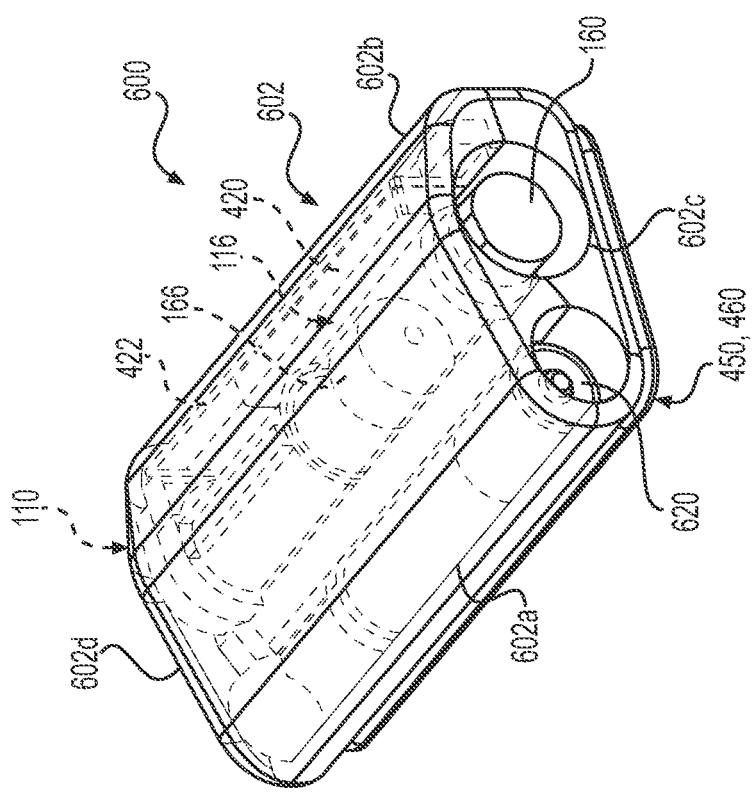
FIG. 33 is a perspective view of an implementation involving a fluid infusion device according to various teachings of the present disclosure.

In this example, the control module 422 is retained within the housing 602 with the power supply 420 between the fluid reservoir system 116 and the power supply 620. It should be noted that in some other embodiments, the control module 422 may be positioned and retained within an alternative location within the housing 602. For example, with reference to FIGS. 33 and 34, the control module 422 is coupled between the fluid reservoir system 116 and a side 602b of the housing 602. In this configuration, the housing 602 is about 15 millimeters (mm.) to about 25 millimeters (mm.) thick, about 35 millimeters (mm.) to about 45 millimeters (mm.) wide and is about 79 millimeters (mm.) to about 89 millimeters (mm.) long.

Referring back to the example of FIGS. 30 and 31, the first housing portion 604 and the second housing portion 606 are coupled together in a manner that forms a seal at an interface 608 between the first housing portion 604 and the second housing portion 606. In these examples, the first housing portion 604 and the second housing portion 406 are coupled together via welding, including, but not limited to laser welding, ultrasonic welding, radiofrequency welding, etc.

The housing 602, when assembled, includes opposed sides 602a, 602b, and opposed ends 602c, 602d. Generally, the end 602c defines an opening 610 to receive the fluid reservoir 160 and an opening 612 to receive the power supply 620. Generally, the power supply 620, the control module 422 and the drive system 110 are accommodated in a pump chamber 612a defined by the housing 602, and the fluid reservoir system 116 is accommodated in a reservoir chamber 612b defined by the housing 602. The opposed sides 602a, 602b and the opposed ends 602c, 602d of the housing 602 define a plurality of faces of the housing 602, and in this example, the faces 602c, 602d have the smallest area (compared to the faces or sides 602a, 602b), and the opening 610, 612 are located on the face or end 602c that has the smallest area.

Figure 36:
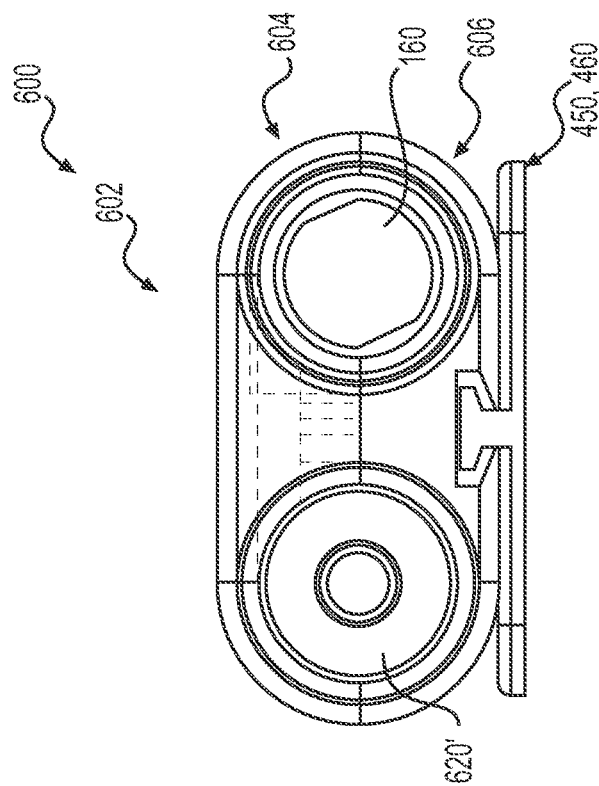
FIG. 36 is an end view of the fluid infusion device of FIG. 35.
Figure 35:
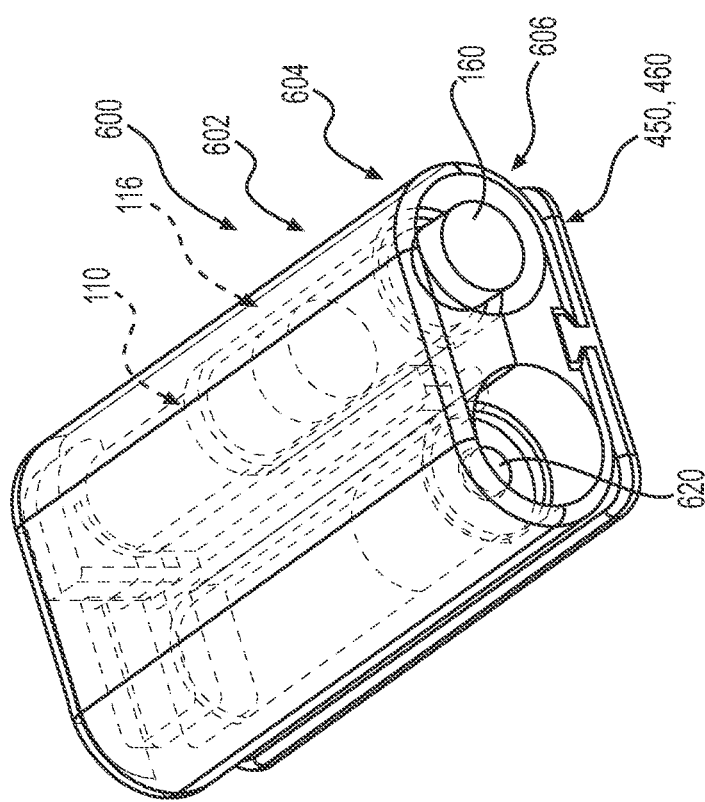
FIG. 35 is a perspective view of an implementation involving a fluid infusion device according to various teachings of the present disclosure.

The power supply 620 is any suitable device for supplying the fluid infusion device 600 with power, including, but not limited to, a battery. In some examples, with reference to FIG. 32, the power supply 620 is a disposable battery, which is received within a battery sleeve 622 associated with the housing 602. In this example, the battery is a AAA battery, however, other disposable battery sizes may be employed. For example, with reference to FIGS. 35 and 36, the fluid infusion device 600 is shown with an AA battery as a power supply 620'. In this configuration, the housing 602 is about 15 millimeters (mm.) to about 25 millimeters (mm.) thick, about 35 millimeters (mm.) to about 45 millimeters (mm.) wide and is about 79 millimeters (mm.) to about 89 millimeters (mm.) long to accommodate the larger power supply. The power supply 420 is a rechargeable battery, which is fixed within the housing 602 and electrically coupled to the control module 422. Generally, the power supply 420 is rechargeable via wireless charging, etc., as discussed. The power supply 420 is chargeable for at least a 7 day use, and in some examples, provides power and/or notifications when the power supply 620 is at low power or needs replacement. It should be noted that the fluid infusion device 600 need not include the rechargeable power supply 420, if desired.

The housing 602 may include a battery cap (not shown) to enclose the power supply 620, 620' when the battery is positioned within the housing 602. The battery sleeve 622 is cylindrical, and receives the power supply 620, 620'. The battery sleeve 622 is coupled or disposed within the housing 602.

The fluid infusion device 600 may be carried by the user, in a pocket of the user's clothing, for example. Alternatively, with reference to FIG. 37A, the fluid infusion device 600 may be coupled or adhered to a body of the user. In this regard, the second housing portion 606 may also include the coupling slot 414 (FIGS. 17A-17C), which may be used to couple the fluid infusion device 600 to the patch plate 450. The rail 456 is shaped and configured to be received within the coupling slot 414 of the second housing portion 606. Generally, the fluid infusion device 600 may be moved or slid over the patch plate 450 such that the rail 456 is received within the coupling slot 414 to couple the fluid infusion device 600 to the patch plate 450 as shown in FIG. 37B. The second plate side 454 includes the biocompatible adhesive 458 for coupling the patch plate 450 to an anatomy of the user. The adhesive 458 may be covered with a liner (not shown) to protect the adhesive 458 during shipping of the patch plate 450, for example.

With reference to FIG. 38A, the fluid infusion device 600 may be coupled or adhered to a body of the user with the patch plate 460. The coupling slot 414 (FIGS. 17A-17C) of the second housing portion 606 may be used to couple the fluid infusion device 600 to the patch plate 460. The rail 466 is shaped and configured to be received within the coupling slot 414. Generally, the fluid infusion device 600 may be moved or slid over the patch plate 460 such that the rail 466 is received within the coupling slot 414 to couple the fluid infusion device 600 to the patch plate 460 as shown in FIG. 38B. The second plate side 464 includes the biocompatible adhesive 468, which may be provided on an adhesive patch coupled to the second plate side 464, for coupling the patch plate 460 to an anatomy of the user. The adhesive 468 may be covered with a liner (not shown) to protect the adhesive 468 during shipping of the patch plate 460, for example.

It should be noted that while the fluid infusion device 600 is described as being coupled to the patch plates 450, 460 via sliding along the rail 456, 466, which mates with the coupling slot 414, the fluid infusion device 600 may be coupled to the patch plate 450, 460 by various other techniques, as discussed with regard to the fluid infusion device 400 of FIGS. 11-26B. For example, the fluid infusion device 600 may be coupled to the patch plate 450, 460 via magnetic coupling. In some examples, the patch plate 450, 460 may include a sleeve, which extends outwardly from the patch plate 450, 460 and defines a receptacle that receives the fluid infusion device 600. In some examples, the patch plate 450, 460 may include one or more mechanical fasteners, such as plastic screws, which are used to mechanically couple the fluid infusion device 600 to the patch plate 450, 460.

Referring back to the example of FIG. 32, with the slide 136, the drive screw 134, the gear box 132 and the motor 130 provided, the motor 130 is coupled to the gear box 132 and the drive screw 134 is coupled to the gear box 132. The slide 136 is positioned over the drive screw 134 and the threads 134a of the drive screw 134 threadably engage the threads 142a of the slide 136. With the second housing portion 606 formed, the assembled drive system 110 is coupled to the second housing portion 606. The control module 422 is coupled to the power supply 420 to be in communication with the power supply 420, and with the charging coil 424, 424' and the antenna 426 coupled and in communication with the control module 422, the control module 422 and the power supply 420 are coupled to the second housing portion 606. The motor 130 is coupled to the control module 422 to receive the one or more control signals to drive the motor 130. The force sensor 138 is positioned within the second housing portion 606 and electrically connected to the printed circuit board 422a to be in communication with the control module 422. With the first housing portion 604 formed, the first housing portion 604 is coupled to the second housing portion 606, via welding, for example.

With the fluid infusion device 600 assembled, the fluid infusion device 600 may be packaged and shipped to an end user. Once received, the end user may remove the packaging and the user may couple the fluid reservoir 160 to the housing 602 by positioning the fluid reservoir 160 through the opening 610 defined in the housing 602. In some embodiments, the fluid reservoir 160 is prefilled with fluid (for example, insulin) such that the stopper 166 is positioned at the distal barrel end 168 (FIG. 32). In some examples, the connector 302 is coupled to the fluid reservoir 160 prior to insertion of the fluid reservoir 160 into the housing 602 for ease of handling by the user. The power supply 620, 620' may be inserted into the opening 612 and enclosed with a battery cap, for example. With the infusion set assembly 300 fixedly coupled or secured to the housing 602, the needle 304 pierces the septum, thereby defining a fluid flow path for the fluid out of the fluid reservoir 160. With the infusion set assembly 300 coupled to the fluid reservoir 160 and the infusion unit 308 coupled to the anatomy of the user, one or more control signals from the control module 422 can drive the motor 130, thereby rotating the drive screw 134, which results in the linear translation of the slide 136. The advancement of the slide 136 into the fluid reservoir 160 moves the stopper 166, causing the fluid to flow from the fluid reservoir 160 through the fluid flow path defined by the infusion set assembly 300.

Alternatively, in the case of the needle connector 470, with the needle connector 470 positioned within the connector chamber 510a coupled to the fluid reservoir 160 such that the needle 474 pierces the septum to define a fluid flow path from the fluid reservoir 160, the exposed end of the needle 474 is inserted into the injection site. One or more control signals from the control module 422 drives the motor 130, thereby rotating the drive screw 134, which results in the linear translation of the slide 136. The advancement of the slide 136 into the fluid reservoir 160 moves the stopper 166, causing the fluid to flow from the fluid reservoir 160 through the fluid flow path defined by the needle 474 and into the injection site.

With reference to FIGS. 37A-38B, it should be noted that the end user may also take one of the patch plates 450, 460 and may slidably couple the coupling slot 414 of fluid infusion device 600 to the respective rail 456, 466 of the patch plate 450, 460. The user may remove the backing from the adhesive 458, 468 of the respective patch plate 450, 460, and couple the adhesive 458, 468, and thus, the fluid infusion device 600, to the anatomy of the user.

While the fluid infusion devices 100, 400, 500, 600 are described herein as using the infusion set assembly 300 to dispense a fluid to a user, it should be noted that the infusion set assembly 300 may exhibit a variety of different configurations. Further, as used herein, an infusion set assembly and a fluid infusion device comprise a fluid infusion system. For example, with reference to FIG. 39, an infusion set assembly 700 is shown coupled to a fluid infusion device 800. Insofar as the infusion set assembly 700 includes the same or similar components as the infusion set assembly 300 discussed with regard to FIGS. 1-38B and insofar as the fluid infusion device 800 includes the same or similar components as the fluid infusion device 400 discussed with regard to FIGS. 11-38B, the same reference numerals may be used to denote the same or similar components.

Figure 39:
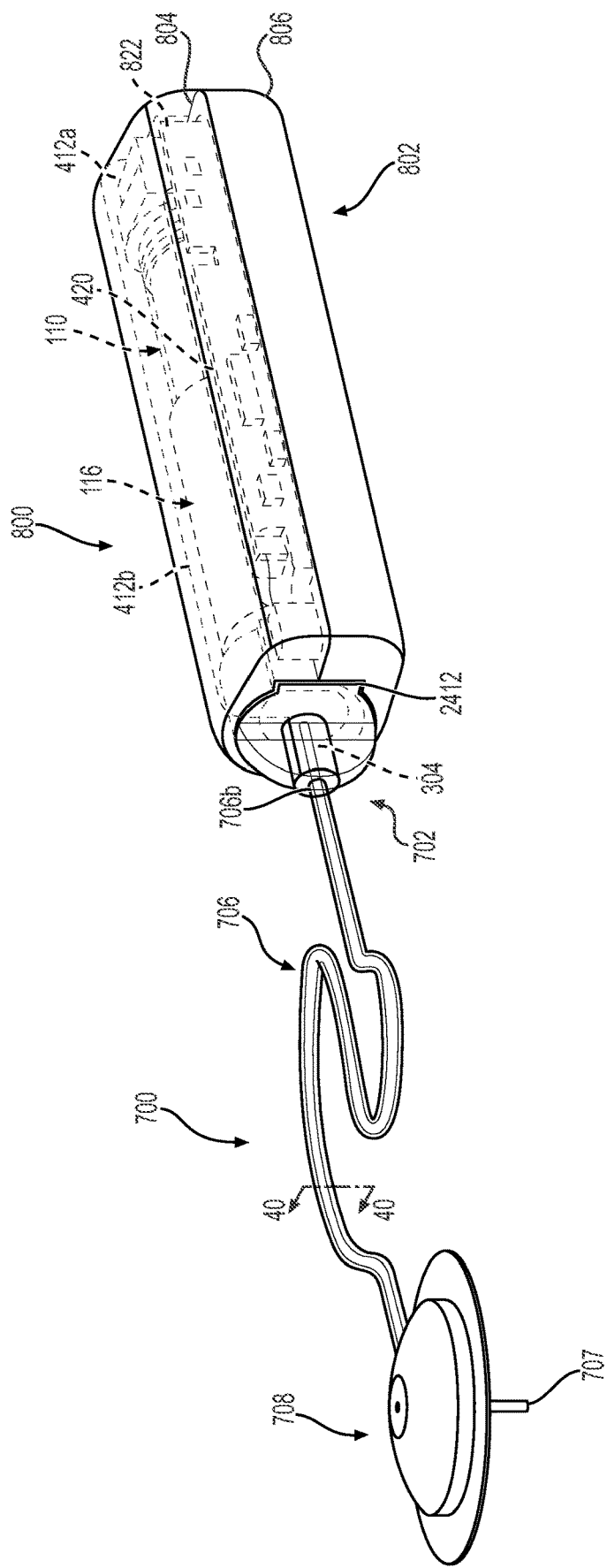
FIG. 39 is a perspective view of an exemplary fluid infusion system comprising an infusion set assembly according to various teachings of the present disclosure.

In the example of FIG. 39, the infusion set assembly 700 includes a connector 702, the hollow instrument or needle 304 and a tube 706. The connector 702 couples with the fluid infusion device 800, and locks into place once coupled to maintain the fluid flow path between the fluid reservoir 160 and an infusion monitor unit 708 via the needle 304 and the tube 706. In this example, as will be discussed, the infusion monitor unit 708 is configured to both dispense a fluid, such as insulin, into the anatomy of the user, and to also monitor, observe or measure a physiological characteristic, such as a blood glucose level or a glucose level, associated with the user.

Figure 40:
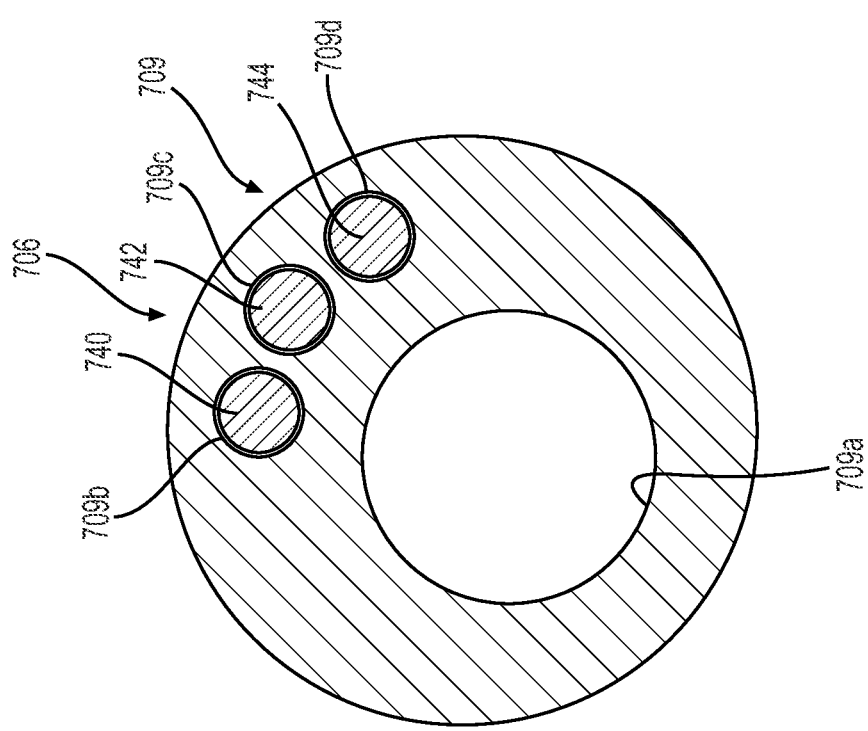
FIG. 40 is a cross-sectional view of a tube of the infusion set assembly, taken along line 40-40 of FIG. 39.

The tube 706 includes a first or proximalmost end 707 and an opposite second end 706b. The proximalmost end 707 is coupled to the infusion monitor unit 708, while the second end 706b is coupled to the connector 702. In this example, the proximalmost end 707 of the tube 706 is inserted into the anatomy to provide the fluid flow path from the fluid reservoir 160 into the anatomy of the user. In some examples, with reference to FIG. 40, a cross-sectional view of the tube 706 is shown. The tube 706 includes a plurality of conduits 709. In this example, the tube 706 includes a fluid delivery conduit 709a, a reference electrode conduit 709b, a counter electrode conduit 709c and a working electrode conduit 709d. The fluid delivery conduit 709a receives the fluid from the fluid reservoir 160 and directs the fluid from the fluid reservoir 160 through the tube 706. In some examples, with reference to FIG. 41, the fluid delivery conduit 709a terminates at a terminal end 707a of the tube 706, such that a fluid outlet is defined at the terminal end 707a. With reference to FIG. 40, the reference electrode conduit 709b accommodates a reference electrode 740 associated with the infusion monitor unit 708, and directs the reference electrode 740 through the tube 706 to the connector 702. The counter electrode conduit 709c accommodates a counter electrode 742 associated with the infusion monitor unit 708, and directs the counter electrode 742 through the tube 706 to the connector 702. The working electrode conduit 709d accommodates a working electrode 744 associated with the infusion monitor unit 708, and directs the working electrode 744 through the tube 706 to the connector 702. As described in greater detail below, a plurality of electrodes (e.g., a reference electrode, a counter electrode, and a working electrode) can work together to determine a physiological characteristic (e.g., a glucose level) of a user. Such a plurality of electrodes may be collectively referred to herein as a physiological characteristic sensor (e.g., a glucose sensor).

Figure 41:
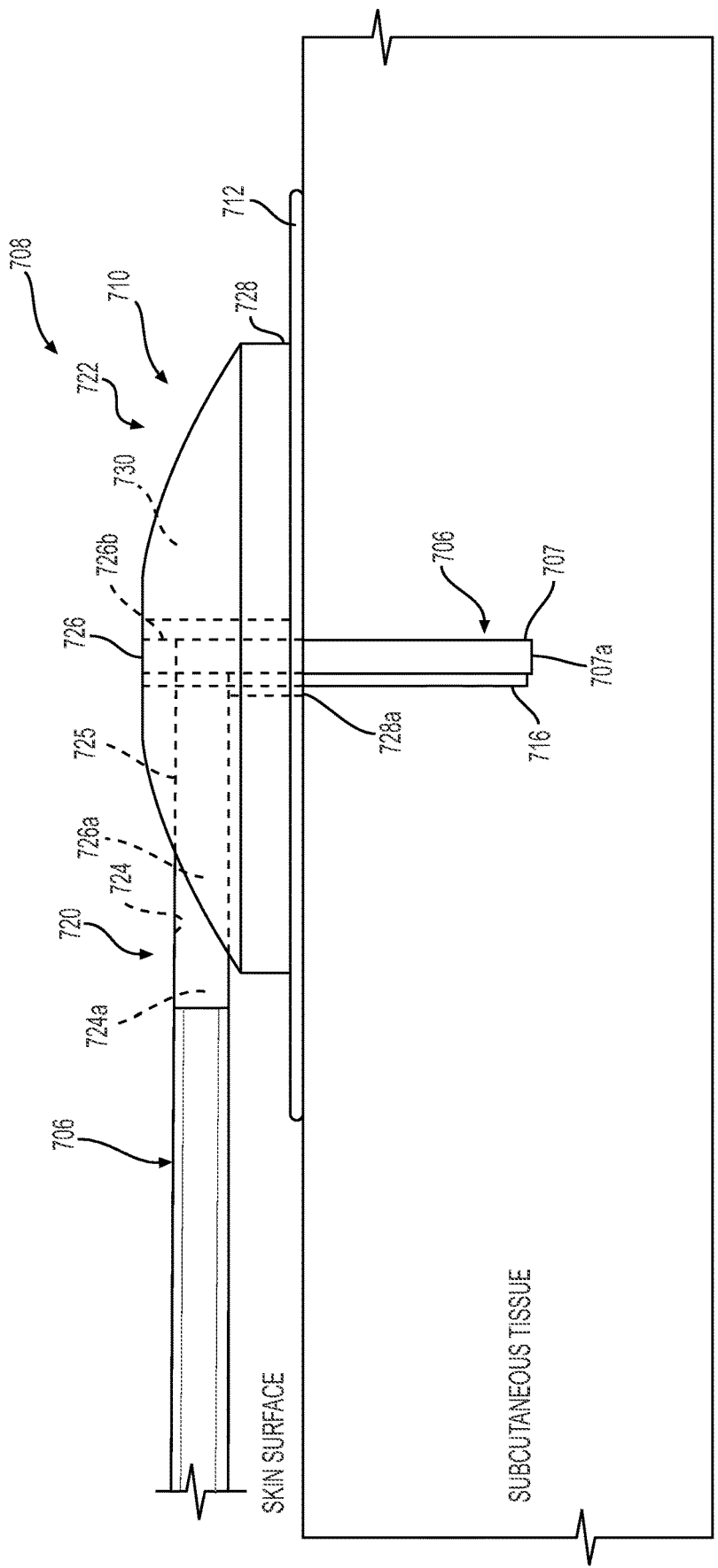
FIG. 41 is a schematic side view of an infusion monitor unit of the infusion set assembly of FIG. 39.

With reference to FIG. 41, the infusion monitor unit 708 is shown in greater detail. The infusion monitor unit 708 includes a housing 710, a coupling member or adhesive patch 712 and a physiological characteristic sensor 716. The housing 710 may be composed of a biocompatible material, including, but not limited to a polymeric material, such as acrylonitrile butadiene styrene (ABS), nylon, an acrylonitrile butadiene styrene polycarbonate blend, polyvinyl chloride, polytetrafluoroethylene (PTFE), polysulfone, polypropylene, polyether ether ketone (PEEK), polycarbonate, polyurethane, silicone, polyethylene terephthalate glycolmodified (PETG) or the like. The housing 710 may be formed through molding, additively manufacturing, etc. The housing 710 comprises a tube connector 720 and a mount 722. The tube connector 720 is coupled to the tube 706 and to the mount 722. The tube connector 720 can have any desired shape and configuration to receive the tube 706 in the infusion monitor unit 708. In the example of FIG. 41, the tube connector 720 is annular and comprises a central bore 724. The central bore 724 defines a passageway 724a, which enables the tube 706 to pass through the tube connector 720 and into a corresponding passageway 725 defined in the mount 722. In this example, the passageways 724a, 725 enable the tube 706 to pass through the tube connector 720 and the mount 722 so that the proximalmost end 707 of the tube 706 may be inserted into the anatomy. The tube 706 can be coupled to the tube connector 720 through any suitable technique, including, but not limited to, press-fit, adhesives, welding, etc.

In some examples, the mount 722 is substantially hemispherical, and includes a first, top mount surface 726 and a second, bottom mount surface 728 opposite the top mount surface 726. Together, the top mount surface 726 and the bottom mount surface 728 enclose a chamber 730. In the example of FIG. 41, the top mount surface 726 is hemispherical and is coupled to the tube connector 720. The top mount surface 726 defines a coupling bore 726a, which is coupled to the tube connector 720 to receive the tube 706. The top mount surface 726 also defines an insertion bore 726b, which is sized to enable an insertion instrument, such as a needle, to be received through the mount 722 to facilitate insertion of the proximalmost end 707 of the tube 706 into the anatomy. The insertion bore 726b is generally sealed with a septum to inhibit fluid flow into and out of the infusion monitor unit 708. The bottom mount surface 728 is coupled to the top mount surface 726 and to the adhesive patch 712. The bottom mount surface 728 defines a bore 728a, through which the tube 706 passes through for insertion into the anatomy. The chamber 730 defines the passageway 725. The passageway 725 receives the tube 706. In this example, the passageway 725 is substantially L-shaped, such that the proximalmost end 707 of the tube 706 extends along an axis that is substantially perpendicular to a remainder of the tube 706.

The adhesive patch 712 is coupled to the bottom mount surface 728 and affixes the infusion monitor unit 708 to an anatomy, such as the skin of the user. The adhesive patch 712 may be covered and protected by a liner. The adhesive patch 712 may be composed of a flexible and breathable material (e.g., a cloth and/or a bandage-like material) with one or more adhesive layers. For example, suitable materials could include polyurethane, polyethylene, polyester, polypropylene, polytetrafluoroethylene (PTFE), or other polymers, to which one or more adhesive layers are applied. Thus, the infusion monitor unit 708 includes the housing 710 that is configured to be adhesively coupled to an anatomy of a user.

In this example, the physiological characteristic sensor 716 is integrated with the tube 706 such that the tube 706 both delivers the fluid from the fluid reservoir 160 and also measures a physiological characteristic (e.g., a glucose level) within the anatomy of the user. It should be noted that the physiological characteristic sensor 716 is not limited to a glucose sensor, but rather, various other physiological characteristic sensors may be employed. In some embodiments, the physiological characteristic sensor 716 is an electrochemical sensor that includes the glucose oxidase enzyme, as is well understood by those familiar with glucose sensor technology. The glucose oxidase enzyme enables the physiological characteristic sensor 716 to monitor glucose levels in a diabetic patient or user by effecting a reaction of glucose and oxygen. Again, although certain embodiments pertain to glucose sensors, the technology described here can be adapted for use with any one of the wide variety of sensors known in the art. In this example, the physiological characteristic sensor 716 is positionable in subcutaneous tissue of the user by the same insertion instrument that inserts the proximalmost end 707 of the tube into the anatomy to measure the glucose oxidase enzyme.

In some examples, the physiological characteristic sensor 716 includes the reference electrode 740, the counter electrode 742 and the working electrode 744. The working electrode 744 may be coated with the glucose oxidase enzyme. The reference electrode 740 maintains a constant voltage to support the reaction at working electrode 744. The counter electrode 742 supplies current to maintain the set potential on the working electrode 744. The electrodes 740, 742, 744 may each be composed of a suitable biocompatible metal or metal alloy, such as copper, platinum, platinum-iridium, silver, gold, etc., and may be extruded. When glucose and oxygen diffuse to the glucose oxidase layer, hydrogen peroxide is formed. Hydrogen peroxide present at the working electrode 744 metallization layer breaks down and generates electrons when a voltage is applied to the working electrode 744. These electrons generates an electrical signal, which is transmitted by the working electrode 744 and communicated to the control module 822 of the fluid infusion device 800, as will be discussed further herein.

As mentioned above, the physiological characteristic sensor 716 can be integrated with the tube 706. However, sensor and tube configurations may vary from implementation to implementation. For example, with reference to FIG. 42, a physiological characteristic sensor (e.g. glucose sensor) 1000 is shown integrated with a tube 1002. Insofar as the physiological characteristic sensor 1000 and the tube 1002 includes the same or similar components as the physiological characteristic sensor 716 and the tube 706 discussed with regard to FIGS. 39-41, the same reference numerals will be used to denote the same or similar components.

Figure 43:
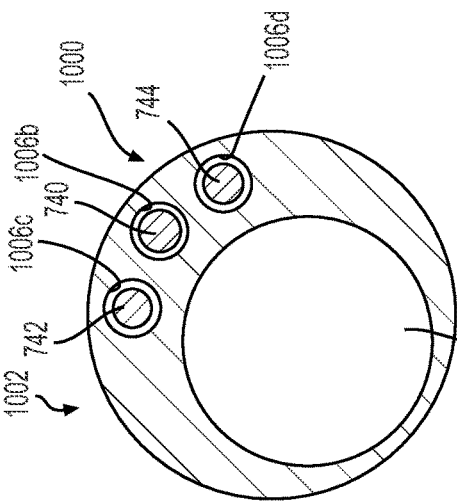
FIG. 43 is a cross-sectional view of the implementation of FIG. 42, taken along line 43-43 of FIG. 42.

The tube 1002 may facilitate a fluidic connection between connector, like the connector 702, and the infusion monitor unit 708, and a proximalmost end 1002a of the tube 1002 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1002. The tube 1002 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane, and may be extruded, molded, cast, additively manufactured, etc. In some examples, the tube 1002 includes a plurality of conduits 1006 and a plurality of windows 1008. With reference to FIG. 43, the plurality of conduits 1006 of the tube 1002 includes a fluid delivery conduit 1006a, a reference electrode conduit 1006b, a counter electrode conduit 1006c and a working electrode conduit 1006d. The fluid delivery conduit 1006a receives the fluid from the fluid reservoir 160 and directs the fluid from the fluid reservoir 160 through the tube 1002. In some examples, with reference back to FIG. 42, the fluid delivery conduit 1006a terminates at a terminal end 1002b of the tube 1002, such that the terminal end 1002b comprises a fluid outlet 1010.

The reference electrode conduit 1006b accommodates the reference electrode 740 associated with the physiological characteristic sensor 1000, and directs the reference electrode 740 through the tube 1002 to a connector, such as the connector 702 of FIG. 39. The counter electrode conduit 1006c accommodates the counter electrode 742 associated with the physiological characteristic sensor 1000, and directs the counter electrode 742 through the tube 1002 to the connector, such as the connector 702 of FIG. 39. The working electrode conduit 1006d accommodates the working electrode 744 associated with the physiological characteristic sensor 1000, and directs the working electrode 744 through the tube 1002 to the connector, such as the connector 702 of FIG. 39.

The plurality of windows 1008 of the tube 1002 includes a reference electrode window 1008*b*, a counter electrode window 1008*c* and a working electrode window 1008*d*. The reference electrode window 1008*b* is defined through an outer surface 1002*c* of the tube 1002, and exposes the reference electrode 740 to interstitial fluid of the user when the proximalmost end 1002*a* of the tube 1002 is inserted into the anatomy. Generally, each of the windows 1008*b*-1008*d* is defined through the outer surface 1002*c* such that the respective electrode 740, 742, 744 is sufficiently exposed to the interstitial fluid. The counter electrode window 1008*c* exposes the counter electrode 742 to interstitial fluid of the user when the proximalmost end 1002*a* of the tube 1002 is inserted into the anatomy. The working electrode window 1008*d* exposes the working electrode 744 to interstitial fluid of the user when the proximalmost end 1002*a* of the tube 1002 is inserted into the anatomy.

Figure 42:
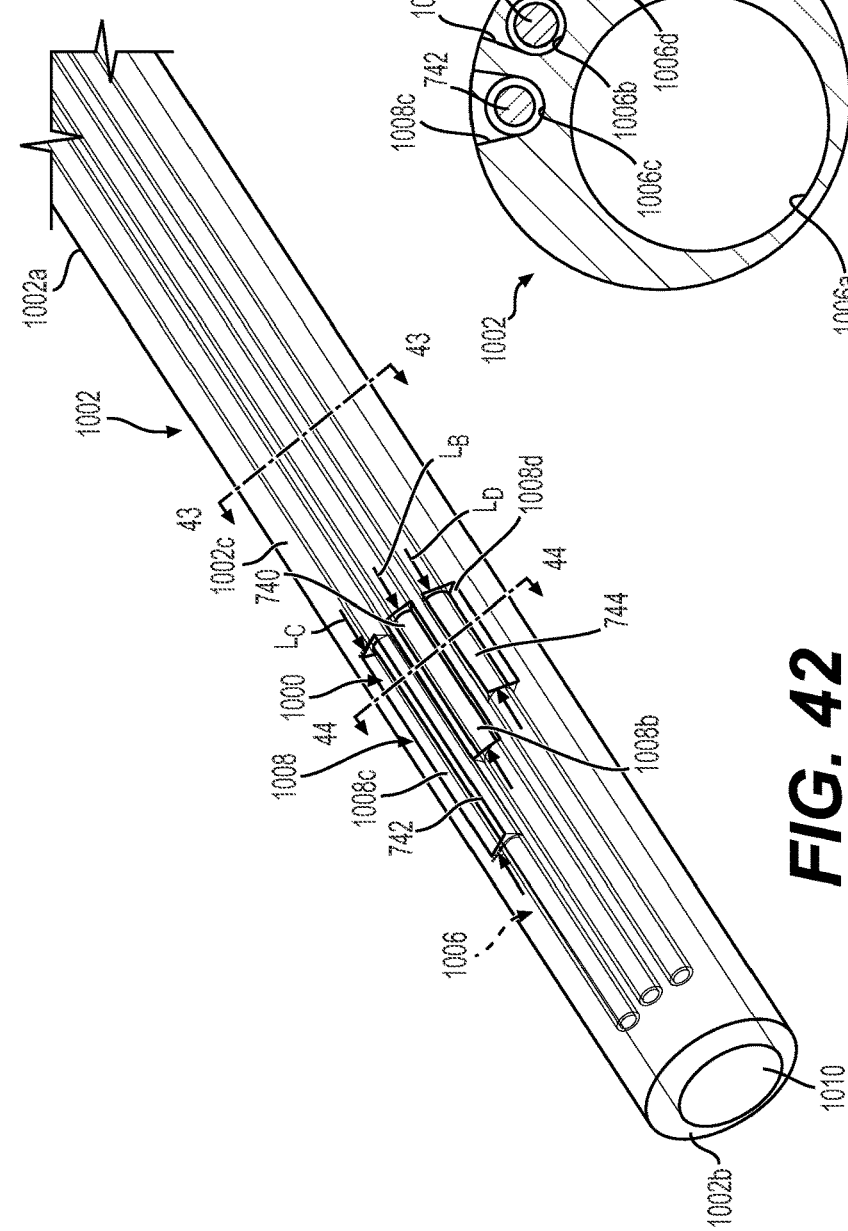
FIG. 42 is a perspective view of an exemplary implementation involving a tube integrated with a physiological characteristic sensor.
Figure 57:
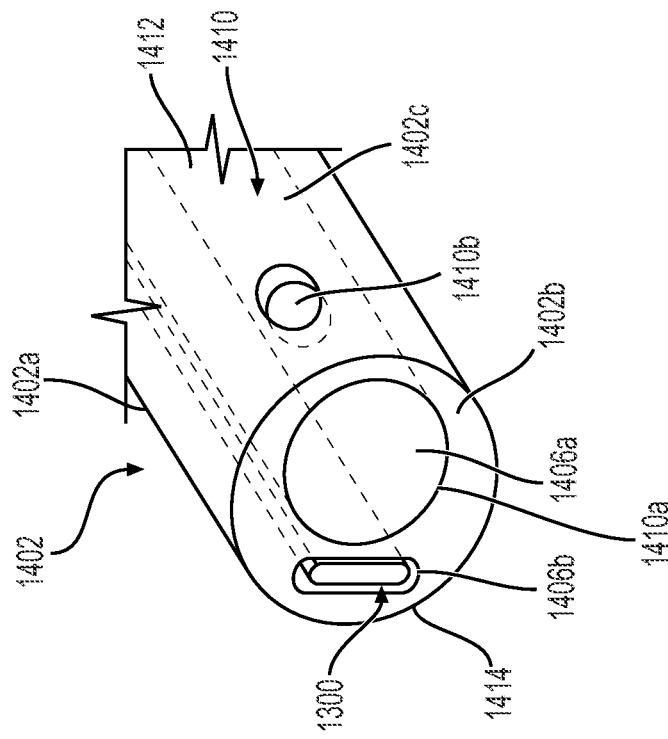
FIG. 57 is a rear perspective view of the implementation of FIG. 56.

In some examples, each of the windows 1008*b*-1008*d* may be defined through the outer surface 1002*c* of the tube 1002 for a different respective length Lb–Ld. In the example of FIG. 42, the length Lc associated with the window 1008*c* is different and greater than the length Lb associated with the window 1008*b* and the length Ld associated with the window 1008*d*. The length Lb is different and greater than the length Ld, and the length Lb is different and less than the length Lc. The length Ld is different and less than the length Lb and the length Lc. In this example, the length Lc is greater than the length Lb and the length Ld to expose more of a surface of the counter electrode 742, which may improve the operation of the physiological characteristic sensor 1000.

In this example, the physiological characteristic sensor 1000 includes the reference electrode 740, the counter electrode 742 and the working electrode 744. The chemical reaction between the glucose and the oxygen at the working electrode 744 generates an electrical signal, which is transmitted by the working electrode 744 and communicated to the control module 822 of the fluid infusion device 800, as will be discussed further herein.

Figure 44:
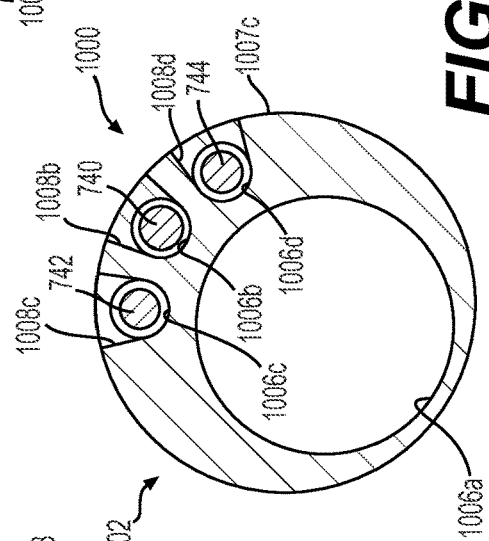
FIG. 44 is a cross-sectional view of the implementation of FIG. 42, taken along line 44-44 of FIG. 42.

It should be noted, however, that other sensor and tube configurations are also contemplated. For example, with reference to FIG. 45, the physiological characteristic sensor 1000 is shown integrated with a tube 1102. Insofar as the physiological characteristic sensor 1000 and the tube 1102 includes the same or similar components as the physiological characteristic sensor 716 and the tube 706 discussed with regard to FIGS. 39-41 and the physiological characteristic sensor 1000 and the tube 1002 discussed with regard to FIGS. 42-44, the same reference numerals will be used to denote the same or similar components.

The tube 1102 may facilitate a fluidic connection between a connector, like the connector 702, and the infusion monitor unit 708, and a proximalmost end 1102*a* of the tube 1102 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1102. The tube 1102 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1102 includes a plurality of conduits 1106 and the plurality of windows 1008.

With reference to FIG. 46, the plurality of conduits 1106 of the tube 1102 includes a fluid delivery conduit 1106*a*, the reference electrode conduit 1006*b*, the counter electrode conduit 1006*c* and the working electrode conduit 1006*d*. The fluid delivery conduit 1106*a* receives the fluid from the fluid reservoir 160 and directs the fluid from the fluid reservoir 160 through the tube 1102. In some embodiments, the tube 1102 may comprise one or more fluid outlets. For example, in FIG. 47, the fluid delivery conduit 1106*a* of the tube 1102 includes a plurality of fluid outlets 1110 defined so as to be spaced apart from a terminal end 1102*b* of the tube 1102. In this example, the terminal end 1102*b* of the tube 1102 is closed, such that the fluid from the fluid reservoir 160 exits the tube 1102 at the fluid outlets 1110. The fluid outlets 1110, in this example, include two circular fluid outlets 1110*a*, 1110*b*; however, in some other examples, the fluid outlets 1110 may include any number of fluid outlets 1110 of any suitable shape. In this example, the fluid outlets 1110*a*, 110*b* are spaced apart from each other and from the terminal end 1102*b*. The fluid outlets 1110*a*, 1110*b* are defined through an outer surface 1102*c* of the tube 1002 to enable fluid delivery to the body of the user via the fluid delivery conduit 1006*a* when the proximalmost end 1102*a* is inserted into the anatomy. In this example, the fluid outlets 1110*a*, 1110*b* are defined through the outer surface 1102*c* on a side 1103 of the tube 1102 that is opposite a side 1105 (FIG. 45) of the tube 1102 that defines the windows 1008. By defining the fluid outlets 1110*a*, 1110*b* on the side 1103 of the tube 1102 opposite the side 1105 with the windows 1008, the dispensing of the fluid is positioned at a location within the anatomy that is different and spaced apart from a location at which the glucose level is being measured, which may improve accuracy of the physiological characteristic sensor 1000.

Referring back to FIG. 46, the reference electrode conduit 1006*b* accommodates the reference electrode 740, the counter electrode conduit 1006*c* accommodates the counter electrode 742, and the working electrode conduit 1006*d* accommodates the working electrode 744 associated with the physiological characteristic sensor 1000. The conduits 1006*b*-1006*d* direct the respective electrodes 740, 742, 744 through the tube 1102 to a connector, such as the connector 702 of FIG. 39. Referring back to FIG. 45, the plurality of windows 1008 of the tube 1002 includes the reference electrode window 1008*b*, the counter electrode window 1008*c* and the working electrode window 1008*d*. The windows 1008*b*-1008*d* are each defined through the outer surface 1102*c* of the tube 1102, and expose the respective electrode 740, 742, 744 to interstitial fluid of the user when the proximalmost end 1102*a* of the tube 1102 is inserted into the anatomy.

In this example, the physiological characteristic sensor 1000 includes the reference electrode 740, the counter electrode 742 and the working electrode 744. The chemical reaction between the glucose and the oxygen at the working electrode 744 generates an electrical signal, which is transmitted by the working electrode 744 and communicated to the control module 822 of the fluid infusion device 800, as will be discussed further herein.

It should be noted, however, that other sensor and tube configurations are also contemplated. For example, with reference to FIG. 48, the physiological characteristic sensor 1000 is shown integrated with a tube 1202. Insofar as the physiological characteristic sensor 1000 and the tube 1202 includes the same or similar components as the physiological characteristic sensor 716 and the tube 706 discussed with regard to FIGS. 39-41, and the physiological characteristic sensor 1000 and the tube 1002 discussed with regard to FIGS. 42-44, the same reference numerals will be used to denote the same or similar components.

The tube 1202 may facilitate a fluidic connection between a connector, like the connector 702, and the infusion monitor unit 708, and a proximalmost end 1202a of the tube 1202 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1202. The tube 1202 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In the example of FIG. 48, the tube 1202 includes a plurality of conduits 1206 and a plurality of windows 1208. The plurality of conduits 1206 of the tube 1202 includes the fluid delivery conduit 1006a, a reference electrode conduit 1206b, a counter electrode conduit 1206c and a working electrode conduit 1206d. In this example, the conduits 1206b-1206d are spaced apart about a perimeter or circumference of the tube 1202, and thus, are spaced apart about a perimeter of the fluid delivery conduit 1006a. The fluid delivery conduit 1006a receives the fluid from the fluid reservoir 160 and directs the fluid from the fluid reservoir 160 through the tube 1202. The fluid delivery conduit 1006a terminates at a terminal end 1202b of the tube 1202, such that the terminal end 1202b includes a fluid outlet 1210.

The reference electrode conduit 1206b accommodates the reference electrode 740 associated with the physiological characteristic sensor 1000, and directs the reference electrode 740 through the tube 1202 to a connector, such as the connector 702 of FIG. 39. The counter electrode conduit 1206c accommodates the counter electrode 742 associated with the physiological characteristic sensor 1000, and directs the counter electrode 742 through the tube 1202 to the connector, such as the connector 702 of FIG. 39. The working electrode conduit 1206d accommodates the working electrode 744 associated with the physiological characteristic sensor 1000, and directs the working electrode 744 through the tube 1202 to the connector, such as the connector 702 of FIG. 39.

The plurality of windows 1208 of the tube 1202 includes a reference electrode window 1208b, a counter electrode window 1208c and a working electrode window 1208d. The reference electrode window 1208b is defined through an outer surface 1202c of the tube 1202, and exposes the reference electrode 740 to interstitial fluid of the user when the proximalmost end 1202a of the tube 1202 is inserted into the anatomy. Generally, each of the windows 1208b-1208d is defined through the outer surface 1202c such that the respective electrode 740, 742, 744 is sufficiently exposed to the interstitial fluid. The counter electrode window 1208c exposes the counter electrode 742 to interstitial fluid of the user when the proximalmost end 1202a of the tube 1202 is inserted into the anatomy. The working electrode window 1208d exposes the working electrode 744 to interstitial fluid of the user when the proximalmost end 1202a of the tube 1202 is inserted into the anatomy. Each of the windows 1208b-1208d may be defined through the outer surface 1202c of the tube 1202 for a respective length Le. In this example, each of the windows 1208b-d has the same length Le.

The physiological characteristic sensor 1000 includes the reference electrode 740, the counter electrode 742 and the working electrode 744. The chemical reaction between the glucose and the oxygen at the working electrode 744 generates an electrical signal, which is transmitted by the working electrode 744 and communicated to the control module 822 of the fluid infusion device 800, as will be discussed further herein.

It should be noted, however, that other sensor and tube configurations are also contemplated. For example, with reference to FIGS. 49-52, the physiological characteristic sensor 1000 is shown being integrated with a tube 1249. Insofar as the physiological characteristic sensor 1000 and the tube 1249 includes the same or similar components as the physiological characteristic sensor 716 and the tube 706 discussed with regard to FIGS. 39-41, the physiological characteristic sensor 1000 and the tube 1002 discussed with regard to FIGS. 42-44, the same reference numerals will be used to denote the same or similar components.

In the example of FIG. 50, the tube 1249 facilitates a fluidic connection between a connector, like the connector 702, and the infusion monitor unit 708, and the proximalmost end 1249a of the tube 1249 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1249. The physiological characteristic sensor 1000 is to be integrated with the tube 1249 to measure a glucose level of the user. In this example, the physiological characteristic sensor 1000 is to be integrated with the tube 1249 about its perimeter such that the insertion of the proximalmost end 1249a of the tube 1249 into the anatomy also inserts the physiological characteristic sensor 1000. In this example, the proximalmost end 1249a of the tube 1249 is shown, along with the reference electrode 740, the counter electrode 742 and the working electrode 744. The reference electrode 740, the counter electrode 742 and the working electrode 744 are spaced apart about the perimeter of the tube 306. With reference to FIG. 51, a heat shrink tube 1250 is disposed about the tube 1249, the reference electrode 740, the counter electrode 742 and the working electrode 744. The heat shrink tube 1250 may be composed of any suitable polymer-based material, which is capable of contracting (shrinking) upon heating from a first large diameter (FIG. 51) to a second, reduced diameter (FIG. 49). It should be noted that a heat shrink wrap may be used in place of the heat shrink tube 1250, and moreover, while the heat shrink tube 1250 is only shown surrounding the proximalmost end 1249a of the tube 1249, the heat shrink tube 1250 may be employed along the length of the tube 1249 to integrate the physiological characteristic sensor 1000 with the tube 1249 between the connector 702 and the proximalmost end 1249a.

With reference to FIG. 49, once heat is applied to the heat shrink tube 1250, the heat shrink tube 1250 contracts to integrate the physiological characteristic sensor 1000 with the tube 1249. As shown in FIG. 52, the heat shrink tube 1250 couples the reference electrode 740, the counter electrode 742 and the working electrode 744 about the perimeter of the tube 1249. In this example, the heat shrink tube 1250 does not cover ends 745 of the reference electrode 740, the counter electrode 742 and the working electrode 744 such that the ends 745 of the reference electrode 740, the counter electrode 742 and the working electrode 744 are exposed to the interstitial fluid to measure the glucose level of the user. As discussed, the chemical reaction between the glucose and the oxygen at the working electrode 744 generates an electrical signal, which is transmitted by the working electrode 744 and communicated to the control module 822 of the fluid infusion device 800, as will be discussed further herein.

It should be noted, however, that other sensor and tube configurations are also contemplated. For example, with reference to FIG. 53, a physiological characteristic sensor (e.g. a glucose sensor) 1300 is shown proximate to but uncoupled with a tube 1301. As the physiological characteristic sensor 1300 and the tube 1301 includes the same or similar components as the physiological characteristic sensor 716 and the tube 706 discussed with regard to FIGS. 39-41, the physiological characteristic sensor 1000 and the tube 1249 discussed with regard to FIGS. 49-52, the same reference numerals will be used to denote the same or similar components.

The tube 1301 facilitates a fluidic connection between a connector, like the connector 702, and the infusion monitor unit 708, and the proximalmost end 1301a of the tube 1301 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1301. The physiological characteristic sensor 1300 is positioned proximate to the proximalmost end 1301a of the tube 1301 to measure a glucose level of the user. In the example of FIG. 54, the physiological characteristic sensor 1300 is proximate to the proximalmost end 1301a of the tube 1301 such that the insertion of the proximalmost end 1301a of the tube 1301 into the anatomy with a hollow needle 1304 also inserts the physiological characteristic sensor 1300 into the anatomy. Referring back to the example of FIG. 53, the proximalmost end 1301a of the tube 1301 is shown, along with the physiological characteristic sensor 1300. The physiological characteristic sensor 1300 is uncoupled with the tube 1301 so as to be free floating relative to the tube 1301 once inserted into the anatomy. Generally, the physiological characteristic sensor 1300 is sized such that an end 1300a of the physiological characteristic sensor 1300 is spaced a distance D13 apart from a terminal end 1301b of the tube 1301. The terminal end 1301b includes a fluid outlet 1301d (FIG. 55). By spacing the end 1300a of the physiological characteristic sensor 1300 away from the fluid outlet 1301d of the tube 1301, the accuracy of the physiological characteristic sensor 1300 may be improved as the measurement of the glucose level and the delivery of fluid or insulin are performed at different locations.

The physiological characteristic sensor 1300 may be is flexible. In the example of FIG. 55, the physiological characteristic sensor 1300 includes a reference electrode 1306, a counter electrode 1308 and a working electrode 1310, which are physically and electrically coupled to a flexible substrate 1312. The working electrode 1310 may be coated with the glucose oxidase enzyme. The reference electrode 1306 maintains a constant voltage to support the reaction at working electrode 1310. The counter electrode 1308 supplies current to maintain the set potential on the working electrode 1310. The electrodes 1306, 1308, 1310 may each be composed of a suitable biocompatible metal or metal alloy, such as copper, platinum, platinum-iridium, silver, gold, etc., and may be extruded. When glucose and oxygen diffuse to the glucose oxidase layer, hydrogen peroxide is formed. Hydrogen peroxide present at the working electrode 1310 metallization layer breaks down and generates electrons when a voltage is applied to the working electrode 1310. These electrons generates an electrical signal, which is transmitted by the working electrode 1310 and communicated to the control module 822 of the fluid infusion device 800, as will be discussed further herein. The substrate 1312 may be flexible, and is composed of a suitable biocompatible polymeric based material, including, but not limited to polyethylene (PE), polyurethane (PU), polyether block amide (PEBA), Nylon, polyester, polyether ether ketone (PEEK), polyimide, polypropylene and silicone.

In order to deploy the tube 1301 and the physiological characteristic sensor 1300, the infusion monitor unit 708 may be pre-packaged with an insertion instrument, such as the needle 1304 (FIG. 54) enveloping or surrounding the physiological characteristic sensor 1300 and the tube 1301. Once the infusion monitor unit 708 is coupled to the anatomy, via the insertion instrument, the needle 1304 can be retracted, leaving the physiological characteristic sensor 1300 and the tube 1301 inserted into the anatomy. In the example of FIG. 55, the physiological characteristic sensor 1300 is positioned proximate to the tube 1301 such that the electrodes 1306, 1308, 1310 face away from the tube 1301.

It should be noted, however, that other sensor and tube configurations are also contemplated. For example, with reference to FIG. 56, the physiological characteristic sensor 1300 is shown integrated within a tube 1402. Insofar as the physiological characteristic sensor 1300 and the tube 1402 includes the same or similar components as the physiological characteristic sensor 716 and the tube 706 discussed with regard to FIGS. 39-41, the physiological characteristic sensor 1000 and the tube 1102 discussed with regard to FIGS. 45-47, and the physiological characteristic sensor 1300 discussed with regard to FIGS. 53-55, the same reference numerals will be used to denote the same or similar components.

The tube 1402 may facilitate a fluidic connection between a connector, like the connector 702, and the infusion monitor unit 708, and a proximalmost end 1402a of the tube 1402 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1402. The tube 1402 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1402 includes a plurality of conduits 1406 and a window 1408.

The plurality of conduits 1406 of the tube 1402 includes a fluid delivery conduit 1406a and a sensor conduit 1406b. The fluid delivery conduit 1406a receives the fluid from the fluid reservoir 160 and directs the fluid from the fluid reservoir 160 through the tube 1402. In some embodiments, the fluid delivery conduit 1406a includes one or more fluid outlets 1410. For example, the fluid delivery conduit 1406a includes a plurality of fluid outlets 1410. The plurality of fluid outlets 1410 includes a first fluid outlet 1410a and a second fluid outlet 1410b. In this example, the terminal end 1402b of the tube 1402 includes the fluid outlet 1410a, and the fluid outlet 1410b is defined through an outer surface 1402c of the tube 1402 and connected to the fluid delivery conduit 1406a. The fluid outlet 1410b is defined so as to be spaced apart from a terminal end 1402b of the tube 1402. The fluid from the fluid reservoir 160 exits the tube 1402 at the fluid outlet 1410b and at the fluid outlet 1410a at the terminal end 1402b. The fluid outlets 1410, in this example, include two circular fluid outlets 1410a, 1410b; however, in some other examples, the fluid outlets 1410 may include any number of fluid outlets 1410 of any shape. In this example, the fluid outlets 1410a, 1410b are spaced apart from each other. In this example, the fluid outlet 1410b is defined through the outer surface 1402c on a side 1412 of the tube 1402 that is opposite a side 1414 of the tube 1402 in which the window 1408 is defined. By defining the fluid outlet 1410b on the side 1412 of the tube 1402 opposite the side 1414 with the window 1008, the dispensing of the fluid is positioned at a location within the anatomy that is different and spaced apart from a location at which the glucose level is being measured, which may improve accuracy of the physiological characteristic sensor 1300.

Figure 56:
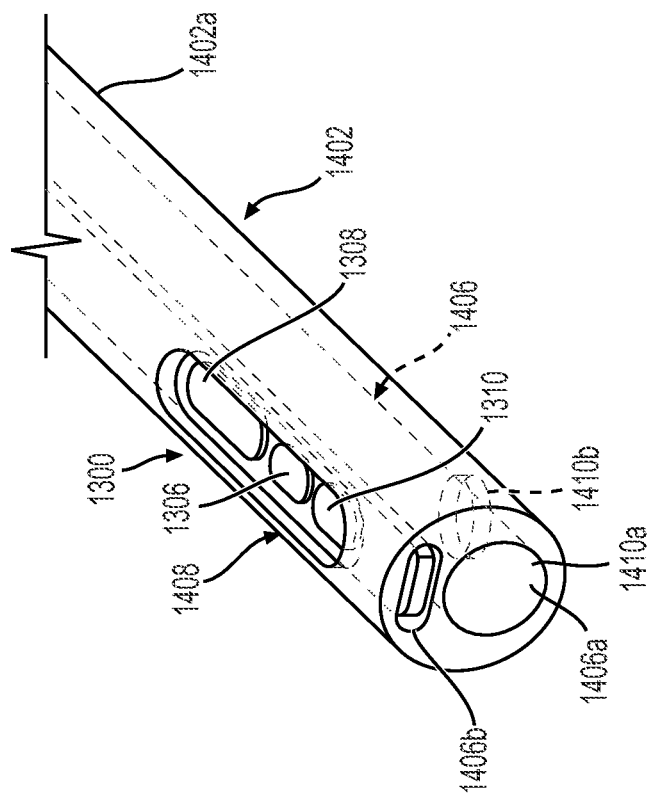
FIG. 56 is a front perspective view of another exemplary implementation involving a tube integrated with a physiological characteristic sensor.

Referring back to the example of FIG. 56, the window 1408 of the tube 1402 is defined through the outer surface 1402c of the tube 1402, and exposes the electrodes 1306, 1308, 1310 of the physiological characteristic sensor 1300 to the interstitial fluid of the user when the proximalmost end 1402a of the tube 1202 is inserted into the anatomy. The window 1408 is defined through the outer surface 1402c to expose the electrodes 1306, 1308, 1310 to the interstitial fluid. Thus, the electrodes 1306, 1308, 1310 face the window 1408, and face away from the fluid outlet 1410b.

In this example, the physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein.

Figure 58:
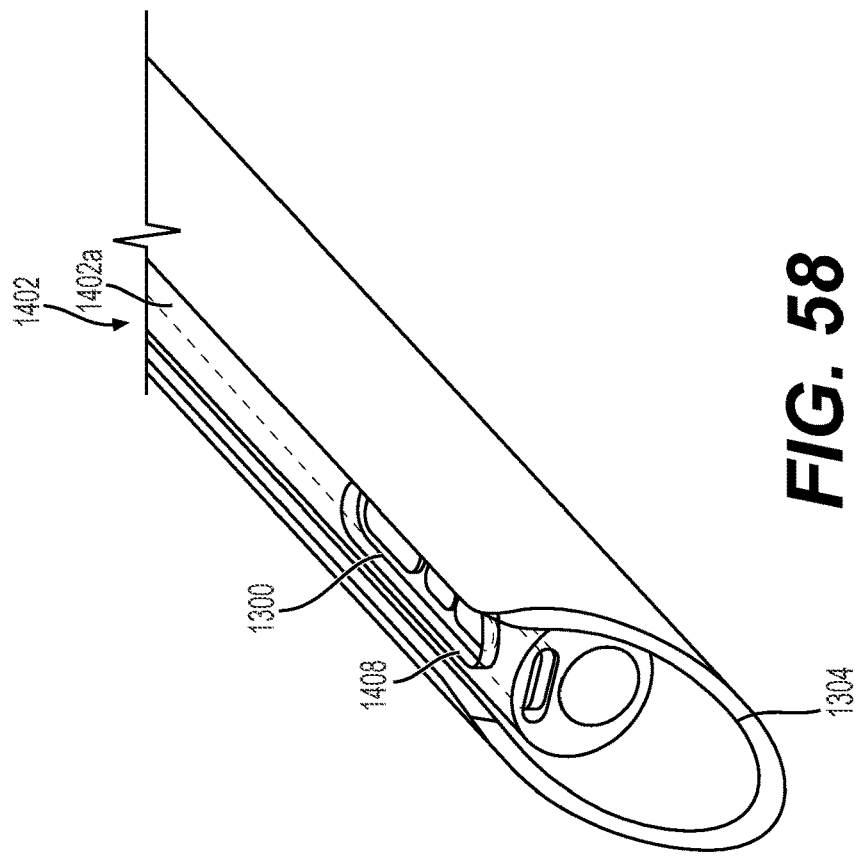
FIG. 58 is a perspective view of the implementation of FIG. 56, in which the tube and the sensor are at least partially enveloped within a needle.

In order to deploy the tube 1402 and the physiological characteristic sensor 1300, the infusion monitor unit 708 may be pre-packaged with an insertion instrument, such as the needle 1304 of FIG. 58. The needle 1304 envelops or surrounds the tube 1402, which includes the physiological characteristic sensor 1300. Once the infusion monitor unit 708 is coupled to the anatomy, via the insertion instrument, the needle 1304 can be retracted, leaving the physiological characteristic sensor 1300 and the tube 1402 inserted into the anatomy.

Figure 59:
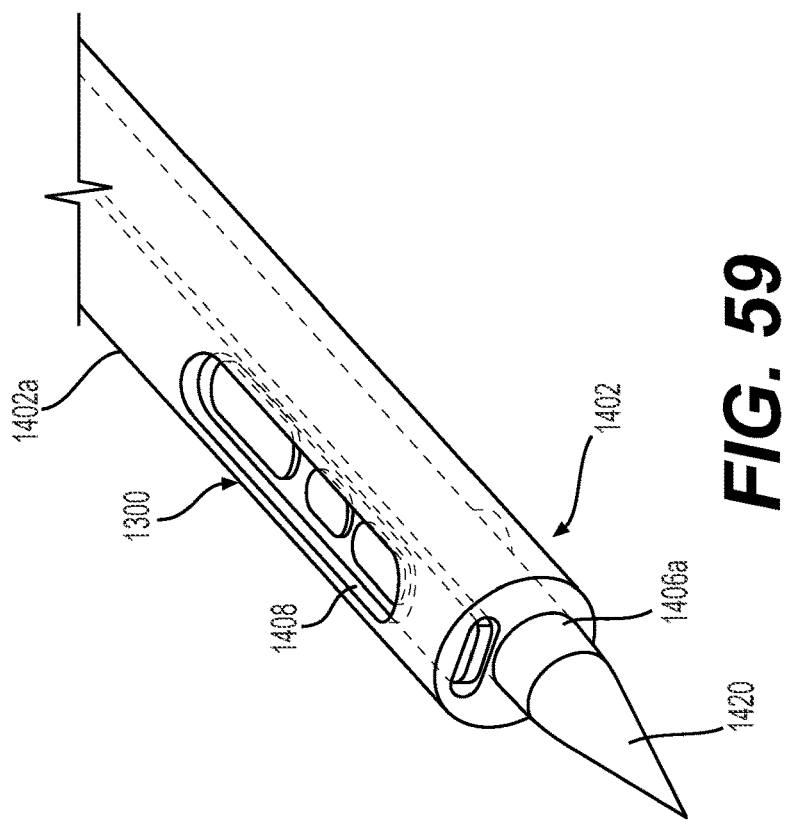
FIG. 59 is a perspective view of the implementation of FIG. 56, in which a solid needle is extended through the tube.

Alternatively, in order to deploy the tube 1402 and the physiological characteristic sensor 1300, the infusion monitor unit 708 may be pre-packaged with an insertion instrument, such as a closed tip needle 1420 (FIG. 59) that extends through the fluid delivery conduit 1406a and exits at the proximalmost end 1402a of the tube 1402. The proximalmost end 1402a of the tube 1402 may include an access opening, which may be sealed by a septum within the infusion monitor unit 708, to seal the opening once the needle 1420 is removed. The needle 1420 may be inserted through the proximalmost end 1402a of the tube 1402. Once the infusion monitor unit 708 is coupled to the anatomy, via the insertion instrument, the needle 1420 can be retracted, leaving the physiological characteristic sensor 1300 and the tube 1402 inserted into the anatomy.

Figure 60:
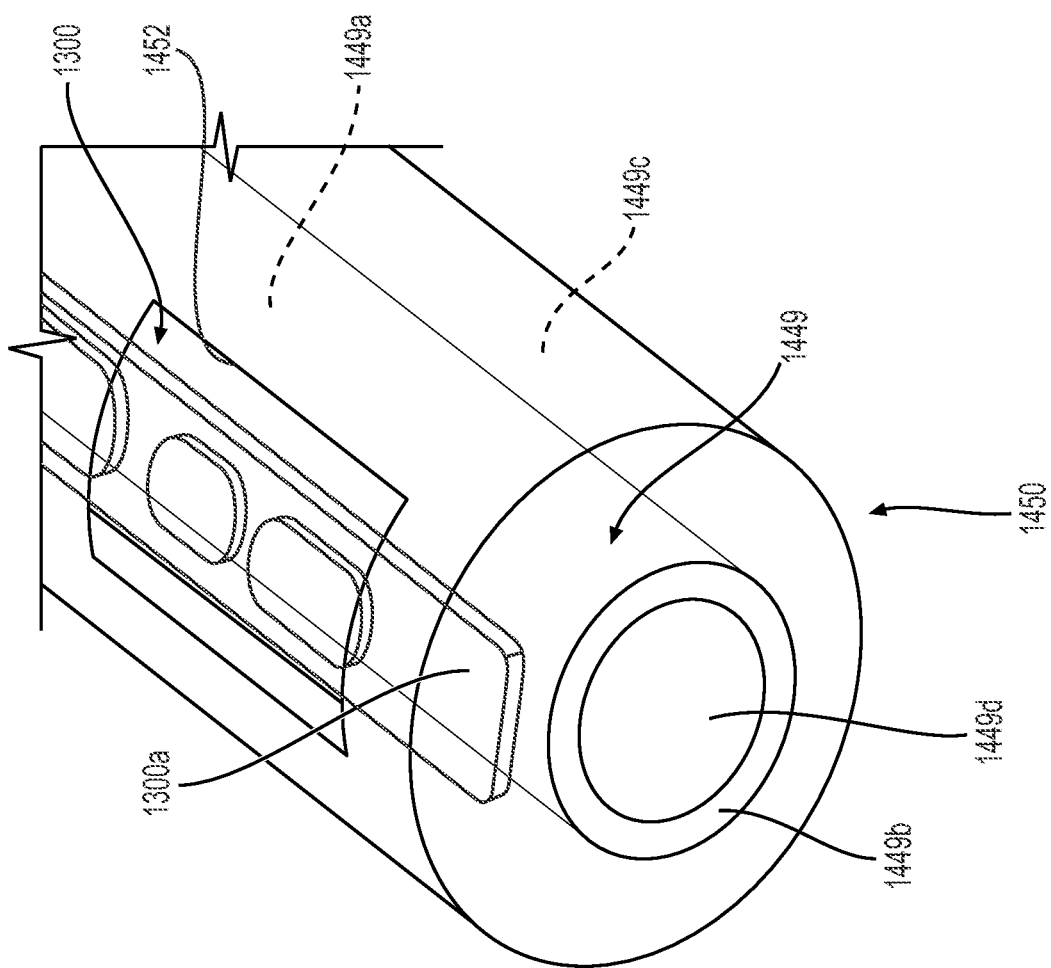
FIG. 60 depicts an exemplary heat shrink tube for integrating a tube with a physiological characteristic sensor.

It should be noted, however, that other sensor and tube configurations are also contemplated. For example, with reference to FIG. 60, the physiological characteristic sensor 1300 is shown integrated with a tube 1449. As the physiological characteristic sensor 1300 and the tube 1449 includes the same or similar components as the physiological characteristic sensor 716 and the tube 706 discussed with regard to FIGS. 39-41, the physiological characteristic sensor 1000 and the tube 1002 discussed with regard to FIGS. 42-44, and the physiological characteristic sensor 1300 discussed with regard to FIGS. 53-55, the same reference numerals will be used to denote the same or similar components.

The tube 1449 may facilitate a fluidic connection between a connector, like the connector 702, and the infusion monitor unit 708, and the proximalmost end 1449a of the tube 1449 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1449. The physiological characteristic sensor 1300 is to be integrated with the proximalmost end 1449a of the tube 1449 to measure a glucose level of the user. In this example, the physiological characteristic sensor 1300 is to be integrated with the tube 1449 along an outer surface 1449c such that the insertion of the proximalmost end 1449a of the tube 1449 into the anatomy also inserts the physiological characteristic sensor 1300. In this example, the proximalmost end 1449a of the tube 1449 is shown, along with the physiological characteristic sensor 1300. A heat shrink tube 1450 is disposed about the tube 1449 and the physiological characteristic sensor 1300. The heat shrink tube 1450 may be composed of any suitable polymer-based material, which is capable of contracting (shrinking) upon heating from a first large diameter to a second, reduced diameter. It should be noted that a heat shrink wrap may be used in place of the heat shrink tube 1450, and moreover, while the heat shrink tube 1450 is only shown surrounding the proximalmost end 1449a of the tube 1449, the heat shrink tube 1450 may be employed along the length of the tube 1449 to integrate the physiological characteristic sensor 1300 with the tube 1449 between the connector 702 and the proximalmost end 1449a. In this example, the heat shrink tube 1450 defines a window 1452, which enables the electrodes 1306, 1308, 1310 of the physiological characteristic sensor 1300 to contact the interstitial fluid when the proximalmost end 1449a is inserted into the anatomy. The window 1452 is defined through the heat shrink tube 1450 with a length sufficient enough to expose each of the electrodes 1306, 1308, 1310. Generally, the physiological characteristic sensor 1300 is sized such that the end 1300a of the physiological characteristic sensor 1300 is spaced a distance apart from a terminal end 306b of the tube 306. The terminal end 1449b defines the fluid outlet 1449d. By spacing the end 1300a of the physiological characteristic sensor 1300 away from the fluid outlet 1449d of the tube 1449, the accuracy of the physiological characteristic sensor 1300 may be improved as the measurement of the blood glucose level is spaced apart from the delivered fluid or insulin.

Once heat is applied to the heat shrink tube 1450, the heat shrink tube 1450 contracts to integrate the physiological characteristic sensor 1300 with the tube 1449 while leaving the electrodes 1306, 1308, 1310 exposed to the interstitial fluid to measure the blood glucose level of the user. The heat shrink tube 1450 couples the physiological characteristic sensor 1300 to the perimeter of the tube 1449. The chemical reaction between the glucose and the oxygen at the working electrode 1310 generates an electrical signal, which is transmitted by the working electrode 1310 and communicated to the control module 822 of the fluid infusion device 800, as will be discussed further herein.

It should be noted, however, that other sensor and tube configurations are also contemplated. For example, with reference to FIG. 61, the physiological characteristic sensor 1300 is shown integrated within a tube 1502. As the physiological characteristic sensor 1300 and the tube 1502 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1402 discussed with regard to FIGS. 56-59, the same reference numerals will be used to denote the same or similar components.

The tube 1502 may facilitate a fluidic connection between a connector, like the connector 702, and the infusion monitor unit 708, and a proximalmost end 1502*a* of the tube 1502 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1502. The tube 1502 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1502 includes a plurality of conduits 1506 and a window 1508. The tube 1502 also includes a beveled surface 1510 at a terminal end 1502*b* for ease of insertion into the anatomy.

With reference to FIG. 62, the plurality of conduits 1506 of the tube 1502 includes a fluid delivery conduit 1506*a* and an electrode conduit 1506*b*. The fluid delivery conduit 1506*a* receives the fluid from the fluid reservoir 160 and directs the fluid from the fluid reservoir 160 through the tube 1502. In some examples, the fluid delivery conduit 1506*a* includes at least one fluid outlet 1512. In this example, the terminal end 1502*b* of the tube 1502 is opened to define the fluid outlet 1512. The fluid from the fluid reservoir 160 exits the tube 1502 at the fluid outlet 1512 at the terminal end 1502*b*. In this example, the fluid outlet 1512 is circular. In this example, the fluid outlet 1512 is defined at the terminal end 1502*b* to be spaced a distance apart from the physiological characteristic sensor 1300. By spacing the fluid outlet 1512 from the physiological characteristic sensor 1300, the dispensing of the fluid is positioned at a location within the anatomy that is different and spaced apart from a location at which the blood glucose level is being measured, which may improve accuracy of the physiological characteristic sensor 1300. The electrode conduit 1506*b* accommodates the physiological characteristic sensor 1300. In this example, the electrode conduit 1506*b* is oval shaped, however, the electrode conduit 1506*b* may have any desired shape.

With reference to FIG. 63, the window 1508 of the tube 1502 is defined through the outer surface 1502*c* of the tube 1502, and exposes the electrodes 1306, 1308, 1310 of the physiological characteristic sensor 1300 to the interstitial fluid of the user when the proximalmost end 1502*a* of the tube 1502 is inserted into the anatomy. The window 1508 may be defined via laser cutting, for example. Generally, the window 1508 is defined through the outer surface 1502*c* to expose the respective electrode 1306, 1308, 1310 to the interstitial fluid. Thus, the electrodes 1306, 1308, 1310 face the window 1508 to measure the blood glucose level of the user.

In this example, the physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein. In some examples, an end 1300*a* (FIG. 62) of the physiological characteristic sensor 1300 may be coupled to the electrode conduit 1506*b* to further secure the physiological characteristic sensor 1300 within the electrode conduit 1506*b*, via adhesives, heat bonding, etc.

In order to deploy the tube 1502 and the physiological characteristic sensor 1300, the infusion monitor unit 708 may be pre-packaged with an insertion instrument, such as a needle 1514. The needle 1514 extends through the fluid delivery conduit 1506*a* and exits at the proximalmost end 1502*a* of the tube 1502. In this example, the proximalmost end 1502*a* of the tube 1502 may include an access opening, which may be sealed by a septum within the infusion monitor unit 708, to seal the opening once the needle 1514 is removed. Once the infusion monitor unit 708 is coupled to the anatomy, via the insertion instrument, the needle 1514 can be retracted, leaving the physiological characteristic sensor 1300 and the tube 1502 inserted into the anatomy. In some examples, the needle 1514 is a 26 gauge needle, however, other sizes may be employed that correspond to the fluid delivery conduit 1506*a*.

Alternatively, with reference to FIG. 64, in order to deploy the tube 1502 and the physiological characteristic sensor 1300, the infusion monitor unit 708 may be prepackaged with an insertion instrument, such as a half needle 1530 that extends through the fluid delivery conduit 1506*a* and exits at the proximalmost end 1502*a* of the tube 1502. In this example, the proximalmost end 1502*a* of the tube 1502 may include an access opening, which may be sealed by a septum within the infusion monitor unit 708, to seal the opening once the needle 1520 is removed. With reference to FIG. 65, the use of the half needle 1530 (which is the needle 1514 cut in half) enables a diameter of the fluid delivery conduit 1506*a* to be reduced, which results in the tube 1502 having a smaller diameter than that shown in FIGS. 61-63. The needle 1530 is inserted through the proximalmost end 1502*a* of the tube 1502 as shown in FIG. 66. Once the infusion monitor unit 708 is coupled to the anatomy, via the insertion instrument, the needle 1530 can be retracted, leaving the physiological characteristic sensor 1300 and the tube 1502 inserted into the anatomy.

It should be noted, however, that other sensor and tube configurations are also contemplated. For example, with reference to FIGS. 67 and 68, the physiological characteristic sensor 1300 is shown integrated within a tube 1552. As the physiological characteristic sensor 1300 and the tube 1552 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1502 discussed with regard to FIGS. 61-66, the same reference numerals will be used to denote the same or similar components.

The tube 1552 may facilitate a fluidic connection between a connector, like the connector 702, and the infusion monitor unit 708, and a proximalmost end 1552a of the tube 1552 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1552. The tube 1552 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1552 includes a plurality of conduits 1556 and a window 1558.

With reference to FIG. 68, the plurality of conduits 1556 of the tube 1552 includes a fluid delivery conduit 1556a and an electrode conduit 1556b. The fluid delivery conduit 1556a receives the fluid from the fluid reservoir 160 and directs the fluid from the fluid reservoir 160 through the tube 1552. In some examples, the fluid delivery conduit 1556a includes at least one fluid outlet 1562. In this example, the terminal end 1552b of the tube 1552 is opened to define the fluid outlet 1562. The fluid from the fluid reservoir 160 exits the tube 1552 at the fluid outlet 1562 at the terminal end 1552b. In this example, the fluid outlet 1562 is oval shaped, and has a major diameter MD that is different and less than a major diameter MD2 of the electrode conduit 1556b. The minor diameter of the fluid delivery conduit 1556a is also different, and less than, the minor diameter of the electrode conduit 1556b. In this example, the fluid outlet 1562 is defined at the terminal end 1552b to be spaced a distance apart from the physiological characteristic sensor 1300. By spacing the fluid outlet 1562 from the physiological characteristic sensor 1300, the dispensing of the fluid is positioned at a location within the anatomy that is different and spaced apart from a location at which the glucose level is being measured, which may improve accuracy of the physiological characteristic sensor 1300. The electrode conduit 1556b accommodates the physiological characteristic sensor 1300. In this example, the electrode conduit 1556b is oval shaped, however, the electrode conduit 1556b may have any desired shape. In this example, the use of the oval shape for the conduits 1556a, 1556b reduces a size of the tube 1552 so that it is substantially contained within a needle 1564 (FIG. 69).

With reference to FIG. 67, the window 1558 of the tube 1552 is defined through the outer surface 1552c of the tube 1552, and exposes the electrodes 1306, 1308, 1310 of the physiological characteristic sensor 1300 to the interstitial fluid of the user when the proximalmost end 1552a of the tube 1552 is inserted into the anatomy. The window 1558 may be defined via laser cutting, for example. Generally, the window 1558 is defined through the outer surface 1552c to expose the electrodes 1306, 1308, 1310 to the interstitial fluid. Thus, the electrodes 1306, 1308, 1310 face the window 1558 to measure the blood glucose level of the user and are positioned on a side of the tube 1552 that is opposite the fluid delivery conduit 1556a.

In this example, the physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein. In some examples, an end 1300a (FIG. 68) of the physiological characteristic sensor 1300 may be coupled to the electrode conduit 1556b to further secure the physiological characteristic sensor 1300 within the electrode conduit 1556b, via adhesives, heat bonding, etc.

In order to deploy the tube 1552 and the physiological characteristic sensor 1300, the infusion monitor unit 708 may be pre-packaged with an insertion instrument, such as a needle 1564. The needle 1564 surrounds the tube 1552, which includes the physiological characteristic sensor 1300. Once the infusion monitor unit 708 is coupled to the anatomy, via the insertion instrument, the needle 1564 can be retracted, leaving the physiological characteristic sensor 1300 and the tube 1552 inserted into the anatomy as shown in FIG. 67.

It should be noted, however, that other sensor and tube configurations are also contemplated. For example, with reference to FIG. 70, the physiological characteristic sensor 1300 is shown integrated within a tube 1602. As the physiological characteristic sensor 1300 and the tube 1602 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1502 discussed with regard to FIGS. 61-66, the same reference numerals will be used to denote the same or similar components.

The tube 1602 may facilitate a fluidic connection between a connector, like the connector 702, and the infusion monitor unit 708, and a proximalmost end 1602a of the tube 1602 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1602. The tube 1602 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1602 includes a plurality of conduits 1606 and a window 1608.

Figure 71:
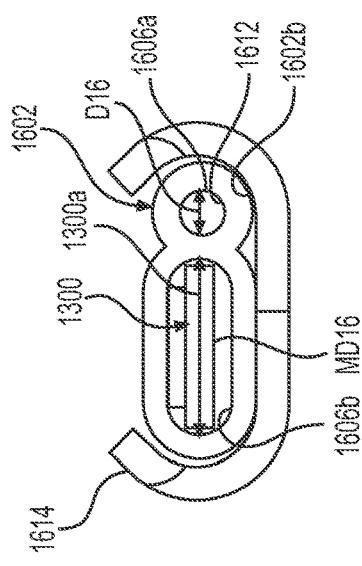
FIG. 71 is an end view of the implementation of FIG. 70.

With reference to FIG. 71, the plurality of conduits 1606 of the tube 1602 includes a fluid delivery conduit 1606a and an electrode conduit 1606b. The fluid delivery conduit 1606a receives the fluid from the fluid reservoir 160 and directs the fluid from the fluid reservoir 160 through the tube 1602. In some examples, the fluid delivery conduit 1606a includes at least one fluid outlet 1612. In this example, the terminal end 1602b of the tube 1602 is circumferentially opened to define the fluid outlet 1612. The fluid from the fluid reservoir 160 exits the tube 1602 at the fluid outlet 1612 at the terminal end 1602b. In this example, the fluid outlet 1612 is circular, and has a diameter D16 that is different and less than a major diameter MD16 of the electrode conduit 1606b. In this example, the fluid outlet 1612 is defined at the terminal end 1602b to be spaced a distance apart from the physiological characteristic sensor 1300. By spacing the fluid outlet 1612 from the physiological characteristic sensor 1300, the dispensing of the fluid is positioned at a location within the anatomy that is different and spaced apart from a location at which the blood glucose level is being measured, which may improve accuracy of the physiological characteristic sensor 1300. The electrode conduit 1606b accommodates the physiological characteristic sensor 1300 and is positioned along a side of the fluid delivery conduit 1606a. In this example, the electrode conduit 1606b is oval shaped, however, the electrode conduit 1606b may have any desired shape. In this example, the use of the oval shape for the electrode conduit 1606b reduces a size of the tube 1602 so that it is substantially contained within a needle 1614.

Figure 70:
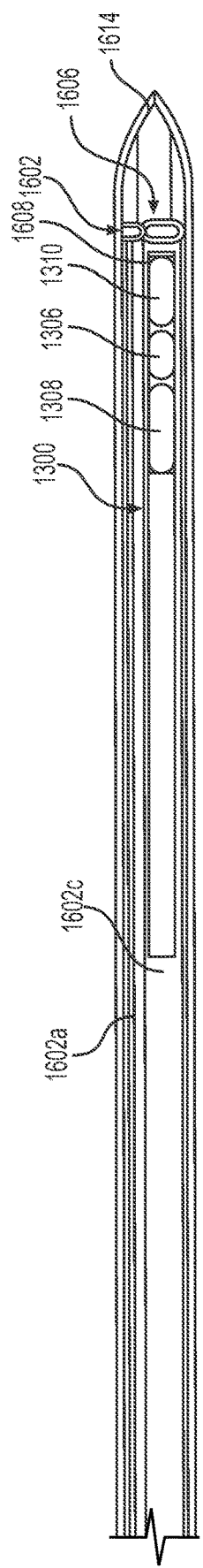
FIG. 70 is a top view of an exemplary implementation involving a tube and a physiological characteristic sensor that are at least partially enveloped within a needle.

With reference to FIG. 70, the window 1608 of the tube 1602 is defined through the outer surface 1602c of the tube 1602, and exposes the electrodes 1306, 1308, 1310 of the physiological characteristic sensor 1300 to the interstitial fluid of the user when the proximalmost end 1602a of the tube 1602 is inserted into the anatomy. The window 1608 may be defined via laser cutting, for example. Generally, the window 1608 is defined through the outer surface 1602c to expose the respective electrode 1306, 1308, 1310 to the interstitial fluid. Thus, the electrodes 1306, 1308, 1310 face the window 1608 to measure the blood glucose level of the user and are positioned on a side of the tube 1602 that is opposite the fluid delivery conduit 1606a.

In this example, the physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein. In some examples, an end 1300a (FIG. 71) of the physiological characteristic sensor 1300 may be coupled to the electrode conduit 1606b to further secure the physiological characteristic sensor 1300 within the electrode conduit 1606b, via adhesives, heat bonding, etc.

In order to deploy the tube 1602 and the physiological characteristic sensor 1300, the infusion monitor unit 708 may be pre-packaged with an insertion instrument, such as the needle 1614. The needle 1614 surrounds the tube 1602, which includes the physiological characteristic sensor 1300. Once the infusion monitor unit 708 is coupled to the anatomy, via the insertion instrument, the needle 1614 can be retracted, leaving the physiological characteristic sensor 1300 and the tube 1602 inserted into the anatomy.

It should be noted, however, that other sensor and tube configurations are also contemplated. For example, with reference to FIG. 72, the physiological characteristic sensor 1300 is shown integrated within a tube 1652. As the physiological characteristic sensor 1300 and the tube 1652 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1502 discussed with regard to FIGS. 61-66, the same reference numerals will be used to denote the same or similar components.

The tube 1652 may facilitate a fluidic connection between a connector, like the connector 702, and the infusion monitor unit 708, and a proximalmost end 1652a of the tube 1652 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1652. The tube 1652 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1652 includes a plurality of conduits 1656 and a slot 1658.

With reference to FIG. 73, the plurality of conduits 1656 of the tube 1652 includes a fluid delivery conduit 1656a and an electrode conduit 1656b. The fluid delivery conduit 1656a receives the fluid from the fluid reservoir 160 and directs the fluid from the fluid reservoir 160 through the tube 1652. In some examples, the fluid delivery conduit 1656a includes at least one fluid outlet 1662. In this example, the terminal end 1652b of the tube 1652 is opened to define the fluid outlet 1662. The fluid from the fluid reservoir 160 exits the tube 1652 at the fluid outlet 1662 at the terminal end 1652b. In this example, the fluid outlet 1662 is oval-shaped, and has a major diameter MD17 that is different and less than a width W18 of the electrode conduit 1656b. In this example, the fluid outlet 1662 is defined at the terminal end 1652b to be spaced a distance apart from the physiological characteristic sensor 1300. By spacing the fluid outlet 1662 from the physiological characteristic sensor 1300, the dispensing of the fluid is positioned at a location within the anatomy that is different and spaced apart from a location at which the blood glucose level is being measured, which may improve accuracy of the physiological characteristic sensor 1300. The electrode conduit 1656b accommodates the physiological characteristic sensor 1300 and is positioned along a side of the fluid delivery conduit 1656a. In this example, the electrode conduit 1656b is semi-oval shaped, however, the electrode conduit 1656b may have any desired shape. In this example, the shape of the conduits 1656a, 1656b reduces a size of the tube 1652 so that it is substantially contained within a needle 1664.

The slot 1658 of the tube 1652 is defined through the outer surface 1652c (FIG. 72) of the tube 1652, and with reference to FIG. 72, exposes the electrodes 1306, 1308, 1310 of the physiological characteristic sensor 1300 to the interstitial fluid of the user when the proximalmost end 1652a of the tube 1652 is inserted into the anatomy. The slot 1658 may be defined via laser cutting, for example. Generally, the slot 1658 is defined through the outer surface 1652c and extends along a length of the tube 1652. The slot 1658 exposes the respective electrode 1306, 1308, 1310 to the interstitial fluid. Thus, the electrodes 1306, 1308, 1310 face the slot 1658 to measure the glucose level of the user and are positioned on a side of the tube 1652 that is opposite the fluid delivery conduit 1656a.

In this example, the physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein. In some examples, with reference to FIG. 74, an end 1300*a* of the physiological characteristic sensor 1300 may be coupled to the electrode conduit 1656*b* to further secure the physiological characteristic sensor 1300 within the electrode conduit 1656*b*, via adhesives, heat bonding, etc. In addition, the physiological characteristic sensor 1300 may be coupled to the electrode conduit 1656*b*, via adhesives, heat bonding, etc., at various points along a length of the physiological characteristic sensor 1300 to retain the physiological characteristic sensor 1300 in the slot 1658.

In order to deploy the tube 1652 and the physiological characteristic sensor 1300, the infusion monitor unit 708 may be pre-packaged with an insertion instrument, such as the needle 1664. The needle 1664 envelops or surrounds the tube 1652, which includes the physiological characteristic sensor 1300. Once the infusion monitor unit 708 is coupled to the anatomy, via the insertion instrument, the needle 1664 can be retracted, leaving the physiological characteristic sensor 1300 and the tube 1652 inserted into the anatomy.

It should be noted, however, that other sensor and tube configurations are also contemplated. For example, with reference to FIG. 75, the physiological characteristic sensor 1300 is shown integrated within a tube 1702. As the physiological characteristic sensor 1300 and the tube 1702 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1502 discussed with regard to FIGS. 61-66, the same reference numerals will be used to denote the same or similar components.

The tube 1702 may facilitate a fluidic connection between a connector, like the connector 702, and the infusion monitor unit 708, and a proximalmost end 1702*a* of the tube 1702 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1702. The tube 1702 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1702 includes a plurality of conduits 1706 and a slot 1708.

Figure 76:
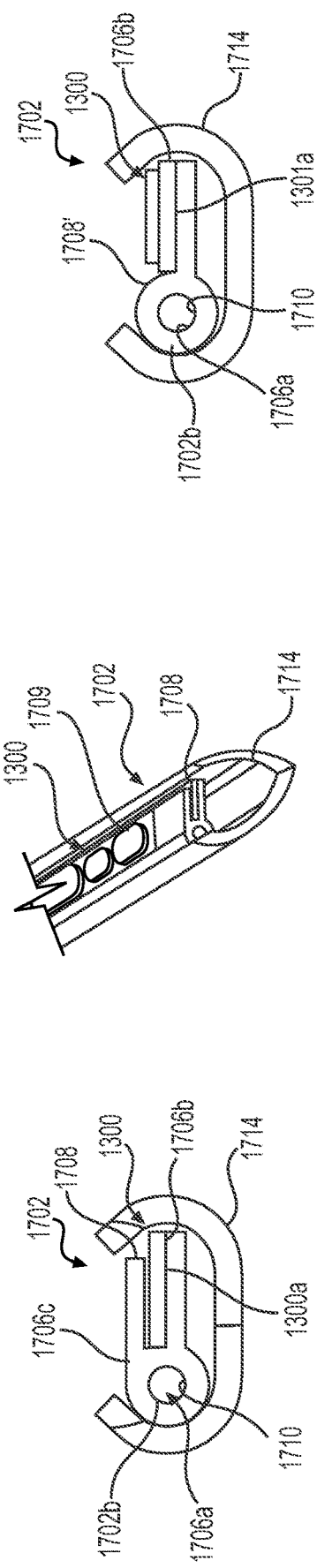
FIG. 76 is an end view of the implementation of FIG. 75 according to some exemplary embodiments.

With reference to FIG. 76, the plurality of conduits 1706 of the tube 1702 includes a fluid delivery conduit 1706*a* and an electrode conduit 1706*b*. The fluid delivery conduit 1706*a* receives the fluid from the fluid reservoir 160 and directs the fluid from the fluid reservoir 160 through the tube 1702. In some examples, the fluid delivery conduit 1706*a* includes at least one fluid outlet 1712. In this example, the terminal end 1702*b* of the tube 1702 is circumferentially opened to define the fluid outlet 1712. The fluid from the fluid reservoir 160 exits the tube 1702 at the fluid outlet 1712 at the terminal end 1702*b*. In this example, the fluid outlet 1712 is defined at the terminal end 1702*b* to be spaced a distance apart from the physiological characteristic sensor 1300. By spacing the fluid outlet 1712 from the physiological characteristic sensor 1300, the dispensing of the fluid is positioned at a location within the anatomy that is different and spaced apart from a location at which the glucose level is being measured, which may improve accuracy of the physiological characteristic sensor 1300. The electrode conduit 1706*b* receives the physiological characteristic sensor 1300 and is positioned along a side of the fluid delivery conduit 1706*a* so that the tube 1702 is receivable within a needle 1714. In this example, the electrode conduit 1706*b* is slotted, however, the electrode conduit 1706*b* may have any desired shape.

Figure 75:
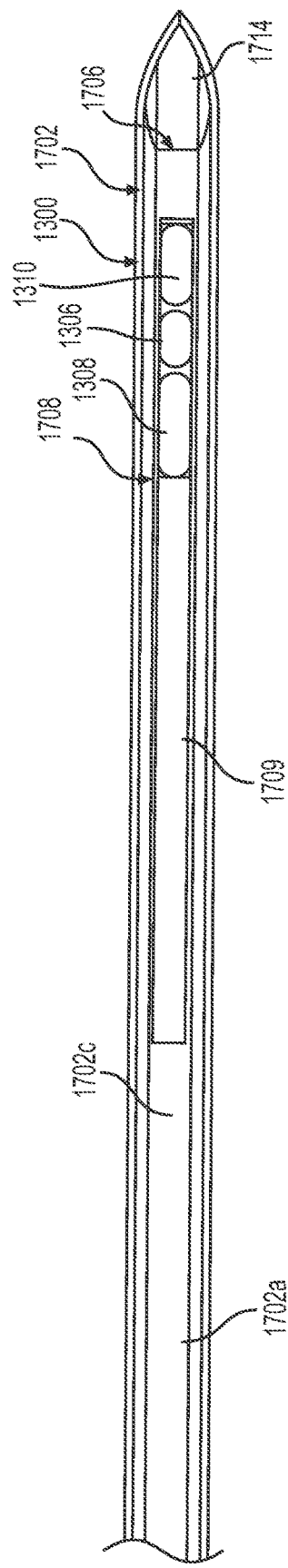
FIG. 75 is a top view of another exemplary implementation involving a tube and a physiological characteristic sensor that are at least partially enveloped within a needle.
Figure 77:
FIG. 77 is a top view of the implementation of FIG. 75.

The slot 1708 of the tube 1652 is defined through the outer surface 1702*c* of the tube 1702, and with reference to FIG. 75, exposes the electrodes 1306, 1308, 1310 of the physiological characteristic sensor 1300 to the interstitial fluid of the user when the proximalmost end 1702*a* of the tube 1702 is inserted into the anatomy. The slot 1708 may be defined via laser cutting, for example. Generally, the slot 1708 is defined through the outer surface 1702*c* and extends for a length of the tube 1702 to expose the electrodes 1306, 1308, 1310 to the interstitial fluid. Thus, the electrodes 1306, 1308, 1310 face the slot 1708 to measure the blood glucose level of the user. In some examples, with reference to FIG. 77, the tube 1702 may also include a window 1709 defined adjacent to the slot 1708 to increase the exposure of the electrodes 1306, 1308, 1310. The window 1709 may be formed by laser cutting, for example.

Figure 78:
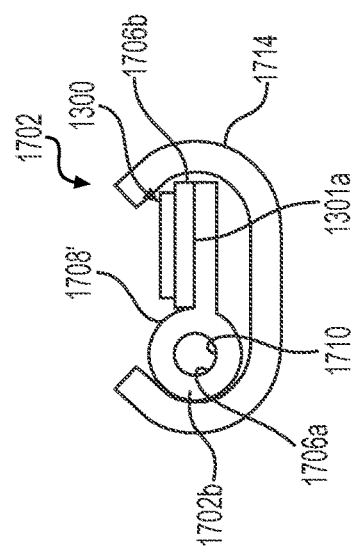
FIG. 78 is an end view of another implementation involving a tube and a physiological characteristic sensor that are at least partially enveloped within a needle according to some exemplary embodiments.

It should be noted in other examples, the slot 1708 may be configured differently to expose the electrodes 1306, 1308, 1310. For example, with reference to FIG. 78, the tube 1702 is shown with a slot 1708'. The slot 1708' is defined through the outer surface 1702*c* such that an entirety of the physiological characteristic sensor 1300 is exposed over a length of the physiological characteristic sensor 1300. The slot 1708 may be defined via laser cutting, for example. Generally, the slot 1708 is defined through the outer surface 1702*c* and extends for a length of the tube 1702 to expose the electrodes 1306, 1308, 1310 to the interstitial fluid.

The physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein. In some examples, with reference to FIGS. 76 and 78, an end 1300*a* of the physiological characteristic sensor 1300 may be coupled to the electrode conduit 1706*b* at various locations along a length of the physiological characteristic sensor 1300 to further secure the physiological characteristic sensor 1300 within the electrode conduit 1706*b*, via adhesives, heat bonding, etc.

In this example, in order to deploy the tube 1702 and the physiological characteristic sensor 1300, the infusion monitor unit 708 may be pre-packaged with an insertion instrument, such as the needle 1714. The needle 1714 envelops or surrounds the tube 1702, which includes the physiological characteristic sensor 1300. Once the infusion monitor unit 708 is coupled to the anatomy, via the insertion instrument, the needle 1714 can be retracted, leaving the physiological characteristic sensor 1300 and the tube 1702 inserted into the anatomy.

It should be noted, however, that other sensor and tube configurations are also contemplated. For example, with reference to FIG. 79, the physiological characteristic sensor 1300 is shown integrated within a tube 1752. As the physiological characteristic sensor 1300 and the tube 1752 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1652 discussed with regard to FIGS. 72-74, the same reference numerals will be used to denote the same or similar components.

The tube 1752 may facilitate a fluidic connection between a connector, like the connector 702, with the infusion monitor unit 708, and a proximalmost end 1752a of the tube 1752 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1752. The tube 1752 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1752 includes a plurality of conduits 1756 and a slot 1758.

With reference to FIG. 80, the plurality of conduits 1756 of the tube 1752 includes a fluid delivery conduit 1756a and an electrode conduit 1756b. The fluid delivery conduit 1756a receives the fluid from the fluid reservoir 160 and directs the fluid from the fluid reservoir 160 through the tube 1752. In some examples, the fluid delivery conduit 1756a includes at least one fluid outlet 1762. In this example, the terminal end 1752b of the tube 1752 is opened to define the fluid outlet 1762. The fluid from the fluid reservoir 160 exits the tube 1752 at the fluid outlet 1762 at the terminal end 1752b. In this example, the fluid outlet 1762 is circular, and has a diameter D20 that is different and less than a width W20 of the electrode conduit 1756b. In this example, the fluid outlet 1762 is defined at the terminal end 1752b to be spaced a distance apart from the physiological characteristic sensor 1300. By spacing the fluid outlet 1762 from the physiological characteristic sensor 1300, the dispensing of the fluid is positioned at a location within the anatomy that is different and spaced apart from a location at which the glucose level is being measured, which may improve accuracy of the physiological characteristic sensor 1300. The electrode conduit 1756b receives the physiological characteristic sensor 1300 and is positioned along a side of the fluid delivery conduit 1756a. In this example, the electrode conduit 1756b is semi-oval shaped, however, the electrode conduit 1756b may have any desired shape. In this example, the shape of the conduits 1756a, 1756b reduces a size of the tube 1752 so that it is substantially contained within a needle 1764.

The slot 1758 of the tube 1752 is defined through the outer surface 1752c of the tube 1752, and with reference to FIG. 79, exposes the electrodes 1306, 1308, 1310 of the physiological characteristic sensor 1300 to the interstitial fluid of the user when the proximalmost end 1752a of the tube 1752 is inserted into the anatomy. The slot 1758 may be defined via laser cutting, for example. Generally, the slot 1758 is defined through the outer surface 1752c and extends along a length of the tube 1752. The slot 1758 exposes the respective electrode 1306, 1308, 1310 to the interstitial fluid. Thus, the electrodes 1306, 1308, 1310 face the slot 1658 to measure the blood glucose level of the user and are positioned on a side of the tube 1752 that is opposite the fluid delivery conduit 1756a.

The physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein. In some examples, with reference to FIG. 81, an end 1300a of the physiological characteristic sensor 1300 may be coupled to the electrode conduit 1756b to further secure the physiological characteristic sensor 1300 within the electrode conduit 1756b, via adhesives, heat bonding, etc. In addition, the physiological characteristic sensor 1300 may be coupled to the electrode conduit 1756b, via adhesives, heat bonding, etc., at various points along a length of the physiological characteristic sensor 1300 to retain the physiological characteristic sensor 1300 in the slot 1758.

In order to deploy the tube 1652 and the physiological characteristic sensor 1300, the infusion monitor unit 708 may be pre-packaged with an insertion instrument, such as the needle 1764. The needle 1764 envelops or surrounds the tube 1752, which includes the physiological characteristic sensor 1300. Once the infusion monitor unit 708 is coupled to the anatomy, via the insertion instrument, the needle 1764 can be retracted, leaving the physiological characteristic sensor 1300 and the tube 1752 inserted into the anatomy.

It should be noted, however, that other sensor and tube configurations are also contemplated. For example, with reference to FIG. 82, a physiological characteristic sensor (e.g. glucose sensor) 1800 is shown integrated within a tube 1802. As the physiological characteristic sensor 1800 and the tube 1802 includes the same or similar components as the physiological characteristic sensor 716 and the tube 706 discussed with regard to FIGS. 39-41, the physiological characteristic sensor 1000 and the tube 1102 discussed with regard to FIGS. 45-47, and the physiological characteristic sensor 1300 and the tube 1652 discussed with regard to FIGS. 72-74, the same reference numerals will be used to denote the same or similar components.

The tube 1802 may facilitate a fluidic connection between a connector, like the connector 702, with the infusion monitor unit 708, and a proximalmost end 1802a of the tube 1802 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1802. The tube 1802 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc. In some examples, the tube 1802 includes a plurality of conduits 1806 and a plurality of windows 1808.

With reference to FIG. 83, the plurality of conduits 1806 of the tube 1802 includes a fluid delivery conduit 1806a, the reference electrode conduit 1806b, the counter electrode conduit 1806c, the working electrode conduit 1806d and an additional electrode conduit 1806e. The fluid delivery conduit 1806a receives the fluid from the fluid reservoir 160 and directs the fluid from the fluid reservoir 160 through the tube 1802. In this example, the fluid outlet 1812 is defined at the terminal end 1802b to be spaced a distance apart from the physiological characteristic sensor 1800. By spacing the fluid outlet 1812 from the physiological characteristic sensor 1800, the dispensing of the fluid is positioned at a location within the anatomy that is different and spaced apart from a location at which the blood glucose level is being measured, which may improve accuracy of the physiological characteristic sensor 1800.

The reference electrode conduit 1806b accommodates the reference electrode 740, the counter electrode conduit 1806c accommodates the counter electrode 742, and the working electrode conduit 1806d accommodates the working electrode 744 associated with the physiological characteristic sensor 1800. The additional electrode conduit 1806e accommodates an additional electrode 1820 associated with the physiological characteristic sensor 1800. The conduits 1806b-1806e direct the respective electrodes 740, 742, 744, 1820 through the tube 1802 to the connector 702 (FIG. 39). The plurality of windows 1808 of the tube 1802 includes the reference electrode window 1808b, the counter electrode window 1808c, the working electrode window 1808d and the additional electrode window 1808e. The windows 1008b-1808e are each defined through the outer surface 1802c of the tube 1802, as shown in FIG. 84, and expose the respective electrode 740, 742, 744, 1820 to interstitial fluid of the user when the proximalmost end 1802a of the tube 1802 is inserted into the anatomy. The windows 1808b-1808e are defined using laser cutting, for example. In this example, the electrodes 740, 742, 744, 1820 are co-extruded with the tube 1802. During the extrusion process, the windows 1808b-1808e may also be employed to segment the insulation over the electrodes 740, 742, 744, 1820 to define the respective windows 1808b-1808e. For example, the extrusion may be paused to create gaps in the outer surface 1802c. The proximal end of the electrodes 740, 742, 744, 1820 may be exposed for connecting to a communication component to communicate with the control module 822, as discussed herein. A narrow strip 1803 of the tube 1802 enables easy termination of the physiological characteristic sensor 1800 and tube 1802, if desired.

In this example, the physiological characteristic sensor 1800 includes the reference electrode 740, the counter electrode 742, the working electrode 744 and the additional electrode 1820. As discussed, the chemical reaction between the glucose and the oxygen at the working electrode 744 generates an electrical signal, which is transmitted by the working electrode 744 and communicated to the control module 822 of the fluid infusion device 800, as will be discussed further herein. It should be noted that the counter electrode 742 does not necessarily have to be coated. The reference electrode 740 does not have to be coated either, but is generally made of silver or silver-chloride. The working electrode 744 is coated with glucose oxidase and a glucose limiting membrane above the glucose oxidase layer. The additional electrode 1820 may be optional. If the additional electrode 1820 is present, the additional electrode 1820 may be an additional working electrode, like the working electrode 744, and the current from both working electrodes 744, 1820 may be averaged by the control module 822. Alternatively, the additional electrode 1820 may be an electrode coated with something other than glucose oxidase in order to detect other analytes of interest (other than glucose), which is transmitted to the control module 822 of the fluid infusion device 800. For example, the additional electrode 1820 may measure ketone, lactate, etc. In addition, the additional electrode 1820 may measure insulin. The additional electrode 1820 may also be employed as a background electrode or may be used to observe a drug interference rejection.

In this example, in order to deploy the tube 1802 and the physiological characteristic sensor 1800, the infusion monitor unit 708 may be pre-packaged with an insertion instrument, such as the needle 1814. The needle 1814 surrounds the tube 1802, which includes the physiological characteristic sensor 1800. Once the infusion monitor unit 708 is coupled to the anatomy, via the insertion instrument, the needle 1814 can be retracted, leaving the physiological characteristic sensor 1800 and the tube 1802 inserted into the anatomy.

Figure 85:
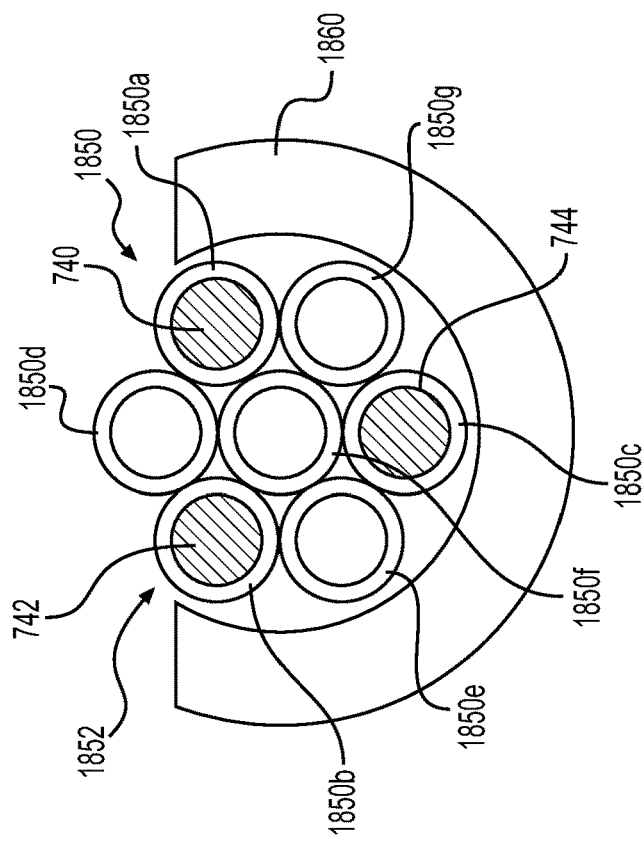
FIG. 85 is an end view of an exemplary implementation involving a plurality of tubules and a physiological characteristic sensor that are at least partially enveloped within a needle.

It should be noted, however, that other sensor and tube configurations are also contemplated. For example, with reference to FIG. 85, the tube comprises a plurality of tubules or fibers 1850. Insofar as the plurality of fibers 1850 includes the same or similar components as the physiological characteristic sensor 716 and the tube 706 discussed with regard to FIGS. 39-41, the physiological characteristic sensor 1000 and the tube 1102 discussed with regard to FIGS. 45-47, and the physiological characteristic sensor 1300 and the tube 1652 discussed with regard to FIGS. 72-74, the same reference numerals will be used to denote the same or similar components.

The plurality of fibers 1850 may facilitate a fluidic connection between a connector, like the connector 702, with the infusion monitor unit 708, and the plurality of fibers 1850 may extend from the housing 710 and be inserted into an anatomy of a user to enable delivering the fluid, such as insulin, while also measuring a glucose level of the user. The plurality of fibers 1850 are each hollow and are composed of a polymer based material that is compatible to the fluid, including, but not limited to polyether block amide, ethylene tetrafluoroethylene and polytetrafluoroethylene. The fibers 1850 are generally extruded; however, other manufacturing techniques, such as additive manufacturing, may be employed. In this example, the fibers 1850 include seven fibers, however, any number of fibers may be employed to measure a blood glucose level of the user and to also dispense the fluid. In this example, three of the fibers 1850a-1850c accommodate a respective one of the reference electrode 740, the counter electrode 742 and the working electrode 744 to define a physiological characteristic sensor 1852. The fibers 1850a-1850c may be co-extruded with the electrodes 740, 742, 744, or the electrodes 740, 742, 744 may be positioned within the respective fiber 1850a-1850c. Generally, the electrodes 740, 742, 744 are insulated with a polymer, including, but not limited to polyether block amide, ethylene tetrafluoroethylene, polytetrafluoroethylene, etc. In some examples, the electrodes 740, 742, 744 and fibers 1850a-1850c are compressed and joined at sidewalls through a heating process where the sidewalls reach a sufficient melt temperature for joining the electrodes 740, 742, 744 to the fibers 1850a-1850c without collapsing the fibers 1850a-1850c. In addition, although not shown herein, the fibers 1850a-1850c include windows, defined via laser cutting or through the extrusion process, to expose the electrodes 740, 742, 744 to the interstitial fluid.

The remainder of the fibers 1850d-1850g dispense or deliver the fluid to the body of the user. At an inlet of the hollow fibers 1850*d*-1850*g*, the fibers 1850*d*-1850*g* are joined to a single source cavity that adapts to an infusion set tube or tube that is connected to a connector, such as the connector 702 of FIG. 39. The connector is fluidly coupled to the fluid reservoir 160 such that the fluid reservoir 160 of the fluid infusion device 800 is a fluid source, which is fluidly connected to the fibers 1850*d*-1850*g*. As the fluid travels from the tube fluidly connected to the fluid reservoir 160 to the inlet of the fibers 1850*d*-1850*g*, the fluid distributes evenly between the fibers 1850*d*-1850*g* and exits from the end of the fibers 1850*d*-1850*g* into the tissue. The quantity of fibers 1850*d*-1850*g* may vary based on the size of the fiber, needle and volume to dispense. In addition, while the fibers 1850*a*-1850*g* are shown as having a circular cross-section, the fibers 1850*a*-1850*g* may have any desired polygonal cross-section, such as oval, triangular, etc.

Figure 86:
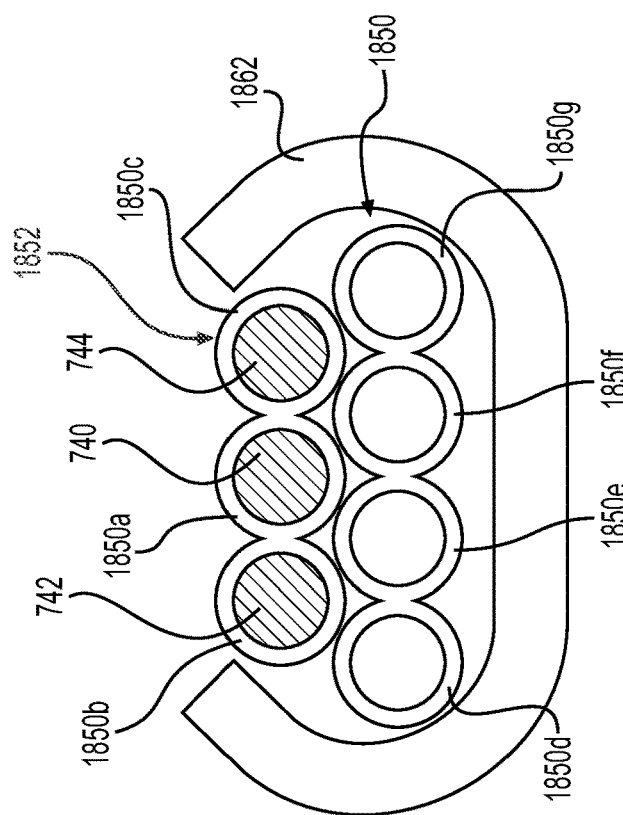
FIG. 86 is an end view of another exemplary implementation involving a plurality of tubules and a physiological characteristic sensor.

It should be noted that while the fibers 1850*a*-1850*g* are arranged to form a substantially circular shape, the fibers 1850*a*-1850*g* may be arranged to define any desired shape to fit within a needle 1860. For example, with reference to FIG. 86, the fibers 1850*a*-1580*g* are arranged to define an oval-shape. The arrangement of the fibers 1850*a*-1580*g* in FIG. 86 enables the fibers 1850*a*-1580*g* to be positioned within a needle 1862, which is also similarly shaped.

In this example, in order to deploy the fibers 1850*a*-1580*g*, the infusion monitor unit 708 may be pre-packaged with an insertion instrument, such as the needle 1860, 1862. The needle 1860, 1862 surrounds the fibers 1850*a*-1580*g*, which includes the electrodes 740, 742, 744 to define the physiological characteristic sensor 1852. Once the infusion monitor unit 708 is coupled to the anatomy, via the insertion instrument, the needle 1860, 1862 can be retracted, leaving the fibers 1850*a*-1580*g* inserted into the anatomy.

It should be noted, however, that other sensor and tube configurations are also contemplated. For example, with reference to FIG. 85, the tube comprises a ribbon cable 1900. As the ribbon cable 1900 includes the same or similar components as the physiological characteristic sensor 716 and the tube 706 discussed with regard to FIGS. 39-41, the physiological characteristic sensor 1000 and the tube 1102 discussed with regard to FIGS. 45-47, and the physiological characteristic sensor 1300 and the tube 1652 discussed with regard to FIGS. 72-74, the same reference numerals will be used to denote the same or similar components.

The ribbon cable 1900 may facilitate a fluidic connection between a connector, like the connector 702, with the infusion monitor unit 708, and the ribbon cable 1900 may extend from the housing 710 and be inserted into an anatomy of a user to enable delivering the fluid, such as insulin, while also measuring a glucose level of the user. The ribbon cable 1900 is composed of a polymer based material that is compatible to the fluid, including, but not limited to polyether block amide, ethylene tetrafluoroethylene and polytetrafluoroethylene. The ribbon cable 1900 is generally extruded; however, other manufacturing techniques, such as additive manufacturing, may be employed. In this example, the ribbon cable 1900 includes eight ribbons, however, any number of ribbons may be employed to measure a blood glucose level of the user and to also dispense the fluid. In this example, five of the ribbons 1900*a*-1900*e* receive a respective one of the reference electrode 740, the counter electrode 742, the working electrode 744 and two additional electrodes 1904, 1906 to define a physiological characteristic sensor (e.g. glucose sensor) 1902, which is in communication with the control module 822. The additional electrodes 1904, 1906 may be optional. If the additional electrodes 1904, 1906 are included, the additional electrodes 1904, 1906 may be an additional working electrode, like the working electrode 744, and the current from both working electrodes 744, 1904, 1906 may be averaged by the control module 822. Alternatively, the additional electrodes 1904, 1906 may be an electrode coated with something other than glucose oxidase in order to detect other analytes of interest (other than glucose), which is transmitted to the control module 822. For example, the additional electrodes 1904, 1906 may measure ketone, lactate, etc. As a further alternative, the additional electrodes 1904, 1906 may comprise counter electrodes, like the counter electrode 742. In another alternative, one of the two additional electrodes 1904, 1906 may comprise a working electrode, like the working electrode 744, and the other of the two additional electrodes 1904, 1906 may comprise a counter electrode, like the counter electrode 742, to provide redundancy and improve response. In addition, the additional electrodes 1904, 1906 may measure insulin. The additional electrodes 1904, 1906 may also be employed as a background electrode or may be used to observe a drug interference rejection.

The ribbon cable 1900 is in a first state in FIG. 87. The ribbons 1900*a*-1900*e* may be co-extruded with the electrodes 740, 742, 744, 1904, 1906 or the electrodes 740, 742, 744 may be positioned within the respective ribbons 1900*a*-1900*e*. Generally, the electrodes 740, 742, 744, 1904, 1906 are insulated with a polymer, including, but not limited to polyether block amide, ethylene tetrafluoroethylene, polytetrafluoroethylene, etc. In some examples, the electrodes 740, 742, 744, 1904, 1906 and ribbons 1900*a*-1900*e* are compressed and joined at sidewalls through a heating process where the sidewalls reach a sufficient melt temperature for joining the electrodes 740, 742, 744, 1904, 1906 to the ribbons 1900*a*-1900*e* without collapsing the ribbons 1900*a*-1900*e*. In addition, although not shown herein, the ribbons 1900*a*-1900*e* include windows, defined via laser cutting, ablation, or through the extrusion process, to expose the electrodes 740, 742, 744 to the interstitial fluid. The windows may be defined through the ribbons 1900*a*-1900*e* at a location that is spaced apart from a terminal end of the ribbons 1900 to provide distance between the fluid dispensed and the electrodes 740, 742, 744, 1904, 1906. The remainder of the ribbons 1900*f*-1900*h* are filler or solid ribbons. It should be noted that while the ribbon cable 1900 is shown with five electrodes, the ribbon cable 1900 may have a lesser or greater number of electrodes depending upon the requirements of the physiological characteristic sensor 1902.

In order to dispense the fluid to the body of the user, the ribbon cable 1900 is formed substantially into a circle in a second state to define a conduit 1901, as shown in FIG. 88. Ends 1908*a*, 1908*b* are coupled together to define the circle, via welding, adhesives, etc. An inlet at a proximal end of the ribbon cable 1900 receives the fluid from an infusion set tube or tube that is connected to a connector, such as the connector 702 of FIG. 39. The connector is fluidly coupled to the fluid reservoir 160 such that the fluid reservoir 160 of the fluid infusion device 800 is a fluid source, which is fluidly connected to the ribbon cable 1900. The fluid reservoir 160 is fluidically coupled to the inlet of ribbon cable 1900, and the ribbon cable 1900 dispenses the fluid from the fluid reservoir 160 at an outlet 1910. It should be noted that while the ribbon cable 1900 is arranged to form a substantially circular shape, the ribbon cable 1900 may be arranged to define any desired shape to fit within a needle.

In this example, in order to deploy the ribbon cable 1900, the infusion monitor unit 708 may be pre-packaged with an insertion instrument, which includes the needle. The needle partially envelopes or surrounds the ribbon cable 1900 that includes the electrodes 740, 742, 744, 1904, 1906 to define the physiological characteristic sensor 1902, or may be received through the conduit 1901. Once the infusion monitor unit 708 is coupled to the anatomy, via the insertion instrument, the needle can be retracted, leaving the ribbon cable 1900 inserted into the anatomy.

It should be noted, however, that other sensor and tube configurations are also contemplated. For example, with reference to FIG. 89, the physiological characteristic sensor 1000 is shown integrally formed with a tube 1950 are shown. As the physiological characteristic sensor 1000 and the tube 1950 include the same or similar components as the physiological characteristic sensor 716 and the tube 706 discussed with regard to FIGS. 39-41, the physiological characteristic sensor 1000 and the tube 1102 discussed with regard to FIGS. 45-47, and the physiological characteristic sensor 1300 and the tube 1652 discussed with regard to FIGS. 72-74, the same reference numerals will be used to denote the same or similar components.

The tube 1952 may facilitate a fluidic connection between a connector, like the connector 702, with the infusion monitor unit 708, and a proximalmost end 1952*a* of the tube 1952 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 1952. The tube 1952 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded.

In some examples, the tube 1952 includes the reference electrode 740, the counter electrode 742 and the working electrode 744 co-extruded with the tube 1952. The electrodes 740, 742, 744 are embedded into a sidewall 1954 of the tube 1952 through the extrusion process, as shown in FIG. 90. It should be noted number of embedded electrodes may vary depending on the sensor design, and thus, the tube 1952 may include a lesser or greater number of electrodes. A fluid delivery conduit 1956 is defined along a center of the tube 1952, and receives the fluid from the fluid reservoir 160 and directs the fluid from the fluid reservoir 160 through the tube 1952. In this example, the fluid outlet 1962 is defined at the terminal end 1952*b* to be spaced a distance apart from the physiological characteristic sensor 1000. By spacing the fluid outlet 1962 from the physiological characteristic sensor 1000, the dispensing of the fluid is positioned at a location within the anatomy that is different and spaced apart from a location at which the blood glucose level is being measured, which may improve accuracy of the physiological characteristic sensor 1000.

It should be noted that co-extrusion of the electrodes 740, 742, 744 with the tube 1952 is merely an example. With reference to FIG. 91, in some examples, the electrodes 740, 742, 744 are printed on the sidewall 1954 of the tube 1952. The conductive inks and adhesives include, but are not limited to, gold, platinum, graphene, carbon, silver, etc., which are printed on the tube 1952 in conjunction with the extrusion process. Generally, the electrodes 740, 742, 744 are printed along the length of the tube 1952. After the electrodes 740, 742, 744 are printed, an insulation layer may be coated on top of the electrodes 740, 742, 744 to control a location of a respective window that exposes the electrodes 740, 742, 744 to the interstitial fluid. The coating may be done as an extrusion process, if desired.

With reference back to FIG. 89, the tube 1952 includes a plurality of windows 1958. The windows 1958 are each defined through the outer surface 1952*c* of the tube 1952 and expose the respective electrode 740, 742, 744 to interstitial fluid of the user when the proximalmost end 1802*a* of the tube 1802 is inserted into the anatomy. The windows 1958 are defined using laser cutting or ablation, for example. In this example, the electrodes 740, 742, 744 are co-extruded with the tube 1952. During the extrusion process, the windows 1958 may also be employed to segment the insulation over the electrodes 740, 742, 744 to define the respective windows 1958. For example, the extrusion may be paused to create gaps in the outer surface 1952*c*. The proximal end of the electrodes 740, 742, 744 are exposed to connect to the control module 822.

In this example, the physiological characteristic sensor 1000 includes the reference electrode 740, the counter electrode 742 and the working electrode 744. The chemical reaction between the glucose and the oxygen at the working electrode 744 generates an electrical signal, which is transmitted by the working electrode 744 and communicated to the control module 822 of the fluid infusion device 800, as will be discussed further herein.

In this example, in order to deploy the tube 1952 and the physiological characteristic sensor 1000, the infusion monitor unit 708 may be pre-packaged with an insertion instrument, such as a needle. The needle may partially surround the tube 1952 or may pass through the tube 1952, which includes the physiological characteristic sensor 1000. Once the infusion monitor unit 708 is coupled to the anatomy, via the insertion instrument, the needle can be retracted, leaving the physiological characteristic sensor 1000 and the tube 1952 inserted into the anatomy.

Figure 92:
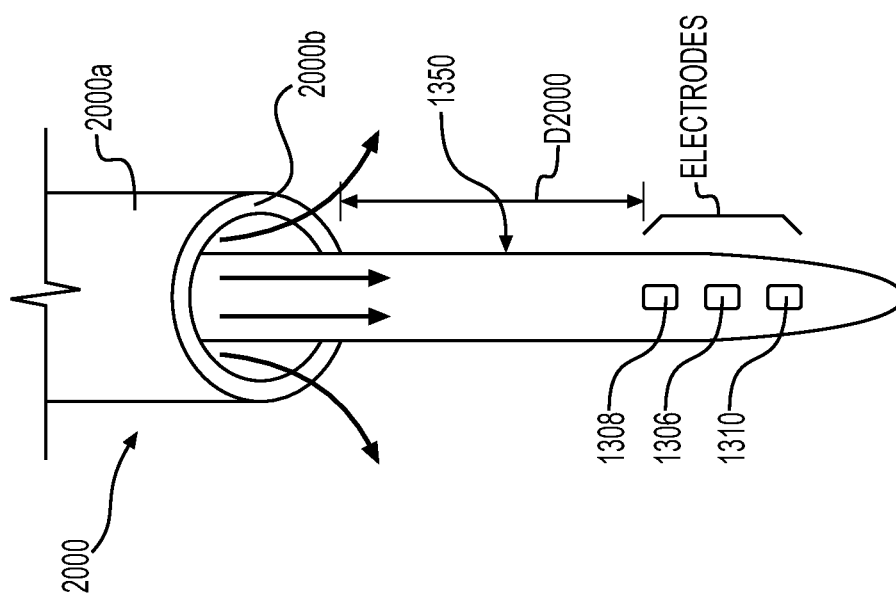
FIG. 92 is a perspective view of an exemplary implementation involving a physiological characteristic sensor that is positioned within a tube.

It should be noted, however, that other sensor and tube configurations are also contemplated. For example, with reference to FIG. 92, the physiological characteristic sensor 1300 is shown coupled to a tube 2000. Insofar as the physiological characteristic sensor 1300 and the tube 2000 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1652 discussed with regard to FIGS. 72-74, the same reference numerals will be used to denote the same or similar components.

The tube 2000 may facilitate a fluidic connection between a connector, like the connector 702, with the infusion monitor unit 708, and a proximalmost end 2000*a* of the tube 2000 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2000. The tube 2000 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc.

In this example, the physiological characteristic sensor 1300 is positioned within the tube 2000 to extend outwardly away from a terminal end 2000*b* of the tube 2000. In this example, the physiological characteristic sensor 1300 is centered within the tube 2000. The terminal end 2000*b* is a distance D2000 from the electrodes 1306, 1308, 1310, and in some examples, the distance D2000 is about 10 millimeters (mm). A fluid outlet 2002 is defined at the terminal end 2000*b*. The fluid from the fluid reservoir 160 exits the tube 2000 at the fluid outlet 2002 at the terminal end 2000*b*. Thus, the fluid outlet 2002 is defined at the terminal end 2000*b* to be spaced a distance apart from the physiological characteristic sensor 1300. By spacing the fluid outlet 2002 from the physiological characteristic sensor 1300, the dispensing of the fluid is positioned at a location within the anatomy that is different and spaced apart from a location at which the blood glucose level is being measured, which may improve accuracy of the physiological characteristic sensor 1300. In some examples, a proximal end of the physiological characteristic sensor 1300 is coupled to the tube 2000 within the infusion monitor unit 708 to secure the physiological characteristic sensor 1300 relative to the tube 2000. The physiological characteristic sensor 1300 is free floating within the tube 2000 itself.

The physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein.

Figure 93:
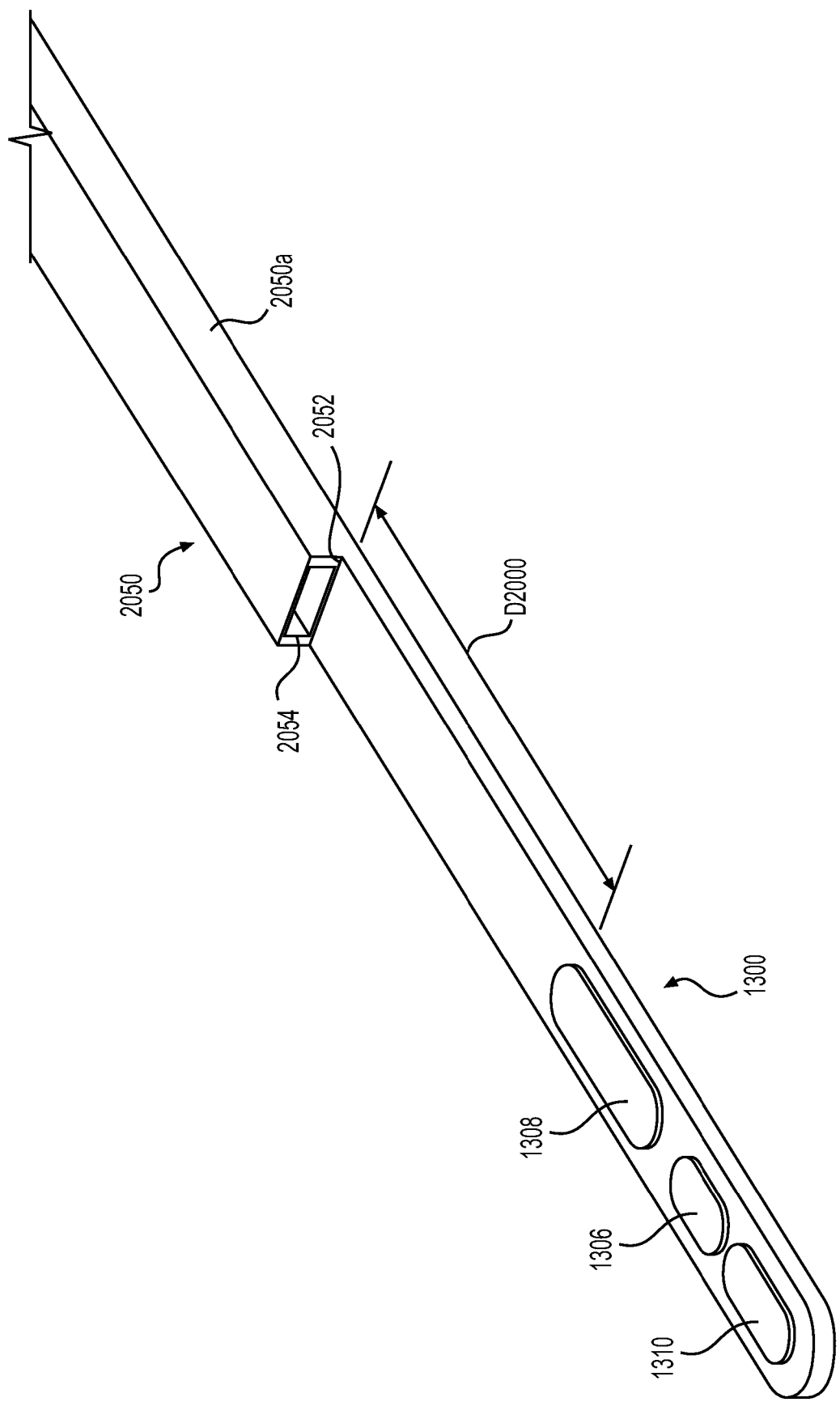
FIG. 93 is a perspective view of another exemplary implementation involving a tube integrated with a physiological characteristic sensor.

It should be noted, however, that other sensor and tube configurations are also contemplated. For example, with reference to FIG. 93, the physiological characteristic sensor 1300 is shown coupled to a tube 2050. As the physiological characteristic sensor 1300 and the tube 2050 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 1652 discussed with regard to FIGS. 72-74, the same reference numerals will be used to denote the same or similar components.

The tube 2050 may facilitate a fluidic connection between a connector, like the connector 702, with the infusion monitor unit 708, and a proximalmost end 2050*a* of the tube 2050 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2050. The tube 2050 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc.

In this example, the physiological characteristic sensor 1300 is integrally formed with the tube 2050 to extend outwardly away from a side 2052 of the tube 2050 that includes a fluid outlet 2054. The physiological characteristic sensor 1300 may be integrally formed with the tube 2050 by overmolding, printing, etc. The fluid outlet 2054 is the distance D2000 from the electrodes 1306, 1308, 1310. The fluid from the fluid reservoir 160 exits the tube 2050 at the fluid outlet 2054. Thus, the fluid outlet 2054 is defined to be spaced a distance apart from the physiological characteristic sensor 1300. By spacing the fluid outlet 2054 from the physiological characteristic sensor 1300, the dispensing of the fluid is positioned at a location within the anatomy that is different and spaced apart from a location at which the glucose level is being measured, which may improve accuracy of the physiological characteristic sensor 1300.

In this example, the physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein.

It should be noted, however, that other sensor and tube configurations are also contemplated. For example, with reference to FIG. 94, the physiological characteristic sensor 1300 is shown coupled to a tube 2100. As the physiological characteristic sensor 1300 and the tube 2100 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 2050 discussed with regard to FIG. 93, the same reference numerals will be used to denote the same or similar components.

The tube 2100 may facilitate a fluidic connection between a connector, like the connector 702, and the infusion monitor unit 708, and a proximalmost end 2100*a* of the tube 2100 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2100. The tube 2100 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc.

In this example, with additional reference to FIG. 95, the physiological characteristic sensor 1300 is integrally formed with the tube 2100 to extend outwardly away from a side 2102 of the tube 2100 that is opposite a side 2104 of the tube 2100 that includes a fluid outlet 2106. The physiological characteristic sensor 1300 may be integrally formed with the tube 2100 by overmolding, printing, etc. The fluid outlet 2106 is the distance D2000 from the electrodes 1306, 1308, 1310. The fluid from the fluid reservoir 160 exits the tube 2100 at the fluid outlet 2106. Thus, the fluid outlet 2106 is defined to be spaced a distance apart from the physiological characteristic sensor 1300. By spacing the fluid outlet 2106 from the physiological characteristic sensor 1300 and on the opposite side 2102, the dispensing of the fluid is positioned at a location within the anatomy that is different and spaced apart from a location at which the blood glucose level is being measured, which may improve accuracy of the physiological characteristic sensor 1300.

The physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein.

Figure 97:
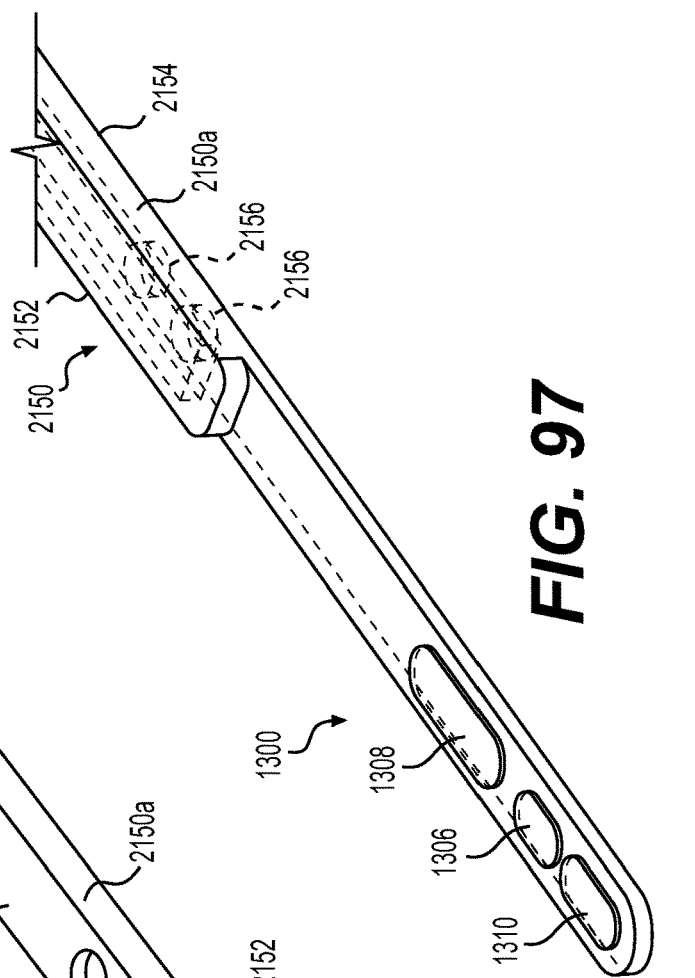
FIG. 97 is a front perspective view of the implementation of FIG. 96.
Figure 96:
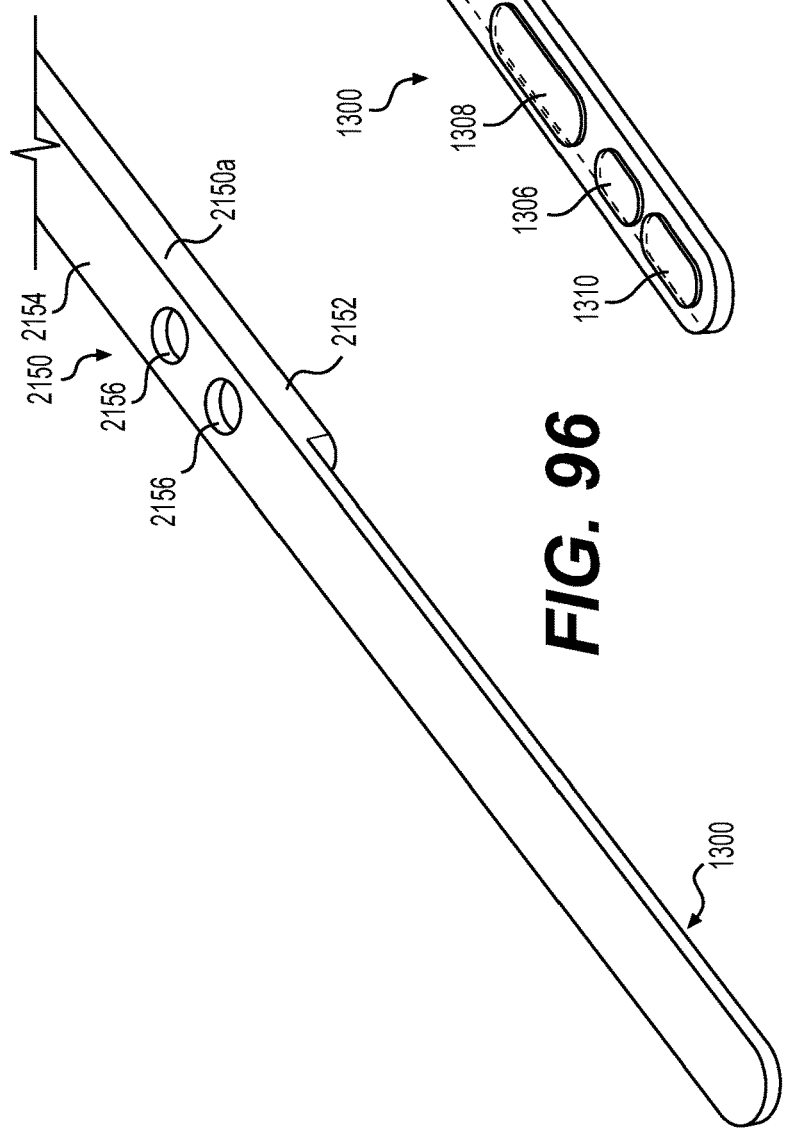
FIG. 96 is a rear perspective view of another exemplary implementation involving a tube integrated with a physiological characteristic sensor.

It should be noted, however, that other sensor and tube configurations are also contemplated. For example, with reference to FIGS. 96 and 97, the physiological characteristic sensor 1300 is shown coupled to a tube 2150. As the physiological characteristic sensor 1300 and the tube 2150 includes the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 2050 discussed with regard to FIG. 93, the same reference numerals will be used to denote the same or similar components.

The tube 2150 may facilitate a fluidic connection between a connector, like the connector 702, and the infusion monitor unit 708, and a proximalmost end 2150a of the tube 2150 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2150. The tube 2150 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene, pellathane and may be extruded, molded, cast, additively manufactured, etc.

Figure 98:
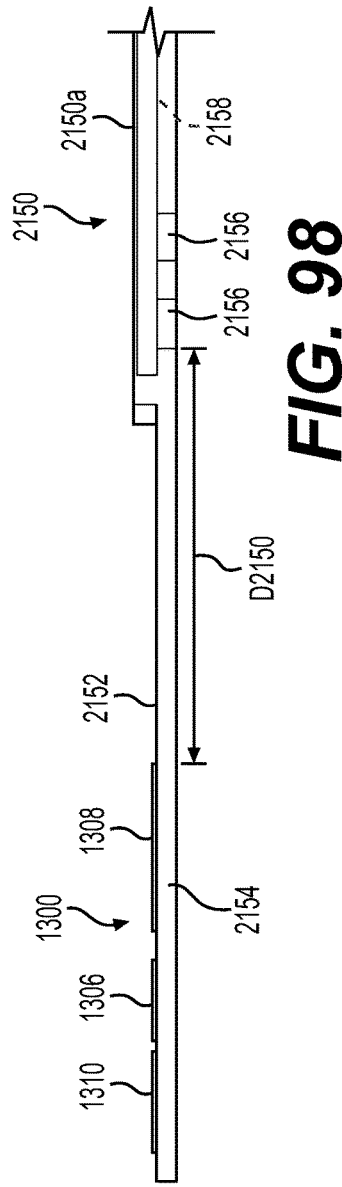
FIG. 98 is a side view of the implementation of FIG. 96.

In this example, with reference to FIG. 98, the physiological characteristic sensor 1300 is integrally formed with the tube 2150 to extend outwardly away from a side 2152 of the tube 2150 that is opposite a side 2154 of the tube 2150 that includes at least one fluid outlet 2156. The physiological characteristic sensor 1300 may be integrally formed with the tube 2150 by overmolding, printing, etc. In this example, a fluid delivery conduit 2158 of the tube 2150 is circumferentially closed, and the fluid from the fluid reservoir 160 exits the tube 2150 at the at least one fluid outlet 2156. In this example, the at least one fluid outlet 2156 comprises two fluid outlets, however, the tube 2150 may include any number of fluid outlets 2156. The fluid outlets 2156 are defined through a surface 2150c of the tube 2150 and are in fluid communication with the fluid delivery conduit 2158. One of the fluid outlets 2156 is at a distance D2150 from the electrodes 1306, 1308, 1310, which in this example is about 15 millimeters (mm). Thus, the fluid outlets 2156 is defined to be spaced a distance apart from the physiological characteristic sensor 1300. By spacing the fluid outlets 2156 from the physiological characteristic sensor 1300 and on the opposite side 2152, the dispensing of the fluid is positioned at a location within the anatomy that is different from a location at which the glucose level is being measured, which may improve accuracy of the physiological characteristic sensor 1300.

The physiological characteristic sensor 1300 includes the reference electrode 1306, the counter electrode 1308 and the working electrode 1310. The chemical reaction between the glucose and the oxygen at the working electrode 1310 generates an electrical signal, which is transmitted by the working electrode 1310 and communicated to the control module 822 of the fluid infusion device 800, as will be discussed further herein.

Figure 99:
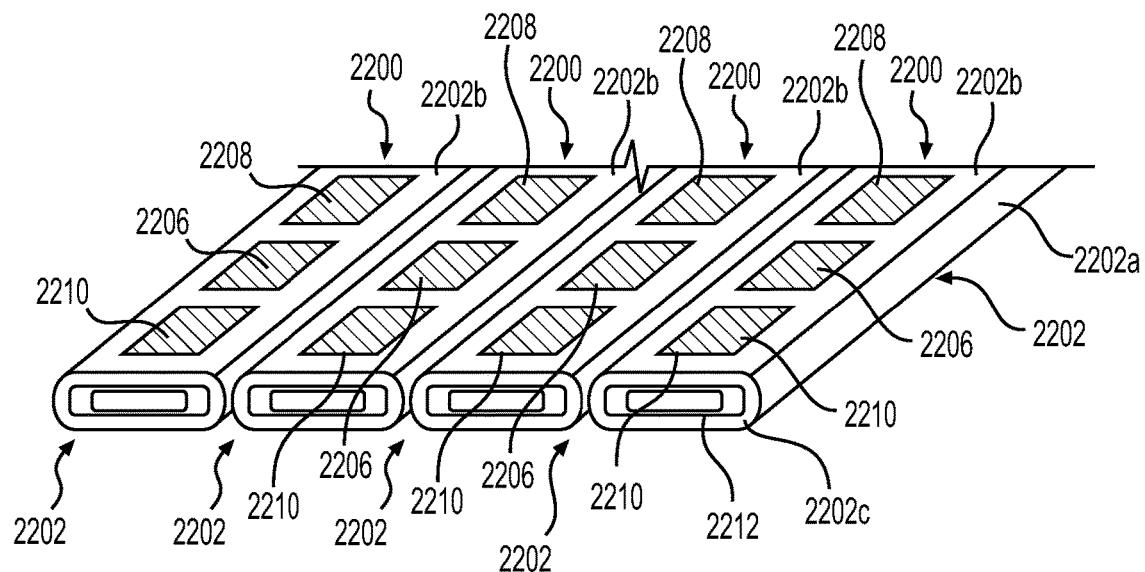
FIG. 99 is a schematic perspective view of a plurality of tubes wherein each tube is integrated with a physiological characteristic sensor.

It should be noted, however, that other sensor and tube configurations are also contemplated. For example, with reference to FIG. 99, a physiological characteristic sensor (e.g. glucose sensor) 2200 is shown coupled to a tube 2202. In the example of FIG. 99, four physiological characteristic sensors 2200 are shown coupled to one of a respective four tubes 2202. As the physiological characteristic sensor 2200 and the tube 2202 include the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 1300 and the tube 2050 discussed with regard to FIG. 93, the same reference numerals will be used to denote the same or similar components. As each of the physiological characteristic sensors 2200 and the tubes 2202 are the same, a single one of the physiological characteristic sensors 2200 and the tubes 2202 will be described herein.

Figure 100:
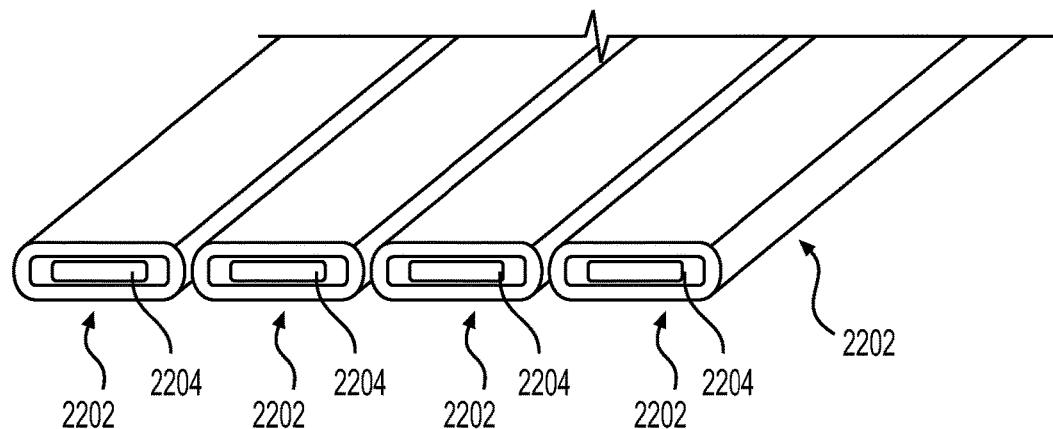
FIG. 100 is another schematic perspective view of the plurality of tubes of FIG. 99.

The tube 2202 may facilitate a fluidic connection between a connector, like the connector 702, and the infusion monitor unit 708, and a proximalmost end 2202a of the tube 2202 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2202. The tube 2202 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP), ethylene tetrafluoroethylene and pellathane. With reference to FIG. 100, the tube 2202 has a rectangular cross-section. The tube 2202 may be supported on a support fixture 2204 during fabrication of the tube 2202 and the physiological characteristic sensor 2200. In some examples, the tube 2202 may be formed by extrusion, micro-electromechanical system/photolithography, additively manufactured, etc. In the example of micro-electromechanical system/photolithography, the tube 2202 may be built directly onto itself, layer by layer. The use of the rectangular tube 2202 enables the physiological characteristic sensor 2200 to be formed directly onto the tube 2202. In some examples, the reference electrode 2206, the counter electrode 2208 and the working electrode 2210 of the physiological characteristic sensor 2200 are fabricated onto a flat surface 2202b of the tube 2202 through printing, screen-printing, laser etching, and/or photolithography. In addition, a coating, such as slot coating, spray coating, etc. may be used for chemistries associated with the working electrode 2210. The support fixture 2204 is removed after the physiological characteristic sensor 2200 is formed on the tube 2202. In this example, the fluid from the fluid reservoir 160 exits the tube 2202 at a fluid outlet 2212. In this example, the fluid outlet 2212 is defined at a terminal end 2202c of the tube 2202.

In this example, the physiological characteristic sensor 2200 includes the reference electrode 2206, the counter electrode 2208 and the working electrode 2210. As the reference electrode 2206, the counter electrode 2208 and the working electrode 2210 are substantially the same as the reference electrode 1306, the counter electrode 1308 and the working electrode 1310 discussed previously herein, the reference electrode 2206, the counter electrode 2208 and the working electrode 2210 will not be discussed in detail. Briefly, the chemical reaction between the glucose and the oxygen at the working electrode 2210 generates an electrical signal, which is transmitted by the working electrode 2210 and communicated to the control module 822 of the fluid infusion device 800, as will be discussed further herein.

It should be noted, however, that other sensor and tube configurations are also contemplated. For example, with reference to FIG. 101, a physiological characteristic sensor (e.g. glucose sensor) 2250 is shown coupled to a tube 2252. As the physiological characteristic sensor 2200 and the tube 2202 include the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 2200 and the tube 2202 discussed with regard to FIGS. 99 and 100, the same reference numerals will be used to denote the same or similar components.

The tube 2252 may facilitate a fluidic connection between a connector, like the connector 702, with the infusion monitor unit 708, and a proximalmost end 2252*a* of the tube 2252 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2252. The tube 2252 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP) ethylene tetrafluoroethylene and pellathane. The tube 2252 is in a first state in FIG. 101. In this example, the tube 2252 is composed of three cannulated sections 2254, which are interconnected via a thin web section 2256. Each of the cannulated sections 2254 provide a fluid delivery conduit for the fluid from the fluid reservoir 160. In some examples, the cannulated sections 2254 include at least one fluid outlet 2257 (FIG. 102), which is defined through a surface 2254*a* of the respective cannulated section 2254. The surface 2254*a* is opposite a surface 2254*b* of the cannulated section 2254 on which a portion of the physiological characteristic sensor 2250 is formed to improve physiological characteristic sensor 2250 accuracy. In this example, the fluid from the fluid reservoir 160 exits the tube 2252 at the fluid outlet 2257 associated with each of the cannulated sections 2254. It should be noted that in other variations, a terminal end of each of the cannulated sections 2254 may define a fluid outlet. The thin web sections 2256 interconnect the three cannulated sections 2254. Generally, the thin web sections 2256 form a living hinge, which enables the cannulated sections 2254 to bend toward each other to define a circular structure or enclosure, as shown in FIG. 102. The tube 2252 is in a second state in FIG. 102. It should be noted that while the tube 2252 is shown in FIG. 102 as being formed such that the physiological characteristic sensor 2250 is on an external perimeter of the tube 2252 while the fluid outlets 2257 are on an internal perimeter, the tube 2252 may be formed such that the physiological characteristic sensor 2250 is along the external perimeter of the tube 2252 and the fluid outlets 2257 are on the internal perimeter.

Figure 101:
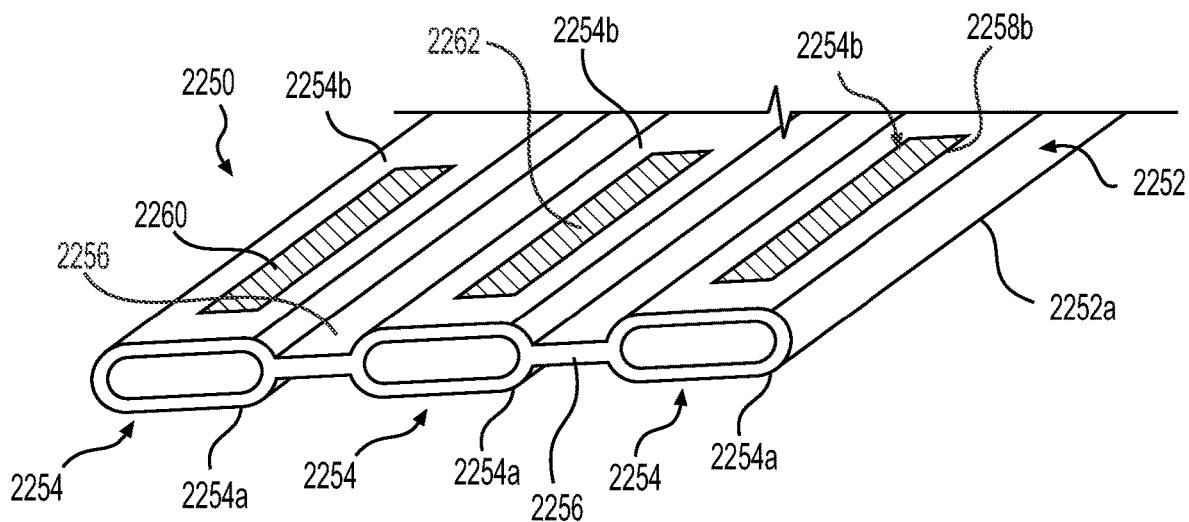
FIG. 101 is a schematic perspective view of an exemplary implementation involving a plurality of tubes that is integrated with a physiological characteristic sensor.
Figure 102:
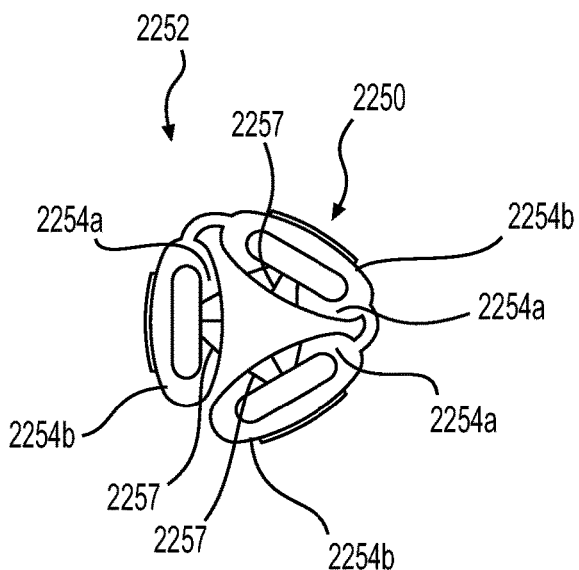
FIG. 102 is a schematic end view of the implementation of FIG. 101 in which the plurality of tubes forms an enclosure.

With reference to FIG. 101, the cannulated sections 2254 have a rectangular cross-section. In some examples, the tube 2252 may be formed by extrusion, micro-electromechanical system/photolithography, additively manufactured, etc. In the example of micro-electromechanical system/photolithography, the tube 2252 may be built directly onto itself, layer by layer. The use of the rectangular tube 2252 enables the physiological characteristic sensor 2250 to be formed directly onto the tube 2252. A support fixture may be used to form the physiological characteristic sensor 2250 on the tube 2252. In some examples, a reference electrode 2258, a counter electrode 2260 and a working electrode 2262 of the physiological characteristic sensor 2250 are fabricated onto a respective one of the surfaces 2254*b* of the cannulated sections 2254 through printing, screen-printing, laser etching, and/or photolithography. In addition, a coating, such as slot coating, spray coating, etc. may be used for chemistries associated with the working electrode 2262.

In this example, the physiological characteristic sensor 2250 includes the reference electrode 2258, the counter electrode 2260 and the working electrode 2262. As the reference electrode 2258, the counter electrode 2260 and the working electrode 2262 are substantially the same as the reference electrode 1306, the counter electrode 1308 and the working electrode 1310 discussed previously herein, the reference electrode 2258, the counter electrode 2260 and the working electrode 2262 will not be discussed in detail. Briefly, the chemical reaction between the glucose and the oxygen at the working electrode 2262 generates an electrical signal, which is transmitted by the working electrode 2262 and communicated to the control module 822 of the fluid infusion device 800, as will be discussed further herein.

It should be noted, however, that other sensor and tube configurations are also contemplated. For example, with reference to FIGS. 103A and 103B, a physiological characteristic sensor (e.g. glucose sensor) 2300 is shown coupled to a tube 2302. Insofar as the physiological characteristic sensor 2300 and the tube 2302 include the same or similar components as the physiological characteristic sensor 716 and the tube 706 discussed with regard to FIGS. 39-41, the physiological characteristic sensor 1300 discussed with regard to FIGS. 53-55, and the physiological characteristic sensor 2200 and the tube 2202 discussed with regard to FIGS. 99 and 100, the same reference numerals will be used to denote the same or similar components.

The tube 2302 may facilitate a fluidic connection between a connector, like the connector 702, with the infusion monitor unit 708, and a proximalmost end 2302*a* of the tube 2302 may extend from the housing 710 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2302. The tube 2302 may be composed of a polymer based material, including, but not limited to polytetrafluroethylene (PTFE), polyethylene (PE), polyurethane (PU), Teflon coated catheters, polyether block amide (PEBA), Nylon, polyester, polyether ether ketone (PEEK), polyimide, polypropylene, perfluoroalkoxy (PFA), fluorinated ethylene propylene (FEP). The tube 2302 provides a fluid delivery conduit for the fluid from the fluid reservoir 160. In some examples, the tube 2302 includes one or more fluid outlets 2304. In this example, the tube 2302 includes a plurality of fluid outlets 2304, which increase in diameter from adjacent to a first, terminal end 2302b of the tube 2302 toward a second end 2303 of the tube 2302. In this example, the tube 2302 includes four fluid outlets 2304a-2304d, which are each defined through a surface 2302c of the tube 2302. The surface 2302c is opposite a surface 2302d of the tube 2302 coupled to the physiological characteristic sensor 2300 to improve physiological characteristic sensor 2300 accuracy. The fluid outlets 2304a-2304d has a respective diameter D23a-D23d, which as discussed, increases monotonically from the fluid outlet 2304a to the fluid outlet 2304d. The increasing diameters of the fluid outlets 2304a-2304d provides for preferential fluid delivery. In the example of increasing diameters, the fluid is delivered in a larger quantity adjacent to a surface of the user's skin where the fluid, such as insulin, is better absorbed by the interstitial tissue. It should be noted, however, that the diameters D23a-D23d may decrease monotonically, such that the fluid is preferentially delivered closer to the terminal end 2302b of the tube 2302.

In some examples, the tube 2302 may be formed by extrusion, micro-electromechanical system/photolithography, additively manufactured, etc. In the example of micro-electromechanical system/photolithography, the tube 2302 may have a rectangular cross-section as shown in FIGS. 103A and 103B. Alternatively, the tube 2302 may be formed using extrusion, and may have a circular cross-section, as shown in FIGS. 104A and 104B.

The physiological characteristic sensor 2300 includes the reference electrode 1306, the counter electrode 1308 and the working electrode 1310. The physiological characteristic sensor 2300 may be integrally formed with the tube 2050 by overmolding, printing, screen-printing, laser etching, photolithography, etc. The chemical reaction between the glucose and the oxygen at the working electrode 1310 generates an electrical signal, which is transmitted by the working electrode 1310 and communicated to the control module 822 of the fluid infusion device 800, as will be discussed further herein.

Figure 106:
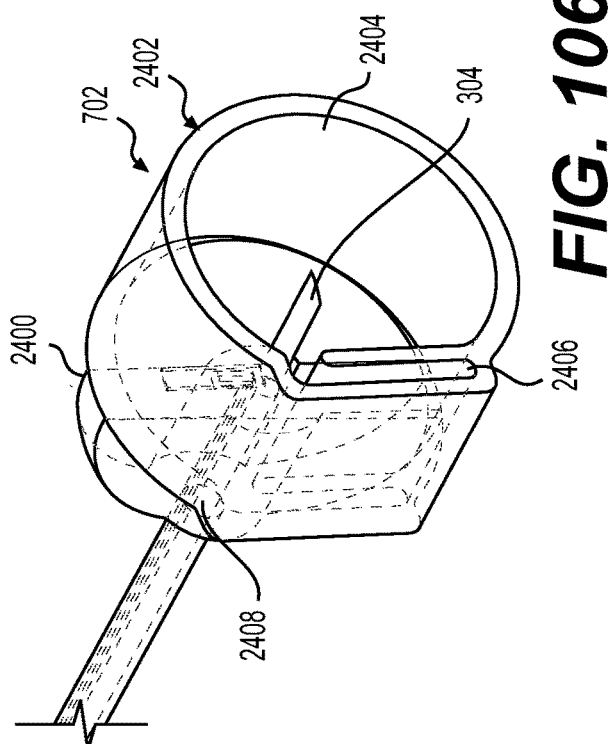
FIG. 106 is an end view of a connector in which a communication component has been removed for clarity.

With reference to FIG. 105, the connector 702 is a removable reservoir cap (or fitting) that is suitably sized and configured to accommodate replacement of the fluid reservoir 160 (which are typically disposable) as needed. The needle 304 defines a flow path for the fluid out of the fluid reservoir 160, through the connector 702 and into the tube 706. In this example, the connector 702 is annular, and includes a first end 2400 and an opposite second end 2402. The first end 2400 is fluidly coupled to the second end 706b of the tube 706, and may include a graspable surface 2400a to enable a user to manipulate the connector 702. With reference to FIG. 106, the second end 2402 is circumferentially open, and defines a counterbore 2404 and a receptacle 2406. The counterbore 2404 is sized and shaped to be positioned about the fluid reservoir 160 to define the fluid flow path from the fluid reservoir 160 to the tube 706. The needle 304 extends through the counterbore 2404, and is fluidly coupled to the first end 2400. The receptacle 2406 is defined along a side 2408 of the connector 702. In some examples, the receptacle 2406 is rectangular, and is sized to extend from the second end 2402 toward the first end 2400. The receptacle 2406 receives a communication component 2410 associated with the infusion monitor unit 708, which is removed from FIG. 106 for clarity.

Figure 107:
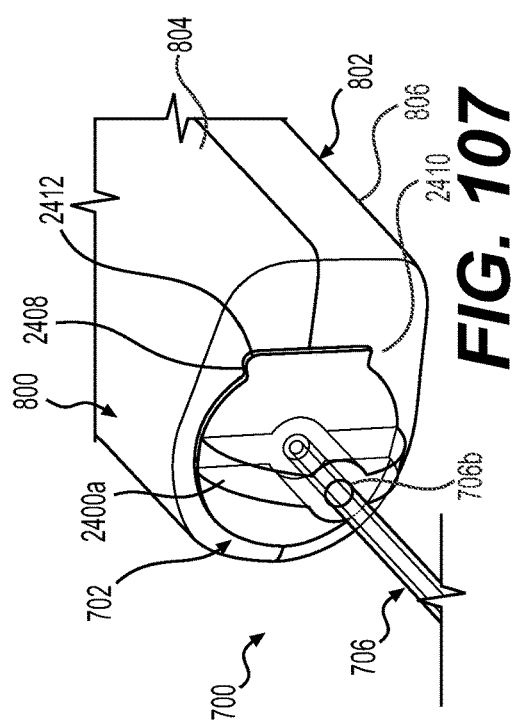
FIG. 107 is a perspective view of the connector of the infusion set assembly coupled to a fluid reservoir of the fluid infusion device of FIG. 105.

With reference to FIG. 107, the connector 702 is sized to be received within a portion of a housing 802 of the fluid infusion device 800 such that the fluid flow path is defined between the fluid reservoir 160 and the tube 706, and electrical communication is established between the infusion monitor unit 708 and the fluid infusion device 800. Generally, the connector 702 establishes a fluidic connection between the tube 706 and the fluid reservoir 160, and also establishes an electrical connection between the physiological characteristic sensor 716 of the infusion monitor unit 708 to communicate the glucose level to the control module 822 of the fluid infusion device 800. It should be noted that the following description of the connector 702 employed to fluidically and electrically connect the tube 706 and the physiological characteristic sensor 716 of the infusion monitor unit 708 with the control module 822 of the fluid infusion device 800 is merely one example. In this regard, the connector 702 may be employed with any of the sensor and tube configurations for use with the infusion monitor unit 708 described herein with regard to FIGS. 39-104B. For example, the connector 702 may be employed to fluidically connect or fluidly couple the respective tube 706, 1002, 1102, 1202, 1249, 1301, 1402, 1449, 1502, 1552, 1602, 1652, 1702, 1752, 1802, 1952, 2000, 2050, 2100, 2150 to the fluid reservoir 160 and to electrically connect or enable communication between the respective physiological characteristic sensor 716, 1000, 1300, 1800, 2200, 2250, 2300 and the control module 822. The connector 702 may also be used to fluidically connect or fluidly couple the plurality of fibers 1850 to the fluid reservoir 160 and to electrically connect or enable communication between the plurality of fibers 1850 and the control module 822. The connector 702 may also be used to fluidically and electrically connect the ribbon cable 1900 to the fluid reservoir 160 and the control module 822, respectively. In this example, the housing 802 of the fluid infusion device 800 includes a slot 2412 in communication with the opening 410 to enable the connector 702 to be received within and coupled to the fluid infusion device 800.

Figure 108:
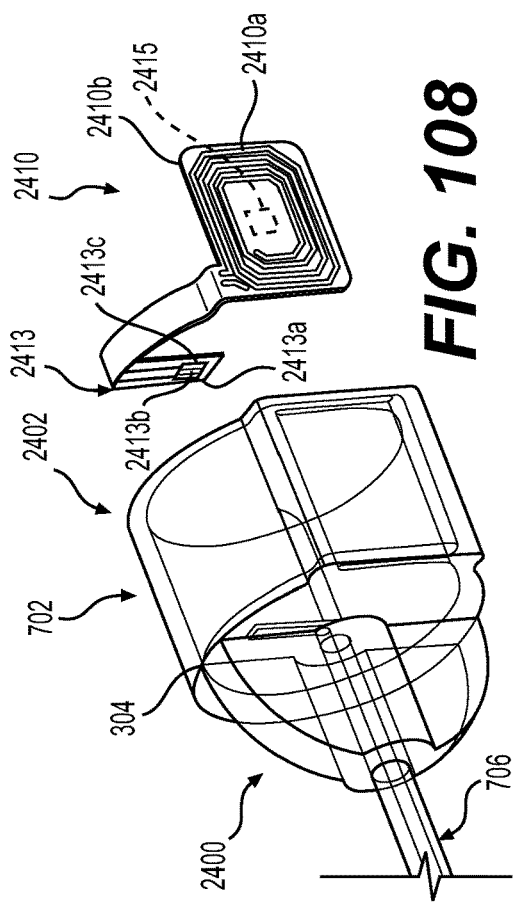
FIG. 108 is an exploded view of the connector and the communication component.

With reference to FIG. 108, the connector 702 is shown exploded from the communication component 2410. In this example, the communication component 2410 is an antenna, including, but not limited to a near-field communication (NFC) antenna. The communication component 2410 transfers data and power between the infusion monitor unit 708 and the fluid infusion device 800. For example, the communication component 2410 transfers data from the infusion monitor unit 708, such as observations or measurements from the physiological characteristic sensor 716 to the fluid infusion device 800 (FIG. 39) and transfers power from the fluid infusion device 800 to the infusion monitor unit 708 to provide power to the physiological characteristic sensor 716 (FIG. 39). In alternative embodiments, the communication component 2410 also transfers data wirelessly between the infusion monitor unit 708 and the fluid infusion device 800.

Figure 110:
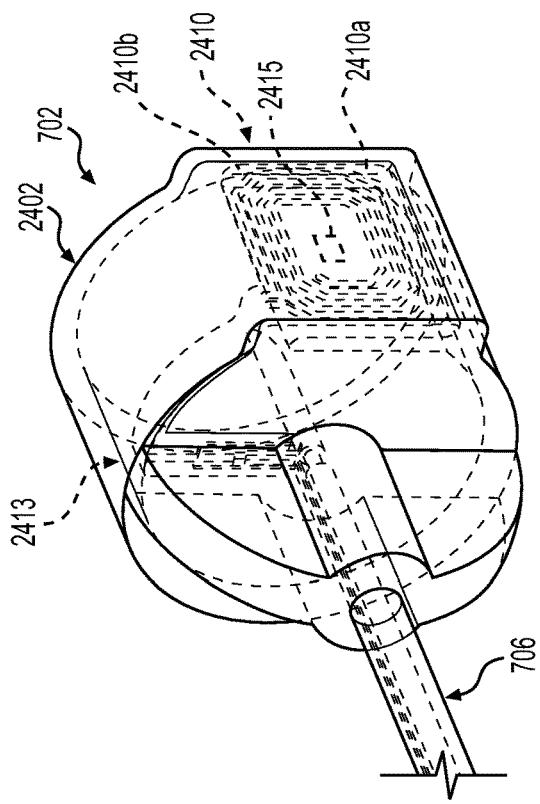
Figure 109:
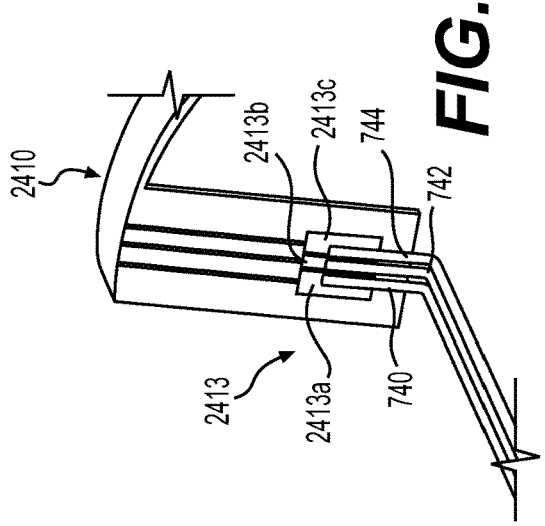

In this example, the communication component 2410 is defined by a plurality of trace coils 2410a embedded into a flexible printed circuit board 2410b. The flexible printed circuit board 2410b also includes a connector 2413 that electrically and mechanically couples the electrodes 740, 742, 744 to the communication component 2410. In this example, the connector 2413 includes a plurality of contact pads 2413a-2413c, however, any suitable technique may be employed. As shown in FIG. 109, which is a detail view of the connector 2413 and the electrodes 740, 742, 744 in isolation, the contact pads 2413a-2413c electrically and mechanically couple each of the electrodes 740, 742, 744 to the communication component 2410, which enables the communication component 2410 to transmit both data and power to and from the electrodes 740, 742, 744. Once coupled together, the contact pads 2413a-2413c and the electrodes 740, 742, 744 may be covered with an electrical insulation coating to inhibit electrical shorts. With reference to FIG. 110, the communication component 2410 may also include a control module 2415, which may be mechanically and electrically coupled to the printed circuit board 2410b to control the transfer of power and data by the communication component 2410 to a device communication component 2414. The control module 2415 may be located on either side of the printed circuit board 2410b, and may be coated with an electrical insulation layer.

Figure 111:
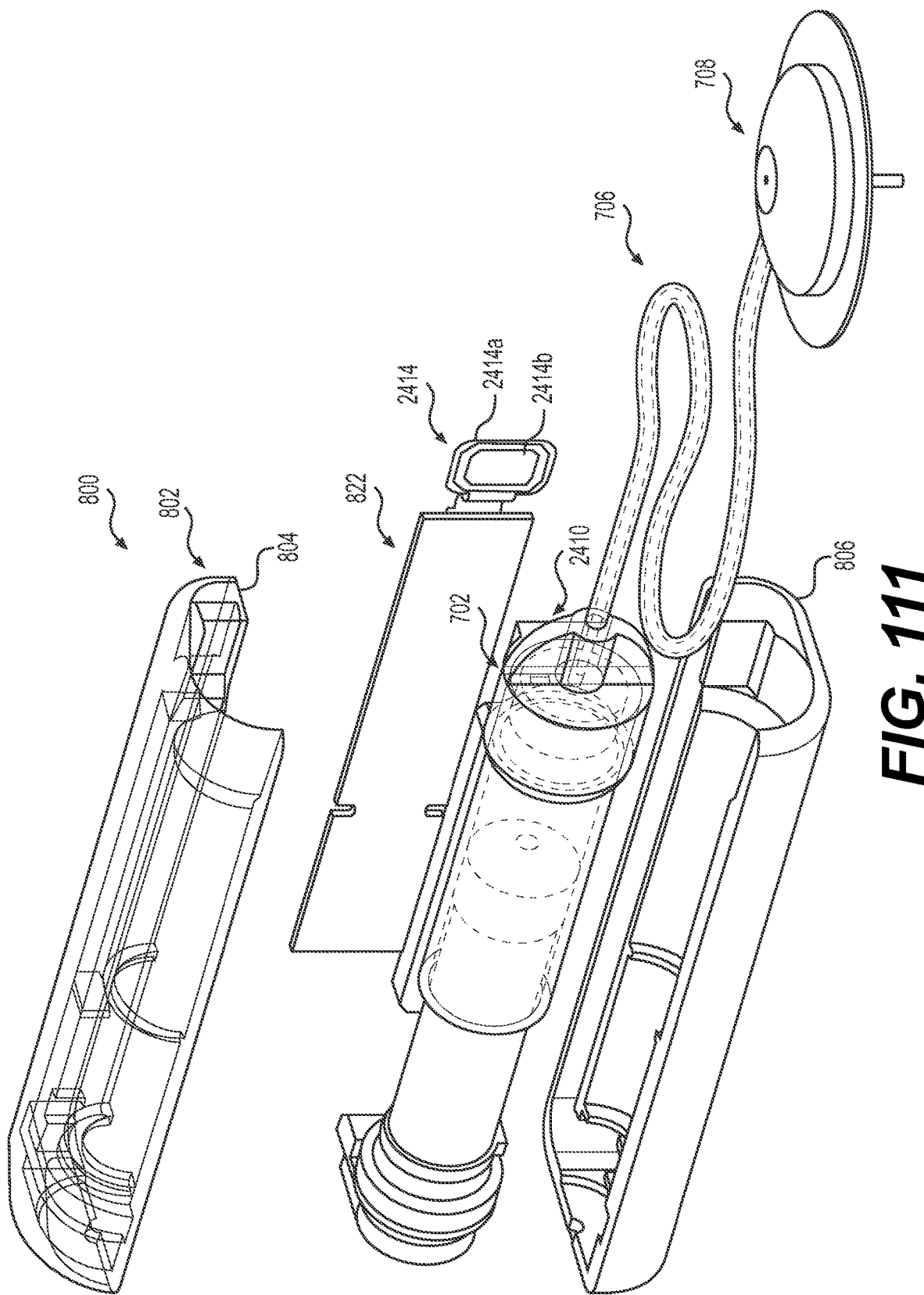

In this example, with reference to FIG. 111, the fluid infusion device 800 includes a device communication component 2414. The device communication component 2414 is in communication with the communication component 2410 to transfer data and power between the infusion monitor unit 708 and the fluid infusion device 800. In some examples, the device communication component 2414 is an antenna, including, but not limited to a near-field communication (NFC) antenna. The device communication component 2414 is electrically and mechanically coupled to the control module 822 of the fluid infusion device 800, and in some examples, may be formed of trace coils 2414a on a portion of a printed circuit board 2414b associated with the control module 822. When the connector 702 is coupled to the housing 802 of the fluid infusion device 800, as shown in FIG. 107, communication is established between the communication component 2410 and the device communication component 2414 due to the proximity of the communication component 2410 to the device communication component 2414.

It should be noted, however, that while the communication component 2410 and the device communication component 2414 are described herein as using antennas to enable the transfer of data and power between the infusion monitor unit 708 and the fluid infusion device 800, it should be noted that the communication component 2410 and the device communication component 2414 may be configured differently to enable communication between the infusion monitor unit 708 and the fluid infusion device 800. For example, with reference to FIG. 112, a communication component 2500 and a device communication component 2502 are shown. As the communication component 2500 and the device communication component 2502 include the same or similar components as the communication component 2410 and the device communication component 2414 discussed with regard to FIGS. 105-111, the same reference numerals will be used to denote the same or similar components.

Figure 113:
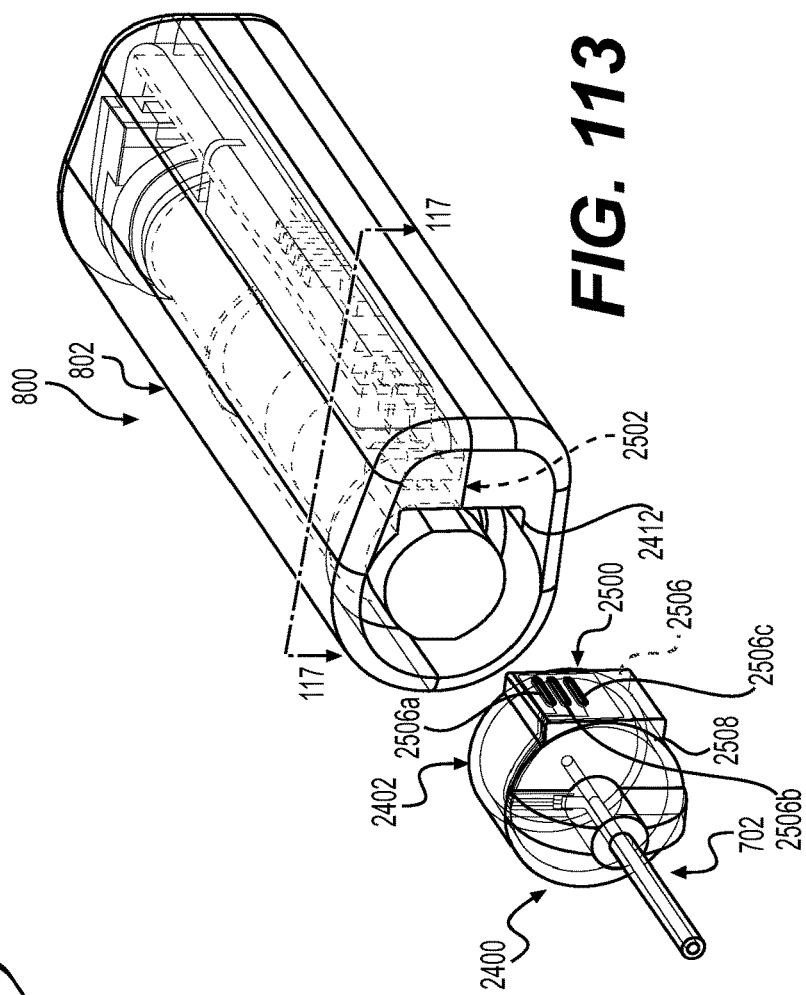

With reference to FIG. 113, the communication component 2500 is coupled to a receptacle 2506 defined in the connector 702. The receptacle 2506 is defined along a side 2508 of the connector 702. In some examples, the receptacle 2506 is rectangular, and is sized to extend from the second end 2402 toward the first end 2400. In this example, the receptacle 2506 includes a plurality of channels 2506a-2506c. The channels 2506a-2506c expose a portion of the communication component 2500 to enable communication between the communication component 2500 and the device communication component 2502. The channels 2506a-2506c are generally defined to extend for a predefined length from proximate the second end 2402 toward the first end 2400. With reference back to FIG. 112, the connector 702 is sized to be received within a portion of the housing 802 of the fluid infusion device 800 such that the fluid flow path is defined between the fluid reservoir 160 and the tube 706, and electrical communication is established between the infusion monitor unit 708 and the fluid infusion device 800. In this example, the housing 802 of the fluid infusion device 800 includes the slot 2412 in communication with the opening 410 to enable the connector 702 to be received within and coupled to the fluid infusion device 800.

With reference to FIG. 114, the connector 702 is shown exploded from the communication component 2500. In this example, the communication component 2500 includes a plurality of contact pads 2500a-2500c, one for each of the electrodes 740, 742, 744. The communication component 2500 transfers data and power between the infusion monitor unit 708 and the fluid infusion device 800. For example, the communication component 2500 transfers data from the infusion monitor unit 708, such as observations or measurements from the physiological characteristic sensor 716, to the fluid infusion device 800 (FIG. 39) and transfers power from the fluid infusion device 800 to the infusion monitor unit 708 to provide power to the physiological characteristic sensor 716 (FIG. 39).

In this example, the communication component 2500 is defined by the contact pads 2500a-2500c, which are embedded into a flexible printed circuit board 2500d. The flexible printed circuit board 2500b also includes the connector 2413 that electrically and mechanically couples the electrodes 740, 742, 744 to the communication component 2410. As shown in FIG. 115, which is a detail view of the contact pads 2500a-2500c, the connector 2413 and the electrodes 740, 742, 744 in isolation, the contact pads 2413a-2413c electrically and mechanically couple each of the electrodes 740, 742, 744 to a respective one of the contact pads 2500a-2500c via the printed circuit board 2500d, which enables the communication component 2500 to transmit both data and power to and from the electrodes 740, 742, 744. With reference to FIG. 116, in this example, the communication component 2500 may also include the control module 2415, which may be mechanically and electrically coupled to the printed circuit board 2500d to control the transfer of power and data by the communication component 2500 to the device communication component 2502. The control module 2415 may be located on either side of the printed circuit board 2500d, and may be coated with an electrical insulation layer. As shown in FIG. 116, each one of the channels 2506a-2506c exposes a respective one of the contact pads 2500a-2500c when the communication component 2500 is coupled to the receptacle 2506. The exposed portion of the contact pads 2500a-2500c enables communication between the communication component 2500 and the device communication component 2502. In addition, the printed circuit board 2500d is also coupled to the receptacle 2506 via heat stake, ultrasonic welding, adhesive, etc. to electrically isolate the contact pads 2500a-2500c in the instance that the connector 702 is exposed to fluids.

Figure 117:
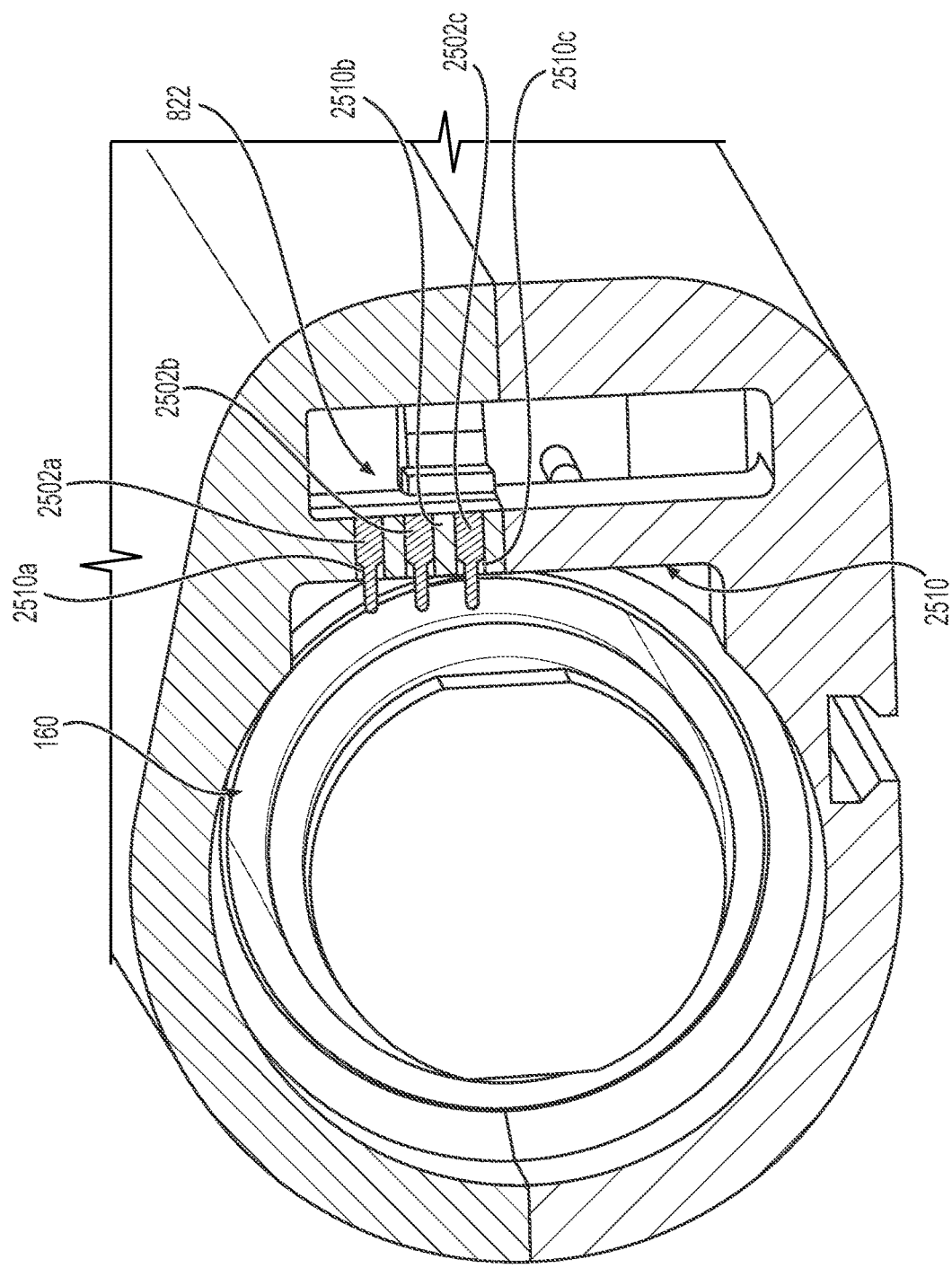

In this example, with reference to FIG. 117, the device communication component 2502 is shown. The device communication component 2502 is in communication with the communication component 2500 to transfer data and power between the infusion monitor unit 708 and the fluid infusion device 800. In some examples, the device communication component 2502 is a pogo pin connector, with three pogo pins 2502a-2502c. Each pogo pin 2502a-2502c is associated with a respective one of the contact pads 2500a-2500c, and establishes electrical communication between the electrodes 740, 742, 744 and the control module 822 of the fluid infusion device 800. Each of the pogo pins 2502a-2502c extend a distance beyond a sidewall 2510 of the housing 802 to enable contact between the pogo pins 2502a-2502c and the contact pads 2500a-2500c. In this example, the sidewall 2510 defines a plurality of bores 2510a-2510c, one for each of the pogo pins 2502a-2502c, however, the sidewall 2510 may be configured with a slot or other opening that enables the pogo pins 2502a-2502c to make contact with the contact pads 2500a-2500c when the connector 702 is coupled to the housing 802.

Figure 118:
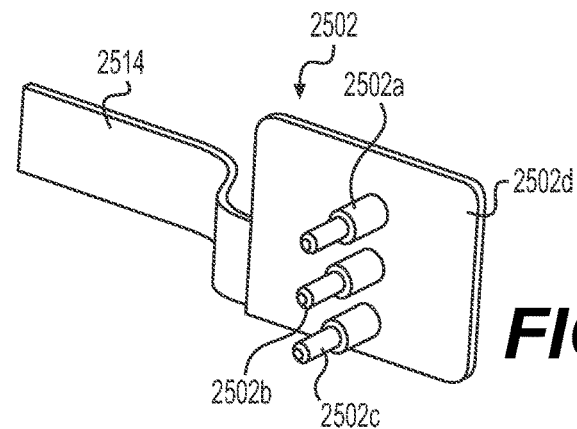
Figure 119:
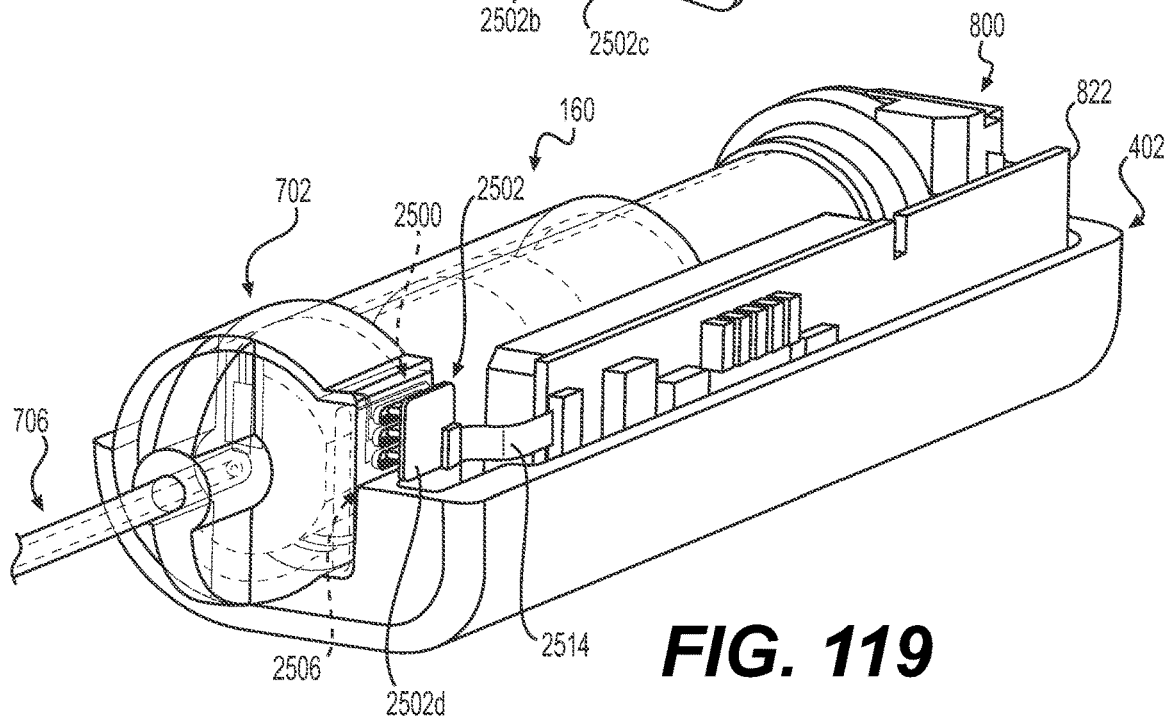
Figure 120:
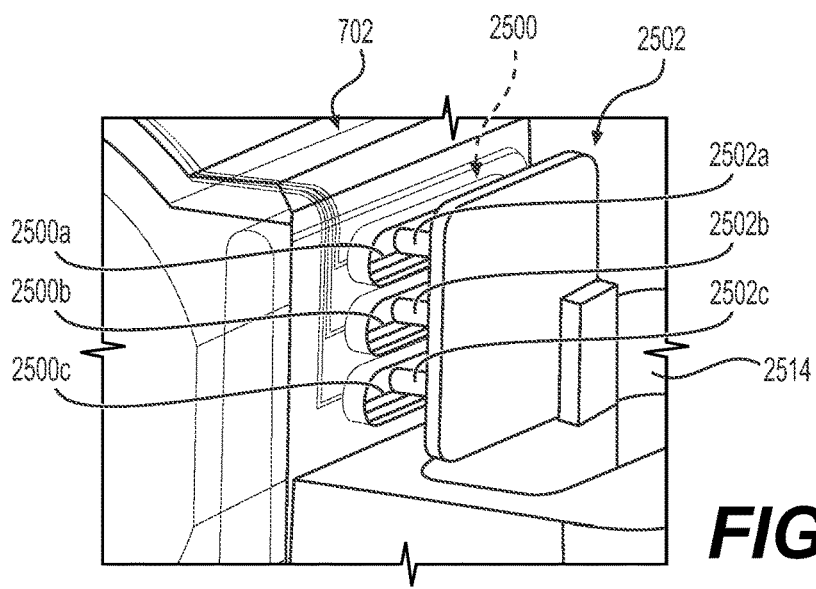

In some examples, with reference to FIG. 118, the device communication component 2502 is shown in greater detail. The device communication component 2502 is electrically and mechanically coupled to the control module 822 of the fluid infusion device 800 via a conductive wire 2514, and in some examples, includes the pogo pins 2502a-2502c, which are coupled to a printed circuit board 2502d. The printed circuit board 2502d is electrically and mechanically coupled to the control module 822 via the conductive wire 2514, as shown in FIG. 119. In addition, with reference back to FIG. 117, the printed circuit board 2502d is also coupled to the sidewall 2510 via heat stake, ultrasonic welding, adhesive, etc. to form a seal that inhibits fluids from entering through the bores 2510a-2510c. Alternatively, or in addition, one or more sealing members, such as O-rings may be positioned about the pogo pins 2502a-2502c to inhibit fluids from entering through the bores 2510a-2510c. With reference to FIG. 120, when the connector 702 is coupled to the housing 802 of the fluid infusion device 800, communication is established between the communication component 2500 and the device communication component 2502 due to the contact between the contact pads 2500a-2500c and the pogo pins 2502a-2502c.

It should be noted, however, that the communication component 2500 may be configured differently to enable communication with the device communication component 2502. For example, with reference to FIG. 121, a communication component 2550 is shown. The communication component 2550 may be employed with the device communication component 2502 to enable communication between the infusion monitor unit 708 and the fluid infusion device 800. As the communication component 2550 and the device communication component 2502 include the same or similar components as the communication component 2500 discussed with regard to FIGS. 112-120, the same reference numerals will be used to denote the same or similar components.

With reference to FIG. 121, the communication component 2550 is coupled to a receptacle 2556 defined in the connector 702. The receptacle 2556 is defined along a side 2558 of the connector 702. In some examples, the receptacle 2556 is rectangular, and is sized to extend from the second end 2402 toward the first end 2400. In this example, the receptacle 2556 includes a plurality of channels 2556a-2556c and includes a gasket 2560. The channels 2556a-2556c expose a portion of the communication component 2550 to enable communication between the communication component 2550 and the device communication component 2502. The channels 2556a-2556c are generally defined to extend for a predefined length from proximate the second end 2402 toward the first end 2400, and in some examples, each of the channels 2556a-2556c include a ramp 2559. The ramp 2559 guides the respective one of the pogo pins 2502a-2502c into the respective channel 2506a-2506c.

The gasket 2560 is compressible upon insertion of the connector 702 into the housing 802 to form a watertight seal about the communication component 2550. The gasket 2560 may be composed of an elastomeric material. With reference to FIG. 122A, a side view of the connector 702 with the communication component 2550 is shown. As shown, further in FIG. 122B, the gasket 2560 extends beyond a surface 2562 of the connector 702 a distance D2560. The distance D2560 is predefined to enable the connector 702 to be inserted into the housing 802 (FIG. 119) of the fluid infusion device 800 without undue force. In this example, the gasket 2560 extends about a perimeter of the channels 2506a-2506c, however, the gasket 2560 may be configured to extend around each of the channels 2506a-2506c individually, for example.

With reference back to FIG. 121, the communication component 2550 includes the plurality of contact pads 2500a-2500c, one for each of the electrodes 740, 742, 744. The communication component 2550 transfers data and power between the infusion monitor unit 708 and the fluid infusion device 800. In this example, the communication component 2550 is defined by the contact pads 2500a-2500c, which are embedded into the flexible printed circuit board 2500d. The communication component 2500 may also include the control module 2415, which may be mechanically and electrically coupled to the printed circuit board 2500d to control the transfer of power and data by the communication component 2500 to the device communication component 2502. Each one of the channels 2556a-2556c exposes a respective one of the contact pads 2500a-2500c when the communication component 2550 is coupled to the receptacle 2556. The exposed portion of the contact pads 2500a-2500c enables communication between the communication component 2550 and the device communication component 2502. In addition, the printed circuit board 2500d is also coupled to the receptacle 2556 via heat stake, ultrasonic welding, adhesive, etc. to electrically isolate the contact pads 2500a-2500c in the instance that the connector 702 is exposed to fluids. When the connector 702 is coupled to the housing 802 of the fluid infusion device 800 (FIG. 119), the gasket 2560 is compressed, and the ramps 2559 guide the respective pogo pins 2502a-2502c into contact with the respective contact pad 2500a-2500c to establish communication between the communication component 2550 and the device communication component 2502.

It should be noted, however, that while the communication component 2410 and the device communication component 2414 are described herein as using antennas to enable the transfer of data and power between the infusion monitor unit 708 and the fluid infusion device 800, it should be noted that the communication component 2410 and the device communication component 2414 may be configured differently to enable communication between the infusion monitor unit 708 and the fluid infusion device 800. For example, with reference to FIG. 123, a communication component 2600 and a device communication component 2602 are shown. As the communication component 2600 and the device communication component 2602 include the same or similar components as the communication component 2410 and the device communication component 2414 discussed with regard to FIGS. 105-111 and the communication component 2500 and the device communication component 2502 discussed with regard to FIGS. 112-120, the same reference numerals will be used to denote the same or similar components.

With reference to FIG. 123, the communication component 2600 is coupled to a receptacle 2606 defined in the connector 702. The receptacle 2606 is defined along a side 2608 of the connector 702. In some examples, the receptacle 2606 is rectangular, and is sized to extend from the second end 2402 toward the first end 2400. In this example, the receptacle 2606 is rectangular. The connector 702 is sized to be received within a portion of the housing 802 of the fluid infusion device 800 such that the fluid flow path is defined between the fluid reservoir 160 and the tube 706, and electrical communication is established between the infusion monitor unit 708 (FIG. 39) and the fluid infusion device 800. In this example, the housing 802 of the fluid infusion device 800 includes the slot 2412 in communication with the opening 410 to enable the connector 702 to be received within and coupled to the fluid infusion device 800.

With reference to FIG. 124, the connector 702 and the communication component 2600 are partially exploded. In this example, the communication component 2600 includes an electrode connector 2610 and a device connector 2612. The device connector 2612 is coupled to and in electrical communication with the electrode connector 2610 and the device communication component 2602 (FIG. 123). With reference to FIG. 125, the electrode connector 2610 is shown exploded from the connector 702. The electrode connector 2610 includes a plurality of contact pads 2610a-2610c, one for each of the electrodes 740, 742, 744. The communication component 2600 transfers data and power between the infusion monitor unit 708 and the fluid infusion device 800 (FIG. 39). For example, the communication component 2600 transfers data from the infusion monitor unit 708, such as observations or measurements from the physiological characteristic sensor 716, to the fluid infusion device 800 (FIG. 39) and transfers power from the fluid infusion device 800 to the infusion monitor unit 708 to provide power to the physiological characteristic sensor 716 (FIG. 39).

In this example, the communication component 2600 is defined by the contact pads 2610a-2610c, which are embedded into a flexible printed circuit board 2610d. The flexible printed circuit board 2610b also includes the connector 2413 that electrically and mechanically couples the electrodes 740, 742, 744 to the communication component 2410. In this example, with reference to FIG. 126, the contact pads 2413a-2413c electrically and mechanically couple each of the electrodes 740, 742, 744 to a respective one of the contact pads 2610a-2610c via the printed circuit board 2610d, which enables the communication component 2500 to transmit both data and power to and from the electrodes 740, 742, 744. With reference to FIG. 124, in this example, the communication component 2600 may also include the control module 2415, which may be mechanically and electrically coupled to the printed circuit board 2610d to control the transfer of power and data by the communication component 2600 to the device communication component 2602. The control module 2415 may be located on either side of the printed circuit board 2600d, and may be coated with an electrical insulation layer. In addition, the printed circuit board 2610d is also coupled to the receptacle 2606 via heat stake, ultrasonic welding, adhesive, etc. to electrically isolate the contact pads 2610a-2610c in the instance that the connector 702 is exposed to fluids.

The device connector 2612 is electrically and mechanically coupled to the electrode connector 2610 and is received within the receptacle 2606. The device connector 2612 is compressible upon insertion of the connector 702 into the housing 802 to form a watertight seal about the communication component 2600. The device connector 2612 may be composed of an elastomeric material. With reference to FIG. 127A, a side view of the connector 702 with the communication component 2600 is shown. As shown, further in FIG. 127B, the device connector 2612 extends beyond a surface 2616 of the connector 702 a distance D2616. The distance D2616 is predefined to enable the connector 702 to be inserted into the housing 802 (FIG. 123) of the fluid infusion device 800 without undue force. In this example, the device connector 2612 includes a plurality of pins 2614a-2614c, which are associated with a respective one of the contact pads 2610a-2610c. The pins 2614a-1614c are composed of an electrically conductive material, including, but not limited to, carbon, and are coupled to a gasket 2615. The gasket 2615 is compressible by the housing 802 (FIG. 123) to form the watertight seal between the connector 702 and the housing 802. The gasket 2615 is composed of an electrically insulative material, including, but not limited to, silicone. The contact between the contact pads 2610a-2610c, the pins 2614a-2614c and the device communication component 2602 enable communication between the infusion monitor unit 708 (FIG. 39) and the fluid infusion device 800 (FIG. 39).

In this example, with reference to FIG. 128, the device communication component 2602 is shown. The device communication component 2602 is in communication with the communication component 2600 to transfer data and power between the infusion monitor unit 708 (FIG. 39) and the fluid infusion device 800. In some examples, the device communication component 2602 is defined by contact pads 2620a-2620c, which are embedded into a flexible printed circuit board 2620d. Each of the contact pads 2620a-2620c is associated with a respective one of the pins 2614a-2614c, and establishes electrical communication between the electrodes 740, 742, 744 and the control module 822 of the fluid infusion device 800 (FIG. 123). Each of the contact pads 2620a-2620c extend along a sidewall 2630 of the housing 802 to enable contact by the pogo pins 2502a-2502c. In this example, the sidewall 2630 defines a bore 2630a, which is sized to receive the printed circuit board 2620d.

In some examples, with reference to FIG. 129, the device communication component 2602 is shown in greater detail. The device communication component 2602 is electrically and mechanically coupled to the control module 822 of the fluid infusion device 800 (FIG. 123) via a conductive wire 2634, and in some examples, includes the contact pads 2620a-2620c, which are coupled to the printed circuit board 2620d. The printed circuit board 2620d is electrically and mechanically coupled to the control module 822 via the conductive wire 2634 (FIG. 123). With reference back to FIG. 128, the printed circuit board 2620d is also coupled to the sidewall 2630 via heat stake, ultrasonic welding, adhesive, etc. to form a seal that inhibits fluids from entering through the bore 2630a. Alternatively, or in addition, one or more sealing members, such as O-rings may be positioned about the bore 2630a to inhibit fluids from entering through the bore 2630a. With reference to FIG. 123, when the connector 702 is coupled to the housing 802 of the fluid infusion device 800, communication is established between the communication component 2600 and the device communication component 2602 due to the contact between the contact pads 2610a-2610c, the pins 2614a-2614c and the contact pads 2620a-2620c.

Thus, with reference back to FIG. 39, the communication component 2410, 2500, 2550, 2600 and the device communication component 2414, 2502, 2602 enable communication between the infusion monitor unit 708 and the fluid infusion device 800. In this example, the fluid infusion device 800 is devoid of a user interface. As the fluid infusion device 800 is substantially the same as the fluid infusion device 400 discussed with regard to FIGS. 11-26B except for the device communication component 2414, 2502, 2602, the fluid infusion device 800 will not be discussed in great detail herein. Briefly, the fluid infusion device 800 includes the power supply 420, the charging coil 424, 424', the antenna 426, the control module 822 and the drive system 110 that are accommodated in the pump chamber 412a defined by a housing 802, and the fluid reservoir system 116 that is accommodated in a reservoir chamber 412b defined by the housing 802. As the housing 802 is substantially the same as the housing 402 except for the device communication component 2414, 2502, 2602 and the slot 2412, only the differences between the housing 802 and the housing 802 will be discussed herein, with the understanding that the remainder of the housing 802 is the same as the housing 802. The housing 802 includes a first housing portion 804 and a second housing portion 806, which are coupled together to form the housing 802. The first housing portion 804 and the second housing portion 806 are each composed of a polymeric material, including, but not limited to polycarbonate, and may be molded, additively manufactured, etc. Briefly, the slot 2412 is defined in each of the first housing portion 804 and the second housing portion 806 to be adjacent to and in communication with the opening 410. The slot 2412 cooperates with the opening 410 to receive the connector 702. The housing 802 has the largest dimension and the smallest dimension as discussed with regard to the housing 402.

The control module 822 includes a processor and a storage media that are mounted on a printed circuit board, but is also physically and electrically coupled to the respective device communication component 2414, 2502, 2602. In some embodiments, the printed circuit board is a rigid printed circuit board that enables communication between the power supply 420, drive system 110, the charging coil 424, 424', the antenna 426, the other components associated with the fluid infusion device 800 and the control module 822. The control module 822 may be in communication with the power supply 420 and drive system 110, and may be in communication with the charging coil 424, 424' to supply power to the power supply 420. The control module 822 may also be in communication with the antenna 426. The processor can be any custom made or commercially available processor, a central processing unit (CPU), an auxiliary processor among several processors associated with the control module 822, a semiconductor based microprocessor (in the form of a microchip or chip set), a macroprocessor, any combination thereof, or generally any device for executing instructions. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electrical, magnetic, and/or optical memory devices capable of storing data, some of which represent executable instructions, used by the control module 822 in controlling components associated with the fluid infusion device 800 and the infusion monitor unit 708.

The instructions may include one or more separate programs, each of which comprises an ordered listing of executable instructions for implementing logical functions. The instructions, when executed by the processor, receive and process input signals, perform logic, calculations, methods and/or algorithms for controlling the components of the fluid infusion device 800, and generate signals to components of the fluid infusion device 800 to control the drive system 110 based on the logic, calculations, methods, and/or algorithms. Although only one control module 822 is shown, embodiments of the fluid infusion device 800 can include any number of control modules that communicate over any suitable communication medium or a combination of communication mediums and that cooperate to process signals received from the portable electronic device, perform logic, calculations, methods, and/or algorithms, and generate control signals to control features of the fluid infusion device 800. In various embodiments, one or more instructions of the control module 822, when executed by the processor, receive and process signals from the portable electronic device associated with a user to generate one or more control signals to the power supply 420 to supply power to the drive system 110, for example. The instructions, when executed by the processor, receive and process input signals, perform logic, calculations, methods and/or algorithms for controlling the components of the infusion monitor unit 708, and generate signals to components of the infusion monitor unit 708 based on the logic, calculations, methods, and/or algorithms. The instructions, when executed by the processor, receive and process input signals received from the infusion monitor unit 708 and determine a glucose level or blood glucose value based on the signal received from the infusion monitor unit 708. The communication between the infusion monitor unit 708 and the fluid infusion device 800 enables the control module 822 of the fluid infusion device 800 to monitor the blood glucose levels of the user and in certain embodiments, may enable the control module 822 of the fluid infusion device 800 to increase and/or decrease the fluid supplied to the user via the infusion monitor unit 708 based on the measured glucose levels. The fluid infusion device 800 may also be coupled to the patch plate 450, 460 via the coupling slot 414 defined in the housing 802, or one of the other techniques described with regard to coupling the fluid infusion device 400 to the patch plate 450, 460 (e.g. magnetically, friction, mechanical fasteners). The fluid infusion device 800 may be charged via the charging mat 432 and/or the wireless charging dongle 434.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 130, a tube 2690 and an infusion monitor unit 2700 are shown. As the tube 2690 and the infusion monitor unit 2700 include the same or similar components as the tube 706 and the infusion monitor unit 708 discussed with regard to FIGS. 39-104B, the same reference numerals will be used to denote the same or similar components.

With reference to FIG. 130, the tube 2690 includes a first end 2690a and the opposite second end 706b (FIG. 39). A first end 2690a is coupled to the infusion monitor unit 2700, while the second end is coupled to a connector, such as the connector 702 (FIG. 39). In this example, a proximalmost end 2692 of the tube 2690 is inserted into the anatomy to provide the fluid flow path from the fluid reservoir 160 (FIG. 39) into the anatomy of the user. The tube 2690 may facilitate a fluidic connection between a connector, like the connector 702, and the infusion monitor unit 2700, and the proximalmost end 2692 of the tube 2690 may extend from a housing 2703 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 800 is a fluid source, which is fluidly connected to the tube 2690. In some examples, with reference to FIG. 131, a cross-sectional view of the tube 2690 is shown. The tube 2690 includes a plurality of conduits 2694. In this example, the tube 2690 includes a fluid delivery conduit 2694a, a power electrode conduit 2694b, a ground electrode conduit 2694c, a transmitter conduit 2694d and a receiver conduit 2694e. The fluid delivery conduit 2694a receives the fluid from the fluid reservoir 160 and directs the fluid from the fluid reservoir 160 through the tube 2690. In some examples, with reference to FIG. 130, the fluid delivery conduit 2694a terminates at the proximalmost end 2692 of the tube 2690, such that a fluid outlet is defined at a terminal end of the proximalmost end 2692. With reference to FIG. 131, the power electrode conduit 2694b receives a power line 2696 associated with the infusion monitor unit 2700, and directs the power line 2696 through the tube 2690 to a unit control module 2702 associated with the infusion monitor unit 2700. The ground electrode conduit 2694c receives a ground line 2697 associated with the infusion monitor unit 2700, and directs the ground line 2697 through the tube 2690 to the unit control module 2702 associated with the infusion monitor unit 2700. The transmitter conduit 2694d receives a transmitter line 2698 associated with the infusion monitor unit 2700, and directs the transmitter line 2698 through the tube 2690 to the unit control module 2702 associated with the infusion monitor unit 2700. The receiver conduit 2694e receives a receiver line 2699 associated with the infusion monitor unit 2700, and directs the receiver line 2699 through the tube 2690 to the unit control module 2702 associated with the infusion monitor unit 2700. Thus, in this example, the proximalmost end 2692 of the tube 2690 or the portion of the tube 2690 that extends into the anatomy, includes merely the fluid delivery conduit 2694a.

With reference back to FIG. 130, the infusion monitor unit 2700 is shown in greater detail. The infusion monitor unit 2700 includes the housing 2703, the coupling member or adhesive patch 712 and a physiological characteristic sensor (e.g. glucose sensor) 2704. The housing 2703 comprises the tube connector 720, the mount 722 and a unit control module 2702. The tube connector 720 is coupled to the tube 706 and to the mount 722. In this example, the first end 2690a of the tube 2690 passes through the housing 2703 so that the proximalmost end 2692 of the tube 2690 may be inserted into the anatomy. The tube 2690 can be coupled to the tube connector 720 through any suitable technique, including, but not limited to, press-fit, adhesives, welding, etc. The first end 2690a of the tube 2690 is mechanically and electrically coupled to the unit control module 2702 to enable communication between the unit control module 2702 and the lines 2696-2699. The adhesive patch 712 is affixes the infusion monitor unit 2700 to an anatomy, such as the skin of the user. Thus, the infusion monitor unit 2700 includes the housing 2703 that is configured to be adhesively coupled to an anatomy of a user. In this example, the physiological characteristic sensor 2704 is coupled to the tube 2690, but is not integral with the tube 2690 such that the tube 2690 delivers the fluid from the fluid reservoir 160 to the anatomy of the user, while the separate glucose sensor 2704 measures a level of blood glucose within the anatomy of the user. It should be noted that the glucose sensor 2704 is not limited to a glucose sensor, but rather, various other physiological characteristic sensors may be employed. Further, it should be noted that the glucose sensor 2704 and the tube 2690 may be integrally formed, as discussed previously herein with regard to FIGS. 39-104B, if desired. The physiological characteristic sensor 2704 is an electrochemical sensor that includes the glucose oxidase enzyme, as is well understood by those familiar with glucose sensor technology. The glucose oxidase enzyme enables the physiological characteristic sensor 2704 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. In this example, the physiological characteristic sensor 2704 is positionable in subcutaneous tissue of the user by the same insertion instrument that inserts the proximalmost end 2692 of the tube 2690 into the anatomy to measure the glucose oxidase enzyme.

In this example, with reference to FIG. 132, FIG. 132 is a schematic circuit diagram of the infusion monitor unit 2700. In this example, the physiological characteristic sensor 2704 includes the reference electrode 740, the counter electrode 742 and the working electrode 744. As is generally known, the working electrode 744 is coated with the glucose oxidase enzyme. The reference electrode 740 maintains a constant voltage to support the chemical reaction at the working electrode 744. The counter electrode 742 supplies current to maintain the set potential on the working electrode 744. The electrodes are powered and sensed by the unit control module 2702 via the power line 2696. When glucose and oxygen diffuse to the glucose oxidase layer, hydrogen peroxide is formed. Hydrogen peroxide present at the working electrode 744 metallization layer breaks down and generates electrons when a voltage is applied at to the working electrode 744. These electrons generates an electrical signal, which is transmitted by the working electrode 744 to the unit control module 2702. The unit control module 2702 processes the electrical signal, and determines the glucose level of the user, which is transmitted as a digital signal to a control module associated with a fluid infusion device, such as the control module 822 of the fluid infusion device 800, via the transmitter line 2698. Thus, in this example, the infusion monitor unit 2700 determines the blood glucose level of the user at the infusion monitor unit 2700 via the unit control module 2702 and transmits this value to the control module 822 of the fluid infusion device 800.

With reference to FIG. 133, the infusion monitor unit 2700 is shown with a portion of the housing 2703 removed. As shown, in some examples, the unit control module 2702 includes a printed circuit board 2710, a first module 2712 and a second module 2714. The printed circuit board 2710 physically and electrically couples the lines 2696-2699 to the first module 2712, physically and electrically couples the electrodes 740, 742, 744 to the second module 2714 and enables communication between the first module 2712 and the second module 2714. The first module 2712 is in communication with the lines 2696-2699 and the second module 2714 via the printed circuit board 2710. The second module 2714 is in communication with the electrodes 740, 742, 744 and the first module 2712 via the printed circuit board 2710. Each of the first module 2712 and the second module 2714 includes at least one processor and a computer readable storage device or media, which are mounted to the printed circuit board 2710. The processor can be any custom made or commercially available processor, a central processing unit (CPU), an auxiliary processor among several processors associated with the first module 2712 and the second module 2714, a semiconductor based microprocessor (in the form of a microchip or chip set), a macroprocessor, any combination thereof, or generally any device for executing instructions. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electrical, magnetic, and/or optical memory devices capable of storing data, some of which represent executable instructions, used by the first module 2712 and the second module 2714 in controlling components associated with the infusion monitor unit 2700.

The instructions may include one or more separate programs, each of which comprises an ordered listing of executable instructions for implementing logical functions. The instructions, when executed by the processor, receive and process input signals, perform logic, calculations, methods and/or algorithms for controlling the components of the glucose sensor 2704, and generate signals to components of the fluid infusion device 800 of the measured/observed blood glucose level based on the logic, calculations, methods, and/or algorithms. Although two modules 2712, 2714 are shown, embodiments of the infusion monitor unit 2700 can include any number of control modules that communicate over any suitable communication medium or a combination of communication mediums and that cooperate to process signals received from the lines 2696, 2697, 2698, 2699 and the electrodes 740, 742, 744, perform logic, calculations, methods, and/or algorithms, and generate signals for transmission to the control module 822 of the fluid infusion device 800. In various embodiments, one or more instructions of the first module 2712, when executed by the processor, receive and process signals from the lines 2696, 2697, 2698, 2699 and the second module 2714 to enable communication between the infusion monitor unit 2700 and the control module 822 of the fluid infusion device 800. In various embodiments, one or more instructions of the second module 2714, when executed by the processor, receive and process signals from the electrodes 740, 742, 744 and the first module 2712 to determine the blood glucose level of the user. Thus, the infusion monitor unit 2700 determines the blood glucose level at the infusion monitor unit 2700 and communicates the blood glucose level value to the control module 822 of the fluid infusion device 800 via the tube 2690.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 134, an infusion monitor unit 2750 is shown. As the infusion monitor unit 2750 includes the same or similar components as the infusion set assembly 300 discussed with regard to FIGS. 11-26B, the infusion monitor unit 708 discussed with regard to FIGS. 39-104B and the infusion monitor unit 2700 discussed with regard to FIGS. 130-133, the same reference numerals will be used to denote the same or similar components.

With reference to FIG. 134, the infusion monitor unit 2750 is fluidly coupled via a tube 2751 to a connector, like the connector 302 (FIG. 11). Thus, in this example, the tube 2751 is devoid of the conduits for electrodes, and only includes a central conduit that defines the fluid flow path for the fluid from the fluid reservoir 160 (FIG. 11) to the infusion monitor unit 2750. A first end 2751*a* is coupled to the infusion monitor unit 2750, while the second end is coupled to a connector, such as the connector 302 (FIG. 11).

In this example, a proximalmost end 2751*b* of the tube 2751 is inserted into the anatomy to provide the fluid flow path from the fluid reservoir 160 (FIG. 39) into the anatomy of the user. The tube 2751 may facilitate a fluidic connection between a connector, like the connector 302, and the infusion monitor unit 2700, and the proximalmost end 2751*b* of the tube 2751 may extend from a housing 2703 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 400 is a fluid source, which is fluidly connected to the tube 2751. The proximalmost end 2751*b* of the tube 306 is inserted into the anatomy, and a fluid outlet is defined at a terminal end of the proximalmost end 2751*b*. The infusion monitor unit 2750 includes the housing 2703, the coupling member or adhesive patch 712, the physiological characteristic sensor (glucose sensor) 2704 and a unit control module 2752. In this example, the tube 2751 is coupled to and passes through the housing 2703 so that the proximalmost end 2751*b* of the tube 2751 may be inserted into the anatomy. The adhesive patch 712 is affixes the infusion monitor unit 2750 to an anatomy, such as the skin of the user. Thus, the infusion monitor unit 2750 includes the housing 2703 that is configured to be adhesively coupled to an anatomy of a user.

In this example, the physiological characteristic sensor 2704 is coupled to the tube 2751, but is not integrally formed with the tube 2751. The tube 2751 delivers the fluid from the fluid reservoir 160 and the glucose sensor 2704 measures a glucose level within the anatomy of the user. It should be noted that the physiological characteristic sensor 2704 is not limited to a glucose sensor, but rather, various other physiological characteristic sensors may be employed. Further, it should be noted that the physiological characteristic sensor 2704 and the tube 2751 may be integrally formed, as discussed previously herein with reference to FIGS. 39-104B, if desired. The physiological characteristic sensor 2704 is an electrochemical sensor that includes the glucose oxidase enzyme, as is well understood by those familiar with glucose sensor technology. The glucose oxidase enzyme enables the physiological characteristic sensor 2704 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. In this example, the physiological characteristic sensor 2704 is positionable in subcutaneous tissue of the user by the same insertion instrument that inserts the proximalmost end 2751*b* of the tube 2751 into the anatomy to measure the glucose oxidase enzyme.

In this example, with reference to FIG. 135, the infusion monitor unit 2750 is shown with a portion of the housing 2703 removed. As shown, in some examples, the unit control module 2752 includes a circuit board 2760, a first module 2762, a power source 2764, a communication component 2766 and the second module 2714. In this example, the infusion monitor unit 2750 determines the blood glucose level of the user at the infusion monitor unit 2750 via the unit control module 2752 and transmits this value to the control module 422 of the fluid infusion device 400 via the communication component 2766, which may improve accuracy of the blood glucose level value.

The printed circuit board 2710 physically and electrically couples the electrodes 740, 742, 744 to the second module 2714 and enables communication between the first module 2762, the second module 2714, the power source 2764 and the communication component 2766. The first module 2762 is in communication with the power source 2764, the communication component 2766 and the second module 2714 via the printed circuit board 2760. The first module 2762 includes at least one processor and a computer readable storage device or media, which are mounted to the printed circuit board 2760. The processor can be any custom made or commercially available processor, a central processing unit (CPU), an auxiliary processor among several processors associated with the first module 2762, a semiconductor based microprocessor (in the form of a microchip or chip set), a macroprocessor, any combination thereof, or generally any device for executing instructions. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electrical, magnetic, and/or optical memory devices capable of storing data, some of which represent executable instructions, used by the first module 2762 in controlling components associated with the infusion monitor unit 2750.

The instructions may include one or more separate programs, each of which comprises an ordered listing of executable instructions for implementing logical functions. The instructions, when executed by the processor, receive and process input signals, perform logic, calculations, methods and/or algorithms for controlling the components of the glucose sensor 2704, and generate signals to be transmitted via the communication component 2766 to the antenna 426 of the fluid infusion device 400 of the measured/observed blood glucose level based on the logic, calculations, methods, and/or algorithms. Although two modules 2762, 2714 are shown, embodiments of the infusion monitor unit 2750 can include any number of control modules that communicate over any suitable communication medium or a combination of communication mediums and that cooperate to process signals received from the electrodes 740, 742, 744, perform logic, calculations, methods, and/or algorithms, and generate signals for transmission to the fluid infusion device 400. In various embodiments, one or more instructions of the first module 2762, when executed by the processor, receive and process signals from the second module 2714 and transmit the signals from the second module 2714 via the communication component 2766 to the antenna 426 of the fluid infusion device 400 to enable communication between the infusion monitor unit 2750 and the fluid infusion device 400 (FIG. 11). In various embodiments, one or more instructions of the second module 2714, when executed by the processor, receive and process signals from the electrodes 740, 742, 744 to determine the blood glucose level of the user.

The power source 2764 supplies power to the first module 2762 and the second module 2714. The power source 2764 is any suitable supply of power, including, but not limited to a coin-cell battery, etc. The first module 2762 supplies the power to the communication component 2766 to transmit the measured blood glucose level value to the fluid infusion device 400 (FIG. 11). The second module 2714 supplies the power from the power source 2764 to the electrodes 740, 742, 744 to measure the blood glucose level of the user.

The communication component 2766 enables communication between the antenna 426 of the fluid infusion device 400 and the infusion monitor unit 2750. Thus, generally, the communication component 2766 cooperates with the antenna 426 to enable wireless communication between the infusion monitor unit 2750 and the fluid infusion device 400. In some examples, the infusion monitor unit 2750 communication component 2766 may include, but is not limited to, near-field communication (NFC) antenna, a radio frequency (RF) communication antenna, a far-field communication antenna, a wireless communication system configured to communicate via a wireless local area network (WLAN) using Institute of Electrical and Electronics Engineers (IEEE) 802.11 standards or by using cellular data communication, a BLUETOOTH antenna, etc. In certain embodiments, the communication component 2766 of the infusion monitor unit 2750 may include more than one communication device, such as a near field communication (NFC) antenna and a BLUETOOTH low energy (BLE) trace antenna. Thus, the infusion monitor unit 2750 determines the blood glucose level at the infusion monitor unit 2750 and communicates the blood glucose level value wirelessly to the control module 422 of the fluid infusion device 400 via the communication component 2766 and the antenna 426.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 136, an infusion monitor unit 2800 is shown. As the infusion monitor unit 2800 includes the same or similar components as the infusion set assembly 300 discussed with regard to FIGS. 11-26B, the infusion monitor unit 708 discussed with regard to FIGS. 39-104B and the infusion monitor unit 2700 discussed with regard to FIGS. 130-133, the same reference numerals will be used to denote the same or similar components.

With reference to FIG. 136, the infusion monitor unit 2800 is fluidly coupled to a tube to define the fluid flow path for the fluid from the fluid reservoir 160 (FIG. 11) to the infusion monitor unit 2800. In this example, the infusion monitor unit 2800 includes a housing 2802, the coupling member or adhesive patch 712, a delivery cannula 2804, a physiological characteristic or glucose sensor 2806 and the unit control module 2752. In FIG. 136, the infusion monitor unit 2800 is shown contained within an insertion instrument or needle 2801. The housing 2802 is composed of a polymeric material, and encloses the unit control module 2752. The housing 2802 may include one or more inlet ports for coupling to a tube to supply the fluid to the infusion monitor unit 2800. The housing 2802 may also include an opening for receiving the insertion needle 2801 through the housing 2802. This opening may be covered by a septum, for example. The adhesive patch 712 is affixes the infusion monitor unit 2800 to an anatomy, such as the skin of the user. Thus, the infusion monitor unit 2800 includes the housing 2802 that is configured to be adhesively coupled to an anatomy of a user.

In this example, with reference to FIG. 137, the delivery cannula 2804 is shown in greater detail. The delivery cannula 2804 includes a fluid conduit 2810 and a shape conduit 2812. The fluid conduit 2810 is fluidly coupled to the tube to define the fluid flow path from the fluid reservoir 160 (FIG. 11) to the anatomy. The tube may facilitate a fluidic connection between a connector, like the connector 302, and the infusion monitor unit 2800, and delivery cannula 2804 may extend from the housing 2802 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 400 is a fluid source, which is fluidly connected to the fluid conduit 2810. The shape conduit 2812 receives a shape-memory wire 2814, such as a nitinol wire or ribbon. The shape-memory wire 2814 is configured to move the delivery cannula 2804 between a first state, shown in FIG. 136, and a second state, shown in FIG. 138. By moving to the second state, with reference to FIG. 138, the shape-memory wire 2814 creates a distance D2800 between the delivery cannula 2804 and the glucose sensor 2806, which may improve the accuracy of the glucose sensor 2806. Generally, the shape-memory wire 2814 has a radius of curvature, which is opposite a radius of curvature of a shape-memory wire 2816 associated with the glucose sensor 2806 such that in the second state, the delivery cannula 2804 is curved away from the glucose sensor 2806. Thus, in the first state the glucose sensor 2806 is proximate the delivery cannula 2804, and in the second state, the glucose sensor 2806 is spaced apart from the delivery cannula 2804. In the first state, the delivery cannula 2804 and the glucose sensor 2806 are contained within the insertion needle 2801, and in the second state, the insertion needle 2801 is retracted or removed from the infusion monitor unit 2800.

With reference to FIG. 139, the glucose sensor 2806 includes the shape-memory wire 2816, a substrate 2818 and a glucose sensor electrode 2820. The shape-memory wire 2816 comprises a nitinol wire or ribbon. The shape-memory wire 2816 is configured to move the glucose sensor 2806 between a first state, shown in FIG. 136, and a second state, shown in FIG. 138. With continued reference to FIG. 139, the substrate 2818 is composed of a polymeric material, such as a polyimide, and encases the shape-memory wire 2816. The glucose sensor electrode 2820 is coupled to the substrate 2818. The glucose sensor electrode 2820 is coated with a glucose sensor chemistry layer 2822, and is configured to determine a blood glucose level associated with the user, as is generally known. It should be noted that a top surface of the glucose sensor electrode 2820 may flush with a top surface of the substrate 2818. Alternatively, the top surface of the electrode 2820 may be set below the top surface of the substrate 2818. It should be noted that in other configurations, the glucose sensor electrode 2820 may face away from the shape-memory wire 2816 in order to not be shadowed by the shape-memory wire 2816. In another configuration, the shape-memory wire 2816 may be a counter or reference electrode through platinization of the shape-memory wire 2816.

The unit control module 2752 includes the circuit board 2760, the first module 2762, the power source 2764, the communication component 2766 and the second module 2714. In this example, the infusion monitor unit 2800 determines the blood glucose level of the user at the infusion monitor unit 2800 via the unit control module 2752 and transmits this value to the control module 422 of the fluid infusion device 400 via the communication component 2766 and the antenna 426, which may improve accuracy of the blood glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 140, an infusion monitor unit 2850 is shown. As the infusion monitor unit 2850 includes the same or similar components as the infusion set assembly 300 discussed with regard to FIGS. 11-26B, the physiological characteristic sensor 1300 discussed with regard to FIGS. 53-55, the infusion monitor unit 2700 discussed with regard to FIGS. 130-133 and the infusion monitor unit 2800 discussed with regard to FIGS. 136-139, the same reference numerals will be used to denote the same or similar components.

With reference to FIG. 140, the infusion monitor unit 2850 is fluidly coupled to a tube to define the fluid flow path for the fluid from the fluid reservoir 160 (FIG. 11) to the infusion monitor unit 2850. In this example, the infusion monitor unit 2850 includes a housing 2852, the coupling member or adhesive patch 712, a delivery cannula 2854, the physiological characteristic sensor 1300 and the unit control module 2752. The housing 2852 is composed of a polymeric material, and encloses the unit control module 2752. The housing 2852 is generally rectangular. The housing 2802 may include one or more inlet ports for coupling to a tube to supply the fluid to the infusion monitor unit 2850. The housing 2802 may also include an opening for receiving the insertion needle 2801 through the housing 2802. This opening may be covered by a septum, for example. In this example, the housing 2852 includes a first housing portion 2856 and a second housing portion 2858. The first housing portion 2856 is coupled to the second housing portion 2858 via welding, such as ultrasonic welding, radiofrequency welding, etc., about a perimeter of the first housing portion 2856 and the second housing portion 2858 to inhibit fluid flow into the housing 2852. The interior of the first housing portion 2856 and the second housing portion 2858 may also include posts 2860, which may be welded together, via ultrasonic welding, radiofrequency welding, etc., to further couple the first housing portion 2856 to the second housing portion 2858 while inhibiting fluid flow into the housing 2852. One or more sealing members 2862, such as O-rings, may be positioned between the first housing portion 2856 and the second housing portion 2858 and may be compressible upon assembly of the first housing portion 2856 to the second housing portion 2858 to further inhibit the flow of fluid into the housing 2852. Generally, one sealing member 2862 may be coupled to the first housing portion 2856 and one sealing member 2862 may be coupled to the second housing portion 2858, with each of the sealing members 2862 coupled about the delivery cannula 2854 and the physiological characteristic sensor 1300 to inhibit fluid from flowing into the housing 2852. The adhesive patch 712 is affixes the infusion monitor unit 2850 to an anatomy, such as the skin of the user.

In this example, with reference to FIG. 140, the delivery cannula 2854 is shown in greater detail. The delivery cannula 2854 is fluidly coupled to the tube to define the fluid flow path from the fluid reservoir 160 (FIG. 11) to the anatomy. The delivery cannula 2854 is fluidly coupled to the tube to define the fluid flow path from the fluid reservoir 160 (FIG. 11) to the anatomy. The tube may facilitate a fluidic connection between a connector, like the connector 302, and the infusion monitor unit 2850, and the delivery cannula 2854 may extend from the housing 2852 and be inserted into an anatomy of a user to enable delivering the fluid, such as insulin. The connector is fluidly coupled to the fluid reservoir 160 such that the fluid reservoir 160 of the fluid infusion device 400 is a fluid source, which is fluidly connected to the delivery cannula 2854. The delivery cannula 2854 is inserted into the anatomy to deliver the fluid to the user when the infusion monitor unit 2850 is coupled to the user. The delivery cannula 2854 is composed of ethylene tetrafluoroethylene (ETFE), polytetrafluoroethylene (PTFE), polyether block amide, etc. and has a length of about 9 millimeters (mm). The physiological characteristic sensor 1300 is coupled to the housing 2852 so as to be sandwiched between the first housing portion 2856 and the second housing portion 2858. Generally, a portion of the physiological characteristic sensor 1300 is sandwiched between the sealing members 2862 to provide a fluid tight seal about the portion of the physiological characteristic sensor 1300 contained within the housing 2852.

The unit control module 2752 includes the circuit board 2760, the first module 2762, the power source 2764, the communication component 2766 and the second module 2714. In this example, the infusion monitor unit 2850 determines the blood glucose level of the user at the infusion monitor unit 2850 via the unit control module 2752 and transmits this value to the control module 422 of the fluid infusion device 400 via the communication component 2766 and the antenna 426, which may improve accuracy of the blood glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 141, an infusion monitor unit 2900 is shown. As the infusion monitor unit 2900 includes the same or similar components as the infusion set assembly 300 discussed with regard to FIGS. 11-26B, the infusion monitor unit 2700 discussed with regard to FIGS. 130-133 and the infusion monitor unit 2800 discussed with regard to FIGS. 136-139, the same reference numerals will be used to denote the same or similar components.

With reference to FIG. 141, the infusion monitor unit 2900 is fluidly coupled to a tube to define the fluid flow path for the fluid from the fluid reservoir 160 (FIG. 11) to the infusion monitor unit 2900. In this example, the infusion monitor unit 2900 includes the housing 2901, the coupling member or adhesive patch 712, a delivery array 2902, a sensing array 2904 and a unit control module 2903. The housing 2901 is composed of a polymeric material, and encloses the unit control module 2903. The housing 2901 may include one or more inlet ports for coupling to a tube to supply the fluid to the infusion monitor unit 2900. The delivery array 2902 and the sensing array 2904 are each coupled to the housing 2901. The delivery array 2902 is coupled to the housing 2901 to be in fluid communication with the fluid flow path to define the fluid flow path from the fluid reservoir 160 (FIG. 11) to subdermal tissue of the user. The sensing array 2904 is in communication with the unit control module 2752 to provide signals from the sensing array 2904 to the unit control module 2752. The adhesive patch 712 is affixes the infusion monitor unit 2900 to an anatomy, such as the skin of the user. The adhesive patch 712 is shown in FIGS. 141, 143 and 144 by general reference for ease of illustration, but the adhesive patch 712 may have the same thickness as that shown in FIG. 138. Thus, the infusion monitor unit 2900 includes the housing 2901 that is configured to be adhesively coupled to an anatomy of a user.

The delivery array 2902 comprises a plurality of microneedles 2906, which are shaded in the drawings for ease of reference. Each of the plurality of microneedles 2906 define a fluid flow path from the fluid reservoir 160 to the subdermal tissue of the user. The plurality of microneedles 2906 is fluidly coupled to the tube to define the fluid flow path from the fluid reservoir 160 (FIG. 11) to the anatomy.

The tube may facilitate a fluidic connection between a connector, like the connector 302, and the infusion monitor unit 2900, and the delivery array 2902 may extend from the housing 2901 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 400 is a fluid source, which is fluidly connected to the delivery array 2902.

The sensing array 2904 comprises a plurality of microneedles 2908, which cooperate to define a glucose sensor that observes or measures a blood glucose level of the user. Each microneedle 2908 is coupled to and in communication with the unit control module 2903. In this example, the delivery array 2902 is shown spaced apart from the sensing array 2904 by a distance D2900, however, the delivery array 2902 and the sensing array 2904 may be arranged in various other configurations, if desired. Each of the microneedles 2906, 2908 are about 500 micrometers (μm) to about 2000 micrometers (μm) long. Each of the microneedles 2906 have an opening at the center to define the fluid flow path. The microneedles 2908 are composed of a silicon, polymer or metal material. A platinum or gold layer is coated on the respective microneedle 2908 and the enzyme and other membranes (such as interference rejection membrane, enzyme, HSA, glucose limiting polymers) are added for measuring glucose. In addition, one or more of the microneedles 2908 may be designated as a reference electrode and may be coated with silver or silver-chloride, while one or more of the microneedles 2908 may be designated as counter electrodes where no chemistry coating is required. Thus, the microneedles 2908 can cooperate to measure a blood glucose level of the user.

Figure 142B:
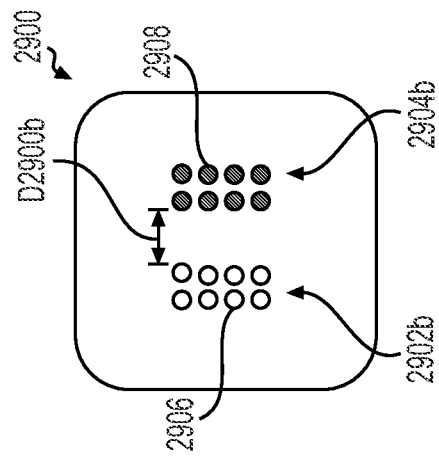
Figure 142D:
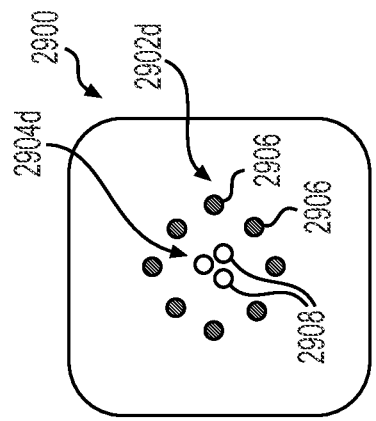
Figure 142A:
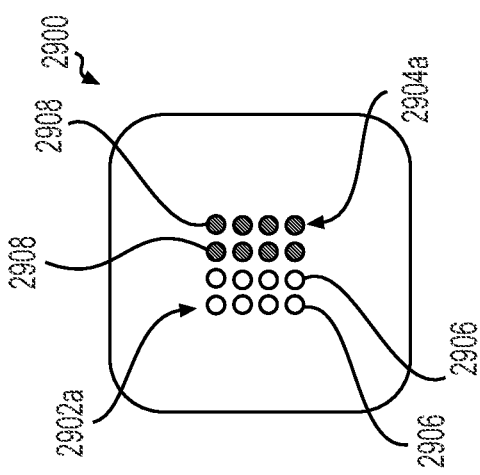
Figure 142C:
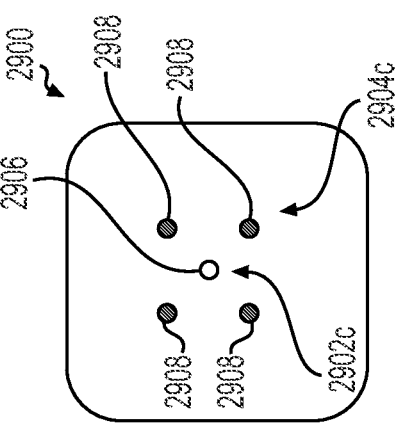

For example, with reference to FIG. 142A-142D, top views of alternative configurations of the delivery array 2902 and the sensing array 2904 are shown. In FIG. 142A, a delivery array 2902a includes the microneedles 2906 in a rectangular pattern next or directly adjacent to the microneedles 2908 of a sensing array 2904a. In FIG. 142B, a delivery array 2902b includes the microneedles 2906 in a rectangular pattern spaced a distance D2900b apart from the microneedles 2908 of a sensing array 2904b. The distance D2900b is different and less than the distance D2900 (FIG. 141). In FIG. 142C, a delivery array 2902c includes a single one of the microneedles 2906 surrounded by the microneedles 2908 of a sensing array 2904c. In this example, the sensing array 2904c includes four microneedles 2908 arranged in a square pattern about the microneedle 2906. In FIG. 142C, the insertion forces are balanced due to the symmetric arrangement. In FIG. 142D, a delivery array 2902d includes the microneedles 2906 surrounded by the microneedles 2908 of a sensing array 2904d. In this example, the sensing array 2904d includes the microneedles 2908 arranged in a circular pattern about a cluster of three microneedles 2906.

As a further alternative configuration, with reference to FIG. 143, a delivery array 2902e includes the microneedle 2908 from the sensing array 2904. By positioning the microneedle 2908 in the delivery array 2902e, the microneedle 2908 may be used by the unit control module 2903 to subtract out any insulin specific background noise present in the sensing array 2904. In this regard, some glucose sensors may be susceptible to insulin and the microneedle 2908 placed in proximity of the delivery array 2902e acts as an insulin sensor that may be used to adjust the glucose reading value from the sensing array 2904. An equation for determining the blood glucose reading value using the sensing array 2904 and the microneedle 2908 in the delivery array 2902e is as follows:

$$\text{Blood Glucose Level Value} = (\text{Msignal} - \text{scaling factor}) * \text{SAsignal} \quad (1)$$

Wherein the Blood Glucose Level Value is the level of glucose measured or observed by the unit control module 2903; the Msignal is the signal reading from the microneedle 2908 in the delivery array 2902e; the scaling factor is a predetermined constant, linear, or non-linear input; and the SAsignal is the signal from the sensing array 2904.

As a further alternative configuration, with reference to FIG. 144, a sensing array 2902f includes an insulin sensor microneedle 2910. By positioning the insulin sensor microneedle 2910 in the sensing array 2902f, the insulin sensor microneedle 2910 may be used by the unit control module 2903 to subtract out any insulin specific background noise present in the sensing array 2904 and to confirm that insulin is being delivered by the delivery array 2902. By including the insulin sensor microneedle 2910, the unit control module 2903 processes the sensor signals from the insulin sensor microneedle 2910 and determines whether insulin is being delivered via the delivery array 2902. The unit control module 2903 may also use the sensor signals from the insulin sensor microneedle 2910 to determine the blood glucose level value. In this regard, as discussed, the insulin sensor microneedle 2910 placed in the sensing array 2902f may be used to adjust the glucose reading value from the sensing array 2904f. An equation for determining the blood glucose reading value using the sensing array 2904f and the insulin sensor microneedle 2910 is as follows:

$$\text{Blood Glucose Level Value} = (\text{IMsignal} - \text{ScalingFactor}) * \text{SAsignal} \quad (2)$$

Wherein the Blood Glucose Level Value is the level of glucose measured or observed by the unit control module 2903; the IMsignal is the signal reading from the insulin sensor microneedle 2910; ScalingFactor is a predetermined constant, linear, or non-linear input; and the SAsignal is the signal from the sensing array 2904f.

As a further alternative configuration, with reference to FIG. 145A, a top view of the delivery array 2902 and the sensing array 2904 are shown, and in FIG. 145B a side view is shown. In FIG. 145A, a delivery array 2902g includes the microneedles 2906 spaced apart in a circular pattern surrounding the microneedles 2908 of a sensing array 2904g. In this example, the microneedle 2906 labeled 1, may be used for a predetermined period of time to dispense the fluid, such as three days, and then the microneedle 2906 labeled 2 would be used for the predetermined period of time to dispense the fluid, such as three days, before switching to the microneedle 2906 labeled 3. The microneedle 2906 labeled 3 would be used for the predetermined period of time to dispense the fluid, such as three days, before switching to the microneedle 2906 labeled 4. This would minimize insulin tissue site loss. The switching between the microneedles 2906 is controlled by the unit control module 2903, which may actuate one or more microvalves, for example, to fluidly couple the respective microneedle 2906 to the fluid source.

With reference back to FIG. 141, the unit control module 2903 includes the circuit board 2760, the first module 2762, the power source 2764, the communication component 2766 and a second module 2914. In this example, the circuit board 2760 physically and electrically couples the sensing array 2904 to the first module 2962 and enables communication between the first module 2762, the second module 2914, the power source 2764 and the communication component 2766. The second module 2914 is in communication with the power source 2764 and the first module 2762 via the printed circuit board 2760. The second module 2914 includes at least one processor and a computer readable storage device or media, which are mounted to the printed circuit board 2760. The processor can be any custom made or commercially available processor, a central processing unit (CPU), an auxiliary processor among several processors associated with the second module 2914, a semiconductor based microprocessor (in the form of a microchip or chip set), a macroprocessor, any combination thereof, or generally any device for executing instructions. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electrical, magnetic, and/or optical memory devices capable of storing data, some of which represent executable instructions, used by the second module 2914 in monitoring components associated with the sensing array 2904.

The instructions may include one or more separate programs, each of which comprises an ordered listing of executable instructions for implementing logical functions. The instructions, when executed by the processor, receive and process input signals, perform logic, calculations, methods and/or algorithms for monitoring the components of the sensing array 2904, and generate signals to the first module 2762 based on the logic, calculations, methods, and/or algorithms. Although two modules 2762, 2914 are shown, embodiments of the infusion monitor unit 2900 can include any number of control modules that communicate over any suitable communication medium or a combination of communication mediums and that cooperate to process signals received from the sensing array 2904, perform logic, calculations, methods, and/or algorithms, and generate signals for transmission to a control module, such as the control module 422, 822 of the respective fluid infusion device 400, 800. In various embodiments, one or more instructions of the first module 2762, when executed by the processor, receive and process signals from the second module 2914 and transmit the signals from the second module 2914 via the communication component 2766 to the antenna 426 of the fluid infusion device 400 to enable communication between the infusion monitor unit 2900 and the fluid infusion device 400 (FIG. 11). In various embodiments, one or more instructions of the second module 2914, when executed by the processor, receive and process signals from the sensing array 2904 to determine the blood glucose level of the user. Thus, in this example, the infusion monitor unit 2900 determines the blood glucose level of the user at the infusion monitor unit 2900 via the unit control module 2903 and transmits this value to the control module 422 of the fluid infusion device 400 via the communication component 2766 and the antenna 426, which may improve accuracy of the blood glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 146, an infusion monitor unit 2950 is shown. As the infusion monitor unit 2950 includes the same or similar components as the infusion set assembly 300 discussed with regard to FIGS. 11-26B, the physiological characteristic sensor 1300 discussed with regard to FIGS. 53-55, the infusion monitor unit 2700 discussed with regard to FIGS. 130-133, the infusion monitor unit 2800 discussed with regard to FIGS. 136-139 and the infusion monitor unit 2900 discussed with regard to FIGS. 141-145B, the same reference numerals will be used to denote the same or similar components.

With reference to FIG. 146, the infusion monitor unit 2900 is fluidly coupled to a tube to define the fluid flow path for the fluid from the fluid reservoir 160 (FIG. 11) to the infusion monitor unit 2950. In this example, the infusion monitor unit 2950 includes a housing 2951, the coupling member or adhesive patch 712, the delivery array 2902, the physiological characteristic sensor 1300 and a unit control module 2953. The housing 2951 is composed of a polymeric material, and encloses the unit control module 2953. The housing 2951 may include one or more inlet ports for coupling to a tube to supply the fluid to the infusion monitor unit 2950. The delivery array 2902 and the physiological characteristic sensor 1300 are each coupled to the housing 2951. The delivery array 2902 is coupled to the housing 2951 to be in fluid communication with the fluid flow path to define the fluid flow path from the fluid reservoir 160 (FIG. 11) to subdermal tissue of the user. The delivery array 2902 is fluidly coupled to the tube to define the fluid flow path from the fluid reservoir 160 (FIG. 11) to the anatomy. The tube may facilitate a fluidic connection between a connector, like the connector 302, and the infusion monitor unit 2900, and delivery array 2902 may extend from the housing 2802 and be inserted into an anatomy of a user to enable delivering the fluid, such as insulin. The connector is fluidly coupled to the fluid reservoir 160 such that the fluid reservoir 160 of the fluid infusion device 400 is a fluid source, which is fluidly connected to the delivery array 2902.

The physiological characteristic sensor 1300 is in communication with the unit control module 2953 to provide signals from the physiological characteristic sensor 1300 to the unit control module 2953. The physiological characteristic sensor 1300 is spaced apart from the delivery array 2902 and is deployed in subcutaneous tissue associated with the user. The adhesive patch 712 is affixes the infusion monitor unit 2900 to an anatomy, such as the skin of the user. The adhesive patch 712 is shown in FIG. 146 by general reference for ease of illustration, but the adhesive patch 712 may have the same thickness as that shown in FIG. 138. Thus, the infusion monitor unit 2950 includes the housing 2951 that is configured to be adhesively coupled to an anatomy of a user.

As the unit control module 2953 is substantially the same as the unit control module 2903, the unit control module 2953 will not be discussed in detail herein. Briefly, the unit control module 2953 includes the circuit board 2760, the first module 2762, the power source 2764, the communication component 2766 and a second module 2954. The second module 2954 includes at least one processor and a computer readable storage device or media, which are mounted to the printed circuit board 2760. The instructions associated with the second module 2954, when executed by the processor, receive and process input signals, perform logic, calculations, methods and/or algorithms for monitoring the components of the physiological characteristic sensor 1300, and generate signals to the first module 2762 based on the logic, calculations, methods, and/or algorithms. In various embodiments, one or more instructions of the first module 2762, when executed by the processor, receive and process signals from the second module 2954 and transmit the signals from the second module 2954 via the communication component 2766 to an antenna of a fluid infusion device, such as the antenna 426 of the fluid infusion device 400, 800, to enable communication between the infusion monitor unit 2900 and a fluid infusion device, such as the fluid infusion device 400 (FIG. 11). In various embodiments, one or more instructions of the second module 2954, when executed by the processor, receive and process signals from the physiological characteristic sensor 1300 to determine the glucose level of the user. Thus, in this example, the infusion monitor unit 2950 determines the glucose level of the user at the infusion monitor unit 2950 via the unit control module 2953 and transmits this value to a control module, such as the control module 422, 822 of the respective fluid infusion device 400, 800 via the communication component 2766 and the antenna 426, which may improve accuracy of the glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 147, an infusion monitor unit 3000 is shown. As the infusion monitor unit 3000 includes the same or similar components as the infusion set assembly 300 discussed with regard to FIGS. 11-26B, the infusion monitor unit 2700 discussed with regard to FIGS. 130-133, the infusion monitor unit 2850 discussed with regard to FIG. 140, the infusion monitor unit 2900 discussed with regard to FIGS. 141-145B and the infusion monitor unit 2950 discussed with regard to FIG. 146, the same reference numerals will be used to denote the same or similar components.

With reference to FIG. 147, the infusion monitor unit 3000 is fluidly coupled to a tube to define the fluid flow path for the fluid from the fluid reservoir 160 (FIG. 11) to the infusion monitor unit 3000. In this example, the infusion monitor unit 3000 includes a housing 3001, the coupling member or adhesive patch 712, the sensing array 2904, the delivery cannula 2854 and a unit control module 3003. The housing 3001 is composed of a polymeric material, and encloses the unit control module 3003. The housing 3001 may include one or more inlet ports for coupling to a tube to supply the fluid to the infusion monitor unit 3000. The sensing array 2904 and the delivery cannula 2854 are each coupled to the housing 3001. The delivery cannula 2854 is coupled to the housing 3001 to be in fluid communication with the fluid flow path to define the fluid flow path from the fluid reservoir 160 (FIG. 11) to the subcutaneous tissue of the user. The sensing array 2904 is in communication with the unit control module 3003 to provide signals from the sensing array 2904 to the unit control module 3003. The adhesive patch 712 is affixes the infusion monitor unit 3000 to an anatomy, such as the skin of the user. The adhesive patch 712 is shown in FIG. 147 by general reference for ease of illustration, but the adhesive patch 712 may have the same thickness as that shown in FIG. 138. Thus, the infusion monitor unit 3000 includes the housing 3001 that is configured to be adhesively coupled to an anatomy of a user.

As the unit control module 3003 is substantially the same as the unit control module 2903, the unit control module 3003 will not be discussed in detail herein. Briefly, the unit control module 2953 includes the circuit board 2760, the first module 2762, the power source 2764, the communication component 2766 and a second module 3006. The second module 3006 includes at least one processor and a computer readable storage device or media, which are mounted to the printed circuit board 2760. The instructions associated with the second module 3006, when executed by the processor, receive and process input signals, perform logic, calculations, methods and/or algorithms for monitoring the components of the sensing array 2904, and generate signals to the first module 2762 based on the logic, calculations, methods, and/or algorithms. In various embodiments, one or more instructions of the first module 2762, when executed by the processor, receive and process signals from the second module 3006 and transmit the signals from the second module 3006 via the communication component 2766 to an antenna of a fluid infusion device, such as the antenna 426 of the fluid infusion device 400, 800 to enable communication between the infusion monitor unit 3000 and the fluid infusion device 400 (FIG. 11), 800 (FIG. 39). In various embodiments, one or more instructions of the second module 3006, when executed by the processor, receive and process signals from the sensing array 2904 to determine the blood glucose level of the user. Thus, in this example, the infusion monitor unit 3000 determines the blood glucose level of the user at the infusion monitor unit 3000 via the unit control module 3003 and transmits this value to a control module, such as the control module 422, 822 of the respective fluid infusion device 400, 800 via the communication component 2766 and the antenna 426, which may improve accuracy of the glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIGS. 148A and 148B, an infusion monitor unit 3050 is shown. As the infusion monitor unit 3050 includes the same or similar components as the infusion set assembly 300 discussed with regard to FIGS. 11-26B, the physiological characteristic sensor 1300 discussed with regard to FIGS. 53-55, the infusion monitor unit 2700 discussed with regard to FIGS. 130-133, the infusion monitor unit 2800 discussed with regard to FIGS. 136-139 and the infusion monitor unit 2900 discussed with regard to FIGS. 141-145B, the same reference numerals will be used to denote the same or similar components.

In FIG. 148A, a top view of the infusion monitor unit 3050 is shown, and in FIG. 148B a side view is shown. In FIG. 148A, the infusion monitor unit 3050 is fluidly coupled to a tube to define the fluid flow path for the fluid from the fluid reservoir 160 (FIG. 11) to the infusion monitor unit 3050. In this example, the infusion monitor unit 3050 includes a housing 3051, the coupling member or adhesive patch 712 (FIG. 148B), the delivery array 2902, the physiological characteristic sensor 1300 and the unit control module 2953. The housing 3051 is composed of a polymeric material, and encloses the unit control module 2953. The housing 3051 may include one or more inlet ports for coupling to a tube to supply the fluid to the infusion monitor unit 3050. The delivery array 2902 and the physiological characteristic sensor 1300 are each coupled to the housing 3051. The delivery array 2902 is coupled to the housing 3051 to be in fluid communication with the fluid flow path to define the fluid flow path from the fluid reservoir 160 (FIG. 11) to subdermal tissue of the user. The microneedles 2906 are spaced apart about the physiological characteristic sensor 1300. The physiological characteristic sensor 1300 is in communication with the unit control module 2953 to provide signals from the physiological characteristic sensor 1300 to the unit control module 2953. The physiological characteristic sensor 1300 is spaced apart from the delivery array 2902 and is deployed in subcutaneous tissue associated with the user. The adhesive patch 712 is affixes the infusion monitor unit 2900 to an anatomy, such as the skin of the user. The adhesive patch 712 is shown in FIG. 148B by general reference for ease of illustration, but the adhesive patch 712 may have the same thickness as that shown in FIG. 138. The infusion monitor unit 3050 includes the housing 3051 that is configured to be adhesively coupled to an anatomy of a user. Thus, in this example, the infusion monitor unit 3050 determines the blood glucose level of the user at the infusion monitor unit 3050 via the unit control module 3053 and transmits this value to a control module, such as the control module 422, 822 of the respective fluid infusion device 400, 800 via the communication component 2766 and the antenna 426, which may improve accuracy of the glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 149, an infusion monitor unit 3100 is shown. As the infusion monitor unit 3100 includes the same or similar components as the infusion set assembly 300 discussed with regard to FIGS. 11-26B, the physiological characteristic sensor 1300 discussed with regard to FIGS. 53-55, the infusion monitor unit 2700 discussed with regard to FIGS. 130-133, the infusion monitor unit 2800 discussed with regard to FIGS. 136-139 and the infusion monitor unit 2900 discussed with regard to FIGS. 141-145B, the same reference numerals will be used to denote the same or similar components.

With reference to FIG. 149, the infusion monitor unit 3100 is fluidly coupled to a tube to define the fluid flow path for the fluid from the fluid reservoir 160 (FIG. 11) to the infusion monitor unit 3100. In this example, the infusion monitor unit 3100 includes the housing 2951, the coupling member or adhesive patch 712, the delivery array 2902, the physiological characteristic sensor 1300, an insulin sensor 3102 and a unit control module 3103. The insulin sensor 3102 is coupled to the physiological characteristic sensor 1300, and observes an amount of insulin. The insulin sensor 3102 is in communication with the unit control module 3103. The sensor signals from the insulin sensor 3102 may be used by the unit control module 3103 to determine whether the delivery array 2902 is dispensing the fluid and to correct a value of the blood glucose level observed by the physiological characteristic sensor 1300. The delivery array 2902 and the physiological characteristic sensor 1300 are each coupled to the housing 2951. The delivery array 2902 is coupled to the housing 2951 to be in fluid communication with the fluid flow path to define the fluid flow path from the fluid reservoir 160 (FIG. 11) to subdermal tissue of the user. The physiological characteristic sensor 1300 is in communication with the unit control module 3103 to provide signals from the physiological characteristic sensor 1300 to the unit control module 3103. The physiological characteristic sensor 1300 is spaced apart from the delivery array 2902 and is deployed in subcutaneous tissue associated with the user. The adhesive patch 712 is affixes the infusion monitor unit 3100 to an anatomy, such as the skin of the user. The adhesive patch 712 is shown in FIG. 147 by general reference for ease of illustration, but the adhesive patch 712 may have the same thickness as that shown in FIG. 138.

Thus, the infusion monitor unit 3100 includes the housing 2951 that is configured to be adhesively coupled to an anatomy of a user.

As the unit control module 3103 is substantially the same as the unit control module 2903, the unit control module 3103 will not be discussed in detail herein. Briefly, the unit control module 3103 includes the circuit board 2760, the first module 2762, the power source 2764, the communication component 2766 and a second module 3104. The second module 3104 includes at least one processor and a computer readable storage device or media, which are mounted to the printed circuit board 2760. The instructions associated with the second module 3104, when executed by the processor, receive and process input signals, perform logic, calculations, methods and/or algorithms for monitoring the components of the physiological characteristic sensor 1300 and the insulin sensor 3102, and generate signals to the first module 2762 based on the logic, calculations, methods, and/or algorithms. In various embodiments, one or more instructions of the first module 2762, when executed by the processor, receive and process signals from the second module 2964 and transmit the signals from the second module 2964 via the communication component 2766 to an antenna of a fluid infusion device, such as the antenna 426 of the fluid infusion device 400, 800 to enable communication between the infusion monitor unit 3100 and the fluid infusion device 400 (FIG. 11), 800 (FIG. 39). In various embodiments, one or more instructions of the second module 3104, when executed by the processor, receive and process signals from the physiological characteristic sensor 1300 and the insulin sensor 3102 to determine the glucose level of the user. In some examples, the unit control module 3103 processes the sensor signals from the insulin sensor 3102 and determines whether insulin is being delivered via the delivery array 2902. The unit control module 3103 may also use the sensor signals from the insulin sensor 3102 to determine the blood glucose level value using equation (2) discussed above. In this regard, as discussed, since some glucose sensors may be susceptible to insulin (meaning, their sensor signal artificially increases in the presence of insulin), the insulin sensor 3102 is used to adjust the glucose reading value from the physiological characteristic sensor 1300. Thus, in this example, the infusion monitor unit 3100 determines the blood glucose level of the user at the infusion monitor unit 3100 via the unit control module 3103 and transmits this value to a control module, such as the control module 422, 822 of the respective fluid infusion device 400, 800 via the communication component 2766 and the antenna 426, which may improve accuracy of the blood glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 150, an infusion monitor unit 3150 is shown. As the infusion monitor unit 3150 includes the same or similar components as the infusion set assembly 300 discussed with regard to FIGS. 11-26B, the physiological characteristic sensor 1300 discussed with regard to FIGS. 53-55, the infusion monitor unit 2700 discussed with regard to FIGS. 130-133, the infusion monitor unit 2800 discussed with regard to FIGS. 136-139 and the infusion monitor unit discussed with regard to FIG. 140, the same reference numerals will be used to denote the same or similar components.

With reference to FIG. 150, the infusion monitor unit 3150 is fluidly coupled to a tube to define the fluid flow path for the fluid from the fluid reservoir 160 (FIG. 11) to the infusion monitor unit 3150. In this example, the infusion monitor unit 3150 includes a housing 3152, the delivery cannula 2854, a glucose sensor 3154 and a unit control module 3156. The housing 3152 is composed of a polymeric material, and encloses the unit control module 3156. The housing 3152 may include one or more inlet ports for coupling to a tube to supply the fluid to the infusion monitor unit 3150. An adhesive patch, not shown, may be used to affix the infusion monitor unit 3150 to an anatomy, such as the skin of the user. In some examples, the adhesive patch may be composed of a breathable material and an adhesive layer. The breathable material layer is composed of a cloth or bandage-like material that is composed of, for example, nonwoven polyurethane. The adhesive layer of the adhesive patch can be composed of a hydrogel based, silicone-based, or acrylic-based adhesive. The adhesive patch is affixed to the infusion monitor unit 3150 via a double sided pressure sensitive adhesive. Thus, the infusion monitor unit 3150 includes the housing 3152 that is configured to be adhesively coupled to an anatomy of a user.

In this example, with reference to FIG. 151, the glucose sensor 3154 is shown in greater detail. The glucose sensor 3154 includes two electrode pairs 3158*a*-3158*b*; 3160*a*-3160*b*; however, the glucose sensor 3154 may include any number of electrode pairs. The electrode pairs 3158*a*-3158*b*; 3160*a*-3160*b* include a positively charged electrode 3158*a*, 3160*a* and a negatively charged electrode 3158*b*, 3160*b*. In this example, the glucose sensor 3154 uses iontophoresis to detect a blood glucose level. The amount of current passed between the electrode pairs 3158*a*-3158*b*; 3160*a*-3160*b* may be minimized to reduce tissue heating. The two sets of electrode pairs 3158*a*-3158*b*; 3160*a*-3160*b* enable redundant sensing. This enables the unit control module 3156 to average the signals from both electrode pairs 3158*a*-3158*b*; 3160*a*-3160*b*. Alternatively, the unit control module 3156 may collect the signal from both electrode pairs 3158*a*-3158*b*; 3160*a*-3160*b* and only use the signal from the electrode 3158*a*-3158*b*; 3160*a*-3160*b* that is believed to be more accurate at a given point in time. As a further alternative, the unit control module 3156 may alternate back-and-forth between which electrode pair 3158*a*-3158*b*; 3160*a*-3160*b* is turn-on to minimize local tissue heating.

As the unit control module 3156 is substantially the same as the unit control module 2903, the unit control module 3156 will not be discussed in detail herein. Briefly, the unit control module 3156 includes the circuit board 2760, the first module 2762, the power source 2764, the communication component 2766 and a second module 3162. The second module 3162 includes at least one processor and a computer readable storage device or media, which are mounted to the printed circuit board 2760. The instructions associated with the second module 3162, when executed by the processor, receive and process input signals, perform logic, calculations, methods and/or algorithms for monitoring the components of the glucose sensor 3154 and supplying power to the components of the glucose sensor 3154, and generate signals to the first module 2762 based on the logic, calculations, methods, and/or algorithms. In various embodiments, one or more instructions of the first module 2762, when executed by the processor, receive and process signals from the second module 3162 and transmit the signals from the second module 3162 via the communication component 2766 to an antenna of a fluid infusion device, such as the antenna 426 of the fluid infusion device 400, 800 to enable communication between the infusion monitor unit 3150 and the fluid infusion device 400 (FIG. 11), 800 (FIG.

39). In various embodiments, one or more instructions of the second module 3162, when executed by the processor, receive and process signals from the glucose sensor 3154 to determine the blood glucose level of the user. Thus, in this example, the infusion monitor unit 3150 determines the blood glucose level of the user at the infusion monitor unit 3150 via the unit control module 3156 and transmits this value to a control module, such as the control module 422, 822 of the respective fluid infusion device 400, 800 via the communication component 2766 and the antenna 426, which may improve accuracy of the glucose level value.

While the infusion set assembly 700 is described herein as using infusion monitor unit 708 to measure a blood glucose level of a user and to deliver a fluid to a user, it should be noted that the infusion monitor unit 708 may be configured differently. For example, with reference to FIG. 152, an infusion monitor unit 3200 is shown. As the infusion monitor unit 3200 includes the same or similar components as the infusion set assembly 300 discussed with regard to FIGS. 11-26B, the physiological characteristic sensor 1300 discussed with regard to FIGS. 53-55, the infusion monitor unit 2700 discussed with regard to FIGS. 130-133, the infusion monitor unit 2800 discussed with regard to FIGS. 136-139 and the infusion monitor unit discussed with regard to FIG. 140, the same reference numerals will be used to denote the same or similar components.

With reference to FIG. 152, the infusion monitor unit 3200 is fluidly coupled to a tube to define the fluid flow path for the fluid from the fluid reservoir 160 (FIG. 11) to the infusion monitor unit 3200. Fluid may be dispensed from the infusion monitor unit 3200 via the glucose sensor 3204. In some examples, the glucose sensor 3204 is fluidly coupled to the tube to define the fluid flow path from the fluid reservoir 160 (FIG. 11) to the anatomy. The tube may facilitate a fluidic connection between a connector, like the connector 302, and the infusion monitor unit 3200, and glucose sensor 3204 may extend from the housing 3202 and be inserted into an anatomy of a user to enable delivering the fluid, such as insulin, while also measuring a glucose level of the user. The connector is fluidly coupled to the fluid reservoir 160 such that the fluid reservoir 160 of the fluid infusion device 400 is a fluid source, which is fluidly connected to the infusion monitor unit 3200. Alternatively, the infusion monitor unit 3200 may include the delivery array 2902 to dispense the fluid.

In this example, the infusion monitor unit 3200 includes a housing 3202, a glucose sensor 3204 and a unit control module 3206. The housing 3202 is composed of a polymeric material, and encloses the unit control module 3206. The housing 3202 may include one or more inlet ports for coupling to a tube to supply the fluid to the infusion monitor unit 3200. An adhesive patch, not shown, may be used to affix the infusion monitor unit 3200 to an anatomy, such as the skin of the user. In some examples, the adhesive patch may be composed of a breathable material and an adhesive layer. The breathable material layer is composed of a cloth or bandage-like material that is composed of, for example, nonwoven polyurethane. The adhesive layer of the adhesive patch can be composed of a hydrogel based, silicone-based, or acrylic-based adhesive. The adhesive patch is affixed to the infusion monitor unit 3200 via a double sided pressure sensitive adhesive. Thus, the infusion monitor unit 3200 includes the housing 3202 that is configured to be adhesively coupled to an anatomy of a user.

In this example, the glucose sensor 3204 includes two glucose sensor assemblies 3204a, 3204b. The glucose sensor assembly 3204a includes the working electrode 1310, the counter electrode 1308 and the reference electrode 1306. The glucose sensor assembly 3204b includes a working electrode 1310b, a counter electrode 1308b and a reference electrode 1306b. The working electrode 1310b is devoid of the glucose oxidase enzyme, and thus, the glucose sensor assembly 3204b observes or measures interferences in the glucose sensor assembly 3204a measurement.

As the unit control module 3206 is substantially the same as the unit control module 2903, the unit control module 3206 will not be discussed in detail herein. Briefly, the unit control module 3156 includes the circuit board 2760, the first module 2762, the power source 2764, the communication component 2766 and a second module 3208. The second module 3208 includes at least one processor and a computer readable storage device or media, which are mounted to the printed circuit board 2760. The instructions associated with the second module 3208, when executed by the processor, receive and process input signals, perform logic, calculations, methods and/or algorithms for monitoring the components of the glucose sensor 3204 and supplying power to the components of the glucose sensor 3204, and generate signals to the first module 2762 based on the logic, calculations, methods, and/or algorithms. In various embodiments, one or more instructions of the first module 2762, when executed by the processor, receive and process signals from the second module 3208 and transmit the signals from the second module 3208 via the communication component 2766 to an antenna of a fluid infusion device, such as the antenna 426 of the fluid infusion device 400, 800 to enable communication between the infusion monitor unit 3200 and the fluid infusion device 400 (FIG. 11), 800 (FIG. 39). In various embodiments, one or more instructions of the second module 3162, when executed by the processor, receive and process signals from the glucose sensor 3204 to determine the blood glucose level of the user based on the following equation:

$$\text{Blood Glucose Level Value} = \text{Signal1} - \text{ScalingFactor} * \text{Signal2} \quad (3)$$

Wherein the Blood Glucose Level Value is the level of glucose measured or observed by the second module 3208; the Signal1 is the signal reading from the glucose sensor assembly 3204a; the ScalingFactor is a predetermined constant, linear, or non-linear input; and the Signal2 is the signal from the glucose sensor assembly 3204b. Thus, in this example, the infusion monitor unit 3200 determines the blood glucose level of the user at the infusion monitor unit 3200 via the unit control module 3156 and transmits this value to a control module, such as the control module 422, 822 of the respective fluid infusion device 400, 800 via the communication component 2766 and the antenna 426, which may improve accuracy of the glucose level value.

In addition, it should be noted that any of the physiological characteristic sensors 716, 1000, 1300, 2200, 2250, 2300, 2704, 2806, 3152, 3204 described herein can include a filter, electrochemical conversion and interference rejection membrane, if desired.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A portable fluid infusion device comprising:
   a housing configured to accommodate a removable fluid reservoir;
   a drive system within the housing and configured to dispense fluid from the removable fluid reservoir;
   a battery within the housing and configured to supply power to the drive system;
   a button on the housing;
   a light emitting element, disposed within the button, wherein the light emitting element is configured to provide a visual indicator, that is viewable outside the housing and through the button, of a status associated with the portable fluid infusion device; and
   processing circuitry configured to:
      generate a first set of data of the portable fluid infusion device, wherein the first set of data includes the status associated with the portable fluid infusion device that is visually indicated by the light emitting element, and wherein the first set of data includes data indicating one or more of: whether the portable fluid infusion device is on, whether the portable fluid infusion device is operating properly, whether the portable fluid infusion device is undergoing wireless charging or done with wireless charging, whether there is an alarm or alert associated with the portable fluid infusion device, or whether the portable fluid infusion device is in pairing mode; and
      generate a second set of data of the portable fluid infusion device, wherein the second set of data includes all data of the portable fluid infusion device that is to be displayed to a user, and wherein at least a portion of the second set of data of the portable fluid infusion device is for displaying on a device other than the portable fluid infusion device, and
   wherein no portion of the portable fluid infusion device includes a display.

2. The portable fluid infusion device of claim 1, further comprising a vibration motor.

3. The portable fluid infusion device of claim 1, wherein the battery has a flat rectangular shape.

4. The portable fluid infusion device of claim 1, wherein the battery has a flat cylindrical shape.

5. The portable fluid infusion device of claim 1, further comprising a force sensor situated between the drive system and the housing.

6. The portable fluid infusion device of claim 1, wherein the housing comprises a plurality of housing portions.

7. The portable fluid infusion device of claim 1, wherein the portable fluid infusion device is an insulin infusion device.

8. The portable fluid infusion device of claim 1, wherein the drive system comprises at least a motor and a slide, wherein in a retracted position, the motor is at least partially within the slide, wherein forward advancement of the slide causes the removable fluid reservoir to dispense fluid, and wherein each of the motor, slide, and the removable fluid reservoir are configured to be serially coupled to one another and be inline with one another to have a combined dimension that is less than or equal to the largest dimension.

9. The portable fluid infusion device of claim 1, wherein the second set of data of the portable fluid infusion device includes an amount of insulin delivered.

10. The portable fluid infusion device of claim 1, wherein the housing has a largest dimension, and wherein the drive system is configured to be serially coupled to the removable fluid reservoir such that a combined dimension of the drive system and the removable fluid reservoir is less than or equal to the largest dimension.

11. The portable fluid infusion device of claim 10, wherein the housing has a smallest dimension, wherein the battery has a plurality of faces comprising one or more faces having a largest area, and wherein the battery is situated such that the one or more faces are parallel to the largest dimension and the smallest dimension.

* * * * *